(12) United States Patent
Pan et al.

(10) Patent No.: US 8,710,035 B2
(45) Date of Patent: Apr. 29, 2014

(54) METHODS AND COMPOSITIONS RELATED TO GLUCOCORTICOID RECEPTOR ANTAGONISTS AND BREAST CANCER

(75) Inventors: Deng Pan, Chicago, IL (US); Masha Kocherginsky, Chicago, IL (US); Suzanne D. Conzen, Park Ridge, IL (US)

(73) Assignee: The University of Chicago, Chicago, IL (US)

( * ) Notice: Subject to any disclaimer, the term of this patent is extended or adjusted under 35 U.S.C. 154(b) by 65 days.

(21) Appl. No.: 13/071,363

(22) Filed: Mar. 24, 2011

(65) Prior Publication Data

US 2011/0269728 A1 Nov. 3, 2011

Related U.S. Application Data

(60) Provisional application No. 61/317,182, filed on Mar. 24, 2010.

(51) Int. Cl.
*A61K 31/575* (2006.01)

(52) U.S. Cl.
USPC .......................................................... 514/171

(58) Field of Classification Search
USPC .......................................................... 514/171
See application file for complete search history.

(56) References Cited

U.S. PATENT DOCUMENTS

| | | | |
|---|---|---|---|
| 2002/0115613 A1* | 8/2002 | Kumar | 514/12 |
| 2008/0287419 A1* | 11/2008 | Bruncko et al. | 514/211.15 |
| 2010/0135956 A1* | 6/2010 | Gant et al. | 424/85.2 |

OTHER PUBLICATIONS

Gaddy et al. (Clin Cancer Res 2004;10:5215-5225).*
Ring et al. (Endocrine-Related Cancer (2004) 11 643-658).*
Klijn et al. (Cancer Research 49, 2851-2856; 1989).*
"Data Sheet: Glucocorticoid Receptor mouse monoclonal antibody NCL-GCR", Novocastra Laboratories Ltd., available at http://www.ebiotrade.com/buyf/Novocastra/data/hrerp/gcr.pdf, accessed on Jun. 7, 2011.
"Identification of Glucocorticoid Receptor (GR) signatures in primary human breast cancer: Association with relapse-free survival time" poster presented by S.D. Conzen as a short talk, presented at Nuclear Receptors: Signaling, Gene Regulation and Cancer, Keystone Symposia on Molecular and Cellular Biology, Keystone Resort, Keystone, Colorado, Thursday, Mar. 25, 2010.
Belanoff et al., "Selective glucocorticoid receptor (type II) antagonists prevent weight gain caused by olanzapine in rats," *Eur. J. Pharmacol.*, 655(1-3):117-120, 2011.
Cho et al., "Role of activation function domain-1, DNA binding, and coactivator GRIP1 in the expression of partial agonist activity of glucocorticoid receptor-antagonist complexes," *Biochemistry*, 44(9):3547-3561, 2005.
Clark, "Glucocorticoid Receptor Antagonists" *Current Topics in Medicinal Chemistry*, 8:813-838, 2008.

Colleoni et al., "Response to primary chemotherapy in breast cancer patients with tumors not expressing estrogen and progesterone receptors" *Annals of Oncology*, 11(8):1057-9, 2000.
Desmedt et al., "Strong Time Dependence of the 76-Gene Prognostic Signature for Node-Negative Breast Cancer Patients in the TRANSBIG Multicenter Independent Validation Series" *Clin. Cancer Res.*, 13:3207-3214, 2007.
Grover and Martin, "The initiation of breast and prostate cancer" *Carcinogenesis*, 23(7): 1095-1102, 2002.
Hein et al., "Click Chemistry, A powerful Tool for Pharmaceutical Sciences" *Pharmaceutical Research*, 25(10):2216-30, 2008.
Henderson et al., "Estrogens as a cause of human cancer: the Richard and Hinda Rosenthal Foundation award lecture" *Cancer Res.*, 48:246-253, 1988.
Keen and Davidson, "The biology of breast carcinoma" *Cancer*, 97 (3 Suppl):825-33, 2003.
Kriaucionis et al., "The nuclear DNA base 5-hydroxymethylcytosine is present in Purkinje neurons and the brain" *Science*, 15;324(5929):929-30, 2009.
Loi et al., "Definition of Clinically Distinct Molecular Subtypes in Estrogen Receptor-Positive Breast Carcinomas Through Genomic Grade" *Journal of Clinical Oncology*, 25:1239-1246, 2006.
Loi et al., "Predicting prognosis using molecular profiling in estrogen receptor-positive breast cancer treated with tamoxifen" *BMC Genomics*, 9:239, 2008.
Ma et al. "IL-21 activates both innate and adaptive immunity to generate potent antitumor responses that require perforin but are independent of IFN-gamma" *J. Immunol*, 171(2):608-615, 2003.
Melhem et al., "Administration of glucocorticoids to ovarian cancer patients is associated with expression of the anti-apoptotic genes SGK1 and MKP1/DUSP1 in ovarian tissues" *Clin. Cancer Res.*, 15(9):3196-204, 2009.
Mikosz et al., "Glucocorticoid receptor-mediated protection from apoptosis is associated with induction of the serine/threonine survival kinase gene, sgk-1" *J. Biol. Chem.*, 276 (20):16649-54, 2001.
Minn et al.. "Genes that mediate breast cancer metastasis to lung". *Nature* 28;436(7050):518-24, 2005.
Moran et al., "The glucocorticoid receptor mediates a survival signal in human mammary epithelial cells" *Cancer Res.*, 60 (4):867-72, 2000.
Moses et al., "The growing applications of click chemistry" *Chem Soc Rev.*, 36(8):1249-62, 2007.
Pan et al., "Activation of the glucocorticoid receptor is associated with poor prognosis in estrogen receptor-negative breast cancer," *Cancer Research*, Published Online First Aug. 25, 2011; doi: 10.1158/0008-5472.CAN-11-0362.
Pang et al., "Dexamethasone decreases xenograft response to Paclitaxel through inhibition of tumor cell apoptosis" *Cancer Biol. Ther.*, 5(8):933-40, 2006.

(Continued)

*Primary Examiner* — Shirley V Gembeh
(74) *Attorney, Agent, or Firm* — Fulbright & Jaworski LLP

(57) ABSTRACT

Embodiments of the invention are directed to methods of determining the prognosis of a breast cancer patient by evaluating the activity of the glucocorticoid receptor in tumor cells. Other embodiment include methods of treating breast cancer cells, particularly, chemo-resistant cells, with a glucocorticoid receptor antagonist and an anticancer agent or compound.

21 Claims, 12 Drawing Sheets

(56) References Cited

OTHER PUBLICATIONS

Peeters et al., "Differential effects of the new glucocorticoid receptor antagonist ORG 34517 and RU486 (mifepristone) on glucocorticoid receptor nuclear translocation in the AtT20 cell line," *Ann. NY Acad. Sci.*, 1148:536-541, 2008.

Pike et al., "Estrogens, progestogens, normal breast cell proliferation, and breast cancer risk" *Epidemiologic Rev.*, 15(1):17-35, 1993.

Robinson et al., "Octahydrophenanthrene-2, 7-diol Analogues as dissociated Glucocorticoid Receptor Agonists Discovery and Lead Exploration" *J. Med. Chem.*,. 52:1731-43, 2009.

Sims et al., "The removal of multiplicative, systematic bias allows integration of breast cancer gene expression datasets—improving meta-analysis and prediction of prognosis" *BMC Medical Genomics*, 1:42, doi:10.1186/1755-8794-1-42, 2008.

Smith et al., "Expression of glucocorticoid and progesterone nuclear receptor genes in archival breast cancer tissue" *Breast Cancer Res.*, 5(1): R9-R12, 2003.

Smith et al., "Progesterone, glucocorticoid, but not estrogen receptor mRNA is altered in breast cancer stroma" *Cancer Lett.*, 255:77-84, 2007.

Sorlie et al., "Gene expression patterns of breast carcinomas distinguish tumor subclasses with clinical implications" *Proc. Natl. Acad. Sci. USA*, 98:10869-10874., 2001.

Sotiriou et al. "Gene expression profiling in breast cancer: understanding the molecular basis of histologic grade to improve prognosis" *J. Natl. Cancer Inst*, 15;98(4):262-72, 2006.

Srinivas et al.,"Proteomics for cancer biomarker discovery" *Clin. Chem.*, 48(8):1160-9, 2002.

Wang et al., "Gene-expression profiles to predict distant metastasis of lymph-node-negative primary breast cancer". *Lancet* 19-25;365(9460):671-9, 2005.

Wu et al., "Glucocorticoid receptor activation signals through forkhead transcription factor 3a in breast cancer cells" *Mol. Endocrinol*, 20(10): 2304-14, 2006.

Wu et al., "Microarray analysis reveals glucocorticoid-regulated survival genes that are associated with inhibition of apoptosis in breast epithelial cells" *Cancer Res.*, 64(5):1757-64, 2004.

Wu et al., "Prevalent expression of the immunostimulatory MHC class I chain-related molecule is counteracted by shedding in prostate cancer" *J. Clin. Invest.*, 114(4):560-8, 2004.

Lucci, et al., "Modification of ceramide metabolism increases cancer cell sensitivity to cytotoxics." *Int J Onco.* 15: 541-546, 1999.

\* cited by examiner

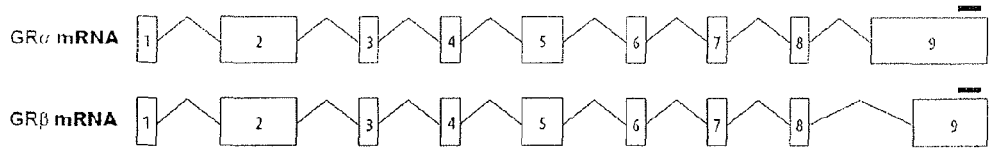

```
Query = GR alpha
Length=6784

18665 = GR beta

ALIGNMENTS

Query   1    GGCGCCGCCTCCACCCGCTCCCCGCTCGGTCCCGCTCGCTCGCCCAGGCCGGGCTGCCCT   60
18665   1    GGCGCCGCCTCCACCCGCTCCCCGCTCGGTCCCGCTCGCTCGCCCAGGCCGGGCTGCCCT   60

Query   61   TTCGCGTGTCCGCGCTCTCTTCCCTCCGCCGCCGCCTCCTCCATTTTGCGAGCTCGTGTC   120
18665   61   TTCGCGTGTCCGCGCTCTCTTCCCTCCGCCGCCGCCTCCTCCATTTTGCGAGCTCGTGTC   120

Query   121  TGTGACGGGAGCCCGAGTCACCGCCTGCCCGTCGGGGACGGATTCTGTGGGTGGAAGGAG   180
18665   121  TGTGACGGGAGCCCGAGTCACCGCCTGCCCGTCGGGGACGGATTCTGTGGGTGGAAGGAG   180

Query   181  ACGCCGCAGCCGGAGCGGCCGAAGCAGCTGGGACCGGGACGGGGCACGCGCGCCCGGAAC   240
18665   181  ACGCCGCAGCCGGAGCGGCCGAAGCAGCTGGGACCGGGACGGGGCACGCGCGCCCGGAAC   240

Query   241  CTCGACCCGCGGAGCCCGGCGCGGGGCGGAGGGCTGGCTTGTCAGCTGGGCAATGGGAGA   300
18665   241  CTCGACCCGCGGAGCCCGGCGCGGGGCGGAGGGCTGGCTTGTCAGCTGGGCAATGGGAGA   300

Query   301  CTTTCTTAAATAGGGGCTCTCCCCCCACCCATGGAGAAAGGGGCGGCTGTTTACTTCCtt   360
18665   301  CTTTCTTAAATAGGGGCTCTCCCCCCACCCATGGAGAAAGGGGCGGCTGTTTACTTCCTT   360

Query   361  ttttttAGaaaaaaaaaaTATATTTCCCTCCTGCTCCTTCTGCGTTCACAAGCTAAGTTGT   420
18665   361  TTTTTAGAAAAAAAAAATATATTTCCCTCCTGCTCCTTCTGCGTTCACAAGCTAAGTTGT   420

Query   421  TTATCTCGGCTGCGGCGGGAACTGCGGACGGTGGCGGGCGAGCGGCTCCTCTGCCAGAGT   480
18665   421  TTATCTCGGCTGCGGCGGGAACTGCGGACGGTGGCGGGCGAGCGGCTCCTCTGCCAGAGT   480

Query   481  TGATATTCACTGATGGACTCCAAAGAATCATTAACTCCTGGTAGAGAAGAAAACCCCAGC   540
18665   481  TGATATTCACTGATGGACTCCAAAGAATCATTAACTCCTGGTAGAGAAGAAAACCCCAGC   540

Query   541  AGTGTGCTTGCTCAGGAGAGGGGAGATGTGATGGACTTCTATAAAACCCTAAGAGGAGGA   600
18665   541  AGTGTGCTTGCTCAGGAGAGGGGAGATGTGATGGACTTCTATAAAACCCTAAGAGGAGGA   600

Query   601  GCTACTGTGAAGGTTTCTGCGTCTTCACCCTCACTGGCTGTCGCTTCTCAATCAGACTCC   660
18665   601  GCTACTGTGAAGGTTTCTGCGTCTTCACCCTCACTGGCTGTCGCTTCTCAATCAGACTCC   660

Query   661  AAGCAGCGAAGACTTTTGGTTGATTTTCCAAAAGGCTCAGTAAGCAATGCGCAGCAGCCA   720
18665   661  AAGCAGCGAAGACTTTTGGTTGATTTTCCAAAAGGCTCAGTAAGCAATGCGCAGCAGCCA   720

Query   721  GATCTGTCCAAAGCAGTTTCACTCTCAATGGGACTGTATATGGGAGAGACAGAAACAAAA   780
18665   721  GATCTGTCCAAAGCAGTTTCACTCTCAATGGGACTGTATATGGGAGAGACAGAAACAAAA   780

Query   781  GTGATGGGAAATGACCTGGGATTCCCACAGCAGGGCCAAATCAGCCTTTCCTCGGGGGAA   840
18665   781  GTGATGGGAAATGACCTGGGATTCCCACAGCAGGGCCAAATCAGCCTTTCCTCGGGGGAA   840

Query   841  ACAGACTTAAAGCTTTTGGAAGAAAGCATTGCAAACCTCAATAGCTCGACCAGTGTTCCA   900
18665   841  ACAGACTTAAAGCTTTTGGAAGAAAGCATTGCAAACCTCAATAGGTCGACCAGTGTTCCA   900
```

FIG. 7A

```
Query   901   GAGAACCCCAAGAGTTCAGCATCCACTGCTGTGTCTGCTGCCCCCACAGAGAAGGAGTTT   960
18665   901   GAGAACCCCAAGAGTTCAGCATCCACTGCTGTGTCTGCTGCCCCCACAGAGAAGGAGTTT   960

Query   961   CCAAAAACTCACTCTGATGTATCTTCAGAACAGCAACATTTGAAGGGCCAGACTGGCACC   1020
18665   961   CCAAAAACTCACTCTGATGTATCTTCAGAACAGCAACATTTGAAGGGCCAGACTGGCACC   1020

Query   1021  AACGGTGGCAATGTGAAATTGTATACCACAGACCAAAGCACCTTTGACATTTTGCAGGAT   1080
18665   1021  AACGGTGGCAATGTGAAATTGTATACCACAGACCAAAGCACCTTTGACATTTTGCAGGAT   1080

Query   1081  TTGGAGTTTTCTTCTGGGTCCCCAGGTAAAGAGACGAATGAGAGTCCTTGGAGATCAGAC   1140
18665   1081  TTGGAGTTTTCTTCTGGGTCCCCAGGTAAAGAGACGAATGAGAGTCCTTGGAGATCAGAC   1140

Query   1141  CTGTTGATAGATGAAAACTGTTTGCTTTCTCCTCTGGCGGAGAAGACGATTCATTCCTT   1200
18665   1141  CTGTTGATAGATGAAAACTGTTTGCTTTCTCCTCTGGCGGAGAAGACGATTCATTCCTT   1200

Query   1201  TTGGAAGGAAACTCGAATGAGGACTGCAAGCCTCTCATTTTACCGGACACTAAACCCAAA   1260
18665   1201  TTGGAAGGAAACTCGAATGAGGACTGCAAGCCTCTCATTTTACCGGACACTAAACCCAAA   1260

Query   1261  ATTAAGGATAATGGAGATCTGGTTTTGTCAAGCCCCAGTAATGTAACACTGCCCCAAGTG   1320
18665   1261  ATTAAGGATAATGGAGATCTGGTTTTGTCAAGCCCCAGTAATGTAACACTGCCCCAAGTG   1320

Query   1321  AAAACAGAAAAAGAAGATTTCATCGAACTCTGCACCCCTGGGGTAATTAAGCAAGAGAAA   1380
18665   1321  AAAACAGAAAAAGAAGATTTCATCGAACTCTGCACCCCTGGGGTAATTAAGCAAGAGAAA   1380

Query   1381  CTGGGCACAGTTTACTGTCAGGCAAGCTTTCCTGGAGCAAATATAATTGGTAATAAAATG   1440
18665   1381  CTGGGCACAGTTTACTGTCAGGCAAGCTTTCCTGGAGCAAATATAATTGGTAATAAAATG   1440

Query   1441  TCTGCCATTTCTGTTCATGGTGTGAGTACCTCTGGAGGACAGATGTACCACTATGACATG   1500
18665   1441  TCTGCCATTTCTGTTCATGGTGTGAGTACCTCTGGAGGACAGATGTACCACTATGACATG   1500

Query   1501  AATACAGCATCCCTTTCTCAACAGCAGGATCAGAAGCCTATTTTTAATGTCATTCCACCA   1560
18665   1501  AATACAGCATCCCTTTCTCAACAGCAGGATCAGAAGCCTATTTTTAATGTCATTCCACCA   1560

Query   1561  ATTCCCGTTGGTTCCGAAAATTGGAATAGGTGCCAAGGATCTGGAGATGACAACTTGACT   1620
18665   1561  ATTCCCGTTGGTTCCGAAAATTGGAATAGGTGCCAAGGATCTGGAGATGACAACTTGACT   1620

Query   1621  TCTCTGGGGACTCTGAACTTCCCTGGTCGAACAGTTTTTTCTAATGGCTATTCAAGCCCC   1680
18665   1621  TCTCTGGGGACTCTGAACTTCCCTGGTCGAACAGTTTTTTCTAATGGCTATTCAAGCCCC   1680

Query   1681  AGCATGAGACCAGATGTAAGCTCTCCTCCATCCAGCTCCTCAACAGCAACAACAGGACCA   1740
18665   1681  AGCATGAGACCAGATGTAAGCTCTCCTCCATCCAGCTCCTCAACAGCAACAACAGGACCA   1740

Query   1741  CCTCCCAAACTCTGCCTGGTGTGCTCTGATGAAGCTTCAGGATGTCATTATGGAGTCTTA   1800
18665   1741  CCTCCCAAACTCTGCCTGGTGTGCTCTGATGAAGCTTCAGGATGTCATTATGGAGTCTTA   1800

Query   1801  ACTTGTGGAAGCTGTAAAGTTTTCTTCAAAAGAGCAGTGGAAGGACAGCACAATTACCTA   1860
18665   1801  ACTTGTGGAAGCTGTAAAGTTTTCTTCAAAAGAGCAGTGGAAGGACAGCACAATTACCTA   1860

Query   1861  TGTGCTGGAAGGAATGATTGCATCATCGATAAAATTCGAAGAAAAAACTGCCCAGCATGC   1920
18665   1861  TGTGCTGGAAGGAATGATTGCATCATCGATAAAATTCGAAGAAAAAACTGCCCAGCATGC   1920

Query   1921  CGCTATCGAAAATGTCTTCAGGCTGGAATGAACCTGGAAGCTCGaaaaacaaagaaaaaa   1980
18665   1921  CGCTATCGAAAATGTCTTCAGGCTGGAATGAACCTGGAAGCTCGAAAAACAAAGAAAAAA   1980

Query   1981  ataaaaGGAATTCAGCAGGCCACTACAGGAGTCTCACAAGAAACCTCTGAAAATCCTGGT   2040
18665   1981  ATAAAAGGAATTCAGCAGGCCACTACAGGAGTCTCACAAGAAACCTCTGAAAATCCTGGT   2040

Query   2041  AACAAAACAATAGTTCCTGCAACGTTACCACAACTCACCCCTACCCTGGTGTCACTGTTG   2100
18665   2041  AACAAAACAATAGTTCCTGCAACGTTACCACAACTCACCCCTACCCTGGTGTCACTGTTG   2100

Query   2101  GAGGTTATTGAACCTGAAGTGTTATATGCAGGATATGATAGCTCTGTTCCAGACTCAACT   2160
18665   2101  GAGGTTATTGAACCTGAAGTGTTATATGCAGGATATGATAGCTCTGTTCCAGACTCAACT   2160
```

FIG. 7B

```
Query  2161  TGGAGGATCATGACTACGCTCAACATGTTAGGAGGGCGGCAAGTGATTGCAGCAGTGAAA  2220
18665  2161  TGGAGGATCATGACTACGCTCAACATGTTAGGAGGGCGGCAAGTGATTGCAGCAGTGAAA  2220

Query  2221  TGGGCAAAGGCAATACCAGGTTTCAGGAACTTACACCTGGATGACCAAATGACCCTACTG  2280
18665  2221  TGGGCAAAGGCAATACCAGGTTTCAGGAACTTACACCTGGATGACCAAATGACCCTACTG  2280

Query  2281  CAGTACTCCTGGATGTTTCTTATGGCATTTGCTCTGGGGTGGAGATCATATAGACAATCA  2340
18665  2281  CAGTACTCCTGGATGTTTCTTATGGCATTTGCTCTGGGGTGGAGATCATATAGACAATCA  2340

Query  2341  AGTGCAAACCTGCTGTGTTTTGCTCCTGATCTGATTATTAATGAGCAGAGAATGACTCTA  2400
18665  2341  AGTGCAAACCTGCTGTGTTTTGCTCCTGATCTGATTATTAATGAGCAGAGAATGACTCTA  2400

Query  2401  CCCTGCATGTACGACCAATGTAAACACATGCTGTATGTTTCCTCTGAGTTACACAGGCTT  2460
18665  2401  CCCTGCATGTACGACCAATGTAAACACATGCTGTATGTTTCCTCTGAGTTACACAGGCTT  2460

Query  2461  CAGGTATCTTATGAAGAGTATCTCTGTATGAAAACCTTACTGCTTCTCTCTTCAGTTCCT  2520
18665  2461  CAGGTATCTTATGAAGAGTATCTCTGTATGAAAACCTTACTGCTTCTCTCTTCAGTTCCT  2520

Query  2521  AAGGACGGTCTGAAGAGCCAAGAGCTATTTGATGAAATTAGAATGACCTACATCAAAGAG  2580
18665  2521  AAGGACGGTCTGAAGAGCCAAGAGCTATTTGATGAAATTAGAATGACCTACATCAAAGAG  2580

Query  2581  CTAGGAAAAGCCATTGTCAAGAGGGAAGGAAACTCCAGCCAGAACTGGCAGCGGTTTTAT  2640
18665  2581  CTAGGAAAAGCCATTGTCAAGAGGGAAGGAAACTCCAGCCAGAACTGGCAGCGGTTTTAT  2640

Query  2641  CAACTGACAAAACTCTTGGATTCTATGCATGAAGTGGTTGAAAATCTCCTTAACTATTGC  2700
18665  2641  CAACTGACAAAACTCTTGGATTCTATGCATGAA                             2673

Query  2701  TTCCAAACATTTTTGGATAAGACCATGAGTATTGAATTCCCCGAGATGTTAGCTGAAATC  2760

Query  2761  ATCACCAATCAGATACCAAAATATTCAAATGGAAATATCAAAAAACTTCTGTTTCATCAA  2820

Query  2821  AAGTGACTGCCTTAATAAGAATGGTTGCCTTAAAGAAAGTCGAATTAATAGCTTTTATTG  2880

Query  2881  TATAAACTATCAGTTTGTCCTGTAGAGgttttgttgttttatttttattgttttcatct  2940

Query  2941  gttgttttgttttAAATACGCACTACATGTGGTTTATAGAGGGCCAAGACTTGGCAACAG  3000

Query  3001  AAGCAGTTGAGTCGTCATCACTTTTCAGTGATGGGAGAGTAGATGGTGAAATTTATTAGT  3060

Query  3061  TAATATATCCCAGAAATTAGAAACCTTAATATGTGGACGTAATCTCCACAGTCAAAGAAG  3120

Query  3121  GATGGCACCTAAACCACCAGTGCCCAAAGTCTGTGTGATGAACTTTCTCTTCATACtttt  3180

Query  3181  tttCACAGTTGGCTGGATGAAATTTTCTAGACTTTCTGTTGGTGTATccccccccTGTAT  3240

Query  3241  AGTTAGGATAGCATTTTTGATTTATGCATGGAAACCTGaaaaaaaaGTTTACAAGTGTATA  3300

Query  3301  TCAGAAAAGGGAAGTTGTGCCTTTTATAGCTATTACTGTCTGGTTTTAACAATTTCCTTT  3360

Query  3361  ATATTTAGTGAACTACGCTTGCTCATTTTTTCTTACATAATTTTTTATTCAAGTTATTGT  3420

Query  3421  ACAGCTGTTTAAGATGGGCAGCTAGTTCGTAGCTTTCCCAAATAAACTCTAAACATTAAT  3480

Query  3481  CAATCATCTGTGTGAAAATGGGTTGGTGCTTCTAACCTGATGGCACTTAGCTATCAGAAG  3540

Query  3541  ACCACAAAAATTGACTCAAATCTCCAGTATTCTTGTCaaaaaaaaaaaaaaaaaaGCTCA  3600

Query  3601  TATTTGTATATATCTGCTTCAGTGGAGAATTATATAGGTTGTGCAAATTAACAGTCCTA  3660

Query  3661  ACTGGTATAGAGCACCTAGTCCAGTGACCTGCTGGGTAAACTGTGGATGATGGTTGCAAA  3720

Query  3721  AGACTAATTTAAAAAATAACTACCAAGAGGCCCTGTCTGTACCTAACGCCCTATTTTTGC  3780
```

FIG. 7C

```
Query  3781  AATGGCTATATGGCAAGAAAGCTGGTAAACTATTTGTCTTTCAGGACCTTTTGAAGTAGT  3840

Query  3841  TTGTATAACTTCTTAAAAGTTGTGATTCCAGATAACCAGCTGTAACACAGCTGAGAGACT  3900

Query  3901  TTTAATCAGACAAAGTAATTCCTCTCACTAAACTTTACCCAAAAACTAAATCTCTAATAT  3960

Query  3961  GGCAAAAATGGCTAGACACCCATTTTCACATTCCCATCTGTCACCAATTGGTTAATCTTT  4020

Query  4021  CCTGATGGTACAGGAAAGCTCAGCTACTGATTTTTGTGATTTAGAACTGTATGTCAGACA  4080

Query  4081  TCCATGTTTGTAAAACTACACATCCCTAATGTGTGCCATAGAGTTTAACACAAGTCCTGT  4140

Query  4141  GAATTTCTTCACTGTTGAAAATTATTTTAAACAAAATAGAAGCTGTAGTAGCCCTTTCTG  4200

Query  4201  TGTGCACCTTACCAACTTTCTGTAAACTCAAAACTTAACATATTTACTAAGCCACAAGAA  4260

Query  4261  ATTTGATTTCTATTCAAGGTGGCCAAATTATTTGTGTAATAGAAAACTGAAAATCTAATA  4320

Query  4321  TTAAAAATATGGAACTTCTAatatattttttatatttagttatagtttcagatatatatca  4380

Query  4381  tatTGGTATTCACTAATCTGGGAAGGGAAGGGCTACTGCAGCTTTACATGCAATTTATTA  4440

Query  4441  AAATGATTGTAAAATAGCTTGTATAGTGTAAAATAAGAATGATTTTAGATGAGATTGTT  4500

Query  4501  TTATCATGACATGTTATATATTTTTTGTAGGGGTCAAAGAAATGCTGATGGATAACCTAT  4560

Query  4561  ATGATTTATAGTTTGTACATGCATTCATACAGGCAGCGATGGTCTCAGAAACCAAACAGT  4620

Query  4621  TTGCTCTAGGGGAAGAGGGAGATGGAGACTGGTCCTGTGTGCAGTGAAGGTTGCTGAGGC  4680

Query  4681  TCTGACCCAGTGAGATTACAGAGGAAGTTATCCTCTGCCTCCCATTCTGACCACCCTTCT  4740

Query  4741  CATTCCAACAGTGAGTCTGTCAGCGCAGGTTTAGTTTACTCAATCTCCCCTTGCACTAAA  4800

Query  4801  GTATGTAAAGTATGTAAACAGGAGACAGGAAGGTGGTGCTTACATCCTTAAAGGCACCAT  4860

Query  4861  CTAATAGCGGGTTACTTTCACATACAGCCCTCCCCCAGCAGTTGAATGACAACAGAAGCT  4920

Query  4921  TCAGAAGTTTGGCAATAGTTTGCATAGAGGTACCAGCAATATGTAAATAGTGCAGAATCT  4980

Query  4981  CATAGGTTGCCAATAATACACTAATTCCTTTCTATCCTACAACAAGAGTTTATTTCCAAA  5040

Query  5041  TAAAATGAGGACAtgttttttgttttctttgaatgcttttgaatgttatttgttattttc  5100

Query  5101  agtatttttggagaaattatttAATaaaaaaaCAATCATTTGCTTTTTGAATGCTCTCTAA  5160

Query  5161  AAGGGAATGTAATATTTTAAGATGGTGTGTAACCCGGCTGGATAAATTTTTGGTGCCTAA  5220

Query  5221  GAAAACTGCTTGAATATTCTTATCAATGACAGTGTTAAGTTTCAAAAAGAGCTTCTAAAA  5280

Query  5281  CGTACATTATCATTCCTTTATAGAATGTTATGTGGTTAAAACCAGAAAGCACATCTCACA  5340
18665  2674                          AATGTTATGTGGTTAAAACCAGAAAGCACATCTCACA  2710

Query  5341  CATTAATCTGATTTTCATCCCAACAATCTTGGCGCTCAAAAAATAGAACTCAATGAGAAA  5400
18665  2711  CATTAATCTGATTTTCATCCCAACAATCTTGGCGCTCAAAAAATAGAACTCAATGAGAAA  2770

Query  5401  AAGAAGATTATGTGCACTTCGTTGTCAATAATAAGTCAACTGATGCTCATCGACAACTAT  5460
18665  2771  AAGAAGATTATGTGCACTTCGTTGTCAATAATAAGTCAACTGATGCTCATCGACAACTAT  2830

Query  5461  AGGAGGCTTTTCATTAAATGGGAAAGAAGCTGTGCCCTTTTAGGATACGTGGGGGAAAA  5520
18665  2831  AGGAGGCTTTTCATTAAATGGGAAAGAAGCTGTGCCCTTTTAGGATACGTGGGGGAAAA  2890

Query  5521  GAAAGTCATCTTAATTATGTTTAATTGTGGATTTAAGTGCTATATGGTGGTGCTGTTTGA  5580
```

FIG. 7D

```
18665  2891  GAAAGTCATCTTAATTATGTTTAATTGTGGATTTAAGTGCTATATGGTGGTGCTGTTTGA  2950

Query  5581  AAGCAGATTTATTTCCTATGTATGTGTTATCTGGCCATCCCAACCCAAACTGTTGAAGTT  5640
18665  2951  AAGCAGATTTATTTCCTATGTATGTGTTATCTGGCCATCCCAACCCAAACTGTTGAAGTT  3010

Query  5641  TGTAGTAACTTCAGTGAGAGTTGGTTACTCACAACAAATCCTGAAAAGTATTTTTAGTGT  5700
18665  3011  TGTAGTAACTTCAGTGAGAGTTGGTTACTCACAACAAATCCTGAAAAGTATTTTTAGTGT  3070

Query  5701  TTGTAGGTATTCTGTGGGATACTATACAAGCAGAACTGAGGCACTTAGGACATAACACTT  5760
18665  3071  TTGTAGGTATTCTGTGGGATACTATACAAGCAGAACTGAGGCACTTAGGACATAACACTT  3130

Query  5761  TTGGGGTATATATATCCAAATGCCTAAAACTATGGGAGGAAACCTTGGCCACCCCAAAAG  5820
18665  3131  TTGGGGTATATATATCCAAATGCCTAAAACTATGGGAGGAAACCTTGGCCACCCCAAAAG  3190

Query  5821  GAAAACTAACATGATTTGTGTCTATGAAGTGCTGGATAATTAGCATGGGATGAGCTCTGG  5880
18665  3191  GAAAACTAACATGATTTGTGTCTATGAAGTGCTGGATAATTAGCATGGGATGAGCTCTGG  3250

Query  5881  GCATGCCATGAAGGAAAGCCACGCTCCCTTCAGAATTCAGAGGCAGGGAGCAATTCCAGT  5940
18665  3251  GCATGCCATGAAGGAAAGCCACGCTCCCTTCAGAATTCAGAGGCAGGGAGCAATTCCAGT  3310

Query  5941  TTCACCTAAGTCTCATAATTTTAGTTCCCTTTTAAAAACCCTGAAAACTACATCACCATG  6000
18665  3311  TTCACCTAAGTCTCATAATTTTAGTTCCCTTTTAAAAACCCTGAAAACTACATCACCATG  3370

Query  6001  GAATGAAAAATATTGTTATACAATACATTGATCTGTCAAACTTCCAGAACCATGGTAGCC  6060
18665  3371  GAATGAAAAATATTGTTATACAATACATTGATCTGTCAAACTTCCAGAACCATGGTAGCC  3430

Query  6061  TTCAGTGAGATTTCCATCTTGGCTGGTCACTCCCTGACTGTAGCTGTAGGTGAAtgtgtt  6120
18665  3431  TTCAGTGAGATTTCCATCTTGGCTGGTCACTCCCTGACTGTAGCTGTAGGTGAATGTGTT  3490

Query  6121  tttgtgtgtgtgtgtCTGGTTTTAGTGTCAGAAGGGAAATAAAAGTGTAAGGAGGACACT  6180
18665  3491  TTTGTGTGTGTGTGTCTGGTTTTAGTGTCAGAAGGGAAATAAAAGTGTAAGGAGGACACT  3550

Query  6181  TTAAACCCTTTGGGTGGAGTTTCGTAATTTCCCAGACTATTTTCAAGCAACCTGGTCCAC  6240
18665  3551  TTAAACCCTTTGGGTGGAGTTTCGTAATTTCCCAGACTATTTTCAAGCAACCTGGTCCAC  3610

Query  6241  CCAGGATTAGTGACCAGGTTTTCAGGAAAGGATTTGCTTCTCTCTAGAAAATGTCTGAAA  6300
18665  3611  CCAGGATTAGTGACCAGGTTTTCAGGAAAGGATTTGCTTCTCTCTAGAAAATGTCTGAAA  3670

Query  6301  GGATTTTATTTTCTGATGAAAGGCTGTATGAAAATACCCTCCTCAAATAACTTGCTTAAC  6360
18665  3671  GGATTTTATTTTCTGATGAAAGGCTGTATGAAAATACCCTCCTCAAATAACTTGCTTAAC  3730

Query  6361  TACATATAGATTCAAGTGTGTCAATATTCTATTTGTATATTAAATGCTATATAATGGGG  6420
18665  3731  TACATATAGATTCAAGTGTGTCAATATTCTATTTGTATATTAAATGCTATATAATGGGG  3790

Query  6421  ACAAATCTATATTATACTGTGTATGGCATTATTAAGAAGCTTTTCATTATTTTTTATCA  6480
18665  3791  ACAAATCTATATTATACTGTGTATGGCATTATTAAGAAGCTTTTCATTATTTTTTATCA  3850

Query  6481  CAGTAATTTTAAAATGTGTAAAAATTAAAACCAGTGACTCCTGTTTAAAAATAAAAGTTG  6540
18665  3851  CAGTAATTTTAAAATGTGTAAAAATTAAAACCAGTGACTCCTGTTTAAAAATAAAAGTTG  3910

Query  6541  TAGTTTTTTATTCATGCTGAATAATAATCTGTAGTTaaaaaaaaaGTGTCTTTTTACCTA  6600
18665  3911  TAGTTTTTTATTCATGCTGAATAATAATCTGTAGTTAAAAAAAAAGTGTCTTTTTACCTA  3970

Query  6601  CGCAGTGAAATGTCAGACTGTAAAACCTTGTGTGGAAATGTTTAACTTTTATTTTTTCAT  6660
18665  3971  CGCAGTGAAATGTCAGACTGTAAAACCTTGTGTGGAAATGTTTAACTTTTATTTTTTCAT  4030

Query  6661  TTAAATTTGCTGTTCTGGTATTACCAAACCACACATTTGTACCGAATTGGCAGTAAATGT  6720
18665  4031  TTAAATTTGCTGTTCTGGTATTACCAAACCACACATTTGTACCGAATTGGCAGTAAATGT  4090

Query  6721  TAGCCATTTACAGCAATGCCAAATATGGAGAAACATCATAATaaaaaaaTCTGCTTTTTC  6780
18665  4091  TAGCCATTTACAGCAATGCCAAATATGGAGAAACATCATAATAAAAAAATCTGCTTTTTC  4150

Query  6781  ATTA  6784
```

FIG. 7E 18665   4151   ATTA   4154

FIG. 7F

SEQUENCE LISTING

<160> NUMBER OF SEQ ID NOS: 46

<210> SEQ ID NO 1
<211> LENGTH: 4794
<212> TYPE: DNA
<213> ORGANISM: Homo sapiens

<400> SEQUENCE: 1

```
tttttagaaa aaaaaaatat atttccctcc tgctccttct gcgttcacaa gctaagttgt      60
ttatctcggc tgcggcggga actgcggacg gtggcgggcg agcggctcct ctgccagagt     120
tgatattcac tgatggactc caaagaatca ttaactcctg gtagagaaga aaaccccagc     180
agtgtgcttg ctcaggagag gggagatgtg atggacttct ataaaaccct aagaggagga     240
gctactgtga aggtttctgc gtcttcaccc tcactggctg tcgcttctca atcagactcc     300
aagcagcgaa gacttttggt tgattttcca aaaggctcag taagcaatgc gcagcagcca     360
gatctgtcca aagcagtttc actctcaatg ggactgtata tgggagagac agaaacaaaa     420
gtgatgggaa atgacctggg attcccacag cagggccaaa tcagccttc ctcgggggaa      480
acagacttaa agcttttgga agaaagcatt gcaaacctca ataggtcgac cagtgttcca     540
gagaacccca agagttcagc atccactgct gtgtctgctg cccccacaga aaggagttt      600
ccaaaaactc actctgatgt atcttcagaa cagcaacatt tgaagggcca gactggcacc     660
aacggtggca atgtgaaatt gtataccaca gaccaaagca cctttgacat tttgcaggat     720
ttggagtttt cttctgggtc cccaggtaaa gagacgaatg agagtccttg gagatcagac     780
ctgttgatag atgaaaactg tttgctttct cctctggcgg gagaagacga ttcattcctt     840
ttggaaggaa actcgaatga ggactgcaag cctctcattt taccggacac taaacccaaa     900
attaaggata tggagatct ggttttgtca gcccccagta atgtaacact gccccaagtg     960
aaaacagaaa aagaagattt catcgaactc tgcacccctg ggtaattaa gcaagagaaa     1020
ctgggcacag tttactgtca ggcaagcttt cctggagcaa atataattgg taataaaatg     1080
tctgccattt ctgttcatgg tgtgagtacc tctggaggac agatgtacca ctatgacatg     1140
aatacagcat ccctttctca acagcaggat cagaagccta ttttaatgt cattccacca     1200
attccgtttg gttccgaaaa ttggaatagg tgccaaggat ctggagatga aacttgact     1260
tctctgggga ctctgaactt ccctggtcga acagttttt ctaatggcta ttcaagcccc     1320
agcatgagac cagatgtaag ctctcctcca tccagctcct caacagcaac aacaggacca     1380
cctcccaaac tctgcctggt gtgctctgat gaagcttcag gatgtcatta tggagtctta     1440
acttgtggaa gctgtaaagt tttcttcaaa agagcagtgg aaggacagca caattaccta     1500
tgtgctggaa ggaatgattg catcatcgat aaaattcgaa gaaaaaactg cccagcatgc     1560
cgctatcgaa aatgtcttca ggctggaatg aacctggaag ctcgaaaaac aaagaaaaaa     1620
ataaaaggaa ttcagcaggc cactacagga gtctcacaag aaacctctga aaatcctggt     1680
aacaaaacaa tagttcctgc aacgttacca caactcaccc ctaccctggt gtcactgttg     1740
gaggttattg aacctgaagt gttatatgca ggatatgata gctctgttcc agactcaact     1800
tggaggatca tgactacgct caacatgtta ggagggcggc aagtgattgc agcagtgaaa     1860
tgggcaaagg caataccagg tttcaggaac ttacacctgg atgaccaaat gaccctactg     1920
cagtactcct ggatgtttct tatggcattt gctctggggt ggagatcata tagacaatca     1980
agtgcaaacc tgctgtgttt tgctcctgat ctgattatta atgagcagag aatgactcta     2040
```

```
ccctgcatgt acgaccaatg taaacacatg ctgtatgttt cctctgagtt acacaggctt    2100
caggtatctt atgaagagta tctctgtatg aaaaccttac tgcttctctc ttcagttcct    2160
aaggacggtc tgaagagcca agagctattt gatgaaatta gaatgaccta catcaaagag    2220
ctaggaaaag ccattgtcaa gagggaagga aactccagcc agaactggca gcggttttat    2280
caactgacaa aactcttgga ttctatgcat gaagtggttg aaaatctcct taactattgc    2340
ttccaaacat ttttggataa gaccatgagt attgaattcc ccgagatgtt agctgaaatc    2400
atcaccaatc agataccaaa atattcaaat ggaaatatca aaaaacttct gtttcatcaa    2460
aagtgactgc cttaataaga atggttgcct taaagaaagt cgaattaata gcttttattg    2520
tataaactat cagtttgtcc tgtagaggtt ttgttgtttt attttttatt gttttcatct    2580
gttgttttgt tttaaatacg cactacatgt ggtttataga gggccaagac ttggcaacag    2640
aagcagttga gtcgtcatca cttttcagtg atgggagagt agatggtgaa atttattagt    2700
taatatatcc cagaaattag aaaccttaat atgtggacgt aatctccaca gtcaaagaag    2760
gatggcacct aaaccaccag tgcccaaagt ctgtgtgatg aactttctct tcatacttt    2820
tttcacagtt ggctggatga aattttctag actttctgtt ggtgtatccc ccccctgta    2880
tagttaggat agcattttg atttatgcat ggaaacctga aaaaagttt acaagtgtat    2940
atcagaaaag ggaagttgtg ccttttatag ctattactgt ctggttttaa caatttcctt    3000
tatatttagt gaactacgct tgctcatttt ttcttacata atttttatt caagttattg    3060
tacagctgtt taagatgggc agctagttcg tagctttccc aaataaactc taaacattaa    3120
tcaatcatct gtgtgaaaat gggttggtgc ttctaacctg atggcactta gctatcagaa    3180
gaccacaaaa attgactcaa atctccagta ttccttgtcaa aaaaaaaaaa aaaaaagctc    3240
atattttgta tatatctgct tcagtggaga attatatagg ttgtgcaaat taacagtcct    3300
aactggtata gagcacctag tccagtgacc tgctgggtaa actgtggatg atggttgcaa    3360
aagactaatt taaaaaataa ctaccaagag gccctgtctg tacctaacgc cctatttttg    3420
caatggctat atggcaagaa agctggtaaa ctatttgtct ttcaggacct tttgaagtag    3480
tttgtataac ttcttaaaag ttgtgattcc agataaccag ctgtaacaca gctgagagac    3540
ttttaatcag acaaagtaat tcctctcact aaactttacc caaaaactaa atctctaata    3600
tggcaaaaat ggctagacac ccattttcac attcccatct gtcaccaatt ggttaatctt    3660
tcctgatggt acaggaaagc tcagctactg attttttgtga tttagaactg tatgtatgtc    3720
agacatccat gtttgtaaaa ctacacatcc ctaatgtgtg ccatagagtt taacacaagt    3780
cctgtgaatt tcttcactgt tgaaaattat tttaaacaaa atagaagctg tagtagccct    3840
ttctgtgtgc accttaccaa ctttctgtaa actcaaaact taacatattt actaagccac    3900
aagaaatttg atttctattc aaggtggcca aattatttgt gtaatagaaa actgaaaatc    3960
taatattaaa aatatggaac ttctaatata ttttttatatt tagttatagt ttcagatata    4020
tatcatattg gtattcacta atctgggaag ggaagggcta ctgcagcttt acatgcaatt    4080
tattaaaatg attgtaaaat agcttgtata gtgtaaaata agaatgattt ttagatgaga    4140
ttgtttatc atgacatgtt atatatttt tgtagggtc aaagaaatgc tgatggataa    4200
cctatatgat ttatagttg tacatgcatt catacaggca gcgatggtct cagaaaccaa    4260
acagtttgct ctaggggaag agggagatgg agactggtcc tgtgtgcagt gaaggttgct    4320
gaggctctga cccagtgaga ttacagagga agttatcctc tgcctcccat tctgaccacc    4380
cttctcattc caacagtgag tctgtcagcg caggtttagt ttactcaatc tccccttgca    4440
```

| | |
|---|---|
| ctaaagtatg taaagtatgt aaacaggaga caggaaggtg gtgcttacat ccttaaaggc | 4500 |
| accatctaat agcgggttac tttcacatac agccctcccc cagcagttga atgacaacag | 4560 |
| aagcttcaga agtttggcaa tagtttgcat agaggtacca gcaatatgta aatagtgcag | 4620 |
| aatctcatag gttgccaata atacactaat tcctttctat cctacaacaa gagtttattt | 4680 |
| ccaaataaaa tgaggacatg ttttttgtttt ctttgaatgc ttttgaatg ttatttgtta | 4740 |
| ttttcagtat tttggagaaa ttatttaata aaaaaaacaa tcatttgctt tttg | 4794 |

<210> SEQ ID NO 2
<211> LENGTH: 6330
<212> TYPE: DNA
<213> ORGANISM: Homo sapiens

<400> SEQUENCE: 2

| | |
|---|---|
| aggagctggc ggagggcgtt cgtcctggga ctgcacttgc tcccgtcggg tcgcccggct | 60 |
| tcaccggacc cgcaggctcc cggggcaggg ccggggccag agctcgcgtg tcggcgggac | 120 |
| atgcgctgcg tcgcctctaa cctcgggctg tgctcttttt ccaggtggcc cgccggtttc | 180 |
| tgagccttct gccctgcggg gacacggtct gcaccctgcc cgcggccacg gaccatgacc | 240 |
| atgaccctcc acaccaaagc atctgggatg gccctactgc atcagatcca agggaacgag | 300 |
| ctggagcccc tgaaccgtcc gcagctcaag atcccctgg agcggcccct gggcgaggtg | 360 |
| tacctggaca gcagcaagcc cgccgtgtac aactaccccg agggcgccgc ctacgagttc | 420 |
| aacgccgcgg ccgccgccaa cgcgcaggtc tacggtcaga ccggcctccc ctacggcccc | 480 |
| gggtctgagg ctgcggcgtt cggctccaac ggcctggggg gtttcccccc actcaacagc | 540 |
| gtgtctccga gccgctgat gctactgcac ccgccgccgc agctgtcgcc tttcctgcag | 600 |
| ccccacggcc agcaggtgcc ctactacctg gagaacgagc ccagcggcta cgcgtgcgc | 660 |
| gaggccggcc cgccggcatt ctacaggcca aattcagata tcgacgcca gggtggcaga | 720 |
| gaaagattgg ccagtaccaa tgacaaggga agtatggcta tggaatctgc caaggagact | 780 |
| cgctactgtg cagtgtgcaa tgactatgct tcaggctacc attatggagt ctggtcctgt | 840 |
| gagggctgca aggccttctt caagagaagt attcaaggac ataacgacta tgtgtgtcca | 900 |
| gccaccaacc agtgcaccat tgataaaaac aggaggaaga gctgccaggc ctgccggctc | 960 |
| cgcaaatgct acgaagtggg aatgatgaaa ggtgggatac gaaaagaccg aagaggaggg | 1020 |
| agaatgttga acacaagcg ccagagagat gatggggagg gcagggtga agtggggtct | 1080 |
| gctggagaca tgagagctgc caacctttgg ccaagcccgc tcatgatcaa cgctctaag | 1140 |
| aagaacagcc tggccttgtc cctgacggcc gaccagatgg tcagtgcctt gttggatgct | 1200 |
| gagcccccca tactctattc cgagtatgat cctaccagac ccttcagtga agcttcgatg | 1260 |
| atgggcttac tgaccaacct ggcagacagg gagctggttc acatgatcaa ctgggcgaag | 1320 |
| agggtgccag gctttgtgga tttgaccctc catgatcagg tccaccttct agaatgtgcc | 1380 |
| tggctagaga tcctgatgat tggtctcgtc tggcgctcca tggagcaccc agggaagcta | 1440 |
| ctgtttgctc ctaacttgct cttggacagg aaccagggaa atgtgtaga gggcatggtg | 1500 |
| gagatcttcg acatgctgct ggctacatca tctcggttcc gcatgatgaa tctgcaggga | 1560 |
| gaggagtttg tgtgcctcaa atctattatt ttgcttaatt ctggagtgta cacatttctg | 1620 |
| tccagcaccc tgaagtctct ggaagagaag gaccatatcc accgagtcct ggacaagatc | 1680 |
| acagacactt tgatccacct gatggccaag gcaggcctga cctgcagca gcagcaccag | 1740 |
| cggctggccc agctcctcct catcctctcc cacatcaggc acatgagtaa caaaggcatg | 1800 |

-continued

```
gagcatctgt acagcatgaa gtgcaagaac gtggtgcccc tctatgacct gctgctggag    1860
atgctggacg cccaccgcct acatgcgccc actagccgtg gagggcatc cgtggaggag    1920 acggaccaaa gccacttggc cactgcgggc tctacttcat cgcattcctt gcaaaagtat   1980
tacatcacgg gggaggcaga gggtttccct gccacggtct gagagctccc tggctcccac   2040
acggttcaga taatccctgc tgcattttac cctcatcatg caccacttta gccaaattct   2100
gtctcctgca tacactccgg catgcatcca acaccaatgg cttctagat gagtggccat    2160 tcatttgctt gctcagttct tagtggcaca tcttctgtct tctgttggga acagccaaag   2220
ggattccaag gctaaatctt tgtaacagct ctctttcccc cttgctatgt tactaagcgt   2280
gaggattccc gtagctcttc acagctgaac tcagtctatg ggttgggct cagataactc    2340 tgtgcattta agctacttgt agagacccag gcctggagag tagacatttt gcctctgata   2400 agcactttt aaatggctct aagaataagc cacagcaaag aatttaaagt ggctccttta    2460
attggtgact tggagaaagc taggtcaagg gtttattata gcaccctctt gtattcctat   2520
ggcaatgcat cctttatga aagtggtaca ccttaaagct tttatatgac tgtagcagag    2580
tatctggtga ttgtcaattc attccccta taggaataca aggggcacac agggaaggca    2640
gatcccctag ttggcaagac tatttaact tgatacactg cagattcaga tgtgctgaaa    2700
gctctgcctc tggcttccg gtcatgggtt ccagttaatt catgcctccc atggacctat    2760
ggagagcagc aagttgatct tagttaagtc tccctatatg agggataagt tcctgatttt   2820 tgttttatt tttgtgttac aaagaaagc cctccctccc tgaacttgca gtaaggtcag     2880
cttcaggacc tgttccagtg ggcactgtac ttggatcttc ccggcgtgtg tgtgccttac   2940
acaggggtga actgttcact gtggtgatgc atgatgaggg taaatggtag ttgaaaggag   3000
caggggccct ggtgttgcat ttagccctgg ggcatggagc tgaacagtac ttgtgcagga   3060
ttgttgtggc tactagagaa caagaggaa agtagggcag aaactggata cagttctgag    3120
gcacagccag acttgctcag ggtggccctg ccacaggctg cagctaccta ggaacattcc   3180
ttgcagaccc cgcattgccc tttggggtg ccctgggatc cctggggtag tccagctctt    3240
cttcatttcc cagcgtggcc ctggttggaa gaagcagctg tcacagctgc tgtagacagc   3300
tgtgttccta caattggccc agcaccctgg ggcacgggag aagggtgggg accgttgctg   3360
tcactactca ggctgactgg ggcctggtca gattacgtat gcccttggtg gtttagagat   3420
aatccaaaat cagggtttgg tttggggaag aaaatcctcc ccttcctcc cccgccccgt    3480 tccctaccgc ctccactcct gccagctcat ttccttcaat ttccttttgac ctataggcta  3540 aaaaagaaag gctcattcca gccacagggc agccttccct gggcctttgc ttctctagca   3600
caattatggg ttacttcctt tttcttaaca aaaagaatg tttgatttcc tctgggtgac    3660
cttattgtct gtaattgaaa ccctattgag aggtgatgtc tgtgttagcc aatgacccag   3720
gtgagctgct cgggcttctc ttggtatgtc ttgtttggaa aagtggattt cattcatttc   3780
tgattgtcca gttaagtgat caccaaagga ctgagaatct gggagggcaa aaaaaaaaa    3840 aaagttttta tgtgcactta aatttgggga caatttatg tatctgtgtt aaggatatgt    3900
ttaagaacat aattcttttg ttgctgtttg tttaagaagc accttagttt gtttaagaag   3960
caccttatat agtataatat atattttttt gaaattacat tgcttgttta tcagacaatt   4020
gaatgtagta attctgttct ggatttaatt tgactgggtt aacatgcaaa aaccaaggaa   4080
aaatatttag ttttttttt tttttttgta tacttttcaa gctaccttgt catgtataca    4140
gtcatttatg cctaaagcct ggtgattatt catttaaatg aagatcacat ttcatatcaa   4200
```

```
cttttgtatc cacagtagac aaaatagcac taatccagat gcctattgtt ggatactgaa    4260
tgacagacaa tcttatgtag caaagattat gcctgaaaag gaaaattatt cagggcagct    4320
aattttgctt ttaccaaaat atcagtagta atattttggg acagtagcta atgggtcagt    4380
gggttctttt taatgtttat acttagattt tcttttaaaa aaattaaaat aaaacaaaaa    4440
aaaatttcta ggactagacg atgtaatacc agctaaagcc aaacaattat acagtggaag    4500
gttttacatt attcatccaa tgtgtttcta ttcatgttaa gatactacta catttgaagt    4560
gggcagagaa catcagatga ttgaaatgtt cgcccagggg tctccagcaa ctttggaaat    4620
ctctttgtat ttttacttga agtgccacta atggacagca gatattttct ggctgatgtt    4680
ggtattgggt gtaggaacat gatttaaaaa aaaactcttg cctctgcttt cccccactct    4740
gaggcaagtt aaaatgtaaa agatgtgatt tatctggggg gctcaggtat ggtgggaag    4800 tggattcagg aatctgggga atggcaaata tattaagaag agtattgaaa gtatttggag    4860
gaaaatggtt aattctgggt gtgcaccagg gttcagtaga gtccacttct gccctggaga    4920
ccacaaatca actagctcca tttacagcca tttctaaaat ggcagcttca gttctagaga    4980
agaaagaaca acatcagcag taaagtccat ggaatagcta gtggtctgtg tttcttttcg    5040
ccattgccta gcttgccgta atgattctat aatgccatca tgcagcaatt atgagaggct    5100
aggtcatcca aagagaagac cctatcaatg taggttgcaa aatctaaccc ctaaggaagt    5160
gcagtctttg atttgatttc cctagtaacc ttgcagatat gtttaaccaa gccatagccc    5220
atgccttttg agggctgaac aaataaggga cttactgata atttactttt gatcacatta    5280
aggtgttctc accttgaaat cttatacact gaaatggcca ttgatttagg ccactggctt    5340
agagtactcc ttcccctgca tgacactgat tacaaatact ttcctattca tactttccaa    5400
ttatgagatg gactgtgggt actgggagtg atcactaaca ccatagtaat gtctaatatt    5460
cacaggcaga tctgcttggg gaagctagtt atgtgaaagg caaatagagt catacagtag    5520
ctcaaaaggc aaccataatt ctctttggtg caggtcttgg gagcgtgatc tagattacac    5580
tgcaccattc ccaagttaat cccctgaaaa cttactctca actggagcaa atgaactttg    5640
gtcccaaata tccatctttt cagtagcgtt aattatgctc tgtttccaac tgcatttcct    5700
ttccaattga attaaagtgt ggcctcgttt ttagtcattt aaaattgttt tctaagtaat    5760
tgctgcctct attatggcac ttcaattttg cactgtcttt tgagattcaa gaaaaatttc    5820
tattcttttt tttgcatcca attgtgcctg aacttttaaa atatgtaaat gctgccatgt    5880
tccaaaccca tcgtcagtgt gtgtgtttag agctgtgcac cctagaaaca acatattgtc    5940
ccatgagcag gtgcctgaga cacagacccc tttgcattca cagagaggtc attggttata    6000
gagacttgaa ttaataagtg acattatgcc agtttctgtt ctctcacagg tgataaacaa    6060 tgcttttttgt gcactacata ctcttcagtg tagagctctt gttttatggg aaaaggctca    6120
aatgccaaat tgtgtttgat ggattaatat gcccttttgc cgatgcatac tattactgat    6180
gtgactcggt tttgtcgcag ctttgctttg tttaatgaaa cacacttgta aacctctttt    6240
gcactttgaa aaagaatcca gcgggatgct cgagcacctg taaacaattt tctcaaccta    6300
tttgatgttc aaataaagaa ttaaactaaa                                    6330
```

<210> SEQ ID NO 3
<211> LENGTH: 4107
<212> TYPE: DNA
<213> ORGANISM: Homo sapiens

<400> SEQUENCE: 3

```
gcgcaaccct ccggaagctg ccgccccttt ccccttttat gggaatactt tttttaaaaa    60
aaaagagttc gctggcgcca ccccgtagga ctggccgccc taaaaccgtg ataaaggagc   120
tgctcgccac ttctcacttc cgcttccttc cagtaaggag tcgggtctt ccccagtttt   180 ctcagccagg cggcggcggc gactggcaat gtttggcctc aaaagaaacg cggtaatcgg   240
actcaacctc tactgtgggg gggccggctt gggggccggc agcggcggcg ccacccgccc   300
gggagggcga cttttggcta cggagaagga ggcctcggcc cggcgagaga taggggagg   360 ggaggccggc gcggtgattg gcggaagcgc cggcgcaagc cccccgtcca ccctcacgcc   420
agactcccgg agggtcgcgc ggccgccgcc cattggcgcc gaggtccccg acgtcaccgc   480 gaccccccgcg aggctgcttt tcttcgcgcc cacccgccgc gcggcgccgc ttgaggagat   540
ggaagccccg gccgctgacg ccatcatgtc gcccgaagag gagctggacg ggtacgagcc   600
ggagcctctc gggaagcggc cggctgtcct gccgctgctg gagttggtcg gggaatctgg   660
taataacacc agtacggacg ggtcactacc ctcgacgccg ccgccagcag aggaggagga   720
ggacgagttg taccggcagt cgctggagat tatctctcgg taccttcggg agcaggccac   780
cggcgccaag gacacaaagc caatgggcag gtctggggcc accagcagga aggcgctgga   840
gaccttacga cggggttgggg atggcgtgca gcgcaaccac gagacggcct tccaaggcat   900
gcttcggaaa ctggacatca aaaacgaaga cgatgtgaaa tcgttgtctc gagtgatgat   960
ccatgttttc agcgacggcg taacaaactg gggcaggatt gtgactctca tttcttttgg  1020
tgcctttgtg gctaaacact tgaagaccat aaaccaagaa agctgcatcg aaccattagc  1080
agaaagtatc acagacgttc tcgtaaggac aaaacgggac tggctagtta aacaaagagg  1140
ctgggatggg tttgtggagt tcttccatgt agaggaccta aaggtggca tcaggaatgt  1200 gctgctggct tttgcaggtg ttgctggagt aggagctggt ttggcatatc taataagata  1260
gccttactgt aagtgcaata gttgactttt aaccaaccac caccaccacc aaaaccagtt  1320
tatgcagttg gactccaagc tgtaacttcc tagagttgca ccctagcaac ctagccagaa  1380
aagcaagtgg caagaggatt atggctaaca agaataaata catgggaaga gtgctcccca  1440
ttgattgaag agtcactgtc tgaaagaagc aaagttcagt ttcagcaaca aacaaacttt  1500
gtttgggaag ctatggagga ggactttag atttagtgaa gatggtaggg tggaaagact  1560
taatttcctt gttgagaaca ggaaagtggc cagtagccag gcaagtcata gaattgatta  1620
cccgccgaat tcattaattt actgtagtgt aagagaagc actaagaatg ccagtgacct  1680
gtgtaaaagt tacaagtaat agaactatga ctgtaagcct cagtactgta caagggaagc  1740
ttttcctctc tctaattagc tttcccagta tacttcttag aaagtccaag tgttcaggac  1800 ttttataccct gttatacttt ggcttggttt ccatgattct tactttatta gcctagttta  1860
tcaccaataa tacttgacgg aaggctcagt aattagttat gaatatggat atcctcaatt  1920
cttaagacag cttgtaaatg tatttgtaaa aattgtatat attttttacag aaagtctatt  1980 tctttgaaac gaaggaagta tcgaatttac attagttttt ttcataccct tttgaacttt  2040
gcaacttccg taattaggaa cctgtttctt acagcttttc tatgctaaac tttgttctgt  2100
tcagttctag agtgtataca gaacgaattg atgtgtaact gtatgcagac tggttgtagt  2160
ggaacaaatc tgataactat gcaggttaaa attttcttat ctgatttgg taagtattcc  2220 ttagataggt ttttctttga aaacctggga ttgagaggtt gatgaatgga aattctttca  2280
cttcattata tgcaagtttt caataattag gtcaagtgg agtttaagg ttactgatga  2340 cttacaaata atgggctctg attgggcaat actcatttga gttccttcca tttgacctaa  2400
```

```
tttaactggt gaaatttaaa gtgaattcat gggctcatct ttaaagcttt tactaaaaga    2460
ttttcagctg aatggaactc attagctgtg tgcatataaa aagatcacat caggtggatg    2520
gagagacatt tgatcccttg tttgcttaat aaattataaa atgatggctt ggaaaagcag    2580
gctagtctaa ccatggtgct attattaggc ttgcttgtta cacacacagg tctaagccta    2640
gtatgtcaat aaagcaaata cttactgttt tgtttctatt aatgattccc aaaccttgtt    2700
gcaagttttt gcattggcat cttttggattt cagtcttgat gtttgttcta tcagacttaa   2760
ccttttattt cctgtccttc cttgaaattg ctgattgttc tgctccctct acagatattt    2820
atatcaattc ctacagcttt ccctgccat ccctgaactc tttctagccc ttttagattt     2880
tggcactgtg aaaccctgc tggaaacctg agtgaccctc cctccccacc aagagtccac     2940 agaccttca tctttcacga acttgatcct gttagcaggt ggtaatacca tgggctgt       3000 gacactaaca gtcattgaga ggtgggagga agtcccttttt ccttggactg gtatctttc    3060 aactattgtt ttatcctgtc tttggggca atgtgtcaaa agtcccctca ggaattttca     3120
gaggaaagaa cattttatga ggctttctct aaagtttcct ttgtatagga gtatgctcac    3180
ttaaatttac agaagaggt gagctgtgtt aaacctcaga gtttaaaagc tactgataaa     3240
ctgaagaaag tgtctatatt ggaactaggg tcatttgaaa gcttcagtct cggaacatga    3300
cctttagtct gtggactcca tttaaaaata ggtatgaata agatgactaa gaatgtaatg    3360
gggaagaact gccctgcctg cccatctcag agccataagg tcatctttgc tagagctatt   3420
tttacctatg tatttatcgt tcttgatcat aagccgctta tttatatcat gtatctctaa    3480
ggacctaaaa gcactttatg tagttttttaa ttaatcttaa gatctggtta cggtaactaa    3540
aaaagcctgt ctgccaaatc cagtggaaac aagtgcatag atgtgaattg gttttttaggg   3600 gccccacttc ccaattcatt aggtatgact gtggaaatac agacaaggat cttagttgat    3660
attttgggct tggggcagtg agggcttagg acaccccaag tggtttggga aggaggagg     3720 ggagtggtgg gtttataggg ggaggaggag gcaggtggtc taagtgctga ctggctacgt    3780
agttcgggca aatcctccaa aagggaaagg gaggatttgc ttagaaggat ggcgctccca    3840
gtgactactt tttgacttct gtttgtctta cgcttctctc agggaaaaac atgcagtcct    3900
ctagtgtttc atgtacattc tgtgggggt gaacaccttg gttctggtta aacagctgta    3960
cttttgatag ctgtgccagg aagggttagg accaactaca aattaatgtt ggttgtcaaa    4020
tgtagtgtgt ttccctaact ttctgttttt cctgagaaaa aaaataaat cttttattca    4080 aatacaggga aaaaaaaaaa aaaaaaa                                        4107

<210> SEQ ID NO 4
<211> LENGTH: 1126
<212> TYPE: DNA
<213> ORGANISM: Homo sapiens

<400> SEQUENCE: 4
tccccatgtg acagtgagcg ggtccccgc tccaggagac gctcgagtct gcgtcccggc      60
cctcagcact gtccactgtt tcggtgccag cagagaccag caggcccggg acagttggtg    120
tttggccgtg ccgctgtcta acttggtgtg cagagtgaat tgccgctgcc ggagcggaga    180
gaggcggagc ggccaggaga gaggggattt ctgtcagcgc cggcctcggg agctcggaga    240
catgaacggc ttcacgcctg acgagatgag ccgcggcggg gatgcggccg ccgcagtggc    300
cgcagtggtc gctgccgcgg ccgccgcgc ctcggcgggg aacggaccg gcgcgggcac      360 cggggctgag gtgccgggcg cggggcggt ctcagcggct gggcccccgg gggcggccgg    420
```

| | |
|---|---|
| gccgggcccc gggcaactgt gctgcctgcg ggaggatggt gagcggtgcg gccgggcggc | 480 |
| aggcaacgcc agcttcagca agaggatcca agaagagcatc tcccagaaga aggtgaagat | 540 |
| cgagctggat aagagcgcaa ggcatctta catatgtgat tatcataaaa acttaattca | 600 |
| gagtgttcga aacagaagaa agagaaaagg gagtgatgat gatggaggtg attcacctgt | 660 |
| tcaagatatt gataccccag aggttgattt ataccaatta caagtaaata cacttaggag | 720 |
| atacaaaaga cacttcaagc taccaaccag accaggactt aataaagcac aacttgttga | 780 |
| gatagttggt tgccacttta ggtctattcc agtgaatgaa aaagacacct aacatatt | 840 |
| catctactca gtgaagaatg acaagaacaa atcagatctc aaggttgata gtggtgttca | 900 |
| ctaggagacg tggaattgag actaataact tggatgttaa cactgtttac tgttttttca | 960 |
| catgtagaaa tgttctttgt gtattttttc tacagaggat tttctctgat tttattttct | 1020 |
| ttgtttctga ctctaataat tagttggaaa ctcatataaa atgagctttc ctaaattaaa | 1080 |
| tctattttaa ataaaggtta ttactattaa aaaaaaaaaa aaaaaa | 1126 |

```
<210> SEQ ID NO 5
<211> LENGTH: 2040
<212> TYPE: DNA
<213> ORGANISM: Homo sapiens

<400> SEQUENCE: 5
```

| | |
|---|---|
| tcgctgcgaa ggacatttgg gctgtgtgtg cgacgcgggt cggaggggca gtcgggggaa | 60 |
| ccgcgaagaa gccgaggagc ccggagcccc gcgtgacgct cctctctcag tccaaaagcg | 120 |
| gcttttggtt cggcgcagag agacccgggg gtctagcttt cctcgaaaa gcgccgccct | 180 |
| gcccttggcc ccgagaacag acaaagagca ccgcagggcc gatcacgctg ggggcgctga | 240 |
| ggccggccat ggtcatggaa gtgggcaccc tggacgctgg aggcctgcgg gcgctgctgg | 300 |
| gggagcgagc ggcgcaatgc ctgctgctgg actgccgctc cttcttcgct ttcaacgccg | 360 |
| gccacatcgc cggctctgtc aacgtgcgct tcagcaccat cgtgcggcgc cgggccaagg | 420 |
| gcgccatggg cctggagcac atcgtgccca cgccgagct ccgcggccgc ctgctggccg | 480 |
| gcgcctacca cgccgtggtg ttgctggacg agcgcagcgc cgcccggac ggcgccaagc | 540 |
| gcgacggcac cctggccctg gcggccggcc cgctctgccg cgaggcgcgc gccgcgcaag | 600 |
| tcttcttcct caaaggagga tacgaagcgt tttcggcttc ctgcccggag ctgtgcagca | 660 |
| aacagtcgac ccccatgggg ctcagccttc ccctgagtac tagcgtccct gacagcgcgg | 720 |
| aatctgggtg cagttcctgc agtaccccac tctacgatca gggtggcccg gtggaaatcc | 780 |
| tgcccttctc gtacctgggc agtgcgtatc acgcttcccg caaggacatg ctggatgcct | 840 |
| tgggcatcac tgccttgatc aacgtctcag ccaattgtcc caaccatttt gagggtcact | 900 |
| accagtacaa gagcatccct gtggaggaca accacaaggc agacatcagc tcctggttca | 960 |
| acgaggccat tgacttcata gactccatca agaatgctgg aggaagggtg tttgtccact | 1020 |
| gccaggcagg catttcccgg tcagccacca tctgccttgc ttaccttatg aggactaatc | 1080 |
| gagtcaagct ggacgaggcc tttgagtttg tgaagcagag gcgaagcatc atctctccca | 1140 |
| acttcagctt catgggccag ctgctgcagt ttgagtccca ggtgctggct ccgcactgtt | 1200 |
| cggcagaggc tgggagcccc gccatggctg tgctcgaccg aggcacctcc accaccaccg | 1260 |
| tgttcaactt ccccgtctcc atccctgtcc actccacgaa cagtgcgctg agctaccttc | 1320 |
| agagccccat tacgacctct cccagctgct gaaaggccac gggaggtgag gctcttcaca | 1380 |
| tcccattggg actccatgct ccttgagagg agaaatgcaa taactctggg aggggctcga | 1440 |

```
gagggctggt ccttatttat ttaacttcac ccgagttcct ctgggtttct aagcagttat    1500
ggtgatgact tagcgtcaag acatttgctg aactcagcac attcgggacc aatatatagt    1560
gggtacatca agtccatctg acaaaatggg gcagaagaga aaggactcag tgtgtgatcc    1620
ggtttctttt tgctcgcccc tgttttttgt agaatctctt catgcttgac atacctacca    1680
gtattattcc cgacgacaca tatacatatg agaatatacc ttatttattt ttgtgtaggt    1740
gtctgccttc acaaatgtca ttgtctactc ctagaagaac caaatacctc aattttttgtt   1800 tttgagtact gtactatcct gtaaatatat cttaagcagg tttgttttca gcactgatgg    1860
aaaataccag tgttgggttt ttttttagtt gccaacagtt gtatgtttgc tgattattta    1920
tgacctgaaa taatatattt cttcttctaa aagacatttt tgttacataa ggatgacttt    1980
tttatacaat ggaataaatt atggcatttc tattgaaatt tcaaaaaaaa aaaaaaaaa     2040

<210> SEQ ID NO 6
<211> LENGTH: 3208
<212> TYPE: DNA
<213> ORGANISM: Homo sapiens

<400> SEQUENCE: 6
agatattcat gaaccgttgc ttcttccagc ctcgccttct cgctccctct gcctttctgg      60
cgctgttctc cctccctccc tctggcttct gctctttctt actccttctc tcagctgctt     120
aactacagct cccactggaa cttgcacaat caaaaacaac tctcctctct caagccgcct     180
ccaggagcgc atcacctgga gaagagcgac tcgctcccgc gccggccgc ggaagagcag      240 ccaggtagct gggggcgggg aggcgtaccc ttctcccgct cggtaagagc cacagcatct     300
ccccggagat tggccgtatc ccaccgtccg gcccccaggg tcctgcagcg gtgatgcata     360
tgtttcggag caatgatgga aggagaaaag ccgctgtcgg tggcaactga agtgggag       420 aggttgctgc agtagctggt gctgcagaat gcgcgagtga agaactgagc cccgctagat     480
tctccatccc gctcagtctt cattaactgt ctgcaggagg taaaccgggg aaacagatat     540
gcactaacca ggcgggtgcc aacctggatc tataactgtg aattcccac ggtgaaaat       600 ggtaaacaaa gacatgaatg gattcccagt caagaaatgc tcagccttcc aattttttaa     660
gaagcgggta cgaaggtgga tcaagagccc aatggtcagt gtggacaagc atcagagtcc     720
cagcctgaag tacaccggct cctccatggt gcacatccct ccaggggagc cagacttcga     780
gtcttccttg tgtcaaacat gcctgggtga acatgctttc caaagagggg ttctccctca     840
ggagaacgag tcatgttcat gggaaactca atctgggtgt gaagtgagag agccatgtaa     900
tcatgccaac atcctgacca agcccgatcc aagaaccttc tggactaatg atgatccagc     960
tttcatgaag cagaggagga tgggtctgaa cgactttatt cagaagattg ccaataactc    1020
ctatgcatgc aaacaccctg aagttcagtc catcttgaag atctcccaac ctcaggagcc    1080 tgagcttat aatgccaacc cttctcctcc accagtcct tctcagcaaa tcaaccttgg      1140
cccgtcgtcc aatcctcatg ctaaaccatc tgactttcac ttcttgaaag tgatcggaaa    1200
gggcagtttt ggaaaggttc ttctagcaag acacaaggca gaagaagtgt tctatgcagt    1260 caaagttta cagaagaaag caatcctgaa aaagaaagag gagaagcata ttatgtcgga    1320
gcggaatgtt ctgttgaaga atgtgaagca ccctttcctg gtgggccttc acttctcttt   1380
ccagactgct gacaaattgt actttgtcct agactacatt aatggtggag agttgttcta    1440
ccatctccag agggaacgct gcttcctgga accacgggct cgtttctatg ctgctgaaat    1500
agccagtgcc ttgggctacc tgcattcact gaacatcgtt tatagagact aaaaccaga    1560
```

-continued

| | |
|---|---|
| gaatattttg ctagattcac agggacacat tgtccttact gacttcggac tctgcaagga | 1620 |
| gaacattgaa cacaacagca caacatccac cttctgtggc acgccggagt atctcgcacc | 1680 |
| tgaggtgctt cataagcagc cttatgacag gactgtggac tggtggtgcc tgggagctgt | 1740 |
| cttgtatgag atgctgtatg gcctgccgcc tttttatagc cgaaacacag ctgaaatgta | 1800 |
| cgacaacatt ctgaacaagc ctctccagct gaaaccaaat attacaaatt ccgcaagaca | 1860 |
| cctcctggag ggcctcctgc agaaggacag gacaaagcgg ctcggggcca aggatgactt | 1920 |
| catggagatt aagagtcatg tcttcttctc cttaattaac tgggatgatc tcattaataa | 1980 |
| gaagattact ccccctttta acccaaatgt gagtgggccc aacgacctac ggcactttga | 2040 |
| ccccgagttt accgaagagc ctgtccccaa ctccattggc aagtcccctg acagcgtcct | 2100 |
| cgtcacagcc agcgtcaagg aagctgccga ggctttccta ggcttttcct atgcgcctcc | 2160 |
| cacggactct ttcctctgaa ccctgttagg gcttggtttt aaaggatttt atgtgtgttt | 2220 |
| ccgaatgttt tagttagcct tttggtggag ccgccagctg acaggacatc ttacaagaga | 2280 |
| atttgcacat ctctggaagc ttagcaatct tattgcacac tgttcgctgg aagcttttttg | 2340 |
| aagagcacat tctcctcagt gagctcatga ggttttcatt tttattcttc cttccaacgt | 2400 |
| ggtgctatct ctgaaacgag cgttagagtg ccgccttaga cggaggcagg agtttcgtta | 2460 |
| gaaagcggac gctgttctaa aaaaggtctc ctgcagatct gtctgggctg tgatgacgaa | 2520 |
| tattatgaaa tgtgcctttt ctgaagagat tgtgttagct ccaaagcttt tcctatcgca | 2580 |
| gtgtttcagt tctttatttt cccttgtgga tatgctgtgt gaaccgtcgt gtgagtgtgg | 2640 |
| tatgcctgat cacagatgga ttttgttata agcatcaatg tgacacttgc aggacactac | 2700 |
| aacgtgggac attgtttgtt tcttccatat ttggaagata aatttatgtg tagacttttt | 2760 |
| tgtaagatac ggttaataac taaaatttat tgaaatggtc ttgcaatgac tcgtattcag | 2820 |
| atgcttaaag aaagcattgc tgctacaaat atttctattt ttagaaaggg ttttttatgga | 2880 |
| ccaatgcccc agttgtcagt cagagccgtt ggtgtttttc attgtttaaa atgtcacctg | 2940 |
| taaaatgggc attatttatg tttttttttt tgcattcctg ataattgtat gtattgtata | 3000 |
| aagaacgtct gtacattggg ttataacact agtatattta aacttacagg cttatttgta | 3060 |
| atgtaaacca ccatttttaat gtactgtaat taacatggtt ataatacgta caatccttcc | 3120 |
| ctcatcccat cacacaactt tttttgtgtg tgataaactg attttggttt gcaataaaac | 3180 |
| cttgaaaaat atttacatat aaaaaaaa | 3208 |

<210> SEQ ID NO 7
<211> LENGTH: 5758
<212> TYPE: DNA
<213> ORGANISM: Homo sapiens

<400> SEQUENCE: 7

| | |
|---|---|
| tttctgtact ctgggtgact cagagaggga agagattcag ccagcacact cctcgcgagc | 60 |
| aagcattact ctactgactg gcagagacag gagaggtaga tgtccacgcc cacagaccct | 120 |
| ggtgcgatgc cccacccagg gccttcgccg gggcctgggc cttcccctgg gccaattctt | 180 |
| gggcctagtc caggaccagg accatcccca ggttccgtcc acagcatgat ggggccaagt | 240 |
| cctggacctc caagtgtctc ccatcctatg ccgacgatgg ggtccacaga cttcccacag | 300 |
| gaaggcatgc atcaaatgca taagcccatc gatggtatac atgacaaggg gattgtagaa | 360 |
| gacatccatt gtggatccat gaagggcact ggtatgcgac cacctcaccc aggcatgggc | 420 |
| cctccccaga gtccaatgga tcaacacagc caaggttata tgtcaccaca cccatctcca | 480 |

```
ttaggagccc cagagcacgt ctccagccct atgtctggag gaggcccaac tccacctcag    540
atgccaccaa gccagccggg ggccctcatc ccaggtgatc cgcaggccat gagccagccc    600
aacagaggtc cctcaccttt cagtcctgtc cagctgcatc agcttcgagc tcagatttta    660
gcttataaaa tgctggcccg aggccagccc ctccccgaaa cgctgcagct tgcagtccag    720
gggaaaagga cgttgcctgg cttgcagcaa cacagcagc agcaacagca gcagcagcag    780
cagcagcagc agcagcagca gcagcaacag cagccgcagc agcagccgcc gcaaccacag    840
acgcagcaac aacagcagcc ggcccttgtt aactacaaca gaccatctgg cccggggccg    900
gagctgagcg gcccgagcac cccgcagaag ctgccggtgc ccgcgcccgg cggccggccc    960
tcgcccgcgc ccccgcagc cgcgcagccg cccgcggccg cagtgcccgg ccctcagtg    1020 ccgcagccgg ccccggggca gccctcgccc gtcctccagc tgcagcagaa gcagagccgc    1080
atcagcccca tccagaaacc gcaaggcctg accccgtgg aaattctgca agagcgggaa    1140
tacagacttc aggcccgcat agctcatagg atacaagaac tggaaaatct gcctggctct    1200
ttgccaccag atttaagaac caaagcaacc gtggaactaa agcacttcg gttactcaat    1260 ttccagcgtc agctgagaca ggaggtggtg gcctgcatgc gcagggacac gaccctggag    1320
acggctctca actccaaagc atacaaacgg agcaagcgcc agactctgag agaagctcgc    1380
atgaccgaga agctggagaa gcagcagaag attgagcagg agaggaaacg ccgtcagaaa    1440
caccaggaat acctgaacag tattttgcaa catgcaaaag attttaagga atatcatcgg    1500
tctgtggccg aaagatccaa gaagctctcc aaagcagtgg caacttggca tgccaacact    1560
gaaagagagc agaagaagga gacagagcgg attgaaaagg agagaatgcg gcgactgatg    1620
gctgaagatg aggagggtta tagaaaactg attgatcaaa agaaagacag gcgtttagct    1680 tacctttgc agcagaccga tgagtatgta gccaatctga ccaatctggt ttgggagcac    1740
aagcaagccc aggcagccaa agagaagaag aagaggagga ggaggaagaa gaaggctgag    1800
gagaatgcag agggtgggga gtctgccctg ggaccggatg agagcccat agatgagagc    1860 agccagatga gtgacctccc tgtcaaagtg actcacacag aaaccggcaa ggttctgttc    1920
ggaccagaag cacccaaagc aagtcagctg gacgcctggc tggaaatgaa tcctggttat    1980
gaagttgccc ctagatctga cagtgaagag agtgattctg attatgagga agaggatgag    2040
gaagaagagt ccagtaggca ggaaaccgaa gagaaaatac tcctggatcc aaatagcgaa    2100
gaagtttctg agaaggatgc taagcagatc attgagacag ctaagcaaga cgtggatgat    2160
gaatacagca tgcagtacag tgccagggggc tcccagtcct actacaccgt ggctcatgcc    2220
atctcggaga gggtggagaa acagtctgcc ctcctaatta atgggaccct aaagcattac    2280
cagctccagg gcctggaatg gatggtttcc ctgtataata caacttgaa cggaatctta    2340 gccgatgaaa tggggcttgg aaagaccata cagaccattg cactcatcac ttatctgatg    2400
gagcacaaaa gactcaatgg cccctatctc atcattgttc cccttttcgac tctatctaac    2460 tggacatatg aatttgacaa atgggctcct tctgtggtga agatttctta caagggtact    2520
cctgccatgc gtcgctccct tgtccccag ctacggagtg gcaaattcaa tgtcctcttg    2580
actacttatg agtatattat aaaagacaag cacattcttg caaagattcg gtggaaatac    2640
atgatagtgg acgaaggcca ccgaatgaag aatcaccact gcaagctgac tcaggtcttg    2700
aacactcact atgtggcccc cagaaggatc ctcttgactg ggaccccgct gcagaataag    2760
ctccctgaac tctgggccct cctcaacttc ctcctcccaa caattttaa gagctgcagc    2820 acatttgaac aatggttcaa tgctccattt gccatgactg gtgaaagggt ggacttaaat    2880
```

```
gaagaagaaa ctatattgat catcaggcgt ctacataagg tgttaagacc attttttacta    2940 aggagactga agaaagaagt tgaatcccag cttcccgaaa aagtggaata tgtgatcaag    3000
tgtgacatgt cagctctgca gaagattctg tatcgccata tgcaagccaa ggggatcctt    3060
ctcacagatg gttctgagaa agataagaag gggaaaggag gtgctaagac acttatgaac    3120
actattatgc agttgagaaa aatctgcaac cacccatata tgtttcagca cattgaggaa    3180
tcctttgctg aacacctagg ctattcaaat ggggtcatca atggggctga actgtatcgg    3240
gcctcaggga agtttgagct gcttgatcgt attctgccaa aattgagagc gactaatcac    3300
cgagtgctgc ttttctgcca gatgacatct ctcatgacca tcatggagga ttatttttgct    3360 tttcggaact tcctttacct acgccttgat ggcaccacca agtctgaaga tcgtgctgct    3420
ttgctgaaga aattcaatga acctggatcc cagtatttca ttttcttgct gagcacaaga    3480
gctggtggcc tgggcttaaa tcttcaggca gctgatacag tggtcatctt tgacagcgac    3540
tggaatcctc atcaggatct gcaggcccaa gaccgagctc accgcatcgg gcagcagaac    3600
gaggtccggg tactgaggct ctgtaccgtg aacagcgtgg aggaaaagat cctcgcggcc    3660
gcaaaataca agctgaacgt ggatcagaaa gtgatccagg cggcatgtt tgaccaaaag    3720 tcttcaagcc acgagcggag ggcattcctg caggccatct tggagcatga ggaggaaaat    3780
gaggaagaag atgaagtacc ggacgatgag actctgaacc aaatgattgc tcgacgagaa    3840
gaagaatttg acctttttat gcggatggac atggaccggc ggagggaaga tgcccggaac    3900
ccgaaacgga agcccgttt aatggaggag gatgagctgc cctcctggat cattaaggat    3960
gacgctgaag tagaaaggct cacctgtgaa gaagaggagg agaaaatatt tgggagggg    4020 tcccgccagc gccgtgacgt ggactacagt gacgccctca cggagaagca gtggctaagg    4080
gccatcgaag acggcaattt ggaggaaatg gaagaggaag tacggcttaa gaagcgaaaa    4140
agacgaagaa atgtggataa agatcctgca aaagaagatg tggaaaaagc taagaagaga    4200
agaggccgcc ctcccgctga gaaactgtca ccaaatcccc ccaaactgac aaagcagatg    4260
aacgctatca tcgatactgt gataaactac aaagataggt gtaacgtgga aaggtgccc    4320 agtaattctc agttggaaat agaaggaaac agttcagggc gacagctcag tgaagtcttc    4380
attcagttac cttcaaggaa agaattacca gaatactatg aattaattag gaagccagtg    4440
gatttcaaaa aaataaagga aaggattcgt aatcataagt accggagcct aggcgacctg    4500
gagaaggatg tcatgcttct ctgtcacaac gctcagacgt tcaacctgga gggatcccag    4560
atctatgaag actccatcgt cttacagtca gtgtttaaga gtgcccggca gaaaattgcc    4620
aaagaggaag agagtgagga tgaaagcaat gaagaggagg aagaggaaga tgaagaagag    4680
tcagagtccg aggcaaaatc agtcaaggtg aaaattaagc tcaataaaaa agatgacaaa    4740
ggccgggaca aagggaaagg caagaaaagg ccaaatcgag gaaaagccaa acctgtagtg    4800
agcgattttg acagcgatga ggagcaggat gaacgtgaac agtcagaagg aagtgggacg    4860
gatgatgagt gatcagtatg gacctttttc cttggtagaa ctgaattcct tcctcccctg    4920
tctcatttct acccagtgag ttcatttgtc atataggcac tgggttgttt ctatatcatc    4980
atcgtctata aactagcttt aggatagtgc cagacaaaca tatgatatca tggtgtaaaa    5040
aacacacaca tacacaaata tttgtaacat attgtgacca aatgggcctc aaagattcag    5100
attgaaacaa acaaaaagct tttgatggaa aatatgtggg tggatagtat atttctatgg    5160
gtgggtctaa tttggtaacg gtttgattgt gcctggtttt atcacctgtt cagatgagaa    5220 gattttttgtc ttttgtagca ctgataacca ggagaagcca ttaaaagcca ctggttattt    5280
```

```
tattttttcat caggcaattt tcgaggtttt tatttgttcg gtattgtttt tttacactgt    5340
ggtacatata agcaacttta ataggtgata aatgtacagt agttagattt cacctgcata    5400
tacatttttc cattttatgc tctatgatct gaacaaaagc ttttgaatt gtataagatt     5460 tatgtcact gtaaacattg cttaattttt ttgctcttga tttaaaaaaa agttttgttg     5520
aaagcgctat tgaatattgc aatctatata gtgtattgga tggcttcttt tgtcaccctg    5580
atctcctatg ttaccaatgt gtatcgtctc cttctcccta aagtgtactt aatctttgct    5640
ttctttgcac aatgtctttg gttgcaagtc ataagcctga ggcaaataaa attccagtaa    5700
tttcgaagaa tgtggtgttg gtgctttcct aataaagaaa taatttagct tgacaaaa     5758
```

<210> SEQ ID NO 8
<211> LENGTH: 837
<212> TYPE: DNA
<213> ORGANISM: Homo sapiens

<400> SEQUENCE: 8

```
gctcctcctg cacacctccc tcgctctccc acaccactgg caccaggccc cggacacccg    60
ctctgctgca ggagaatggc tactcatcac acgctgtgga tgggactggc cctgctgggg    120
gtgctgggcg acctgcaggc agcaccggag gcccaggtct ccgtgcagcc caacttccag    180
caggacaagt tcctggggcg ctggttcagc gcgggcctcg cctccaactc gagctggctc    240
cgggagaaga aggcggcgtt gtccatgtgc aagtctgtgg tggcccctgc cacggatggt    300
ggcctcaacc tgacctccac cttcctcagg aaaaaccagt gtgagacccg aaccatgctg    360
ctgcagcccg cggggtccct cggctcctac agctaccgga gtccccactg gggcagcacc    420
tactccgtgt cagtggtgga gaccgactac gaccagtacg cgctgctgta cagccagggc    480
agcaagggcc ctggcgagga cttccgcatg gccaccctct acagccgaac ccagacccc    540 agggctgagt taaaggagaa attcaccgcc ttctgcaagg cccagggctt cacagaggat    600
accattgtct tcctgcccca aaccgataag tgcatgacgg aacaatagga ctccccaggg    660
ctgaagctgg gatcccggcc agccaggtga cccccacgct ctggatgtct ctgctctgtt    720
ccttccccga gcccctgccc cggctcccc ccaaagcaac cctgcccact caggcttcat     780
cctgcacaat aaactccgga agcaagtcag taaaaaaaaa aaaaaaaaa aaaaaaa       837
```

<210> SEQ ID NO 9
<211> LENGTH: 6001
<212> TYPE: DNA
<213> ORGANISM: Homo sapiens

<400> SEQUENCE: 9

```
caaggaggga tcccacagat gtcacagggc tgtcacagag ctgtggtggg aatttcccat    60
gagaccccgc ccctggctga gtcaccgcac tcctgtgttt gacctgaagt cctctcgagc   120
tgcagaagcc tgaagaccaa ggagtggaaa gttctccggc agccctgaga tctcaagagt   180
gacatttgtg agaccagcta atttgattaa aattctcttg gaatcagctt tgctagtatc   240
atacctgtgc cagatttcat catgggaaac agctgttaca acatagtagc cactctgttg   300
ctggtcctca actttgagag gacaagatca ttgcaggatc cttgtagtaa ctgcccagct   360
ggtacattct gtgataataa caggaatcag atttgcagtc cctgtcctcc aaatagtttc   420
tccagcgcag gtggacaaag gacctgtgac atatgcaggc agtgtaaagg tgttttcagg   480
accaggaagg agtgttcctc caccagcaat gcagagtgtg actgcactcc agggtttcac   540
tgcctggggg caggatgcag catgtgtgaa caggattgta acaaggtca agaactgaca    600
```

```
aaaaaaggtt gtaaagactg ttgctttggg acatttaacg atcagaaacg tggcatctgt    660
cgaccctgga caaactgttc tttggatgga aagtctgtgc ttgtgaatgg gacgaaggag    720
agggacgtgg tctgtggacc atctccagcc gacctctctc cgggagcatc ctctgtgacc    780
ccgcctgccc ctgcgagaga gccaggacac tctccgcaga tcatctcctt ctttcttgcg    840
ctgacgtcga ctgcgttgct cttcctgctg ttcttcctca cgctccgttt ctctgttgtt    900
aaacggggca gaaagaaact cctgtatata ttcaaacaac catttatgag accagtacaa    960
actactcaag aggaagatgg ctgtagctgc cgatttccag aagaagaaga aggaggatgt   1020
gaactgtgaa atgaagtcaa atagggctgt tgggactttc ttgaaaagaa gcaaggaaat   1080
atgagtcatc cgctatcaca gctttcaaaa gcaagaacac catcctacat aatacccagg   1140
attcccccaa cacacgttct tttctaaatg ccaatgagtt ggcctttaaa aatgcaccac   1200
tttttttttt tttttgacag gtctcactc tgtcacccag gctggagtgc agtggcacca   1260
ccatggctct ctgcagcctt gacctctggg agctcaagtg atcctcctgc ctcagtctcc   1320
tgagtagctg aactacaag gaagggccac cacacctgac taacttttt gttttttgtt   1380
tggtaaagat ggcatttcac catgttgtac aggctggtct caaactccta ggttcacttt   1440
ggcctcccaa agtgctggga ttacagacat gaactgccag gcccggccaa ataatgcac    1500
cacttttaac agaacagaca gatgaggaca gagctggtga taaaaaaaaa aaaaaaaag    1560
cattttctag ataccactta acaggtttga gctagttttt ttgaaatcca agaaaatta    1620
tagtttaaat tcaattacat agtccagtgg tccaactata attataatca aaatcaatgc   1680
aggtttgttt tttggtgcta atatgacata tgacaataag ccacgaggtg cagtaagtac   1740
ccgactaaag tttccgtggg ttctgtcatg taacacgaca tgctccaccg tcagggggga   1800
gtatgagcag agtgcctgag tttagggtca aggacaaaaa acctcaggcc tggaggaagt   1860
tttggaaaga gttcaagtgt ctgtatatcc tatggtcttc tccatcctca caccttctgc   1920
ctttgtcctg ctcccttta agccaggtta cattctaaaa attcttaact tttaacataa    1980
tattttatac caaagccaat aaatgaactg catatgatag gtatgaagta cagtgagaaa   2040
attaacacct gtgagctcat tgtcctacca cagcactaga gtgggggccg ccaaactccc   2100
atggccaaac ctggtgcacc atttgccttt gtttgtctgt tggtttgctt gagacagtct   2160
tgctctgttg cccaggctgg aatggagtgg ctattcacag gcacaatcat agcacacttt   2220
agccttaaac tcctgggctc aagtgatcca cccgcctcag tctcccaagt agctgggatt   2280
acaggtgcaa acctggcatg cctgccattg tttggcttat gatctaagga tagcttttta   2340
aatttttattc attttatttt ttttttgagac agtgtctcac tctgtctccc aggctggagt   2400
acagtggtac aatcttggat caccgcctcc cagtttcaag tgatctccct gcctcagcct   2460
cctaagtagc tgggactaca ggtatgtgcc accacgcctg gctaattttt atatttttag   2520
tagagacggg gtttcaccat gttgtccagg ctggtctcaa actcctgacc tcaggtgatc   2580
tgcccacctc tgcctcccaa agtgctggga ttacaggcat gagccaccat gcctggccat   2640
ttcttacact tttgtatgac atgcctattg caagcttgcg tgcctctgtc ccatgttatt   2700
ttactctggg atttaggtgg agggagcagc ttctatttgg aacattggcc atcgcatggc   2760
aaatgggtat ctgtcacttc tgctcctatt tagttggttc tactataacc tttagagcaa   2820
atcctgcagc caagccaggc atcaataggg cagaaaagta tattctgtaa ataggggtga   2880
ggagaagata tttctgaaca atagtctact gcagtaccaa attgcttttc aaagtggctg   2940
ttctaatgta ctcccgtcag tcatataagt gtcatgtaag tatcccattg atccacatcc   3000
```

```
ttgctaccct ctggtactat caggtgccct taattttgcc aagccagtgg gtatagaatg    3060
agatctcact gtggtcttag tttgcatttg cttggttact gatgagcacc ttgtcaaata    3120
tttatatacc atttgtgttt attttttaa  ataaaatgct tgctcatgct tttttgccca    3180
tttgcaaaaa aacttggggc cggtgcagt  ggctcatgcc tgtagtccca gctctttggg    3240
aggccaaggt gggcagatcg cttgagccca ggagttcgag accagccttg caacatggc     3300 gaaaccctgt ctttacaaaa aatacaaaaa ttagccgggt gtggtggtgt gcacctgaag    3360
tcccagctac tcagtaggtt cgctttgagc ctgggaggca gaggttgcag tgagctggga    3420
ccgcatcact acacttcagc ctgggcaaca gagaaaaacc ttttctcaga aacaaacaaa    3480
cccaaatgtg gttgtttgtc ctgattccta aaaggtcttt atgtattcta gataataatc    3540
tttggtcagt tatatgtgtt aaaaaatatc ttctttgtgg ccaggcacgg tagctcacac    3600
ctgtaatccc agcactttgc ggggctgagg tgggtggatc atctgaggtc aagagttcaa    3660
gatcagcctg gccaacacag tgaaacccca tctctactaa acatgtacaa aacttagctg    3720
ggtatggtgg cgggtgcctg taaccccagc tgctccagag gctgtggcag aagaatcgct    3780
tgaacccagg aggcagaggt tgcagcgagc caagattgtg ccattgcact ccagactggg    3840
tgacaagagt gaaattctgc ctatctatct atctatctat ctatatctat atatatatat    3900
atatatatcc tttgtaattt atttttccct ttttaaaatt tttataaaa  ttctttttta    3960 tttttatttt tagcagaggt gaggtttctg aggtttcatt atgttgccca ggctggtctt    4020
gaactcctga gctcaagtga tcctcccacc tcagccttcc aaagtgctgg aattgcagac    4080
atgagccacc gcgcccctcc tgtttttctc taattaatgg tgtctttctt tgtctttctg    4140
gtaataagca aaaagttctt catttgattt ggttaaattt ataactgttt tctcatatgg    4200
ttaacatttt ttcttgcctg gctaaagaaa tccttttctg cccaatacta taagagggtt    4260
tgcccacatt ttattccaaa agttttaagt tttgtctttc atcttgaagt ctaatgtatc    4320
aggaactggc ttttgtgcct gttgggaggt agtgatccaa ttccatgtct tgcatgtagg    4380
taaccactgg tccctgcgcc atgtattcaa tacgtcgtct ttctcctgcg ggtctgcaat    4440
ctcacctacc atccatcaag tttccatagg gccatgggtc tgcttctggg ctccctgttc    4500
tgttccattg tcaatttgtc tatcctgtgc cagtatcaca ctgtgtttat tacaatagct    4560
ttgtaacagc tctcgatatc cggtaggaca tctccctcca ccttctttt  ctacttcaga    4620 agtgtcttag ctaggtcagg cacggtggct cacgcctgta atcccagcac tttgggaggc    4680
cgacgcggat ggatcacctg aggtcaggag ttttgagaca gcctggccaa catggtgaaa    4740
ccccatctct actaaaaaat acaaaaatta gtcaggcatg gtggcatgtg cctgtaatcc    4800
cagctatttg ggaggctgag gccggagaat tgcttgaacc cgggggcgg  aggttgcagt    4860 gagccgagat cgtaccattg cactccagcc tgggtgacag agcgaaactc tgtctcagga    4920 aaaaaagaa  aagagatgtc ttggttattc ttggttcttt attattcaat ataaattta     4980 gaagctgaat ttgaaaagat ttggattgga atttcattaa atctacaggt caatttaggg    5040
agagttgata attttacaga attgagtcat ctggtgttcc aataagaata agagaacaat    5100
tattggctgt acaattcttg ccaaatagta ggcaaagcaa agcttaggaa gtatactggt    5160
gccatttcag gaacaaagct aggtgcgaat attttgtct  ttctgaatca tgatgctgta    5220
agttctaaag tgatttctcc tcttggcttt ggacacatgg tgtttaatta cctactgctg    5280
actatccaca aacagaaaga gactggtcat gccccacagg gttggggtat ccaagataat    5340
ggagcgaggc tctcatgtgt cctaggttac acaccgaaaa tccacagttt attctgtgaa    5400
```

| | |
|---|---|
| gaaaggaggc tatgttatg atacagactg tgatattttt atcatagcct attctggtat | 5460 |
| catgtgcaaa agctataaat gaaaaacaca ggaacttggc atgtgagtca ttgctccccc | 5520 |
| taaatgacaa ttaataagga aggaacattg agacagaata aaatgatccc cttctgggtt | 5580 |
| taatttagaa agttccataa ttaggtttaa tagaaataaa tgtaaatttc tatgattaaa | 5640 |
| aataaattag cacatttagg gatacacaaa ttataaatca ttttctaaat gctaaaaaca | 5700 |
| agctcaggtt tttttcagaa gaaagtttta attttttttc tttagtggaa gatatcactc | 5760 |
| tgacggaaag ttttgatgtg aggggcggat gactataaag tgggcatctt cccccacagg | 5820 |
| aagatgtttc catctgtggg tgagaggtgc ccaccgcagc tagggcaggt tacatgtgcc | 5880 |
| ctgtgtgtgg taggacttgg agagtgatct ttatcaacgt ttttatttaa aagactatct | 5940 |
| aataaaacac aaaactatga tgttcacagg aaaaaaagaa taagaaaaaa agaaaaaaaa | 6000 |
| a | 6001 |

<210> SEQ ID NO 10
<211> LENGTH: 1336
<212> TYPE: DNA
<213> ORGANISM: Homo sapiens

<400> SEQUENCE: 10

| | |
|---|---|
| gagagacaca gagtccggca ttggtcccag gcagcagtta gcccgccgcc cgcctgtgtg | 60 |
| tccccagagc catggagaga gccagtctga tccagaaggc caagctggca gagcaggccg | 120 |
| aacgctatga ggacatggca gccttcatga aggcgccgt ggagaagggc gaggagctct | 180 |
| cctgcgaaga gcgaaacctg ctctcagtag cctataagaa cgtggtgggc ggccagaggg | 240 |
| ctgcctggag ggtgctgtcc agtattgagc agaaaagcaa cgaggagggc tcggaggaga | 300 |
| aggggcccga ggtgcgtgag taccgggaga aggtggagac tgagctccag ggcgtgtgcg | 360 |
| acaccgtgct gggcctgctg gacagccacc tcatcaagga ggccggggac gccgagagcc | 420 |
| gggtcttcta cctgaagatg aagggtgact actaccgcta cctggccgag gtggccaccg | 480 |
| gtgacgacaa gaagcgcatc attgactcag cccggtcagc ctaccaggag gccatggaca | 540 |
| tcagcaagaa ggagatgccg cccaccaacc ccatccgcct gggcctggcc ctgaactttt | 600 |
| ccgtcttcca ctacgagatc gccaacagcc ccgaggaggc catctctctg gccaagacca | 660 |
| cttttcgacga ggccatggct gatctgcaca ccctcagcga ggactcctac aaagacagca | 720 |
| ccctcatcat gcagctgctg cgagacaacc tgacactgtg gacggccgac aacgccgggg | 780 |
| aagaggggg cgaggctccc caggagcccc agagctgagt gttgcccgcc accgcccgc | 840 |
| cctgccccct ccagtccccc accctgccga gaggactagt atgggtggg aggccccacc | 900 |
| cttctccct aggcgctgtt cttgctccaa agggctccgt ggagagggac tggcagagct | 960 |
| gaggccacct ggggctgggg atcccactct tcttgcagct gttgagcgca cctaaccact | 1020 |
| ggtcatgccc ccaccctgc tctccgcacc cgcttcctcc cgaccccagg accaggctac | 1080 |
| ttctcccctc ctcttgcctc cctcctgccc ctgctgcctc tgatcgtagg aattgaggag | 1140 |
| tgtcccgcct gtggctgag aactggacag tggcaggggc tggagatggg tgtgtgtgtg | 1200 |
| tgtgtgtgtg tgtgtgtgtg tgtgcgcgcg cgccagtgca agaccgagat tgagggaaag | 1260 |
| catgtctgct gggtgtgacc atgtttcctc tcaataaagt tcccctgtga cactcaaaaa | 1320 |
| aaaaaaaaaa aaaaaa | 1336 |

<210> SEQ ID NO 11
<211> LENGTH: 2240
<212> TYPE: DNA

<213> ORGANISM: Homo sapiens

<400> SEQUENCE: 11

```
ggagggcagc cagcagcttc cccttctctg ccctgctcca ggcaccaggc tctttcccct      60
tcagtgtctc agaggagggg acggcagcac catggacccc cgcttgtcca ctgtccgcca     120
gacctgctgc tgcttcaatg tccgcatcgc aaccaccgcc ctggccatct accatgtgat     180
catgagcgtc ttgttgttca tcgagcactc agtagaggtg gcccatggca aggcgtcctg     240
caagctctcc cagatgggct acctcaggat cgctgacctg atctccagct tcctgctcat     300
caccatgctc ttcatcatca gcctgagcct actgatcggc gtagtcaaga accgggagaa     360
gtacctgctg cccttcctgt ccctgcaaat catggactat ctcctgtgcc tgctcaccct     420
gctgggctcc tacattgagc tgcccgccta cctcaagttg gcctcccgga gccgtgctag     480
ctcctccaag ttcccccctga tgacgctgca gctgctggac ttctgcctga gcatcctgac     540
cctctgcagc tcctacatgg aagtgccccac ctatctcaac ttcaagtcca tgaaccacat     600
gaattacctc cccagccagg aggatatgcc tcataaccag ttcatcaaga tgatgatcat     660
cttttccatc gccttcatca ctgtccttat cttcaaggtc tacatgttca agtgcgtgtg     720
gcggtgctac agattgatca agtgcatgaa ctcggtggag gagaagagaa actccaagat     780
gctccagaag gtggtcctgc cgtcctacga ggaagccctg tctttgccat cgaagacccc     840
agaggggggc ccagcaccac ccccatactc agaggtgtga ccctcgccag gccccagccc     900
cagtgctggg aggggtggag ctgcctcata atctgctttt ttgctttggt ggcccctgtg     960
gcctgggtgg gccctcccgc ccctccctgg caggacaatc tgcttgtgtc tccctcgctg    1020
gcctgctcct cctgcagggc ctgtgagctg ctcacaactg ggtcaacgct ttaggctgag    1080
tcactcctcg ggtctctcca taattcagcc caacaatgct tggtttattt caatcagctc    1140
tgacacttgt ttagacgatt ggccattcta aagttggtga gtttgtcaag caactatcga    1200
cttgatcagt tcagccaagc aactgacaaa tcaaaaaccc acttgtcagt tcagtaaaat    1260
aatttggtca acaacagtc tattgcattg atttataaat agttgtcagt tcacatagca    1320
atttaatcaa gtaatcatta attagttacc ccctatatat aaatatatgt aatcaatttc    1380
ttcaaatagc ttgcttacat gataatcaat tagccaacca tgagtcattt agaatagtga    1440
taaatagaat acacagaata gtgatgaaat tcaatttaaa aaatcacgtt agcctccaaa    1500
ccatttaatt caaatgaacc catcaactgg atgccaactc tggcgaatgt aggacctctg    1560
agtggctgta taattgttaa ttcaaatgaa attcatttaa acagttgaca aactgtcatt    1620
caacaattag ctccaggaaa taacagttat ttcatcataa aacagtccct tcaaacacac    1680
aattgttctg ctgaagagtt gtcatcaaca atccaatgct cacctattca gttgctctgt    1740
ggtcagtgtg gctgcataac agtggattcc atgaaaggag tcatttagt gatgagctgc    1800
cagtccattc ccaggccagg ctgtcgctgg ccatccattc agtcgattca gtcataggcg    1860
aatctgttct gcccgaggct tgtggtcaag caaaaattca gccctgaaat caggcacatc    1920
tgttcgttgg actaaaccca caggttagtt cagtcaaagc aggcaacccc cttgtgggca    1980
ctgaccctgc cactggggtc atggcggttg tggcagctgg ggaggtttgg ccccaacagc    2040
cctcctgtgc ctgcttccct gtgtgtcggg gtcctccagg gagctgaccc agaggtggag    2100
gccacggagg cagggtctct ggggactgtc gggggtaca gagggagaag gctctgcaag    2160
agctccctgg caatacccccc ttgtgtaatt gctttgtgtg cgacagggag gaagtttcaa    2220
taaagcagca acaagcttct                                                2240
```

<210> SEQ ID NO 12
<211> LENGTH: 3039
<212> TYPE: DNA
<213> ORGANISM: Homo sapiens

<400> SEQUENCE: 12

| | | | | | |
|---|---|---|---|---|---|
| aggcgcagag | gagggcggtg | ttgagaccgg | cggagcggcg | ggacccctag | gtggcggagg | 60 |
| gacgctccgg | gaaagcgagg | ggcgctacga | gctctgggcc | acgtgacctg | ccggggggcgg | 120 |
| gagcaggggg | cgcgccggcc | tcctgcggtg | cccctgcctt | ggggaggggc | cgtgaccacc | 180 |
| cgtctgtcgc | ccgaggcggc | cgccgctgca | ccttcaccgc | gtacccggga | cccgcccgcc | 240 |
| cgcgggagaa | atgttgctga | agtgctgctg | aaagggccag | agatgcaagg | atttgggata | 300 |
| cattttgaac | cttttaagctg | tctgacattg | acctccttttc | attattaata | aagaagaatc | 360 |
| aggagcttag | gatgtattaa | caccaactca | ttaatatact | aaccggacaa | tgttctacaa | 420 |
| acaattctac | attgtaaagg | actggattgg | cacaaaataa | aataattta | ttttattcag | 480 |
| cttataatat | gactcgatgg | aggaaaattt | gataagcatg | agagaagacc | attcttttca | 540 |
| tgttcgttac | agaatggaag | cttcttgcct | agagctggcc | ttggaagggg | aacgtctatg | 600 |
| taaatcagga | gactgccgcg | ctggcgtgtc | attctttgaa | gctgcagttc | aagttggaac | 660 |
| tgaagaccta | aaacactta | gcgctattta | cagccagttg | ggcaatgctt | atttctatttt | 720 |
| gcatgattat | gccaaagcat | agaatatca | ccatcatgat | ttaacccttg | caaggactat | 780 |
| tggagaccag | ctgggggaag | cgaaagctag | tggtaatctg | ggaaacaccct | taaaagttct | 840 |
| tgggaattttt | gacgaagcca | tagtttgttg | tcagcgacac | ctagatatttt | ccagagagct | 900 |
| taatgacaag | gtgggagaag | caagagcact | ttacaatctt | gggaatgtgt | atcatgccaa | 960 |
| agggaaaagt | tttggttgcc | ctggtcccca | ggatgtagga | gaatttccag | aagaagtgag | 1020 |
| agatgctctg | caggcagccg | tggattttta | tgaggaaaac | ctatcattag | tgactgcttt | 1080 |
| gggtgaccga | gcggcacaag | gacgtgcctt | tggaaatctt | ggaaacacac | attacctcct | 1140 |
| tgcaacttc | agggatgcag | ttatagctca | tgagcagcgt | ctccttattg | caaaagaatt | 1200 |
| tggagataaa | gcagctgaaa | gaagagcata | tagcaacctt | ggaaatgcat | atatatttct | 1260 |
| tggtgaattt | gaaactgcct | cggaatacta | caagaagaca | ctactgttgg | cccgacagct | 1320 |
| taaagaccga | gctgtagaag | cacagtcttg | ttacagtctt | ggaaatacat | atactttact | 1380 |
| tcaagactat | gaaaaggcca | ttgattatca | tctgaagcac | ttagcaattg | ctcaagagct | 1440 |
| gaatgataga | attggtgaag | gaagagcatg | ttggagctta | ggaaatgcat | acacagcact | 1500 |
| aggaaatcat | gatcaagcaa | tgcatttttgc | tgaaaagcac | ttggaaatttt | caagagaggt | 1560 |
| tggggataaa | agtggtgaac | taacagcacg | acttaatctc | tcagaccttc | aaatggttct | 1620 |
| tggtctgagc | tacagcacaa | ataactccat | aatgtctgaa | atactgaaa | ttgatagcag | 1680 |
| tttgaatggt | gtacgcccca | agttgggacg | ccggcatagt | atggaaaata | tggaacttat | 1740 |
| gaagttaaca | ccagaaaagg | tacagaactg | gaacagtgaa | attcttgcta | agcaaaaacc | 1800 |
| tcttattgcc | aaaccttctg | caaagctact | ctttgtcaac | agactgaagg | ggaaaaaata | 1860 |
| caaaacgaat | tcctccacta | aagttctcca | agatgccagt | aattctattg | accaccgaat | 1920 |
| tccaaattct | cagaggaaaa | tcagtgcaga | tactattgga | gatgaagggt | tctttgactt | 1980 |
| attaagccga | tttcaaagca | ataggatgga | tgatcagaga | tgttgcttac | aagaaaagaa | 2040 |
| ctgccataca | gcttcaacaa | caacttcttc | cactccccct | aaaaatgatgc | taaaaacatc | 2100 |
| atctgttcct | gtggtatccc | ccaacacgga | tgagttttta | gatcttcttg | ccagctcaca | 2160 |

```
gagtcgccgt ctggatgacc agagggctag tttcagtaat ttgccagggc ttcgtctaac    2220
acaaaacagc cagtcggtac ttagccacct gatgactaat gacaacaaag aggctgatga    2280
agatttcttt gacatccttg taaaatgtca aggatccaga ttagatgatc aaagatgtgc    2340
tccaccacct gctaccacaa agggtccgac agtaccagat gaagactttt tcagccttat    2400
tttacggtcc cagggaaaga gaatggatga acagagagtt cttttacaaa gagatcaaaa    2460
cagagacact gactttgggc taaaggactt tttgcaaaat aatgctttgt tggagtttaa    2520
aaattcaggg aaaaaatcgg cagaccatta gttactatgg atttattttt tttcctttca    2580
aacacggtaa ggaaacaatc tattacttt  ttccttaaaa ggagaattta tagcactgta    2640
atacagctta aaatatttt  agaatgatgt aaatagttaa ccttcagtag tctattaagg    2700
cattaatact tctctggaca tgcgcgtttg agggtggagg ggtcctgtaa ggtgcttcat    2760
cgtctgtgat tactgcttgg gatgtgttct ttggcagctt gtgagattac tttacctagt    2820
gtttataaag taggaagtta agtgaatcat agattagaat ttaatactct tatggaaata    2880
attttttaac atcttaattg acaatggcgt ttttttatac ataaccatgg atgtagtggg    2940
aaacaatgtt gtttggtaaa aataatgtac ttgatcaatg taaaaagta  tataaaatag    3000 tcttactaaa aatctaggtt tttttttcct ccaaaaaaa                           3039

<210> SEQ ID NO 13
<211> LENGTH: 7018
<212> TYPE: DNA
<213> ORGANISM: Homo sapiens

<400> SEQUENCE: 13
ggcgggcgcg ccgggcggca ggtgtcggcg tcggcggcat tcggcggcga tggagcggcc      60
ctggggagct gcggacggcc tctcgcgctg gccccatggc ctcggcctcc tcctcctcct     120
gcagctgctg ccgccgtcga ccctcagcca ggaccggctg acgcgccgc  cgccgcccgc     180 tgcgccgctg ccgcgctggt ctggccccat cggggtgagc tggggctgc  gggcggccgc     240 agccgggggc gcgtttcccc cggcggccg  ttggcgtcgc agcgcgccgg gcgaggacga     300
ggagtgcggc cgggtccggg acttcgtcgc caagctggcc aacaacacgc accagcatgt     360
gtttgatgat ctcagaggct cagtatcctt gtcctgggtt ggagatagca ctggggtcat     420
tctagtcttg actaccttcc atgtaccact ggtaattatg acttttggac agtccaagct     480
atatcgaagt gaggattatg ggaagaactt taaggatatt acagatctca tcaataacac     540
ctttattcgg actgaatttg gcatggctat tggtcctgag aactctggaa aggtggtgtt     600
aacagcagag gtgtctggag gaagtcgtgg aggaagaatc ttcagatcat cagattttgc     660
gaagaatttt gtgcaaacag atctcccttt tcatcctctc actcagatga tgtatagccc     720
tcagaattct gattatcttt tagctctcag cactgaaaat ggcctgtggg tgtccaagaa     780 ttttgggga aaatgggaag aaatccacaa agcagtatgt ttggccaaat ggggatcaga     840
caacaccatc ttctttacaa cctatgcaaa tggctcctgc aaagctgacc ttggggctct     900
ggaattatgg agaacttcag acttgggaaa agcttcaaa  actattggtg tgaaaatcta     960
ctcatttggt cttggggggac gtttcctttt tgcctctgtg atggctgata aggataccac    1020
aagaaggatc cacgtttcaa cagatcaagg ggacacatgg agcatggccc agctccctc     1080 cgtgggacag gaacagttct attctattct ggcagcaaat gatgacatgg tattcatgca    1140
tgtagatgaa cctggagaca ctgggtttgg cacaatcttt acctcagatg atcgaggcat    1200
tgtctattcc aagtctttgg accgacatct ctacactacc acaggcggag agacggactt    1260
```

```
taccaacgtg acctccctcc gcggcgtcta cataacaagc gtgctctccg aagataattc    1320
tatccagacc atgatcactt ttgaccaagg aggaaggtgg acgcacctga ggaagcctga    1380
aaacagtgaa tgtgatgcta cagcaaaaaa caagaatgag tgcagccttc atattcatgc    1440
ttcctacagc atctcccaga aactgaatgt tccaatggcc ccactctcag agccgaatgc    1500
cgtaggcatt gtcattgctc atggtagcgt gggggatgcc atctcagtga tggttccaga    1560
tgtgtacatc tcagatgatg ggggttactc ctggacaaag atgctggaag acccccacta    1620
ttacaccatc ctggattctg gaggcatcat tgtggccatt gagcacagca gccgtcctat    1680
caatgtgatt aagttctcca cagacgaagg tcaatgctgg caaacctaca cgttcaccag    1740 ggacccccatc tatttcactg gcctagcttc agaacctgga gctaggtcca tgaatatcag    1800
catttggggc ttcacagaat cttttcctgac cagccagtgg gtctcctaca ccattgattt    1860
taaagatatc cttgaaagga actgtgaaga aaggactat accatatggc tggcacactc    1920 cacagacccct gaagattatg aagatggctg cattttgggc tacaaagaac agtttctgcg    1980
gctacgcaag tcatccgtgt gtcagaatgg tcgagactat gttgtgacca agcagccctc    2040
catctgcctc tgttccctgg aggactttct ctgtgatttt ggctactacc gtccagaaaa    2100
tgactccaag tgtgtggaac agccagaact gaagggccac gacctggagt tttgtctgta    2160
cggaagagaa gaacacctaa caacaaatgg gtaccggaaa attccagggg acaaatgcca    2220
gggtggggta aatccagttc gagaagtaaa agacttgaaa aagaaatgca caagcaactt    2280
tttgagtccg gaaaaacaga attccaagtc aaattctgtt ccaattatcc tggccatcgt    2340
gggattgatg ctggtcacag tcgtagcagg agtgctcatt gtgaagaaat atgtctgtgg    2400
gggaaggttc ctggtgcatc gatactctgt gctgcagcag catgcagagg ccaatggtgt    2460
ggatggtgtg gatgctttgg acacagcctc ccacactaat aaaagtggtt atcatgatga    2520
ctcagatgag gacctcttgg aatagctctt cagaggagct ggaccccagca tggatggtgg    2580 aaccacagta cctcttacac tccctgtggc tccaacttca ggaaataaat ttcccattgc    2640
gagggaccca gctctgtttc tgctgcttcc atcaaagcca aaaggaccta cactaaagaa    2700
atgcagggtg ggggtgggga accctgagca ctttttttaca attggctctg agaaaaaggg    2760
agacatttta aattctttaa cttcttatt ctcgtcctgt ctctttgcaa agtatgggct    2820
tttttgtttt tgtttttaa gggaaacgaa atggaattcg aagggacctt ttcactaacc    2880
ccacttctgt gtgttctgca tggcgcctgc cccagggcat ctgccaactc cagtatcagc    2940
tctcacagtg tacttggtac catccctggg ctctgctggc gagacgaaac agctgtagag    3000
atgaaaacag gctgcagagg ctggcacagc ctggccggct tttctccatc tggggacagt    3060
cctactccaa gaacactgca caccagctcc tcacacagat cccacttact cttttttttt    3120
ttttcagaga ccacagacca cagtgatttt tcttttccct tgtttaatta ggcaataccc    3180
ttgttaattg cccctttggca actaacttaa ccatgtgctt cccacacagt acatcaggaa    3240
aacttacagg gcaatatttt taacttgggg caggaagaag ggagcagcag agaattgact    3300
agatatagca cctattaaaa gagaactctt gcttcttctg agattttttca agctgtgctt    3360 tgtgtgtgtg ccagtagact tacgcaagga cagggtacaa acttagctgg aagtctgccc    3420 aggctgaatat atctcttccc tagagttgat tgtcgggtac acagtgtgaa ccccgaaga    3480 cggaacctca cagtcttcca tgttcccttc ttaactgtcg tgtggctcgt tgctaaatca    3540
tgacaatggc tgcctatctg ctgcttctta ggttgctgtt gtacatggaa ccaggactag    3600
agattttttc agatttatag acttaaaaaa ttagaatttt attaccaggc tttccttctc    3660
```

```
accccttttt tctgactttg ccaagtaatt tgttgacacg aaaattttgg aggaaccaat    3720
tgaaaacaca cttccagtct agatgatgct ttgtgtgata cattaagttc ttattttgga    3780
ttaaaagaag ttttccattt gatacttctc taaattaaat aaattataga atgtagttgg    3840
gtggattttg gggtggccat atagtaatgg aaagctgcaa taattagttt taatacagct    3900
tgaatatttg ctatatagaa atatagtatg gaaagttttt ggtcttaatg tagctactgt    3960
gcgggtcaca gttctcccca atgattatga ctgggacatt ctttggtaga taccatttgc    4020
tactagttta ttttgtggct agaaagtcag ttttgtgtgt ttttttttt ttttatttga     4080
agtgccaaat taactttagt cagaatgtga gcagatggc aagttctctc ctccccagaa     4140
tggattaaca gctgcgtgga aagtggggga gagagtggat ggagactttt agagatgtta    4200
aaactgcagt agaatgaaat gagtcaggga gcttcagtta gaaataaag ttgaggcagt     4260
ttttgtgaag ataatatggt tagggctgga gtgcactagt cttttttgctt attcattttg   4320
catggtttta aaattaaaaa taattccgaa gatacaccag ctcacaaatg aaaacgtcag    4380
cctctgcccc accctccctc ctgcccaaag tgaatttggt actcagaaaa gaactgttta   4440
taccactcac ctttctccca gcatgtactc actgtgggca gatgcaccaa tacatggtaa    4500
tcctcttact cattttaaga cgtaggaaac tcaatattct tctctaacca tatacgatag    4560
ggctcttcgc ttttaatgat atctgggatt tctgtggaac ttggcaaatt ttcagagcac    4620
cttcactcac ataatgtcat ttgaacctca caatgttctt gggatggagt cagttgttca    4680
gggtccccgt gtgtgtgata agcagtgctg gctggctgtc ttcagaactc ttggaaatct    4740
ttacacatgc gagtgctaac cactttgagc aaggctgcct tcttgtagat gacttgctgt    4800
tctttatgac agggatcagt ggcatttgtt tcctagcagt atttagcacc ttttgccac     4860
cttggtgaac agaaaattgt attttcctgt ctttcatggc tgaaaacaaa agtaatggga    4920
attttaaata cgtttgcaga aactgcccct cccctcattg agggtcactg ctcaagagtg    4980
caggagtgga ctctccactg atgggtctcc ctccccatcc tggtttccac cccgggctgg    5040
ctagctctgt tggttttgaag actgacagcc agcctggctc attctcatta ttggctagtt   5100
agctttctt atcaacctgc tcactcacaa atgtgtgccc tcagccagag agtaagaaag     5160
cccaaatctg ttacagcttc taaaaaaata gatttctaat ttgtcctact catgttagga    5220
gcattatctt tgaaggtaaa acatagtgta tcattgtgta aactcccagg cttgatgtag    5280
cagaagagat catttctgga ggcttcagca atggaattta gcattataag agagattgga    5340
caaaccagtc caaagtggtc cgagttctta aatccaggta gggaactcac tcttcttct     5400
tctctggacc taattgggca ttgggcttta gtgagaccac agaccaggcc cgtctctcct   5460
gtaggctttt aattcaatgg caactctatt tcaaagaata aaagcctttg gagagttgcg    5520
gcagttctgg gggcgggctc aggagagtcc atagatcagc cgtaactgga acgtagaatc    5580
tacgtctgcc tctgaatgga cttcccacct cctctctctt gctctgatgc ttgcctctgg    5640
gcctctccat gcccaaggtg gtctttcatc cttgacaggc tggtaatgtg ctggccacct    5700
ccagctcctg catcgagtct gtaaaccaga gctggttctc atggccttcg tcacgatacc    5760
aggatacgga ggggagccca gggccatcca taccaccccc agggtaacgg ggctggcctg    5820
gcattagtca ttatttagtt tccaggccaa ccatccagat agagattccc tctttccttt    5880
gagcagtgct ctcaagagct ccgtgcctgt ccacaatgac ctagagtgca tcctgctcat    5940
tgtcagtgta gcccctcgcc cctatattca tccaggatac ttggaagtgc taaaatagga    6000
agggattcgg ctttcaactt tgctaccatc ttccctgaag caggaaaatg aacatggact    6060
```

```
taaatgttct tgaaaaaac caaagttttta agatttgctg tgtgatgaag tgacagggag    6120
ggccggagtc agcaggtgcc agactttctg ttctgtctgc catgggtttg tccagctcag    6180
gtagctctag gagcaccatc ctgccctagc agagcccagg ccttgccctc atgaagcatc    6240
attgaaatag caggagcatg ttgatttctt ggttaggttg cattataata acaagagtca    6300
gaacattaat tcgaaacaac ttgcagtatg catttcttca caccagtaca ttcttaagtg    6360
tacttgttta taaggaataa cataaactaa tctgtacctt tatatatatg tgtgtgtaca    6420
tatatacata tataaactgt atagtgtaca tggtaatgat ttattgctat gccccagatc    6480
cttaatgtag ttctcatcct ccgcatgccc tcagccacaa gcgggtgact gactgttccc    6540
tgatgatttg gcccacctcc tgtgtttgga cctctaggga ggagggtttt ggtcatactc    6600
tccttatcct cgtgcacaga aatgctcagg gtccccatgt gcctgttgtt cagccctctc    6660
tcttgttccc tttctgagca tgtggtcctt ccccaggctg tgggacagct gccttcccac    6720
gaaagtgtaa agcagtatta agatcattac tgcatgtgcc ctaaaaaccc aagttttcta    6780
ttcccttagg acagaaaatt gcatgtgagg tgggataatc gagtttcagt gacccacgtc    6840
agttacacat aaagccaga ccccatgata aaattccaca aaatggaaat aaaactcaaa    6900
tttctttagc attgtgtaaa taaatctgaa tgtgtttaac tttgtactgg taattttctg    6960
tatatttgga atatttgggt taaaaataaa acagactgga ctttgttacc tgacctac     7018

<210> SEQ ID NO 14
<211> LENGTH: 1749
<212> TYPE: DNA
<213> ORGANISM: Homo sapiens

<400> SEQUENCE: 14
gtgacattgt ttgccaaaat cccaggcagc atggacctca gtcttctctg gtacttctg      60 cccctagtca ccatggcctg gggccagtat ggcgattatg atacccata ccagcagtat     120 catgactaca gcgatgatgg gtgggtgaat ttgaaccggc aaggcttcag ctaccagtgt     180
ccccaggggc aggtgatagt ggccgtgagg agcatcttca gcaagaagga aggttctgac     240
agacaatgga actacgcctg catgcccacg ccacagagcc tcggggaacc cacggagtgc     300
tggtgggagg agatcaacag ggctggcatg gaatggtacc agacgtgctc caacaatggg     360
ctggtggcag gattccagag ccgctacttc gagtcagtgc tggatcggga gtggcagttt     420
tactgttgtc gctacagcaa gaggtgccca tattcctgct ggctaacaac agaatatcca     480
ggtcactatg tgaggaaat ggacatgatt tcctacaatt atgattacta tatccgagga     540
gcaacaacca ctttctctgc agtggaaagg atcgccagt ggaagttcat aatgtgccgg     600
atgactgaat cgactgtgaa atttgcaaat gtttagattt gccacatacc aaatctgggt     660
gaaaggaaag gggccgggga caggagggtg tccacatatg ttaacatcag ttggatctcc     720
tatagaagtt tctgctgctc tctttccttc tccctgagct ggtaactgca atgccaactt     780
cctgggcctt tctgactagt atcacacttc taataaaatc cacaattaaa ccatgtttct     840
cacttttcac atgtttcata gcaactgctt tatatgactg atgatggctt ccttgcacac     900
cacatataca gtgcgcatgc ttacagccgg gcttctggag caccagctgc agcctggcta     960
ctgcttttta ctgcagaatg aactgcaagt tcagcatagt gggggagga ggcagaactg    1020 gaggagaggt gcagtgaagg ttctctacag ctaagcctgt ttgaatgata cgtaggttcc    1080
ccaccaaaag caggctttct gccctgaggg acatcttccc actcccctgc tccacatgag    1140
ccatgcatgc ttagcaatcc aagtgcagag ctctttgctc caggagtgag gagactggga    1200
```

```
ggtgaaatgg ggaaatggaa gggtttggag gcagagctga aaacagggtt ggaaggattt    1260
cctgaattag aagacaaacg ttagcatacc cagtaaggaa aatgagtgca ggggccaggg    1320
gaacccgtga ggatcactct caaatgagat taaaaacaag gaagcagaga atggtcagag    1380
aatgggattc agattgggaa cttgtgggga tgagagtgac caggttgaac tgggaagtgg    1440
aaaaaggagt ttgagtcact ggcacctaga agcctgccca cgattcctag gaaggctggc    1500
agacaccctg gaaccctggg gagctactgg caaactctcc tggattgggc ctgattttt     1560 tggtgggaaa ggctgccctg ggatcaact  ttccttctgt gtgtggctca ggagttcttc    1620
tgcagagatg cgctatcttt tcctcctcct gtgatgtcct gctcccaacc atttgtactc    1680
ttcattacaa aagaaataaa aatattaacg ttcactatgc tgaaaataaa aaaaaaaaaa    1740
aaaaaaaaa                                                           1749

<210> SEQ ID NO 15
<211> LENGTH: 2478
<212> TYPE: DNA
<213> ORGANISM: Homo sapiens

<400> SEQUENCE: 15
gcagttggtg aaactcctct gtctcccgct catcttttca ttgctcgttc ccctccttcc      60
cgcagacacc cggaccctcc ctgggcgcca gctccgcggc tccaacgggt ccagaaacaa     120
gccggatttt ttttttttct tcctggaaat tggctttggt gtgtgttgcc ctacctccct     180 cctcccctc ccacccacag cccccccccg gccttttttt tttttttttt tttttttgag     240
acatggcccg ggcagtggct cctggaagag gaacaagtgt gggaaaaggg agaggaagcc     300
ggagctaaat gacaggatgc aggcgacttg agacacaaaa agagaagcgt tcctctcgga     360
tccaggcatt gcctcgctgc tttctttct ccaagacggg ctgaggattg tacagctcta     420
ggcggagttg ggctcttcg gatcgcttag attctcctct ttgctgcatt tcccccacg      480 tcctcgttct cccgcgtctg cctgcggacc cggagaaggg agaatggaga gggggctgcc     540
gctcctctgc gccgtgctcg ccctcgtcct cgccccggcc ggcgcttttc gcaacgataa     600
atgtggcgat actataaaaa ttgaaagccc cgggtacctt acatctcctg ttatcctca     660 ttcttatcac ccaagtgaaa aatgcgaatg gctgattcag gctccggacc cataccagag     720
aattatgatc aacttcaacc ctcacttcga tttggaggac agagactgca agtatgacta     780
cgtggaagtc ttcgatggag aaaatgaaaa tggacatttt aggggaaagt tctgtggaaa     840 gatagccccct cctcctgttg tgtcttcagg gccatttctt tttatcaaat ttgtctctga     900
ctacgaaaca catggtgcag gattttccat acgttatgaa attttcaaga gaggtcctga     960
atgttcccag aactacacaa cacctagtgg agtgataaag tcccccggat tccctgaaaa    1020
atatcccaac agccttgaat gcacttatat tgtctttgcg ccaaagatgt cagagattat    1080
cctgaatttt gaaagctttg acctggaagc ctgactcaaat cctccagggg ggatgttctg    1140
tcgctacgac cggctagaaa tctgggatgg attccctgat gttggccctc acattgggcg    1200
ttactgtgga cagaaaacac caggtcgaat ccgatcctca tcgggcattc tctccatggt    1260
tttttacacc gacagcgcga tagcaaaaga aggtttctca gcaaactaca gtgtcttgca    1320
gagcagtgtc tcagaagatt tcaaatgtat ggaagctctg ggcatggaat caggagaaat    1380
tcattctgac cagatcacag cttcttccca gtatagcacc aactggtctg cagagcgctc    1440
ccgcctgaac tacctgaga atgggtggac tccggagag gattcctacc gagagtggat    1500
acaggtagac ttgggccttc tgcgctttgt cacggctgtc gggacacagg gcgccatttc    1560
```

-continued

| | |
|---|---|
| aaaagaaacc aagaagaaat attatgtcaa gacttacaag atcgacgtta gctccaacgg | 1620 |
| ggaagactgg atcaccataa aagaaggaaa caaacctgtt ctctttcagg gaaacaccaa | 1680 |
| ccccacagat gttgtggttg cagtattccc caaaccactg ataactcgat tgtccgaat | 1740 |
| caagcctgca acttgggaaa ctggcatatc tatgagattt gaagtatacg gttgcaagat | 1800 |
| aacagattat ccttgctctg gaatgttggg tatggtgtct ggacttattt ctgactccca | 1860 |
| gatcacatca tccaaccaag gggacagaaa ctggatgcct gaaaacatcc gcctggtaac | 1920 |
| cagtcgctct ggctgggcac ttccacccgc acctcattcc tacatcaatg agtggctcca | 1980 |
| aatagacctg ggggaggaga agatcgtgag gggcatcatc attcagggtg ggaagcaccg | 2040 |
| agagaacaag gtgttcatga ggaagttcaa gatcgggtac agcaacaacg gctcggactg | 2100 |
| gaagatgatc atggatgaca gcaaacgcaa ggcgaagtct tttgagggca caacaacta | 2160 |
| tgatacacct gagctgcgga cttttccagc tctctccacg cgattcatca ggatctaccc | 2220 |
| cgagagagcc actcatggcg gactggggct cagaatggag ctgctgggct gtgaagtgga | 2280 |
| agcccctaca gctggaccga ccactcccaa cgggaacttg gtggatgaat gtgatgacga | 2340 |
| ccaggccaac tgccacagtg aacaggtga tgacttccag ctcacaggtg gcaccactgt | 2400 |
| gctggccaca gaaaagccca cggtcataga cagcaccata caatcaggta tcaaataaaa | 2460 |
| tacgaaatgt gacagatt | 2478 |

<210> SEQ ID NO 16
<211> LENGTH: 3372
<212> TYPE: DNA
<213> ORGANISM: Homo sapiens

<400> SEQUENCE: 16

| | |
|---|---|
| taaaaccagg aagtgaagtc cccgagcacg ttagaaagcc tgacatggcc tgactcggga | 60 |
| cagctcagag cagggcagaa ctggggacac tctgggccgg ccttctgcct gcatggacgc | 120 |
| tctgaagcca ccctgtctct ggaggaacca cgagcgaggg aagaaggaca gggactcgtg | 180 |
| tggcaggaag aactcagagc cgggaagccc ccattcacta gaagcactga gagatgcggc | 240 |
| cccctcgcag ggtctgaatt tcctgctgct gttcacaaag atgcttttta tctttaactt | 300 |
| tttgttttcc ccacttccga ccccggcgtt gatctgcatc ctgacatttg gagctgccat | 360 |
| cttcttgtgg ctgatcacca gacctcaacc cgtcttacct cttcttgacc tgaacaatca | 420 |
| gtctgtggga attgagggag gagcacggaa gggggtttcc cagaagaaca atgacctaac | 480 |
| aagttgctgc ttctcagatg ccaagactat gtatgaggtt ttccaaagag gactcgctgt | 540 |
| gtctgacaat gggccctgct gggatatag aaaaccaaac cagccctaca gatggctatc | 600 |
| ttacaaacag gtgtctgata gagcagagta cctgggttcc tgtctcttgc ataaaggtta | 660 |
| taaatcatca ccagaccagt tgtcggcat cttttgctcag aataggccag agtggatcat | 720 |
| ctccgaattg gcttgttaca cgtactctat ggtagctgta cctctgtatg acaccttggg | 780 |
| accagaagcc atcgtacata ttgtcaacaa ggctgatatc gccatggtga tctgtgacac | 840 |
| accccaaaag gcattggtgc tgataggaa tgtagagaaa gcttcaccc cgagcctgaa | 900 |
| ggtgatcatc cttatggacc ccttgatga tgacctgaag caaagagggg agaagagtgg | 960 |
| aattgagatc ttatccctat atgatgctga gaacctaggc aaaagagcact tcagaaaacc | 1020 |
| tgtgcctcct agcccagaag acctgagcgt catctgcttc accagtggga ccacaggtga | 1080 |
| ccccaaagga gccatgataa cccatcaaaa tattgtttca aatgctgctg ccttttctcaa | 1140 |
| atgtgtggag catgcttatg agcccactcc tgatgatgtg ccatatcct acctccctct | 1200 |

```
ggctcatatg tttgagagga ttgtacaggc tgttgtgtac agctgtggag ccagagttgg   1260
attcttccaa ggggatattc ggttgctggc tgacgacatg aagactttga agcccacatt   1320
gtttcccgcg gtgcctcgac tccttaacag gatctacgat aaggtacaaa atgaggccaa   1380
gacacccttg aagaagttct tgttgaagct ggctgtttcc agtaaattca aagagcttca   1440
aaagggtatc atcaggcatg atagtttctg ggacaagctc atctttgcaa agatccagga   1500
cagcctgggc ggaagggttc gtgtaattgt cactggagct gcccccatgt ccacttcagt   1560
catgacattc ttccgggcag caatgggatg tcaggtgtat gaagcttatg gtcaaacaga   1620
atgcacaggt ggctgtacat ttacattacc tggggactgg acatcaggtc acgttggggt   1680
gcccctggct tgcaattacg tgaagctgga agatgtggct gacatgaact actttacagt   1740
gaataatgaa ggagaggtct gcatcaaggg tacaaacgtg ttcaaaggat acctgaagga   1800
ccctgagaag acacaggaag ccctggacag tgatggctgg cttcacacag gagacattgg   1860
tcgctggctc ccgaatggaa ctctgaagat catcgaccgt aaaaagaaca ttttcaagct   1920
ggcccaagga gaatacattg caccagagaa gatagaaaat atctacaaca ggagtcaacc   1980
agtgttacaa atttttgtac acggggagag cttacggtca tccttagtag gagtggtggt   2040
tcctgacaca gatgtacttc cctcatttgc agccaagctt ggggtgaagg gctcctttga   2100
ggaactgtgc caaaaccaag ttgtaaggga agccattta  aagacttgc agaaaattgg   2160 gaaagaaagt ggccttaaaa cttttgaaca ggtcaaagcc atttttcttc atccagagcc   2220
attttccatt gaaatgggc tcttgacacc aacattgaaa gcaaagcgag gagagctttc   2280
caaatacttt cggacccaaa ttgacagcct gtatgagcac atccaggatt aggataaggt   2340
acttaagtac ctgccggccc actgtgcact gcttgtgaga aaatggatta aaaactattc   2400
ttacatttgt tttgcctttc ctcctattt  tttttaacct gttaaactct aaagccatag   2460
cttttgtttt atattgagac atataatgtg taaacttagt tcccaaataa atcaatcctg   2520
tctttcccat cttcgatgtt gctaatatta aggcttcagg gctacttta  tcaacatgcc   2580 tgtcttcaag atcccagttt atgttctgtg tccttcctca tgatttccaa ccttaatact   2640
attagtaacc acaagttcaa gggtcaaagg gaccctctgt gccttcttct ttgttttgtg   2700
ataaacataa cttgccaaca gtctctatgc ttatttacat cttctactgt tcaaactaag   2760 agattttaa  attctgaaaa actgcttaca attcatgttt tctagccact ccacaaacca   2820
ctaaaatttt agttttagcc tatcactcat gtcaatcata tctatgagac aaatgtctcc   2880
gatgctcttc tgcgtaaatt aaattgtgta ctgaagggaa aagtttgatc ataccaaaca   2940
tttcctaaac tctctagtta gatatctgac ttgggagtat taaaaattgg gtctatgaca   3000
tattgtccaa aaggaatgct gttcttaaag cattatttac agtaggaact ggggagtaaa   3060
tctgttccct acagtttgct gctgagctgg aagctgtggg ggaaggagtt gacaggtggg   3120
cccagtgaac ttttccagta aatgaagcaa gcactgaata aaaacctcct gaactgggaa   3180
caaagatcta caggcaagca agatgcccac acaacaggct tattttctgt gaaggaacca   3240
actgatctcc cccacccttg gattagagtt cctgctctac cttacccaca gataacacat   3300
gttgtttcta cttgtaaatg taaagtcttt aaaataaact attacagata cttaaaaaaa   3360 aaaaaaaaa aa                                                        3372

<210> SEQ ID NO 17
<211> LENGTH: 5243
<212> TYPE: DNA
<213> ORGANISM: Homo sapiens
```

<400> SEQUENCE: 17

```
agcgtgagac tcgcgccctc cggcacggaa aaggccaggc gacaggtgtc gcttgaaaag      60
actgggcttg tccttgctgg tgcatgcgtc gtcggcctct gggcagcagg tttacaaagg     120
aggaaaacga cttcttctag attttttttt cagtttcttc tataaatcaa acatctcaa     180
aatggagacc taaaatcctt aaagggactt agtctaatct cgggaggtag ttttgtgcat     240
gggtaaacaa attaagtatt aactggtgtt ttactatcca aagaatgcta attttataaa     300
catgatcgag ttatataagg tataccataa tgagtttgat tttgaatttg atttgtggaa     360
ataaaggaaa agtgattcta gctggggcat attgttaaag cattttttttc agagttggcc     420
aggcagtctc ctactggcac attctcccat tatgtagaat agaaatagta cctgtgtttg     480
ggaaagattt taaaatgagt gacagttatt tggaacaaag agctaataat caatccactg     540
caaattaaag aaacatgcag atgaaagttt tgacacatta aaatacttct acagtgacaa     600
agaaaaatca gaacaaagc ttttgtatat gtgcaacaaa tttagaggaa gtaaaaagat     660
aaatgtgatg attggtcaag aaattatcca gttatttaca aggccactga tattttaaac     720
gtccaaaagt ttgtttaaat gggctgttac cgctgagaat gatgaggatg agaatgatgg     780
ttgaaggtta cattttagga aatgaagaaa cttagaaaat taatataaag acagtgatga     840
atacaaagaa gatttttata acaatgtgta aaattttttgg ccagggaaag gaatattgaa     900
gttagataca attacttacc tttgagggaa ataattgttg gtaatgagat gtgatgtttc     960
tcctgccacc tggaaacaaa gcattgaagt ctgcagttga aaagcccaac gtctgtgaga    1020
tccaggaaac catgcttgca aaccactggt aaaaaaaaaa aaaaaaaaa aaaaaagcca    1080
cagtgacttg cttattggtc attgctagta ttatcgactc agaacctctt tactaatggc    1140
tagtaaatca taattgagaa attctgaatt ttgacaaggt ctctgctgtt gaaatggtaa    1200
atttattatt ttttttgtca tgataaaattc tggttcaagg tatgctatcc atgaaataat    1260
ttctgaccaa aactaaattg atgcaatttg attatccatc ttagcctaca gatggcatct    1320
ggtaactttt gactgttttta aaaaataaat ccactatcag agtagatttg atgttggctt    1380
cagaaacatt tagaaaaaca aaagttcaaa atgttttttca ggaggtgata agttgaataa    1440
ctctacaatg ttagttcttt gagggggaca aaaaatttaa aatctttgaa aggtcttatt    1500
ttacagccat atctaaatta tcttaagaaa attttttaaca aagggaatga aatatatatc    1560
atgattctgt ttttccaaaa gtaacctgaa tatagcaatg aagttcagtt ttgttattgg    1620
tagtttgggc agagtctctt tttgcagcac ctgttgtcta ccataattac agaggacatt    1680
tccatgttct agccaagtat actattagaa taaaaaaact taacattgag ttgcttcaac    1740
agcatgaaac tgagtccaaa agaccaaatg aacaaacaca ttaatctctg attatttatt    1800
ttaaatagaa tatttaattg tgtaagatct aatagtatca ttatacttaa gcaatcatat    1860
tcctgatgat ctatgggaaa taactattat ttaattaata ttgaaaccag ttttaagat    1920
gtgttagcca gtcctgttac tagtaaatct ctttatttgg agagaaattt tagattgttt    1980
tgttctcctt attagaagga ttgtagaaag aaaaaaatga ctaattggag aaaaattggg    2040
gatatatcat atttcactga attcaaaatg tcttcagttg taaatcttac cattattttta    2100
cgtacctcta agaaataaaa gtgcttctaa ttaaatatg atgtcattaa ttatgaaata    2160
cttcttgata acagaagttt taaaatagcc atcttagaat cagtgaaata tggtaatgta    2220
ttatttttcct cctttgagtt aggtcttgtg ctttttttttc ctggccacta aatttcacaa    2280
tttccaaaaa gcaaaataaa catattctga atattttgc tgtgaaacac ttgacagcag    2340
```

```
agctttccac catgaaaaga agcttcatga gtcacacatt acatctttgg gttgattgaa    2400
tgccactgaa acattctagt agcctggaga agttgaccta cctgtggaga tgcctgccat    2460
taaatggcat cctgatggct taatacacat cactcttctg tgaagggttt taattttcaa    2520
cacagcttac tctgtagcat catgtttaca ttgtatgtat aaagattata caaaggtgca    2580
attgtgtatt tcttccttaa aatgtatcag tataggattt agaatctcca tgttgaaact    2640
ctaaatgcat agaaataaaa ataataaaaa attttcatt ttggcttttc agcctagtat     2700
taaaactgat aaaagcaaag ccatgcacaa aactacctcc ctagagaaag gctagtccct    2760
tttcttcccc attcatttca ttatgaacat agtagaaaac agcatattct tatcaaattt    2820
gatgaaaagc gccaacacgt ttgaactgaa atacgacttg tcatgtgaac tgtaccgaat    2880
gtctacgtat tccactttc ctgctggggt tcctgtctca gaaaggagtc ttgctcgtgc     2940
tggtttctat tacactggtg tgaatgacaa ggtcaaatgc ttctgttgtg gcctgatgct    3000
ggataactgg aaaagaggag acagtcctac tgaaaagcat aaaaagttgt atcctagctg    3060
cagattcgtt cagagtctaa attccgttaa caacttggaa gctacctctc agcctacttt    3120
tccttcttca gtaacaaatt ccacacactc attacttccg ggtacagaaa acagtggata    3180
tttccgtggc tcttattcaa actctccatc aaatcctgta aactccagag caaatcaaga    3240
tttttctgcc ttgatgagaa gttcctacca ctgtgcaatg aataacgaaa atgccagatt    3300
acttactttt cagacatggc cattgacttt tctgtcgcca acagatctgg caaaagcagg    3360
cttttactac ataggacctg agacagagt ggcttgcttt gcctgtggtg aaaattgag      3420 caattgggaa ccgaaggata atgctatgtc agaacacctg agacattttc ccaaatgccc    3480
atttatagaa aatcagcttc aagacacttc aagatacaca gtttctaatc tgagcatgca    3540
gacacatgca gcccgcttta aaacattctt taactggccc tctagtgttc tagttaatcc    3600
tgagcagctt gcaagtgcgg ttttttatta tgtgggtaac agtgatgatg tcaaatgctt    3660
ttgctgtgat ggtggactca ggtgttggga atctggagat gatccatggg ttcaacatgc    3720
caagtggttt ccaaggtgtg agtacttgat aagaattaaa ggacaggagt tcatccgtca    3780
agttcaagcc agttaccctc atctacttga acagctgcta tccacatcag acagcccagg    3840
agatgaaaat gcagagtcat caattatcca ttttgaacct ggagaagacc attcagaaga    3900
tgcaatcatg atgaatactc ctgtgattaa tgctgccgtg gaaatgggct ttagtagaag    3960
cctggtaaaa cagacagttc agagaaaaat cctagcaact ggagagaatt atagactagt    4020
caatgatctt gtgttagact tactcaatgc agaaatgaa ataagggaag aggagagaga     4080
aagagcaact gaggaaaaag aatcaaatga tttattatta atccggaaga atagaatggc    4140
acttttccaa catttgactt gtgtaattcc aatcctggat agtctactaa ctgccggaat    4200
tattaatgaa caagaacatg atgttattaa acagaagaca cagacgtctt tacaagcaag    4260
agaactgatt gatacgattt tagtaaaagg aaatattgca gccactgtat tcagaaactc    4320
tctgcaagaa gctgaagctg tgttatatga gcatttattt gtgcaacagg acataaaata    4380
tattcccaca gaagatgttt cagatctacc agtggaagaa caattgcgga gactacaaga    4440
agaaagaaca tgtaaagtgt gtatggacaa agaagtgtcc atagtgttta ttccttgtgg    4500
tcatctagta gtatgcaaag attgtgctcc ttctttaaga aagtgtccta tttgtaggag    4560
tacaatcaag ggtacagttc gtacatttct ttcatgaaga agaaccaaaa catcgtctaa    4620
actttagaat taatttatta aatgtattat aactttaact tttatcctaa tttggttccc    4680
ttaaaatttt tatttatta caactcaaaa aacattgttt tgtgtaacat atttatatat     4740
```

| gtatctaaac catatgaaca tatattttt agaaactaag agaatgatag gcttttgttc | 4800 |
| ttatgaacga aaaagaggta gcactacaaa cacaatattc aatcaaaatt tcagcattat | 4860 |
| tgaaattgta agtgaagtaa aacttaagat atttgagtta acctttaaga attttaaata | 4920 |
| ttttggcatt gtactaatac cgggaacatg aagccaggtg tggtggtatg tgcctgtagt | 4980 |
| cccaggctga ggcaagagaa ttacttgagc ccaggagttt gaatccatcc tgggcagcat | 5040 |
| actgagaccc tgccttaaa aacaaacaga acaaaaacaa acaccaggg acacatttct | 5100 |
| ctgtcttttt tgatcagtgt cctatacatc gaaggtgtgc atatatgttg aatgacattt | 5160 |
| tagggacatg gtgttttat aaagaattct gtgagaaaaa atttaataaa gcaacaaaaa | 5220 |
| ttactcttaa aaaaaaaaaa aaa | 5243 |

<210> SEQ ID NO 18
<211> LENGTH: 1579
<212> TYPE: DNA
<213> ORGANISM: Homo sapiens

<400> SEQUENCE: 18

| gaggaggtgc ttgccagaca ctgggtcatg gcagtggtcg gtgaagctgc agttgcctag | 60 |
| ggcagggatg gagagagagt ctgggcatga ggagagggtc tcgggatgtt tggctggact | 120 |
| agattttaca gaaagcctta tccaggcttt taaaattact cttccagac ttcatctgag | 180 |
| actccttctt cagccaacat tccttagccc tgaatacatt tcctatcctc atctttccct | 240 |
| tcttttttt cctttctttt acatgtttaa atttaaacca ttcttcgtga ccccttttct | 300 |
| tgggagattc atggcaagaa cgagaagaat gatggtgctt gttaggggat gtcctgtctc | 360 |
| tctgaacttt ggggtcctat gcattaaata attttcctga cgagctcaag tgctccctct | 420 |
| ggtctacaat ccctggcggc tggccttcat cccttgggca agcattgcat acagctcatg | 480 |
| gccctccctc taccataccc tccacccccg ttcgcctaag ctccctctc cgggaatttc | 540 |
| atcatttcct agaacagcca gaacattgt ggtctatttc tctgttagtg tttaaccaac | 600 |
| catctgttct aaaagaaggg ctgaactgat ggaaggaatg ctgttagcct gagactcagg | 660 |
| aagacaactt ctgcagggtc actccctggc ttctggagga aagagaagga gggcagtgct | 720 |
| ccagtggtac agaagtgaga cataatggaa tcaggcttca cctccaagga cacctatcta | 780 |
| agccatttta accctcggga ttacctagaa aaatattaca agtttggttc taggcactct | 840 |
| gcagaaagcc agattcttaa gcaccttctg aaaaatcttt tcaagatatt ctgcctagac | 900 |
| ggtgtgaagg gagacctgct gattgacatc ggctctggcc ccactatcta tcagctcctc | 960 |
| tctgcttgtg aatcctttaa ggagatcgtc gtcactgact actcagacca gaacctgcag | 1020 |
| gagctggaga agtggctgaa gaaagagcca gaggcctttg actggtcccc agtggtgacc | 1080 |
| tatgtgtgtg atcttgaagg gaacagagtc aagggtccag agaaggagga gaagttgaga | 1140 |
| caggcggtca gcaggtgct gaagtgtgat gtgactcaga gccagccact gggggccgtc | 1200 |
| cccttacccc cggctgactg cgtgctcagc acactgtgtc tggatgccgc ctgcccagac | 1260 |
| ctccccacct actgcagggc gctcaggaac ctcggcagcc tactgaagcc agggggcttc | 1320 |
| ctggtgatca tggatgcgct caagagcagc tactacatga ttggtgagca gaagttctcc | 1380 |
| agcctccccc tgggccggga ggcagtagag gctgctgtga agaggctggg ctacacaatc | 1440 |
| gaatggtttg aggtgatctc gcaaagttat tcttccacca tggccaacaa cgaaggactt | 1500 |
| ttctcccctgg tggcgaggaa gctgagcaga cccctgtgat gcctgtgacc tcaattaaag | 1560 |
| caattccttt gacctgtca | 1579 |

<210> SEQ ID NO 19
<211> LENGTH: 980
<212> TYPE: DNA
<213> ORGANISM: Homo sapiens

<400> SEQUENCE: 19

| | | | | | |
|---|---|---|---|---|---|
| gcggcggcgg | gcagcagctg | cgctgcgact | gctctggaag | gagaggacgg | ggcacaaacc | 60 |
| ctgaccatga | ccccccacag | gctgctgcca | ccgctgctgc | tgctgctagc | tctgctgctc | 120 |
| gctgccagcc | caggaggcgc | cttggcgcgg | tgcccaggct | gcgggcaagg | ggtgcaggcg | 180 |
| ggttgtccag | ggggctgcgt | ggaggaggag | gatggggggt | cgccagccga | gggctgcgcg | 240 |
| gaagctgagg | gctgtctcag | gagggagggg | caggagtgcg | gggtctacac | ccctaactgc | 300 |
| gccccaggac | tgcagtgcca | tccgcccaag | gacgacgagg | cgcctttgcg | ggcgctgctg | 360 |
| ctcggccgag | gccgctgcct | tccggcccgc | gcgcctgctg | ttgcagagga | gaatcctaag | 420 |
| gagagtaaac | cccaagcagg | cactgcccgc | ccacaggatg | tgaaccgcag | agaccaacag | 480 |
| aggaatccag | gcacctctac | cacgcccrcc | cagcccaatt | ctgcgggtgt | ccaagacact | 540 |
| gagatgggcc | catgccgtag | acatctggac | tcagtgctgc | agcaactcca | gactgaggtc | 600 |
| taccgagggg | ctcaaacact | ctacgtgccc | aattgtgacc | atcgaggctt | ctaccggaag | 660 |
| cggcagtgcc | gctcctccca | ggggcagcgc | cgaggtccct | gctggtgtgt | ggatcggatg | 720 |
| ggcaagtccc | tgccagggtc | tccagatggc | aatggaagct | cctcctgccc | cactgggagt | 780 |
| agcggctaaa | gctgggggat | agaggggctg | caggccact | ggaaggaaca | tggagctgtc | 840 |
| atcactcaac | aaaaaaccga | ggccctcaat | ccaccttcag | gccccgcccc | atgggcccct | 900 |
| caccgctggt | tggaaagagt | gttggtgttg | gctggggtgt | caataaagct | gtgcttgggg | 960 |
| tcgctgaaaa | aaaaaaaaaa | | | | | 980 |

<210> SEQ ID NO 20
<211> LENGTH: 7346
<212> TYPE: DNA
<213> ORGANISM: Homo sapiens

<400> SEQUENCE: 20

| | | | | | |
|---|---|---|---|---|---|
| gcgaggagga | aacggtgccg | gagcgcgcag | ggcttgctgc | cgccaccgcc | gctgcacagg | 60 |
| ctgccggagc | gagcctgccg | cgcgccgccc | tcccgctct | ccttcctggg | cgagctgcgg | 120 |
| ggatggggcg | gccgcgggag | cccgagcgcg | cgcaggaacc | gccgccgccg | ccgcccgcgt | 180 |
| ctccgttgcc | gcgcgcctga | gccgccgtcg | ccgccgcgcg | cctgcccgg | gggcggcccc | 240 |
| cccagcccca | tggaggtctc | ccggaggaag | gcgccgccgc | gcccccgcg | cccgcagcg | 300 |
| ccactgcccc | tgctcgccta | tctgctggca | ctggcggctc | ccggccgggg | cgcggacgag | 360 |
| cccgtgtggc | ggtcggagca | agccatcgga | gccatcgcgg | cgagccagga | ggacggcgtg | 420 |
| tttgtggcga | gcgcagctg | cctggaccag | ctggactaca | gctggagcca | gcctctcg | 480 |
| cgcctgtacc | gggaccaagc | gggcaactgc | acagagccgg | tctcgctggc | gcccccgcg | 540 |
| cggccccggc | ccgggagcag | cttcagcaag | ctgctgctgc | cctaccgcga | ggggcggcc | 600 |
| ggcctcgggg | ggctgctgct | caccggctgg | accttcgacc | ggggcgcctg | cgaggtgcgg | 660 |
| cccctgggca | acctgagccg | caactccctg | cgcaacggca | ccgaggtggt | gtcgtgccac | 720 |
| ccgcagggct | cgacggccgg | cgtggtgtac | cgcgcgggcc | ggaacaaccg | ctggtacctg | 780 |
| gcggtggccg | ccacctacgt | gctgcctgag | ccggagacgg | cgagccgctg | caaccccgcg | 840 |
| gcatccgacc | acgacacggc | catcgcgctc | aaggacacgg | aggggcgcag | cctggccacg | 900 |

```
caggagctgg ggcgcctcaa gctgtgcgag ggcgcgggca gcctgcactt cgtggacgcc    960
tttctctgga acggcagcat ctacttcccc tactacccct acaactacac gagcggcgct   1020
gccaccggct ggcccagcat ggcgcgcatc gcgcagagca ccgaggtgct gttccagggc   1080
caggcatccc tcgactgcgg ccacggccac cccgacggcc gccgcctgct cctctcctcc   1140
agcctagtgg aggccctgga cgtctgggcg ggagtgttca gcgcggccgc tggagagggc   1200
caggagcggc gctcccccac caccacggcg ctctgcctct tcagaatgag tgagatccag   1260
gcgcgcgcca agagggtcag ctgggacttc aagacggccg agagccactg caaagaaggg   1320
gatcaacctg aaagagtcca accaatcgca tcatctacct tgatccattc cgacctgaca   1380
tccgtttatg gcaccgtggt aatgaacagg actgttttat tcttgggac tggagatggc    1440 cagttactta aggttattct tggtgagaat ttgacttcaa attgtccaga ggttatctat   1500
gaaattaaag aagagacacc tgttttctac aaactcgttc ctgatcctgt gaagaatatc   1560
tacatttatc taacagctgg gaagagtg aggagaattc gtgttgcaaa ctgcaataaa     1620
cataaatcct gttcggagtg tttaacagcc acagaccctc actgcggttg gtgccattcg   1680
ctacaaaggt gcactttca aggagattgt gtacattcag agaacttaga aaactggctg    1740
gatatttcgt ctggagcaaa aaagtgccct aaaattcaga taattcgaag cagtaaagaa   1800
aagactacag tgactatggt gggaagcttc tctccaagac actcaaagtg catggtgaag   1860
aatgtggact ctagcaggga gctctgccag aataaaagtc agcccaaccg gacctgcacc   1920
tgtagcatcc caaccagagc aacctacaaa gatgtttcag ttgtcaacgt gatgttctcc   1980
ttcggttctt ggaatttatc agacagattc aactttacca actgctcatc attaaaagaa   2040
tgcccagcat gcgtagaaac tggctgcgcg tggtgtaaaa gtgcaagaag gtgtatccac   2100
cccttcacag cttgcgaccc ttctgattat gagagaaacc aggaacagtg tccagtggct   2160
gtcgagaaga catcaggagg aggaagaccc aaggagaaca aggggaacag aaccaaccag   2220
gctttacagg tcttctacat taagtccatt gagccacaga agtatcgac attagggaaa    2280 agcaacgtga tagtaacggg agcaaacttt acccgggcat cgaacatcac aatgatcctg   2340
aaaggaacca gtacctgtga taaggatgtg atacaggtta gccatgtgct aaatgacacc   2400
cacatgaaat tctctcttcc atcaagccgg aaagaaatga aggatgtgtg tatccagttt   2460
gatggtggga actgctcttc tgtgggatcc ttatcctaca ttgctctgcc acattgttcc   2520
cttatatttc ctgctaccac ctggatcagt ggtggtcaaa atataaccat gatgggcaga   2580
aattttgatg taattgacaa cttaatcatt tcacatgaat aaaaggaaa cataaatgtc    2640 tctgaatatt gtgtggcgac ttactgcggg ttttagccc ccagtttaaa gagttcaaaa    2700
gtgcgcacga atgtcactgt gaagctgaga gtacaagaca cctacttgga ttgtggaacc   2760
ctgcagtatc gggaggaccc cagattcacg gggtatcggg tggaatccga ggtggacaca   2820
gaactggaag tgaaaattca aaagaaaat gacaacttca acatttccaa aaagacatt    2880 gaaattactc tcttccatgg ggaaaatggg caattaaatt gcagttttga aatattact    2940 agaaatcaag atcttaccac catcctttgc aaaattaaag gcatcaagac tgcaagcacc   3000
attgccaact cttctaagaa agttcgggtc aagctgggaa acctggagct ctacgtcgag   3060
caggagtcag ttccttccac atggtatttt ctgattgtgc tccctgtctt gctagtgatt   3120
gtcatttttg cggccgtggg ggtgaccagg cacaaatcga aggagctgag tcgcaaacag   3180
agtcaacaac tagaattgct ggaaagcgag ctccggaaag agatacgtga cggctttgct   3240
gagctgcaga tggataaatt ggatgtggtt gatagttttg gaactgttcc cttccttgac   3300
```

```
tacaaacatt ttgctctgag aactttcttc cctgagtcag gtggcttcac ccacatcttc    3360
actgaagata tgcataacag agacgccaac gacaagaatg aaagtctcac agctttggat    3420
gccctaatct gtaataaaag cttctcttgtt actgtcatcc acaccttga aaagcagaag    3480 aacttttctg tgaaggacag gtgtctgttt gcctccttcc taaccattgc actgcaaacc    3540
aagctggtct acctgaccag catcctagag gtgctgacca gggacttgat ggaacagtgt    3600
agtaacatgc agccgaaact catgctgaga cgcacggagt ccgtcgtcga aaactcctc     3660 acaaactgga tgtccgtctg cctttctgga tttctccggg agactgtcgg agagcccttc    3720
tatttgctgg tgacgactct gaaccagaaa attaacaagg gtcccgtgga tgtaatcact    3780
tgcaaagccc tgtacacact taatgaagac tggctgttgt ggcaggttcc ggaattcagt    3840
actgtggcat taaacgtcgt ctttgaaaaa atcccggaaa acgagagtgc agatgtctgt    3900
cggaatattt cagtcaatgt tctcgactgt gacaccattg gccaagccaa agaaaagatt    3960
ttccaagcat tcttaagcaa aaatggctct ccttatggac ttcagcttaa tgaaattggt    4020
cttgagcttc aaatgggcac acgacagaaa gaacttctgg acatcgacag ttcctccgtg    4080
attcttgaag atggaatcac caagctaaac accattggcc actatgagat atcaaatgga    4140
tccactataa aagtctttaa gaagatagca aattttactt cagatgtgga gtactcggat    4200
gaccactgcc atttgatttt accagattcg gaagcattcc aagatgtgca aggaaagaga    4260
catcgaggga agcacaagtt caaagtaaaa gaaatgtatc tgacaaagct gctgtcgacc    4320
aaggtggcaa ttcattctgt gcttgaaaaa cttttttagaa gcatttggag tttacccaac    4380
agcagagctc catttgctat aaaatacttt tttgactttt tggacgccca ggctgaaaac    4440
aaaaaaatca cagatcctga cgtcgtacat atttggaaaa caaacagcct tcctcttcgc    4500
ttctgggtaa acatcctgaa gaaccctcag tttgtctttg acattaagaa gacaccacat    4560
atagacggct gtttgtcagt gattgcccag gcattcatgg atgcatttc tctcacagag     4620 cagcaactag ggaaggaagc accaactaat aagcttctct atgccaagga tatcccaacc    4680
tacaaagaag aagtaaaatc ttattacaaa gcaatcaggg atttgcctcc attgtcatcc    4740
tcagaaatgg aagaattttt aactcaggaa tctaagaaac atgaaaatga atttaatgaa    4800
gaagtggcct tgacagaaat ttacaaatac atcgtaaaat attttgatga gattctaaat    4860
aaactagaaa gagaacgagg gctggaagaa gctcagaaac aactcttgca tgtaaaagtc    4920
ttatttgatg aaaagaagaa atgcaagtgg atgtaagcac tctggggcct ggcttaatct    4980
ggcaaagttc ttcagcgac ttgggagcaa aatggctgct tgagctactc tgtgtcgtta     5040
atttgttgtt tgcacatagg ttccactttg ggcactgtct ttttaagaga ccaaggcaca    5100
tgcacagctt ttagaaagca taccaaccct tgtgcctgtg tgtataccgt gggaaccctt    5160
ctgtaaatag agttgaagtg gttgttgcaa acagcctcct tgtttacaga gaatacaagg    5220
ccagtaagcg aatgtcagta ttgtaactac agtctccact taagcacaat gatataagtg    5280
gttttgtttg aaaactacag ctatgtagca cttgtgctac actgcacctc tgcattgtaa    5340
agggatactg ccagtgctca aaacaaaatg tgaaatgagt catttggaaa caaggtgggg    5400
gtgttagggc aacctcgagg atttgcagca ttgaaacttt ccccagtagt tcttggaaaa    5460
gctgaccgca gaatttggta gtgtacactt agcatttgtg agtgtgtgtg tgtgtttaaa    5520
ccaaaaacta acagtgttgc aacattgttg aaagggctcg tgttttttcag tggtcatcaa    5580 ctgcactcca tcaaactcac ctccatttca ccaaggagct ctaaagtaag gagagtgggc    5640
tttatttaaa tgaacagcat tttaaccaga tactttgtcc taatgtatgt tcctttctct    5700
```

| | |
|---|---:|
| catctgtttt ttcatactaa atgtatttga tagtggacat gttggatatt atacaaaaaa | 5760 |
| atcattaatt catttctgtt ccaaaacctt tgatcagaac gatctgtgga agagtaactc | 5820 |
| catttctata tgagtgagtg tctccttgct ttagatttct ggtgaaccct gtggttatga | 5880 |
| atacttgtgt gtgatttaaa aaaaaaaaga tacattttac atttcatcga attgctgttc | 5940 |
| acactggagt attatatata aatatatata tttgaggccc aaggcctgaa aaatattagt | 6000 |
| atacaacttg gtatcttagt cttactatgt acttttttgaa agtattcctc gcaggagaaa | 6060 |
| gaatttaaaa tacccatttt attcatgcct ttctttttaa agaattctct atccagttat | 6120 |
| actgtagtct tttttagtgct gattttttaa ttcctgaatt tttgctgctc atgaccagtt | 6180 |
| ttaataccac tgtgttttcc ttctattaaa ccagaagaag taaacagcat aattggcaac | 6240 |
| tcttgagctt tcttgtggc aggcaccttt tacccttggt gctccaaatc ccccatctag | 6300 |
| gaaagaaaat ttttcaagt caaataacat tgatcacata ttccttgaaa tcatttacca | 6360 |
| acactgtatg gagcattagg atttaaatat gaatttgtct taaaggcaat tccttttttgc | 6420 |
| ttctgtatta tctggaaaag catgagagag gtgacacctc aacaaactga tcagagaaaa | 6480 |
| taagcagtta ctaccctgat aggcaccttc ccaatcctgt tgcttttgac cattgtctgt | 6540 |
| ccaacggaca cacctcaaac aaacaaaact accaaataga tgacagatca gaataaaggt | 6600 |
| gagaggtctg gtccccattg aaggctgcta cagtcttcaa agaggtgaag gagttcataa | 6660 |
| gagaacaaca gtaggaaagt tgagagccaa gggtaggaga gttgcccaaa agacttcccc | 6720 |
| tactacttta gggtactgaa aactcaaagg atcagctaca gctttatcta agtatttact | 6780 |
| aaatgctaca tgagggtgtc cctgtccagc tttctggcac atgagtcctg tgtggagagt | 6840 |
| tacctcctct tccagggact gtgctgttgg gaactttggg caagtcactt acctctttgt | 6900 |
| gcctcaattt ctgtataata tttctaagct acctcactga ggtggtatga agattcacta | 6960 |
| atgtatgtag cgtgtttgtc aatcctccag tgaaaagcac tatctagatc acattttgga | 7020 |
| tcacattagc caaatgcagt aaatggccaa attagatgtg tgctgaagac aatcagtcac | 7080 |
| tgggtctata ttaaacagca accagagcaa caaatggcaa acaatttcta ttttcaagtt | 7140 |
| tctttgcata tttttttggt gcaaaaccat ttataaactt tttttttctaa cactagtgtc | 7200 |
| tacagcagca ttcaaaaaaa ttctgttacc ttttctgtat taggatttaa agtctatttc | 7260 |
| ttattgtata cctgattgaa gctgttcttg gagatgaatg ttttaaatgt ctatatccaa | 7320 |
| aaaataaaca ttttgatgta actgtg | 7346 |

```
<210> SEQ ID NO 21
<211> LENGTH: 2828
<212> TYPE: DNA
<213> ORGANISM: Homo sapiens

<400> SEQUENCE: 21
```

| | |
|---|---:|
| agaacagtga cagcgccgcg gcagccgacc ccgcctcctc ggcggacagc gatgctcagc | 60 |
| tggctgcggc cgagtcatcg cctagcgctg gcagggccgc tgaccgaccg acggaggcgc | 120 |
| cgattggccg attgtccact gcgcagaagg agcagctgct ccgcgccccg ccgcgccgcg | 180 |
| ctgaggccga ggtccgcagg gccgcgggga agccgagggc tgccggagaa ccctgcaggt | 240 |
| gtcactcggg acgcggaagt gcgccttgcg aggtttgctt tacaatacgc ttgagactcc | 300 |
| ccgacaagcg taatttggtc gagttcgacg ggaaagtact ctccccaccc cagcgccggc | 360 |
| cgcgtagtcc gaggttactg tccccggcgc gtcctctgtt gccccagtcc agaggctgcc | 420 |
| cttgaacccg ggcgcgcacg agcgcagggc atccgaggcg acagcccctg gcacggcccg | 480 |

```
acctgtaccc agcctggcag gaagactgta atcgtgggaa tacagctacc tacccaggca    540
atatgaagat tttatttgta gaacctgcca ttttccttag tgcatttgct atgactttga    600
ccggtccact gacaacgcaa tatgtttatc ggagaatatg ggaagaaact ggcaactaca    660
cttttttcatc tgatagcaat atttctgagt gtgaaaaaaa caaaagcagc ccaattttg    720
cattccagga ggaagttcag aaaaaagtgt cacgttttaa tctgcagatg gacataagtg    780
gattaattcc tggtctagtg tctacattca tacttttgtc tattagtgat cactacggac    840
gaaaattccc tatgattttg tcttccgttg gtgctcttgc aaccagcgtt tggctctgtt    900
tgctttgcta ttttgccttt ccattccagc ttttgattgc atctaccttc attggtgcat    960
tttgtggcaa ttataccaca ttttggggag cttgctttgc ctatatagtt gatcagtgta   1020
aagaacacaa acaaaaaaca attcgaatag ctatcattga ctttctactt ggacttgtta   1080
ctggactaac aggactgtca tctggctatt ttattagaga gctaggtttt gagtggtcgt   1140
ttctaattat tgctgtgtct cttgctgtta atttgatcta tattttattt tttctcggag   1200
atccagtgaa agagtgttca tctcagaatg ttactatgtc atgtagtgaa ggcttcaaaa   1260
acctatttta ccgaacttac atgctttta agaatgcttc tggtaagaga cgattttgc    1320
tctgtttgtt actttttaca gtaatcactt atttttttgt ggtaattggc attgccccaa   1380
tttttatcct ttatgaattg gattcaccac tctgctggaa tgaagttttt ataggttatg   1440
gatcagcttt gggtagtgcc tcttttttga ctagtttcct aggaatatgg ctttttttctt   1500
attgtatgga agatattcat atggccttca ttgggatttt taccacgatg acaggaatgg   1560
ctatgaccgc gtttgccagt acaacactga tgatgttttt agccagggtg ccgttcctt    1620
tcactattgt gccattctct gttctacggt ccatgttgtc aaaagtggtt cgttcgactg   1680
aacaaggtac cctgtttgct tgtattgctt tcttagaaac acttggagga gtcactgcag   1740
tttctactt taatggaatt tactcagcca ctgttgcttg gtaccctggc ttcactttcc   1800
tgctgtctgc tggtctgtta ctacttccag ccatcagtct atgtgttgtc aagtgtacca   1860
gctggaatga gggaagctat gaacttctta tacaagaaga atccagtgaa gatgcttcag   1920
acagagcctg ttaagctgct attgatagtc ggagcttata tactgtgact tctgaagact   1980
atacatgaat tccacaatca gtgctttgtt gatacaaaat ccttaaaagg gaggcacttt   2040
aaagaatatg tattttttcac ttttcttaat atgtttcatc ggtgacaggc atgataatat   2100
ttctatatgt aatgggtaat tgggaaaaaa tagatgataa ataaaattgc tctaaagaag   2160
ttaaaaaact gaatgaacag ctaatactgg tataaagtaa ctaatgtttg gagccaacat   2220
ttgttccttg tgtcagcaaa aggatattca cattccatga tccctggctg agaattctgc   2280
ctctagtctt tcttacccag ctgttgtcta tccttgttca attataaata ctgctaaggg   2340
cattttaaa atacgatctt gtactcctta aatttgaatc cgtcagcacg gtcactcata   2400
ggaaaatgat caaacaagca agccagtcat gatttgactc cttcccatct catttcttac   2460
tgccttacgc tcatcctgag gtccaccttg gtctctaaaa acaccatgtg ttctcatgcc   2520
tccatgtctt ttcacacact gttccatttg ctcttcctcc cacattacat tgaaactttc   2580
aagcctcagt cgaaacattg cttcttctgg atagcagcct tcttgacatc cctcctcact   2640
ccccagtccc tacagggctt ccatagctct tgtgtgcac ttcgatccca gcattttcca    2700
tcgacttgta attgtttctg ctacctgaca atcatcgcct tgagtactgg gacaaccttt   2760
gattactcat tatatcctca ataaatattt gttgaactaa aaaaaaaaaa aaaaaaaaa    2820
aaaaaaaa                                                           2828
```

<210> SEQ ID NO 22
<211> LENGTH: 2840
<212> TYPE: DNA
<213> ORGANISM: Homo sapiens

<400> SEQUENCE: 22

```
gttttttgtgc aggaacagcc cctcccgtct ttgtcctggc ggtgagcacc cagggctaag      60
cttttgaaca ctttctttgt gtttggattc agcccaggca atgcatattt gctttcattt     120
cttcttgagc ttgaggagct cctgggtgca aatcttggaa aatgaggatc tctgagcctt     180
tccaggccag ctctttgttt tgtagcagac aattgaggct ttgaaaagga aagtgggtgg     240
gggcacccca caggtggccc tcatcaccca attgccagtg cctgcaggct gcttcagcag     300
aggcccagag tcaaagagga cttaaaacca gctgtcgttt ctcccttagc ttctgtgtat     360
gagagaaacg acttctgttt ttcaaagtaa gaacaaggag gaatttgttt ctaaaagaac     420
attaaaacac aggctcgtgg tctaaaagca aatggttcag caggatgttc agggccttaa     480
agcacagtca gcaggactca gcatctccca gcacctgctc tccggttgtc atggtaacat     540
catccccaac ccaaccacct tgtccagccg agagacagca atcataagga gggacctcgg     600
tttcccccga ggatcctggg cttcctttct gaaacgcttg cttctgagct cagcaaccag     660
gaacaccagg ccagcccatc cccagcacct ctgtggagat gagggacaaa gtcctacagt     720
ccctcttcct gttctgatga aaagggagg gaagaaaaca taccccgagc gcctgcaata     780
tggtcatgac actttcaaaa agcctgtgct atggagtcat gatcagaaac cagagtgtgg     840
agagggtcag cagcctgcct cagagcagcc agctaggcgg ggagtggtaa atttgggact     900
tgtacccagg catgactggc tccgagccca gtgctccact ctatggaatg ttccctgggc     960
ctcagttgct ttcctttcct ttgcaggccg cgggctgctg ccactctggc agctggtgag    1020
ttagctggag ggcaacattc caaagcaggg gcagcatgct gctttcctcc tgtgcccact    1080
cctgcgggga agtccgttga ctcccaccgc tgaagggagc tggcaacacc aggatgaggt    1140
cccaggggac gggagcaggt acccactgtc tgtctaccct cccactggaa aagcacggac    1200
aggccagccc ttgcggggc aggcagagga cagagttggc tttgcgcggt ctctgcctgc    1260
tgagcagttc caattcctct catgggagaa acaaggaggc agtcgcttgt gcatgttcca    1320
gaagttttac tggggaggag gaagcggaca gaggaagctg tgtgtgcatg tgaaggggtg    1380
ggcagggtgg gagggatgca cgcgtatgtg agcatagcat gtgtgagtac tacacacatc    1440
tccatgcaga agcacaactg ggcagccctg gcttccagct ctgggcttca gcacaacaga    1500
caccagcctg tggtctctca gaagccaggg agaccacatc gggctcagga cgttttaccc    1560
aaagtccaga gtttttatgc ctctccctgg cattctccat aaagaaggga aggtcagatg    1620
acccccttaga tctgtgtcat ctgggaattt ccttgggctg gtttagacac gatgccctct    1680
ttttctcaga atagcagata acctgctttg aaagagggct taattctgtg ggtcctaaat    1740
tttctccttt ctctctctct ttctgtgtgt gtgtgttggg aaaatggcaa gtttccaata    1800
ccagctttgg aggaacgatt acgttttccc tccaatttca agtccgaaag accagagccc    1860
tcattccaaa gccccccacc cagatggatt ttttcgtttc atttgtcatc cgtcccatgg    1920
gagggcccca tgtctcctca gaacccatcc tggaggcagc aggtcgggta gagtgagttt    1980
ggcctgctca tgacctccac ccctgagatt gtgaacaagg atgtctgggg cgatgctgag    2040
aatgttttg aagctgctcc cagatgacgc tgatgatcac accagattga gtgctgcgat    2100
cgccttgagt ccaacctctg cataaacgag gttctcataa acaagttcac tctaccctaa    2160
```

```
gctaagtcta tgtgagcaaa cccacttcat cctttgtacc tggagacctg gttacactaa   2220
cctgatactg acctgttcat gtagctggaa tggtgtgttt catgcagtgt ggaccaagca   2280
atggcatggg gtgtgtgtgt gtgtgtgtgt gtgtctgtgt gtgtgtgttt gtgtatgcgt   2340
tcacacttgt gtgtgtatat gtgcatgtag atgctgcata aatgattttt gatgtcaaag   2400
acaaacacat tccattgttt taaatattct attatgtaaa caatacgcag agggaccata   2460
tctactcttg tcatattatt tgtgatggta aacatgcatt tgcaataaa ttaagctttc    2520 tgggaaggca agcagtattg gagccaaacg actgtctcgg aacatgtgtg tgttatctcg   2580
gttcatatca agtccaaagc taatggagcc ttccccgcca tccagggagg aacaccagga   2640
ccccggagtt tcttcttagt gctatatttt aaagttgcat tgacgttttc ctcccccttcc   2700 ttttgtgcaa gttggaagta gcagtgttct aaaagatggt ttgacgtttt tgctgttgtt   2760
ttatgttttt aaaaatgtat ctgctttgtg tttggaaata aaaatctcta ttttggtcta   2820
tgaaaaaaaa aaaaaaaaaa                                               2840

<210> SEQ ID NO 23
<211> LENGTH: 2309
<212> TYPE: DNA
<213> ORGANISM: Homo sapiens

<400> SEQUENCE: 23 gcggggggcgg gccggggcgg ggccaggccg gctagagggg cgggtctagc ggcggccccc     60
ggcgaagttc actgcgcttg cgctgacaga cgcaagatgg cggacagtgc ggaactaaag    120
caaatggtta tgagccttag agtttctgaa ctccaagtac tgttgggcta cgccgggaga    180
aacaagcacg gacgcaaaca cgaacttctc acaaaagccc tgcatttgct aaaggctggc    240
tgtagtcctg ctgtgcaaat gaaaattaag gaactctata ggcggcggtt cccacagaaa    300
atcatgacgc ctgcagactt gtccatcccc aacgtacatt caagtcctat gccagcaact    360
ttgtctccat ctaccattcc acaactcact tacgatggtc accctgcatc atcgccatta    420
ctccctgttt ctcttctggg acctaaacat gaactggaac tcccacatct tacatcagct    480
cttcacccag tccatccgga tataaaactt caaaaattac cattttatga tttactggat    540
gaactgataa aacccaccag tctagcatca gacaacagtc agcgctttcg agaaacctgt    600
tttgcatttg ccttgacacc acaacaagtg cagcaaatca gtagttccat ggatatttct    660
gggaccaaat gtgacttcac agtacaggtc cagttaaggt tttgtttatc agaaaccagt    720
tgtccacaag aagatcactt cccacccaat cttttgtgtga agtgaatac aaaaccttgc    780 agccttccag gttaccttcc acctacaaaa aatggcgtgg aaccaaagcg acccagccga    840
ccaattaata tcacctcact tgtccgactg tccacaacag taccaaacac gattgttgtt    900
tcttggactg cagaaattgg aagaaactat tccatggcag tatatcttgt aaaacagttg    960
tcctcaacag ttcttcttca gaggttacga gcaaagggaa taaggaatcc ggatcattct   1020
agagctttaa ttaaagagaa gttgactgcg gatccagaca gtgaaatagc tacaaccagc   1080
ctaagggttt tctactatg tccacttggt aaaatgcggc tgacaattcc gtgtcgggcc   1140
cttacatgtt ctcatctaca atgttttgac gcaactcttt acattcagat gaatgagaaa   1200
aaaccaacct gggtttgtcc tgtctgtgat aagaaggctc catatgaaca ccttattatt   1260
gatggcttgt ttatggaaat cctaaagtac tgtacagact gtgatgaaat acaatttaag   1320
gaggatggca cttgggcacc gatgagatca aaaaaggaag tacaggaagt ttctgcctct   1380
tacaatggag tcgatggatg cttgagctcc acattggagc atcaggtagc gtctcaccac   1440
```

```
cagtcctcaa ataaaaacaa gaaagtagaa gtgattgacc taaccataga cagttcatct    1500
gatgaagagg aagaagagcc atctgccaag aggacctgtc cttccctatc tcccacatca    1560
ccactaaata ataaaggcat tttaagtctt ccacatcaag catctccagt atcccgcacc    1620
ccaagccttc ctgctgtaga cacaagctac attaatacct ccctcatcca agactatagg    1680
catcctttcc acatgacacc catgccttac gacttacaag gattagattt ctttcctttc    1740
ttatcaggag acaatcagca ttacaacacc tccttgcttg ccgctgcagc agcagcagtt    1800
tcagatgatc aagacctcct acactcgtct cggttttcc cgtatacctc ctcacagatg    1860
tttcttgatc agttaagtgc aggaggcagt acttctctgc caaccaccaa tggaagcagt    1920
agtggcagta acagcagcct ggtttcttcc aacagcctaa gggaaagcca tagccacacc    1980
gtcacaaaca ggagcagcac ggacacggca tccatctttg gcatcatacc agacattatt    2040
tcattggact gattcccagg ccctgctgct cccatcccca ccccagatcg aatgaacttg    2100
gcagaaagaa gagaactttg tgctctgttt taccttactc tgtttagaaa agtatacaag    2160 cgtgttttt ttccttttt tagggaaaaa attaaaagaa atgtacagag aacaaaacta    2220
tattttcagt tttacttttg tatataaatc taagactgcc tgtgtgataa aacacttgtt    2280
taaaaaaaaa aaaaaaaaa aaaaaaaa                                       2309

<210> SEQ ID NO 24
<211> LENGTH: 1740
<212> TYPE: DNA
<213> ORGANISM: Homo sapiens

<400> SEQUENCE: 24
ccagcgttag cccgcggcca ggcagccggg aggagcggcg cgcgctcgga cctctcccgc      60
cctgctcgtt cgctctccag cttgggatgg ccggctacct gcgggtcgtg cgctcgctct     120
gcagagcctc aggctcgcgg ccggcctggg cgccggcggc cctgacagcc cccacctcgc     180
aagagcagcc gcggcgccac tatgccgaca aaaggatcaa ggtggcgaag cccgtggtgg     240
agatggatgg tgatgagatg acccgtatta tctggcagtt catcaaggag aagctcatcc     300
tgccccacgt ggacatccag ctaaagtatt ttgacctcgg gctcccaaac cgtgaccaga     360
ctgatgacca ggtcaccatt gactctgcac tggccaccca gaagtacagt gtggctgtca     420
agtgtgccac catcacccct gatgaggccc gtgtggaaga gttcaagctg aagaagatgt     480
ggaaaagtcc caatggaact atccggaaca tcctgggggg gactgtcttc cgggagccca     540
tcatctgcaa aaacatccca cgcctagtcc ctggctggac caagcccatc accattggca     600
ggcacgccca tggcgaccag tacaaggcca cagactttgt ggcagaccgg gccggcactt     660
tcaaaatggt cttcaccccca aaagatgcga gtggtgtcaa ggagtgggaa gtgtacaact     720
tccccgcagg cggcgtgggc atgggcatgt acaacaccga cgagtccatc tcaggtttg     780 cgcacagctg cttccagtat gccatccaga gaaatggcc gctgtacatg agcaccaaga     840
acaccatact gaaagcctac gatgggcgtt tcaaggacat cttccaggag atctttgaca     900
agcactataa gaccgacttc gacaagaata agatctggta tgagcaccgg ctcattgatg     960
acatggtggc tcaggtcctc aagtcttcgg gtggctttgt gtgggcctgc aagaactatg    1020
acggagatgt gcagtcagac atcctggccc agggctttgg ctcccttggc ctgatgacgt    1080
ccgtcctggt ctgccctgat gggaagacga ttgaggctga ggccgctcat gggaccgtca    1140
cccgccacta tgggagcac cagaagggcc ggccccaccag caccaacccc atcgccagca    1200
tctttgcctg gacacgtggc ctggagcacc gggggaagct ggatgggaac caagacctca    1260
```

```
tcaggtttgc ccagatgctg gagaaggtgt gcgtggagac ggtggagagt ggagccatga   1320
ccaaggacct ggcgggctgc attcacggcc tcagcaatgt gaagctgaac gagcacttcc   1380
tgaacaccac ggacttcctc gacaccatca agagcaacct ggacagagcc ctgggcaggc   1440 agtagggga ggcgccaccc atggctgcag tggaggggcc agggctgagc cggcgggtcc    1500
tcctgagcgc ggcagagggt gagcctcaca gcccctctct ggaggccttt ctagggatg    1560 ttttttata agccagatgt ttttaaaagc atatgtgtgt ttcccctcat ggtgacgtga    1620
ggcaggagca gtgcgtttta cctcagccag tcagtatgtt ttgcatactg taatttatat   1680
tgcccttgga acacatggtg ccatatttag ctactaaaaa gctcttcaca aaaaaaaaa    1740
```

<210> SEQ ID NO 25
<211> LENGTH: 1552
<212> TYPE: DNA
<213> ORGANISM: Homo sapiens

<400> SEQUENCE: 25

```
ggtcgcttta agaaaggagt agctgtaatc tgaagcctgc tggacgctgg attagaaggc     60
agcaaaaaaa gctctgtgct ggctggagcc ccctcagtgt gcaggcttag agggactagg    120
ctgggtgtgg agctgcagcg tatccacagg ccccaggatg caggccctgg tgctactcct    180
ctgcattgga gccctcctcg gcacagcag ctgccagaac cctgccagcc ccccggagga    240
gggctcccca gaccccgaca gcacaggggc gctggtggag gaggaggatc ctttcttcaa    300
agtccccgtg aacaagctgg cagcggctgt ctccaacttc ggctatgacc tgtaccgggt    360
gcgatccagc acgagcccca cgaccaacgt gctcctgtct cctctcagtg tggccacggc    420
cctctcggcc ctctcgctgg gagcggagca gcgaacagaa tccatcattc accgggctct    480
ctactatgac ttgatcagca gcccagacat ccatggtacc tataaggagc tccttgacac    540
ggtcactgcc ccccagaaga acctcaagag tgcctcccgg atcgtctttg agaagaagct    600
gcgcataaaa tccagctttg tggcacctct ggaaaagtca tatgggacca ggcccagagt    660
cctgacgggc aaccctcgct tggacctgca agagatcaac aactgggtgc aggcgcagat    720
gaaagggaag ctcgccaggt ccacaaagga aattcccgat gagatcagca ttctccttct    780
cggtgtggcg cacttcaagg ggcagtgggt aacaaagttt gactccagaa agacttccct    840
cgaggatttc tacttggatg aagagaggac cgtgagggtc cccatgatgt cggaccctaa    900
ggctgtttta cgctatggct tggattcaga tctcagctgc aagattgccc agctgcccct    960
gaccggaagc atgagtatca tcttcttcct gcccctgaaa gtgacccaga atttgacctt   1020
gatagaggag agcctcacct ccgagttcat tcatgacata gaccgagaac tgaagaccgt   1080
gcaggcggtc ctcactgtcc ccaagctgaa gctgagttat gaaggcgaag tcaccaagtc   1140
cctgcaggag atgaagctgc aatccttgtt tgattcacca gactttagca agatcacagg   1200
caaacccatc aagctgactc aggtggaaca ccgggctggc tttgagtgga acgaggatgg   1260
ggcgggaacc acccccagcc cagggctgca gcctgcccac ctcaccttcc cgctggacta   1320
tcaccttaac cagcctttca tcttcgtact gagggacaca gacacagggg cccttctctt   1380
cattggcaag attctggacc ccagggggccc ctaatatccc agtttaatat tccaataccc   1440
tagaagaaaa ccccgagggac agcagattcc acaggcacg aaggctgccc ctgtaaggtt   1500
tcaatgcata caataaaaga gctttatccc taaaaaaaaa aaaaaaaaa aa            1552
```

<210> SEQ ID NO 26
<211> LENGTH: 4816
<212> TYPE: DNA

<213> ORGANISM: Homo sapiens

<400> SEQUENCE: 26

```
gttcccggat ttttgtgggc gcctgccccg cccctcgtcc ccctgctgtg tccatatatc      60
gaggcgatag ggttaaggga aggcggacgc ctgatgggtt aatgagcaaa ctgaagtgtt     120
ttccatgatc ttttttgagt cgcaattgaa gtaccacctc ccgagggtga ttgcttcccc     180
atgcgggta gaacctttgc tgtcctgttc accactctac ctccagcaca gaatttggct     240
tatgcctact caatgtgaag atgatgagga tgaaaacctt tgtgatgatc cacttccact     300
taatgaatgg tggcaaagca aagctatatt caagaccaca tgcaaagcta ctccctgagc     360
aaagagtcac agataaaacg ggggcaccag tagaatggcc aggacaaacg cagtgcagca     420
cagagactca gaccctggca gccatgcctg cgcaggcagt gatgagagtg acatgtactg     480
ttgtggacat gcacaaaagt gagtgtgcac cggcacagac atgaagctgc ggctccctgc     540
cagtcccgag acccacctgg acatgctccg ccacctctac cagggctgcc aggtggtgca     600
gggaaacctg gaactcacct acctgcccac caatgccagc ctgtccttcc tgcaggatat     660
ccaggaggtg cagggctacg tgctcatcgc tcacaaccaa gtgaggcagg tcccactgca     720
gaggctgcgg attgtgcgag gcacccagct cttttgaggac aactatgccc tggccgtgct     780
agacaatgga gacccgctga caataccac ccctgtcaca ggggcctccc caggaggcct     840
gcgggagctg cagcttcgaa gcctcacaga gatcttgaaa ggaggggtct tgatccagcg     900
gaaccccag ctctgctacc aggacacgat tttgtggaag acatcttcc acaagaacaa      960
ccagctggct ctcacactga tagacaccaa ccgctctcgg gcctgccacc cctgttctcc    1020
gatgtgtaag ggctcccgct gctggggaga gagttctgag gattgtcaga gcctgacgcg    1080
cactgtctgt gccggtggct gtgcccgctg caaggggcca ctgcccactg actgctgcca    1140
tgagcagtgt gctgccggct gcacgggccc aagcactct gactgctgg cctgcctcca    1200
cttcaaccac agtggcatct gtgagctgca ctgcccagcc ctggtcacct acaacacaga    1260
cacgtttgag tccatgccca atcccgaggg ccggtataca ttcggcgcca gctgtgtgac    1320
tgcctgtccc tacaactacc tttctacgga cgtgggatcc tgcaccctcg tctgcccct     1380
gcacaaccaa gaggtgacag cagaggatgg aacacagcgg tgtgagaagt gcagcaagcc    1440
ctgtgcccga gtgtgctatg gtctgggcat ggagcacttg cgagaggtga gggcagttac    1500
cagtgccaat atccaggagt ttgctggctg caagaagatc tttgggagcc tggcatttct    1560
gccggagagc tttgatgggg acccagcctc caacactgcc ccgctccagc cagagcagct    1620
ccaagtgttt gagactctgg aagagatcac aggttaccta tacatctcag catggccgga    1680
cagcctgcct gacctcagcg tcttccagaa cctgcaagta atccggggac gaattctgca    1740
caatggcgcc tactcgctga cccctgcaagg gctgggcatc agctggctgg gctgcgctc    1800
actgagggaa ctgggcagtg gactggccct catccaccat aacacccacc tctgcttcgt    1860
gcacacggtg ccctgggacc agctctttcg gaacccgcac caagctctgc tccacactgc    1920
caaccggcca gaggacgagt gtgtgggcga gggcctggcc tgccaccagc tgtgcgcccg    1980
agggcactgc tgggtccag ggcccaccca gtgtgtcaac tgcagccagt ccttcggggg    2040
ccaggagtgc gtggaggaat gccgagtact gcagggctc cccagggagt atgtgaatgc    2100
caggcactgt ttgccgtgcc accctgagtg tcagcccag aatggctcag tgacctgttt    2160
tggaccggag gctgaccagt gtgtggcctg tgcccactat aaggaccctc ccttctgcgt    2220
ggcccgctgc cccagcggtg tgaaacctga cctctcctac atgcccatct ggaagtttcc    2280
```

```
agatgaggag ggcgcatgcc agccttgccc catcaactgc acccactcct gtgtggacct    2340
ggatgacaag ggctgccccg ccgagcagag agccagccct ctgacgtcca tcatctctgc    2400
ggtggttggc attctgctgg tcgtggtctt ggggtggtc tttgggatcc tcatcaagcg     2460
acggcagcag aagatccgga agtacacgat gcggagactc ctgcaggaaa cggagctggt    2520
ggagccgctg acacctagcg gagcgatgcc caaccaggcg cagatgcgga tcctgaaaga    2580
gacggagctg aggaaggtga aggtgcttgg atctggcgct tttggcacag tctacaaggg    2640
catctggatc cctgatgggg agaatgtgaa aattccagtg gccatcaaag tgttgaggga    2700
aaacacatcc cccaaagcca acaaagaaat cttagacgaa gcatacgtga tggctggtgt    2760
gggctcccca tatgtctccc gccttctggg catctgcctg acatccacgg tgcagctggt    2820
gacacagctt atgccctatg gctgcctctt agaccatgtc cgggaaaacc gcggacgcct    2880
gggctcccag gacctgctga actggtgtat gcagattgcc aaggggatga gctacctgga    2940
ggatgtgcgg ctcgtacaca gggacttggc cgctcggaac gtgctggtca agagtcccaa    3000
ccatgtcaaa attacagact cgggctggc tcggctgctg acattgacg agacagagta     3060 ccatgcagat gggggcaagg tgcccatcaa gtggatggcg ctggagtcca ttctccgccg    3120
gcggttcacc caccagagtg atgtgtggag ttatggtgtg actgtgtggg agctgatgac    3180 ttttgggggcc aaaccttacg atgggatccc agcccgggag atccctgacc tgctggaaaa    3240
gggggagcgg ctgccccagc cccccatctg caccattgat gtctacatga tcatggtcaa    3300
atgttggatg attgactctg aatgtcggcc aagattccgg gagttggtgt ctgaattctc    3360
ccgcatggcc agggaccccc agcgctttgt ggtcatccag aatgaggact gggcccagc    3420 cagtcccttg gacagcacct tctaccgctc actgctggag gacgatgaca tggggggacct    3480 ggtggatgct gaggagtatc tggtacccca gcagggcttc ttctgtccag accctgcccc    3540
gggcgctggg ggcatggtcc accacaggca ccgcagctca tctaccagga gtggcggtgg    3600
ggacctgaca ctagggctgg agccctctga agaggaggcc cccaggtctc cactggcacc    3660
ctccgaaggg gctggctccg atgtatttga tggtgacctg ggaatgggg cagccaaggg    3720 gctgcaaagc ctccccacac atgaccccag ccctctacag cggtacagtg aggaccccac    3780 agtaccctg ccctctgaga ctgatggcta cgttgccccc ctgacctgca gccccagcc     3840 tgaatatgtg aaccagccag atgttcggcc ccagccccct cgccccgag agggccctct    3900 gcctgctgcc cgacctgctg gtgccactct ggaaaggccc aagactctct ccccagggaa    3960
gaatggggtc gtcaaagacg ttttgcctt tgggggtgcc gtggagaacc ccgagtactt    4020
gacaccccag ggaggagctg cccctcagcc ccaccctcct cctgccttca gcccagcctt    4080
cgacaacctc tattactggg accaggaccc accagagcgg ggggctccac ccagcacctt    4140
caaagggaca cctacggcag agaacccaga gtacctgggt ctggacgtgc agtgtgaac     4200 cagaaggcca gtccgcaga agccctgatg tgtcctcagg gagcagggaa ggcctgactt     4260
ctgctggcat caagaggtgg gagggccctc cgaccacttc caggggaacc tgccatgcca    4320
ggaacctgtc ctaaggaacc ttccttcctg cttgagttcc cagatggctg aagggtcc     4380 agcctcgttg gaagaggaac agcactgggg agtcttttg gattctgagg ccctgcccaa    4440
tgagactcta gggtccagtg gatgccacag cccagcttgg ccctttcctt ccagatcctg    4500
ggtactgaaa gccttaggga agctggcctg agaggggaag cggccctaag ggagtgtcta    4560
agaacaaaag cgacccattc agagactgtc cctgaaacct agtactgccc cccatgagga    4620
aggaacagca atggtgtcag tatccaggct ttgtacagag tgctttttctg tttagttttt    4680
```

-continued

```
actttttttg ttttgttttt ttaaagatga aataaagacc caggggagga atgggtgttg      4740
tatgggaggg caagtgtggg gggtccttct ccacacccac tttgtccatt tgcaaatata      4800
ttttggaaaa cagcta                                                       4816
```

<210> SEQ ID NO 27
<211> LENGTH: 6831
<212> TYPE: DNA
<213> ORGANISM: Homo sapiens

<400> SEQUENCE: 27

```
ccaggcccca ttgttcccgg tttccagcca tggctgccat tacctgacca gcgccacagc        60
cggtctctct gcaggcgccg ggagaagtga ccagagcaat ttctgctttt cacagggcgg       120
gtttctcaac ggtgacttgt gggcagtgcc ttctgctgag cgagtcatgg cccgaaggca       180
gaactaactg tgcctgcagt cttcactctc aggatgcagc cgaggtgggc caagggggcc       240
acgatgtggc ttggagtcct gctgaccctt ctgctctgtt caagccttga gggtcaagaa       300
aactctttca caatcaacag tgttgacatg aagagcctgc cggactggac ggtgcaaaat       360
gggaagaacc tgaccctgca gtgcttcgcg gatgtcagca ccacctctca cgtcaagcct       420
cagcaccaga tgctgttcta aggatgacg tgctgttttt acaacatctc ctccatgaag       480
agcacagaga gttatttat tcctgaagtc cggatctatg actcagggac atataaatgt       540
actgtgattg tgaacaacaa agagaaaacc actgcagagt accaggtgtt ggtggaagga       600
gtgcccagtc ccagggtgac actggacaag aaagaggcca tccaaggtgg gatcgtgagg       660
gtcaactgtt ctgtcccaga ggaaaaggcc ccaatacact tcacaattga aaaacttgaa       720
ctaaatgaaa aaatggtcaa gctgaaaaga gagaagaatt ctcgagacca gaattttgtg       780
atactggaat tccccgttga ggaacaggac cgcgttttat ccttccgatg tcaagctagg       840
atcatttctg ggatccatat gcagacctca gaatctacca agagtgaact ggtcaccgtg       900
acggaatcct tctctacacc caagttccac atcagcccca ccggaatgat catggaagga       960
gctcagctcc acattaagtg caccattcaa gtgactcacc tggcccagga gtttccagaa      1020
atcataattc agaaggacaa ggcgattgtg gcccacaaca acatggcaa caaggctgtg      1080 tactcagtca tggccatggt ggagcacagt ggcaactaca cgtgcaaagt ggagtccagc      1140
cgcatatcca aggtcagcag catcgtggtc aacataacag aactattttc caagcccgaa      1200
ctggaatctt ccttcacaca tctggaccaa ggtgaaagac tgaacctgtc ctgctccatc      1260
ccaggagcac ctccagccaa cttccaccatc agaaggaag atacgattgt gtcacagact      1320
caagatttca ccaagatagc ctcaaagtcg acagtgggga cgtatatctg cactgcaggt      1380
attgacaaag tggtcaagaa aagcaacaca gtccagatag tcgtatgtga atgctctcc      1440 cagcccagga tttcttatga tgcccagttt gaggtcataa aaggacagac catcgaagtc      1500
cgttgcgaat cgatcagtgg aactttgcct atttcttacc aacttttaaa aacaagtaaa      1560
gttttggaga atagtaccaa gaactcaaat gatcctgcgg tattcaaaga caaccccact      1620
gaagacgtcg aataccagtg tgttgcagat aattgccatt cccatgccaa atgttaagt      1680 gaggttctga gggtgaaggt gatagccccg gtggatgagg tccagatttc tatcctgtca      1740
agtaaggtgg tggagtctgg agaggacatt gtgctgcaat gtgctgtgaa tgaaggatct      1800
ggtcccatca cctataagtt ttacagagaa aaagagggca aacccttcta tcaaatgacc      1860
tcaaatgcca cccaggcatt ttggaccaag cagaaggcta gcaaggaaca ggagggagag      1920
tattactgca cagccttcaa cagagccaac cacgcctcca gtgtccccag aagcaaaata      1980
```

```
ctgacagtca gagtcattct tgccccatgg aagaaaggac ttattgcagt ggttatcatc   2040
ggagtgatca ttgctctctt gatcattgcg gccaaatgtt attttctgag gaaagccaag   2100
gccaagcaga tgccagtgga aatgtccagg ccagcagtac cacttctgaa ctccaacaac   2160
gagaaaatgt cagatcccaa tatggaagct aacagtcatt acggtcacaa tgacgatgtc   2220
agaaaccatg caatgaaacc aataaatgat aataaagagc ctctgaactc agacgtgcag   2280
tacacggaag ttcaagtgtc ctcagctgag tctcacaaag atctaggaaa gaaggacaca   2340
gagacagtgt acagtgaagt ccggaaagct gtccctgatg ccgtggaaag cagatactct   2400
agaacggaag gctcccttga tggaacttag acagcaaggc cagatgcaca tccctggaag   2460
gacatccatg ttccgagaag aacagataat ccctgtattt caagacctct gtgcacttat   2520
ttatgaacct gccctgctcc cacagaacac agcaattcct caggctaagc tgccggttct   2580
taaatccatc ctgctaagtt aatgttgggt agaaagagat acagagggc tgttgaattt    2640 cccacatacc ctccttccac caagttggaa catccttgga aattggaaga gcacaagagg   2700
agatccaggg caaggccatt gggatattct gaaacttgaa tattttgttt tgtgcagaga   2760
taaagacctt ttccatgcac cctcatacac agaaaccaat tttcttttt atactcaatc    2820 atttctagcg catggcctgg ttagaggctg gttttttctc ttttcctttg gtccttcaaa   2880
ggcttgtagt tttggctagt ccttgttctt tggaaataca cagtgctgac cagacagcct   2940 cccctgtcc cctctatgac ctcgccctcc acaaatggga aaaccagact acttgggagc    3000
accgcctgtg aaataccaac ctgaagacac cgttcattca ggcaacgcac aaaacagaaa   3060
atgaaggtgg aacaagcaca gatgttcttc aactgttttt gtctacactc tttctcttt    3120 cctctaccat gctgaaggct gaaagacagg aagatggtgc catcagcaaa tattattctt   3180
aattgaaaac ttgaaatgtg tatgtttctt actaattttt aaaaatgtat tccttgccag   3240
ggcaggcaag gtggctcacg cctgtaatcc cagcacttca ggaggctgag gtgggcggat   3300
cacctgaggt caggagtttg agaccagcct gatgaaaccc tgtctctact aaaaatacaa   3360
gaattagccg ggcgtggtgg cgcatgcctg tagtatcagc tactcaagag gctgaggtga   3420
gattatcgct tgaacccagg aaacggaggt tgtagtgagc ggagatcgcg ccactgcact   3480
ccagcctgag tgacagagtg agaatccatc tcaaaaaaaa caaaaaacaa aattgcttgc   3540
taaagaagtg gtctcctgag gtcttaagac attcctgaca gtgtcttgag tgggtgggag   3600
agaggctgct gtcattgcgc gtgtggaattt cacagatgag aaccacgcct agccaaaatc   3660
acttttcctg tttgcctcag tgacacagct gcagggaccc tcgtggatgt tgtattaaat   3720
aaatttgacc tttgctcttt gcagatctgt gaaatgttgt cttctgaggg gccacatgca   3780
tctatagtgc tgaggactcc ttgggcctct gaagtcacag agagaaccga gcaggtctat   3840 gttttgttt tgttgttttg agacggagat tcgctcttgt tgcccgggct ggactgcagc    3900
ggcgcaacct ctgctcactg caacctccgc ctcctgggtt caagcagttc tcctgtctca   3960
gcctcccgag tagctgggat tacaggcaca tgtcaccacg cctggctaat ttttgtattt   4020
ttagtagaga tgggggtttca ccacgttggc caggctgatc tcgaatgcct gacctttggt   4080
gatctgcccg ccttgtcctc atgtgtgctc cacaggcctt tgggttggga ttgcaggcgt   4140
gagccaccat gcccagccta gactcttttg acaatatgat gaaagctgtt ggttcctttc   4200
cccaacacac acacaccgag ttgtatcacg aaaatgtcat acaatttcca ggttttctga   4260
gtggtgggct cagattgagg tcaaaggatc agacgacctc taacgacctt catgtctctg   4320
ttgatgatct ggggacagcc agatcccctg tgtccaggga gttccttagt cccttgccac   4380
```

| | |
|---|---|
| caccagagaa gggcaattgc cacgggagct gcaaagaccc tattcctact cctggtgcct | 4440 |
| tacttatgca gcacgactga attttttgtt ttgttttgtt ttgttgagac agggggcttgc | 4500 |
| tctgttgccc aggctggagt gcagtggcac aacaatggct caccgcagcc tcgaacccct | 4560 |
| gggctcaagc gatcctccca tctcagcttc ctgggtagct gggaccagag gcgtgagccg | 4620 |
| ccatagctgg ctaattttta attttttttt tgcagagatg aggtttcacc atggtgccca | 4680 |
| ggctggtctc gaacttctgg gctcaagtga tcctccctcc ttggcctcgc aaagtgctgg | 4740 |
| gattgcaggc atgagccacc gcccccggcc tgtggagcac acatgagttt aaaattactt | 4800 |
| tcccttctgc ctatatttcc gaggaggaaa cttcatgcgc agggatcttt cttagtggat | 4860 |
| ttaatggcta aaaggtctgt ctgaatccag gacgctggct ttagccttcc tcggcagctg | 4920 |
| ccgtaaccc ggtgtctaaa cctgaagcat cccaggagca cccactccag gagttttctc | 4980 |
| ggccgcggaa ctcattagtt agagcgccct cttgtgttct catgtggtaa tcggtcactg | 5040 |
| aaggacttaa aatggtcctt agccaacaca cagtaaaact tttccctctt ctgaccccaa | 5100 |
| gaggtcagcc acccatttca tgagcatata ctggtcgccc catcagcgtt ctctgattgg | 5160 |
| ctaactgaac ccactccccg acctagactc aagacaggcg aagtgacgct taggtcaaca | 5220 |
| ttcactcact aaagcaacga ctgtcgggcg attttgtctc ccgctggttt tggaatggtg | 5280 |
| tctggagaca tttttggttg tcacagctgg gtgggtgtgc tcccggcatc tggtgggtag | 5340 |
| aaaccaagca tgctcctaaa catcctacag gcacagaacc gtctcccacg accaagcatg | 5400 |
| atcaagtccc aaatgccaat aatgccagg ttgagaaact ctgcacagaa gcatccagtt | 5460 |
| atttgtctgt ttgctcaaca agcttgtgct catcatgctc tgtgttcctg acgctgtgct | 5520 |
| gggtgttggc ggtgggaaga ttacaagagt cacatggcag ctgtcctcct ggaaggtaca | 5580 |
| acccagtaga gatgcagact aacagagagc caattacaaa gcagtgtgac aagcgtcatg | 5640 |
| gtggaaaatt aaaagctcaa acaagggcac atgggagggg cttccaacac agactttggg | 5700 |
| ggatccagga aggtctaaga ggaaagtggg tctcaccaaa gccttgacca taggcagagg | 5760 |
| gtaccagtgg aaaaggtggg gtgaagaaca ttgaggacaa aaggaagaag tgcaggaagg | 5820 |
| ccctgaggca agggagtggg gggtgccctg gagggatggc agcagggcag tctgtcagac | 5880 |
| ccaagtggcc tccagcccta gaagccaatt agtcctcctc aaaaagctgt cactgtcccc | 5940 |
| taagaattgc tgccaggctc ccactggcct gactcagtct ttgagagtct taaggaggag | 6000 |
| gtctctgaaa ggtacacacc aagaactctc cccagcacag ctgtttttaa gactctccac | 6060 |
| cagcgtcatt ggcgtgttgg gaagaaaccc tctgccacag aggccagctt cagcctttgc | 6120 |
| ctaacaccgc aagggcaaat ggaaaggtaa acgggaagga gatgtctccc cagcaggcta | 6180 |
| tttgaggaca gtcttccctg cagaagatct caacctgggg tccacagagt ggaaatgtta | 6240 |
| gagtagggag ctaggcaaac atgagcagga caggtgaggg cccccacagg aatgtcaggc | 6300 |
| taccatcagg tgatggtcag gtggttgtta aactgtctct gtaaaataat aattggttgc | 6360 |
| agccagctcc aagcaaggac agtctctcaa tagatacaaa acaccctgat ctggtgatca | 6420 |
| gccgcttccc gataagatct caggagctgg gcaagcagcc tggagcatgc gcaccaagag | 6480 |
| gcaaaatggc ggaatttaac cagtatatga cctaccttcc tctgggaacg cacgactggt | 6540 |
| aaggggaaaa atgcctcaag tgagcatgcg cgcaacttca gtaatcacac tgtgcatgcg | 6600 |
| acccccttcca agtgctggca ggtcaccaca tacgcggaca gcctgctgca agggaagaat | 6660 |
| caggggagat gagacgtaaa tcccagaact atgccaaata cataaaaccc caagttaagg | 6720 |
| gtcaggcagg gcacttagat ctctcaagtt gcctgcctga cccaagtgta gtgtacttcc | 6780 |

-continued ttttgttcct gctctaaaac tttttaataa actctcactc ctgctctaaa a        6831

<210> SEQ ID NO 28
<211> LENGTH: 2956
<212> TYPE: DNA
<213> ORGANISM: Homo sapiens

<400> SEQUENCE: 28
ggggctgagt gctcagtgga gagcggggag ttgtgtccac cttgccgacg tcgctagccg    60
tggggctgtc ctgggaaggc ggacggcgag cgcccggtgt ccgcactcgg ccgcctgccg   120
tgcccgtctg cgcccgtgtc atcctcactc gggacgcagg gaccgttttt aaatcacagg   180
ggcgtgtgtc agcctgccct aggacttcat gtctatatat ttccccattc actgccccga   240
ctatctgaga tcggccaaga tgactgaggt gatgatgaac acccagccca tggaggagat   300
cggcctcagc ccccgcaagg atggcctttc ctaccagatc ttcccagacc cgtcagattt   360
tgaccgctgc tgcaaactga aggaccgtct gccctccata gtggtggaac ccacagaagg   420
ggaggtggag agcggggagc tccggtggcc ccctgaggag ttcctggtcc aggaggatga   480
gcaagataac tgcgaagaga cagcgaaaga aaataaagag cagtagagtc cctgtggact   540
cccatgggtc ataccagcca gcatctgttc ctgaactgtg ttttcccat catgacggaa    600
gaagagagtg agccgcaatt gttctgaaaa tgtcaaacga ggcttctgtt ttgcacctgc   660
agatcaccga gttggttttc tttcttttc ttgccttttt tttttttga aatttgccga    720
gcagtggagc cctctgacaa tttgcaaggc cctctgagaa aggaagctgc ttagagccag   780
ggggttagtg ggtgagggga gcgagtgctg tttttgagat cattatctga actcaggcag   840
cctagtagag gcagtggtgg gattccaatg ggtcttggtg ggtgggaggt ggggcatgtg   900
caaagcaagc aaggaacatt tggggtaaga aaacaaacat gaggcaaaag aaaaaataca   960
tgtttttaag aaaacattga gcagagaact gcagccagga tgcgctcagc agacattcac  1020
tctggctgct gggacatcag aaaacaaagt cttcatctct ctctccagtt tcacccaccc  1080
cacccttttgc tttcatttca ggtgtgttgg tctatatgac agggaggaga gtaaaggaga  1140
gcaggagcaa ttggctgcct gcaaagccag ctggaggtga agtgcaggaa aggaaaggtc  1200
accccattct actccatggc ctctctgctc ccagctgtgg taggctcaca tagccagtgt  1260
gatcggtttt taagaggcag tgcttttcag ctttttctccc tgatatatcc attttgcttc  1320
ccagcacttt ttaggagtag tgagagcact tcctgcccctt gttggaagcc cagggtgga   1380
cactcagcac gaaggtctct cccttaactg ctgcccttcc aagacttgct cccgagatgg  1440
agtgggcgtg gtcttccagg ctggcccttc cttctcctca ccgccacctt ccctgcccca  1500
gccccagcag ccatgggtac atgggtcccc agctcaccta tggattcccg ccagtctgcc  1560
cagctgcagt actcacgccc catgggggat cttggtctgt ttttcttgtg ggagcctagt  1620
ggagagcaga cgtggctttt tatgtgtctt gttggggagg tgacttgcat ggtgggaca   1680
aggctgtcgt ggcaaccttg ggatcgagtt tgagactaaa ggatgtcatg agatccctgg  1740
cttctcccca tgttgttccc ggacaagggc agaaggagg catggcaagg gacctctgct   1800
gtccttactc aacagtggtc ctcatccctc cccacctccc actgcttcct gcaagggcac  1860
cagttgtatg agaaagttgg cctttggact taggattct tattgtagct aagagccatc    1920
tgaagcagca ggttgcagga caaatgcttc agtccgccga gagcagtacc gtgtggccaa  1980
gaggtggact cagagccttc cttgagctaa actcggccaa ccaaggcacg cagcatgtcc  2040
cctcaggtct ccagtcagtc caggttgacc ctcagttctg gacgtgtgta tatagctgta  2100

-continued

| | |
|---|---|
| tttaatacct caaggtcatt gtggctctgg ggatgccggg gcaggaggac gagggtgcgc | 2160 |
| tgtggacaca gcagtccgcg gaattccgtt ctgggaagcc aatggtcgcc ggcacccctt | 2220 |
| gcttcctccc tctgttgtct gcctgtgtga cacacatcaa tggcaataac ttcttccaac | 2280 |
| tcctcgcaga agtgggagag gccggcagcc tgcaccgaga ggggctttcc tctctcttgc | 2340 |
| tccccgcttc gttctgtttt ggctgcagag agtggttcat ccatactctc attccctcgc | 2400 |
| ctccccttgt ggacggggt cttgcctttt caattcctgt gttttggtgt cttcccttat | 2460 |
| ctgctaccct gaatcacctg tcctggtctt gctgtgtgat gggaacatgc ttgtaaactg | 2520 |
| cgtaacaaat ctactttgtg tatgtgtctg tttatggggg tggtttatta ttttttgctgg | 2580 |
| tccctagacc actttgtatg accgtttgca gtctgagcag gccaggggct gacagctaat | 2640 |
| gtcaggaccc tcagcggtgg agcctgctgg ggggacccag ctgctcttgg acaagtggct | 2700 |
| gagctcctat ctggcctcct ctttttttt ttttcaagta atttgtgtgt atttctaact | 2760 |
| gattgtattg aaaaaattcc tagtatttca gtaaaaatgc ctgttgtgag atgaacctcc | 2820 |
| tgtaacttct atctgttctt ttttgaggct cagggagaaa ctagcattt tttttttcca | 2880 |
| aactactttt tgtcactgtg acagttgtaa ataaagtttg aaaatgcttt ccactctgaa | 2940 |
| aaaaaaaaaa aaaaaa | 2956 |

<210> SEQ ID NO 29
<211> LENGTH: 2262
<212> TYPE: DNA
<213> ORGANISM: Homo sapiens

<400> SEQUENCE: 29

| | |
|---|---|
| ctggggagta atagcatggg caaccattat cctgtctcgc cgccacccag gacatggctt | 60 |
| ctgttccaat gccaagtgag tacacctatg tgaaactgag aagtgattgc tcgaggcctt | 120 |
| ccctgcaatg gtacacccga gctcaaagca agatgagaag gcccagcttg ttattaaaag | 180 |
| acatcctcaa atgtacattg cttgtgtttg gagtgtggat cctttatatc ctcaagttaa | 240 |
| attatactac tgaagaatgt gacatgaaaa aaatgcatta tgtggaccct gaccatgtaa | 300 |
| agagagctca gaaatatgct cagcaagtct tgcagaagga atgtcgtccc aagttttgcca | 360 |
| agacatcaat ggcgctgtta tttgagcaca ggtatagcgt ggacttactc ccttttgtgc | 420 |
| agaaggcccc caaagacagt gaagctgagt ccaagtacga tcctcctttt gggttccgga | 480 |
| agttctccag taaagtccag accctcttgg aactcttgcc agagcacgac ctccctgaac | 540 |
| acttgaaagc caagacctgt cggcgctgtg tggttattgg aagcggagga atactgcacg | 600 |
| gattagaact gggccacacc ctgaaccagt tcgatgttgt gataaggtta acagtgcac | 660 |
| cagttgaggg atattcagaa catgttggaa ataaaactac tataaggatg acttatccag | 720 |
| agggcgcacc actgtctgac cttgaatatt attccaatga cttatttgtt gctgttttat | 780 |
| ttaagagtgt tgatttcaac tggcttcaag caatggtaaa aaaggaaacc ctgccattct | 840 |
| gggtacgact cttcttttgg aagcaggtgg cagaaaaaat cccactgcag ccaaaacatt | 900 |
| tcaggatttt gaatccagtt atcatcaaag agactgcctt tgacatccett cagtactcag | 960 |
| agcctcagtc aaggttctgg ggccgagata agaacgtccc cacaatcggt gtcattgccg | 1020 |
| ttgtcttagc cacacatctg tgcgatgaag tcagttggc gggttttgga tatgacctca | 1080 |
| atcaacccag aacacctttg cactacttcg acagtcaatg catggctgct atgaactttc | 1140 |
| agaccatgca taatgtgaca acggaaacca agttcctctt aaagctggtc aaagagggag | 1200 |
| tggtgaaaga tctcagtgga ggcattgatc gtgaattttg aacacagaaa acctcagttg | 1260 |

-continued

```
aaaatgcaac tctaactctg agagctgttt ttgacagcct tcttgatgta tttctccatc    1320
ctgcagatac tttgaagtgc agctcatgtt tttaactttt aatttaaaaa cacaaaaaaa    1380
attttagctc ttcccacttt ttttttccta tttatttgag gtcagtgttt gttttttgcac   1440 accattttgt aaatgaaact taagaattga attggaaaga cttctcaaag agaattgtat    1500
gtaacgatgt tgtattgatt tttaagaaag taatttaatt tgtaaaactt ctgctcgttt    1560
acactgcaca ttgaatacag gtaactaatt ggaaggagag gggaggtcac tcttttgatg   1620
gtggccctga acctcattct ggttccctgc tgcgctgctt ggtgtgaccc acggaggatc    1680
cactcccagg atgacgtgct ccgtagctct gctgctgata ctgggtctgc gatgcagcgg    1740
cgtgaggcct gggctggttg gagaaggtca aacccttct ctgttggtct gccttctgct    1800
gaaagactcg agaaccaacc agggaagctg tcctggaggt ccctggtcgg agagggacat    1860
agaatctgtg acctctgaca actgtgaagc caccctgggc tacagaaacc acagtcttcc    1920
cagcaattat tacaattctt gaattccttg gggattttt actgcccttt caaagcactt     1980
aagtgttaga tctaacgtgt tccagtgtct gtctgaggtg acttaaaaaa tcagaacaaa    2040
acttctatta tccagagtca tgggagagta caccctttcc aggaataatg ttttgggaaa    2100
cactgaaatg aaatcttccc agtattataa attgtgtatt taaaaaaag aaacttttct      2160 gaatgcctac ctggcggtgt ataccaggca gtgtgccagt ttaaaaagat gaaaagaat     2220 aaaaactttt gaggaaaaaa aaaaaaaaaa aaaaaaaaa aa                       2262
```

```
<210> SEQ ID NO 30
<211> LENGTH: 4909
<212> TYPE: DNA
<213> ORGANISM: Homo sapiens

<400> SEQUENCE: 30
```

```
tagacgcacc ctctgaagat ggtgactccc tcctgagaag ctggacccct tggtaaaaga     60
caaggccttc tccaagaaga atatgaaagt gttactcaga cttatttgtt tcatagctct    120
actgatttct tctctggagg ctgataaatg caaggaacgt gaagaaaaaa taattttagt    180
gtcatctgca aatgaaattg atgttcgtcc ctgtcctctt aacccaaatg aacacaaagg    240
cactataact tggtataaag atgacagcaa gacacctgta tctacagaac aagcctccag    300
gattcatcaa cacaaagaga aactttggtt tgttcctgct aaggtggagg attcaggaca    360
ttactattgc gtggtaagaa attcatctta ctgcctcaga attaaaataa gtgcaaaatt    420
tgtggagaat gagcctaact tatgttataa tgcacaagcc atatttaagc agaaactacc    480
cgttgcagga gacggaggac ttgtgtgccc ttatatggag tttttaaaa atgaaaataa    540 tgagttacct aaaattacagt ggtataagga ttgcaaacct ctacttcttg acaatataca   600
ctttagtgga gtcaaagata ggctcatcgt gatgaatgtg gctgaaaagc atagagggaa    660
ctatacttgt catgcatcct acacatactt gggcaagcaa tatcctatta cccgggtaat     720
agaatttatt actctagagg aaaacaaacc cacaaggcct gtgattgtga gcccagctaa    780
tgagacaatg gaagtagact ggggatccca gatacaattg atctgtaatg tcaccggcca    840
gttgagtgac attgcttact ggaagtggaa tgggtcagta attgatgaag atgacccagt    900
gctaggggaa gactattaca gtgtggaaaa tcctgcaaac aaaagaagga gtaccctcat    960
cacagtgctt aatatatcgg aaattgaaag tagatttat aaacatccat ttacctgttt    1020
tgccaagaat acacatggta tagatgcagc atatatccag ttaatatatc cagtcactaa    1080
tttccagaag cacatgattg gtatatgtgt cacgttgaca gtcataattg tgtgttctgt    1140
```

```
tttcatctat aaaatcttca agattgacat tgtgctttgg tacagggatt cctgctatga    1200
ttttctccca ataaaagctt cagatggaaa gacctatgac gcatatatac tgtatccaaa    1260
gactgttggg gaagggtcta cctctgactg tgatattttt gtgtttaaag tcttgcctga    1320
ggtcttggaa aaacagtgtg gatataagct gttcatttat ggaagggatg actacgttgg    1380
ggaagacatt gttgaggtca ttaatgaaaa cgtaaagaaa agcagaagac tgattatcat    1440
tttagtcaga gaaacatcag gcttcagctg gctgggtggt tcatctgaag agcaaatagc    1500
catgtataat gctcttgttc aggatggaat taaagttgtc ctgcttgagc tggagaaaat    1560
ccaagactat gagaaaatgc cagaatcgat taaattcatt aagcagaaac atggggctat    1620
ccgctggtca ggggacttta cacagggacc acagtctgca aagacaaggt tctggaagaa    1680
tgtcaggtac cacatgccag tccagcgacg gtcaccttca tctaaacacc agttactgtc    1740
accagccact aaggagaaac tgcaaagaga ggctcacgtg cctctcgggt agcatggaga    1800
agttgccaag agttctttag gtgcctcctg tcttatggcg ttgcaggcca ggttatgcct    1860
catgctgact tgcagagttc atggaatgta actatatcat cctttatccc tgaggtcacc    1920
tggaatcaga ttattaaggg aataagccat gacgtcaata gcagcccagg cacttcaga    1980 gtagagggct tgggaagatc ttttaaaaag gcagtaggcc cggtgtggtg gctcacgcct    2040
ataatcccag cactttggga ggctgaagtg ggtggatcac cagaggtcag gagttcgaga    2100
ccagcccagc caacatggca aaaccccatc tctactaaaa atacaaaaat gagctaggca    2160
tggtggcaca cgcctgtaat cccagctaca cctgaggctg aggcaggaga attgcttgaa    2220
ccggggagac ggaggttgca gtgagccgag tttgggccac tgcactctag cctggcaaca    2280
gagcaagact ccgtctcaaa aaagggcaa taaatgccct ctctgaatgt ttgaactgcc    2340
aagaaaaggc atggagacag cgaactagaa gaaagggcaa gaaggaaata gccaccgtct    2400
acagatggct tagttaagtc atccacagcc caagggcggg gctatgcctt gtctggggac    2460
cctgtagagt cactgacccct ggagcggctc tcctgagagg tgctgcaggc aaagtgagac    2520
tgacacctca ctgaggaagg gagacatatt cttggagaac tttccatctg cttgtatttt    2580
ccatacacat ccccagccag aagttagtgt ccgaagaccg aatttatttt tacagagctt    2640
gaaaactcac ttcaatgaac aaagggattc tccaggattc caaagttttg aagtcatctt    2700
agctttccac aggagggaga gaacttaaaa aagcaacagt agcagggaat tgatccactt    2760
cttaatgctt tcctccctgg catgaccatc ctgtcctttg ttattatcct gcattttacg    2820
tctttggagg aacagctccc tagtggcttc ctccgtctgc aatgtccctt gcacagccca    2880
cacatgaacc atccttccca tgatgccgct cttctgtcat cccgctcctg ctgaaacacc    2940
tcccaggggc tccacctgtt caggagctga agcccatgct ttcccaccag catgtcactc    3000
ccagaccacc tccctgccct gtcctccagc ttcccctcgc tgtcctgctg tgtgaattcc    3060
caggttggcc tggtggccat gtcgcctgcc cccagcactc ctctgtctct gctcttgcct    3120
cgacccttcc tcctccttg cctaggaggc cttctcgcat tttctctagc tgatcagaat    3180
tttaccaaaa ttcagaacat cctccaattc cacagtctct gggagacttt ccctaagagg    3240
cgacttcctc tccagccttc tctctctggt caggcccact gcagagatgg tggtgagcac    3300
atctgggagg ctggtctccc tccagctgga attgctgctc tctgagggag aggctgtggt    3360
ggctgtctct gtccctcact gccttccagg agcaatttgc acatgtaaca tagatttatg    3420
taatgcttta tgtttaaaaa cattcccaa ttatcttatt taatttttgc aattattcta    3480
attttatata tagagaaagt gacctatttt ttaaaaaaat cacactctaa gttctattga    3540
```

| | |
|---|---|
| acctaggact tgagcctcca tttctggctt ctagtctggt gttctgagta cttgatttca | 3600 |
| ggtcaataac ggtccccct cactccacac tggcacgttt gtgagaagaa atgacatttt | 3660 |
| gctaggaagt gaccgagtct aggaatgctt ttattcaaga caccaaattc caaacttcta | 3720 |
| aatgttggaa ttttcaaaaa ttgtgtttag attttatgaa aaactcttct actttcatct | 3780 |
| attctttccc tagaggcaaa catttcttaa aatgtttcat tttcattaaa aatgaaagcc | 3840 |
| aaatttatat gccaccgatt gcaggacaca agcacagttt taagagttgt atgaacatgg | 3900 |
| agaggacttt tggttttat atttctcgta tttaatatgg gtgaacacca acttttattt | 3960 |
| ggaataataa ttttcctcct aaacaaaaac acattgagtt taagtctctg actcttgcct | 4020 |
| ttccacctgc tttctcctgg gcccgctttg cctgcttgaa ggaacagtgc tgttctggag | 4080 |
| ctgctgttcc aacagacagg gcctagcttt catttgacac acagactaca gccagaagcc | 4140 |
| catggagcag ggatgtcacg tcttgaaaag cctattagat gttttacaaa tttaattttg | 4200 |
| cagattattt tagtctgtca tccagaaaat gtgtcagcat gcatagtgct aagaaagcaa | 4260 |
| gccaatttgg aaacttaggt tagtgacaaa attggccaga gagtgggggt gatgatgacc | 4320 |
| aagaattaca agtagaatgg cagctggaat ttaaggaggg acaagaatca atggataagc | 4380 |
| gtgggtggag gaagatccaa acagaaaagt gcaaagttat tccccatctt ccaagggttg | 4440 |
| aattctggag gaagaagaca cattcctagt tccccgtgaa cttcctttga cttattgtcc | 4500 |
| ccactaaaac aaaacaaaaa acttttaatg ccttccacat taattagatt ttcttgcagt | 4560 |
| ttttttatgg catttttta aagatgccct aagtgttgaa gaagagtttg caaatgcaac | 4620 |
| aaaatattta attaccggtt gttaaaactg gtttagcaca atttatattt tccctctctt | 4680 |
| gcctttctta tttgcaataa aaggtattga gccatttttt aaatgacatt tttgataaat | 4740 |
| tatgtttgta ctagttgatg aaggagtttt ttttaacctg tttatataat tttgcagcag | 4800 |
| aagccaaatt ttttgtatat taaagcacca aattcatgta cagcatgcat cacggatcaa | 4860 |
| tagactgtac ttattttcca ataaaatttt caaactttgt actgttaaa | 4909 |

<210> SEQ ID NO 31
<211> LENGTH: 2210
<212> TYPE: DNA
<213> ORGANISM: Homo sapiens

<400> SEQUENCE: 31

| | |
|---|---|
| cgcgcccctc cctcctcgcg gacctggcgg tgccggcgcc cggagtggcc ctttaaaagg | 60 |
| cagcttattg tccggagggg gcgggcgggg ggcgccgacc gcggcctgag gcccggcccc | 120 |
| tcccctctcc ctccctctgt ccccgcgtcg ctcgctggct agctcgctgg ctcgctcgcc | 180 |
| cgtccggcgc acgctccgcc tccgtcagtt ggctccgctg tcgggtgcgc ggcgtggagc | 240 |
| ggcagccggt ctggacgcgc ggcggggct gggggctggg agcgcggcgc gcaagatctc | 300 |
| cccgcgcgag agcggcccct gccaccgggc gaggcctgcg ccgcgatggc agagatgggc | 360 |
| agtaaagggg tgacggcggg aaagatcgcc agcaacgtgc agaagaagct cacccgcgcg | 420 |
| caggagaagg ttctccagaa gctggggaag gcagatgaga ccaaggatga gcagtttgag | 480 |
| cagtgcgtcc agaatttcaa caagcagctg acggagggca cccggctgca aaggatctc | 540 |
| cggacctacc tggcctccgt caaagccatg cacgaggctt ccaagaagct gaatgagtgt | 600 |
| ctgcaggagg tgtatgagcc cgattggccc ggcagggatg aggcaaacaa gatcgcagag | 660 |
| aacaacgacc tgctgtggat ggattaccac cagaagctgg tggaccaggc gctgctgacc | 720 |
| atggacacgt acctgggcca gttccccgac atcaagtcac gcattgccaa gcgggggcgc | 780 |

| | |
|---|---|
| aagctggtgg actacgacag tgcccggcac cactacgagt cccttcaaac tgccaaaaag | 840 |
| aaggatgaag ccaaaattgc caaggccgag gaggagctca tcaaagccca gaaggtgttt | 900 |
| gaggagatga atgtggatct gcaggaggag ctgccgtccc tgtggaacag ccgcgtaggt | 960 |
| ttctacgtca acacgttcca gagcatcgcg ggcctggagg aaaacttcca caaggagatg | 1020 |
| agcaagctca accagaacct caatgatgtg ctggtcggcc tggagaagca cacgggagc | 1080 |
| aacaccttca cggtcaaggc ccagcccaga aagaaaagta aactgttttc gcggctgcgc | 1140 |
| agaaagaaga acagtgacaa cgcgcctgca aagggaaca agagcccttc gcctccagat | 1200 |
| ggctcccctg ccgccacccc cgagatcaga gtcaaccacg agccagagcc ggccggcggg | 1260 |
| gccacgcccg ggccacccct ccccaagtcc ccatctcagc cagcagaggc ctcggaggtg | 1320 |
| gcgggtggga cccaacctgc ggctggagcc caggagccag gggagacggc ggcaagtgaa | 1380 |
| gcagcctcca gctctcttcc tgctgtcgtg gtggagacct tcccagcaac tgtgaatggc | 1440 |
| accgtggagg gcggcagtgg ggccgggcgc ttggacctgc ccccaggttt catgttcaag | 1500 |
| gtacaggccc agcacgacta cacggccact gacacagacg agctgcagct caaggctggt | 1560 |
| gatgtggtgc tggtgatccc cttccagaac cctgaagagc aggatgaagg ctggctcatg | 1620 |
| ggcgtgaagg agagcgactg gaaccagcac aaggagctgg agaagtgccg tggcgtcttc | 1680 |
| cccgagaact tcactgagag ggtcccatga cggcggggcc caggcagcct ccgggcgtgt | 1740 |
| gaagaacacc tcctcccgaa aaatgtgtgg ttctttttt tgttttgttt tcgttttca | 1800 |
| tcttttgaag agcaaaggga aatcaagagg agacccccag gcagggggc gttctcccaa | 1860 |
| agattaggtc gttttccaaa gagccgcgtc ccggcaagtc cggcggaatt caccagtgtt | 1920 |
| cctgaagctg ctgtgtcctc tagttgagtt tctggcgccc ctgcctgtgc cgcatgtgt | 1980 |
| gcctggccgc agggcggggc tgggggctgc cgagccacca tgcttgcctg aagcttcggc | 2040 |
| cgcgccaccc gggcaagggt cctctttttcc tggcagctgc tgtgggtggg gcccagacac | 2100 |
| cagcctagcc tggctctgcc ccgcagacgg tctgtgtgct gtttgaaaat aaatcttagt | 2160 |
| gttcaaaaca aatgaaaca aaaaaaaat gataaaaact ctcaaaaaaa | 2210 |

<210> SEQ ID NO 32
<211> LENGTH: 4664
<212> TYPE: DNA
<213> ORGANISM: Homo sapiens

<400> SEQUENCE: 32

| | |
|---|---|
| gcagcctccc ggcgctgagc gcttttcctg cccgcccggc tcagccctgc ggaccccggg | 60 |
| agaagtttcc cagaaaaaat gcccagcgcg gcgcggggct gcggagtcgt ccggagccgc | 120 |
| tgcgcgattt atcagcaaga ctgttgaacg cataactgcc caagatgcct gtccctcccc | 180 |
| ctccagcacc cccgccgccc ccgacgtttg cactggccaa tacagagaag cctaccttga | 240 |
| ataagacaga gcaggctggg agaaatgctc tcctttctga tatcagcaaa gggaagaaac | 300 |
| taaagaagac ggtcaccaat gacagaagtg caccaatact ggacaaacct aaaggagctg | 360 |
| gtgctggagg cggtggtggt ggcttttgtg gaggcggcgg atttggcgga ggaggtggtg | 420 |
| gcggaggcgg tggaagtttt ggagggggcg gacctccagg tctgggagga ttgttccagg | 480 |
| ctggaatgcc gaagctgaga tccacggcca acagggataa tgattctgga ggaagccgac | 540 |
| caccattgtt gccaccggga ggaagatcca catctgcgaa accttttca cccccaagtg | 600 |
| gcccaggag gtttcctgtg ccttctccag gccacagaag tggtccccca gagcctcaga | 660 |
| ggaaccgaat gccgccccca aggcccgacg tgggctcaaa gcctgatagc attcctcctc | 720 |

```
cagtacctag tactccaaga cccattcaat caagtccgca caaccggggg tccccaccag    780
tgcccggagg ccccaggcag cccagccccg ggcccactcc tcccccttc cctggaaacc      840 gcggcactgc tttgggagga ggctcaatac gtcagtcccc cttgagctcc tcctcgccct    900
tctccaaccg gcctcccctg ccgcctaccc cagcagggc cttggatgac aaacccctc      960 caccacctcc tccagtgggc aacaggccct ccatccacag ggaagcggtt cccctcctc   1020 ctcctcagaa caacaagcct ccagtgcctt ccactccgcg gccttcggcc tcctcacagg   1080
ccccacctcc gccgccacct cccagcaggc ccgggccgcc tcctctgcct ccaagttcca   1140
gcggcaatga cgaaacccca agactcccac agcggaatct gtccctcagt tcgtccacgc   1200
ccccgttacc ttcgccagga cgttcaggtc ctcttcctcc cccgcccagt gagagacccc   1260
cacctccagt gagggacccg ccaggccgat caggcccct cccaccacct cctccagtaa     1320
gcagaaacgg cagcacatct cgggccctgc ctgctacccc tcagttgcca tccaggagtg   1380
gagtagacag tcccaggagt ggacccaggc ctccccttcc tcctgatagg cccagtgctg   1440
gggcacctcc cccacctcca ccatcaacat ctattagaaa tggcttccaa gactctccat   1500
gtgaagatga gtgggaaagc agattctact tccatccgat ttccgatttg ccacctccag   1560
agccatatgt acaaacgacc aaaagttatc ccagcaaact ggcaagaaac gaaagccgga   1620
gtggatccaa ccgaagagaa aggggtgctc caccactccc tcccatcccg aggtgatctt   1680
tgcctgctct tctctaccca agctcaagag ctgcttctgt tgctatctaa gaactgcata   1740
ccctcctccc tgcttcttcc cttgtgcctc atgtatgggc aggaggaaag gtgggagggg   1800
gagtgggaat atgcgtgtgt gggtgggaat cggtaagaaa tgcacctagc ttttcatatt   1860
gtgtttattc tccaggctat tgcttgcttc agctgcagcc tgcctgtgct ggctgctggg   1920
gtcgataggc ttttgtcgta ataggcagag atgacttgca tcccagcttt ccaccaacca   1980
aattcaaaca ttcactgctt atttgttaca gactgtaatt attaaagtcc ctgagagctg   2040
ttttctcccg ttccttttc gcatgcttgg cctcctctct gtttctatga accacagacc   2100
acctaagcaa gctgctgagt aagggctcac tggaaacttg cagtcacagg atgtccaatc   2160
tttggcagtc cgagcttggc tctaggacag agctgtccaa tagaaatata atgtgagccc   2220
catatacaat ttttacattt ctaatatatt ttaaacaagt gaagttaata tgcatccaaa   2280
atatttcaac ctgtaatcaa cataaaattt taatgagata ttttatatta tttttggta   2340 ctgaatcttc aaaatccaga gtgtatttta cacttaccgc acatctccat tcagactagt   2400
cacattttta agtgctcagt agccacatgt ggctggtggc tactggatta gacagcacga   2460
gtctggaaga tggaagctag tgcagaaacc tcttgtttaa aaacaaaaa aggcaagatg   2520 ggcttgagcg attcaagagg caactaaaaa taaaattagg acccagcacc ttgtttgaca   2580
cacagtttga ccttcgattt tcctcccta acttccctct tcccttaata tctgtataca   2640
agtgttgctt caaagtacca aggtcagaaa ttgattcagt acggtttact aaagtcatgt   2700
ggaataaagc cattggaaac aaatggaaag cctgtcggga cttctgggct cagaaccagc   2760
tggctcacgc actccacttg tcagctggac ttctgccttg tgaaatggaa gcagcctttg   2820
ttcctttctg gctgagcaag ctcctgaggc tgggagagac taggaaggct tggtaggagg   2880
ggaaaaaagt caggaaaaga tatcaaatca gaaacatgga agaagaaggg aaccgatttg   2940
agttggtggg caaaactcta aaaatctaaa tctgatgctt atgtaagggt tgagcgaatt   3000
agggagattg ctagtggaaa ttggagggaa tttgttttgc atcatttgtc taggatctat   3060
gcaaatatag ctccactaaa ggaccatagg gaagagccag ccttgccttt tcttatatga   3120
```

```
ttttgtttac aaaattttac tgggactttt aaatctagct atagagttgg gaaaaaatat    3180
ttccacttag atattttaca tggttttgtt taaaattacc attacttgtt ttttaaaaac    3240
acatgaccac atatgtatat gtatatctac ctaaacattg tatcatggtt tcagtatgtt    3300
attcatgtat tactgggaga tgctaccaag aaaccaaccc aaagaaaatt ctgaaaaata    3360
catttctatt tatagaataa atgtttcatt tatataaaag caaagaaact tagagttcta    3420
ataaatggga tgtctaataa attatgaagt tactgatttg aatatattat atttttataa    3480
cttccttgcc aaagtcctga tttagtacat tagagaacct gtgtttcctc tctcctctac    3540
cattcatctc tcttccatac agtcatttgg gctttttact caaagagaat caagaaataa    3600
taaggtataa caagcttggc aaagtgttgg cttttttaaa aaaaatttt ttaatctcta    3660
gcagtttggt aatttagcag catcattat ttgggattct tttatctgat ttcaacagtg    3720
aaaaacatcc ctatgataaa gcctaatgac ccatttcaca aaagatggaa tttgcccttc    3780
ctagaaaata tgacggagaa aagtctgact cagagaaagt gagtctgaat tttataaggg    3840
gtagtaagaa ttggacaatt cctttgcata tctgaacttg gcaggtaccg ttctaaatct    3900
gaaacagggt gatagctcaa agttgccatt catccagaat agattgtttt agaatgtagt    3960
gtttaagtga ctgtttcatt aatacaccta cacccttct ttgaaagttt gcaacctaat    4020
tgcatctaaa actatgaata agttctgtgg taaaatctta aactatggaa aattacaaaa    4080
atgaattttt cttccctgaa atcagagctt acatgtgtgt ttttttataa cattttcaga    4140
taaatgtatt caacatgtaa tacagtattt taacattcac ctcttatttt atattgaaat    4200
gtattacagt attaaaactc agtgttcagt atttatttca ctatgcattt tatttagtaa    4260
aagccaggag aaatgtttaa tccaatggtg ccttactttg tgatttaaaa gaaatcaact    4320
tttttttatg tctaagtagt agattatttg catatttgta aaaactgtta ggtctttata    4380
ttttaaagtg taataccagt tttgttattt tagtagcaga aatgggatga ttgttaaagt    4440
tccccaaaaa tgttggcatg aaattaattt ttccctcctt atagtcaagg accgtagagg    4500
aagaaaaact ttttttttcat accatgcact atgtaaacag acacattttg ctatctgtgt    4560
catcaggata gtgtaagtgg tagggtagag actaccctag acatctgcat ctttgtaagt    4620
tagccagaca ataaagaaaa gcagaatgaa aaaaaaaaaa aaaa                    4664

<210> SEQ ID NO 33
<211> LENGTH: 1166
<212> TYPE: DNA
<213> ORGANISM: Homo sapiens

<400> SEQUENCE: 33
attcccaact gccagtgatc tctgaagccg actctgaggc tccctctttg ctctaacaga      60
cagcagcgac tttaggctgg ataatagtca aattcttacc tcgctctttc actgctagta     120
agatcagatt gcgtttcttt cagttactct tcaatcgcca gtttcttgat ctgcttctaa     180
aagaagaagt agagaagata atcctgtct tcaatacctg gaaggaaaaa caaaataacc     240
tcaactccgt tttgaaaaaa acattccaag aactttcatc agagatttta cttagatgat     300
ttacacaatg aagaaagtac atgcactttg ggcttctgta tgcctgctgc ttaatcttgc     360
ccctgccct cttaatgctg attctgagga agatgaagaa cacacaatta tcacagatac     420
ggagttgcca ccactgaaac ttatgcattc attttgtgca ttcaaggcgg atgatggccc     480
atgtaaagca atcatgaaaa gattttctct caatatttc actcgacagt gcgaagaatt     540
tatatatggg ggatgtgaag gaaatcagaa tcgatttgaa agtctggaag agtgcaaaaa     600
```

| | |
|---|---|
| aatgtgtaca agagataatg caaacaggat tataaagaca acattgcaac aagaaaagcc | 660 |
| agatttctgc tttttggaag aagatcctgg aatatgtcga ggttatatta ccaggtattt | 720 |
| ttataacaat cagacaaaac agtgtgaacg tttcaagtat ggtggatgcc tgggcaatat | 780 |
| gaacaatttt gagacactgg aagaatgcaa gaacatttgt gaagatggtc cgaatggttt | 840 |
| ccaggtggat aattatggaa cccagctcaa tgctgtgaat aactccctga ctccgcaatc | 900 |
| aaccaaggtt cccagccttt tgttacaaa gaaggaaca aatgatggtt ggaagaatgc | 960 |
| ggctcatatt taccaagtct ttctgaacgc cttctgcatt catgcatcca tgttctttct | 1020 |
| aggattggat agcatttcat gcctatgtta atatttgtgc ttttggcatt tccttaatat | 1080 |
| ttatatgtat acgtgatgcc tttgatagca tactgctaat aaagttttaa tatttacatg | 1140 |
| catagtaaaa aaaaaaaaaa aaaaaa | 1166 |

<210> SEQ ID NO 34
<211> LENGTH: 8449
<212> TYPE: DNA
<213> ORGANISM: Homo sapiens

<400> SEQUENCE: 34

| | |
|---|---|
| gcccgcgccg gctgtgctgc acaggggag gagagggaac cccaggcgcg agcgggaaga | 60 |
| ggggacctgc agccacaact tctctggtcc tctgcatccc ttctgtccct ccacccgtcc | 120 |
| ccttccccac cctctggccc ccaccttctt ggaggcgaca accccgggga ggcattagaa | 180 |
| gggatttttc ccgcaggttg cgaagggaag caaacttggt ggcaacttgc ctcccggtgc | 240 |
| gggcgtctct cccccaccgt ctcaacatgc ttaggggtcc ggggcccggg ctgctgctgc | 300 |
| tggccgtcca gtgcctgggg acagcggtgc cctccacggg agcctcgaag agcaagaggc | 360 |
| aggctcagca aatggttcag ccccagtccc cggtggctgt cagtcaaagc aagcccggtt | 420 |
| gttatgacaa tggaaaacac tatcagataa atcaacagtg ggagcggacc tacctaggca | 480 |
| atgcgttggt ttgtacttgt tatggaggaa gccgaggttt taactgcgag agtaaacctg | 540 |
| aagctgaaga gacttgcttt gacaagtaca ctgggaacac ttaccgagtg ggtgacactt | 600 |
| atgagcgtcc taaagactcc atgatctggg actgtacctg catcggggct gggcgaggga | 660 |
| gaataagctg taccatcgca aaccgctgcc atgaggggg tcagtcctac aagattggtg | 720 |
| acacctggag gagaccacat gagactggtg gttacatgtt agagtgtgtg tgtcttggta | 780 |
| atggaaaagg agaatggacc tgcaagccca gctgagaa gtgttttgat catgctgctg | 840 |
| ggacttccta tgtggtcgga gaaacgtggg agaagcccta ccaaggctgg atgatggtag | 900 |
| attgtacttg cctgggagaa ggcagcggac gcatcacttg cacttctaga aatagatgca | 960 |
| acgatcagga cacaaggaca tcctatagaa ttggagacac ctggagcaag aaggataatc | 1020 |
| gaggaaacct gctccagtgc atctgcacag gcaacggccg aggagagtgg aagtgtgaga | 1080 |
| ggcacacctc tgtgcagacc acatcgacg gatctggccc cttcaccgat gttcgtgcag | 1140 |
| ctgtttacca accgcagcct caccccagc ctcctcccta tggccactgt gtcacagaca | 1200 |
| gtggtgtggt ctactctgtg gggatgcagt ggctgaagac acaaggaaat aagcaaatgc | 1260 |
| tttgcacgtg cctgggcaac ggagtcagct gccaagagac agctgtaacc cagacttacg | 1320 |
| gtggcaactc aaatgagag ccatgtgtct taccattcac ctacaatggc aggacgttct | 1380 |
| actcctgcac cacagaaggg cgacaggacg gacatctttg gtgcagcaca acttcgaatt | 1440 |
| atgagcagga ccagaaatac tctttctgca gagaccacac tgttttggtt cagactcgag | 1500 |
| gaggaaattc caatggtgcc ttgtgccact tcccttcct atacaacaac cacaattaca | 1560 |

```
ctgattgcac ttctgagggc agaagagaca acatgaagtg gtgtgggacc acacagaact    1620
atgatgccga ccagaagttt gggttctgcc ccatggctgc ccacgaggaa atctgcacaa    1680
ccaatgaagg ggtcatgtac cgcattggag atcagtggga taagcagcat gacatgggtc    1740
acatgatgag gtgcacgtgt gttgggaatg gtcgtgggga atggacatgc attgcctact    1800
cgcagcttcg agatcagtgc attgttgatg acatcactta caatgtgaac gacacattcc    1860
acaagcgtca tgaagagggg cacatgctga actgtacatg cttcggtcag ggtcggggca    1920
ggtggaagtg tgatcccgtc gaccaatgcc aggattcaga gactgggacg ttttatcaaa    1980
ttggagattc atgggagaag tatgtgcatg gtgtcagata ccagtgctac tgctatggcc    2040
gtggcattgg ggagtggcat tgccaacctt tacagaccta tccaagctca agtggtcctg    2100
tcgaagtatt tatcactgag actccgagtc agcccaactc ccacccatc cagtggaatg    2160 caccacagcc atctcacatt tccaagtaca ttctcaggtg gagacctaaa aattctgtag    2220
gccgttggaa ggaagctacc ataccaggcc acttaaactc ctacaccatc aaaggcctga    2280
agcctggtgt ggtatacgag ggccagctca tcagcatcca gcagtacggc caccaagaag    2340
tgactcgctt tgacttcacc accaccagca ccagcacacc tgtgaccagc aacaccgtga    2400
caggagagac gactcccttt tctcctcttg tggccacttc tgaatctgtg accgaaatca    2460
cagccagtag ctttgtggtc tcctgggtct cagcttccga caccgtgtcg ggattccggg    2520
tggaatatga gctgagtgag gagggagatg agccacagta cctggatctt ccaagcacag    2580
ccacttctgt gaacatccct gacctgcttc ctggccgaaa atacattgta aatgtctatc    2640
agatatctga ggatggggag cagagtttga tcctgtctac ttcacaaaca acagcgcctg    2700 atgccctcc tgacccgact gtggaccaag ttgatgacac ctcaattgtt gttcgctgga    2760
gcagacccca ggctcccatc acagggtaca gaatagtcta ttcgccatca gtagaaggta    2820
gcagcacaga actcaacctt cctgaaactg caaactccgt caccctcagt gacttgcaac    2880
ctggtgttca gtataacatc actatctatg ctgtggaaga aaatcaagaa agtacacctg    2940
ttgtcattca acaagaaacc actggcaccc cacgctcaga tacagtgccc tctcccaggg    3000
acctgcagtt tgtggaagtg acagacgtga aggtcaccat catgtggaca ccgcctgaga    3060
gtgcagtgac cggctaccgt gtggatgtga tccccgtcaa cctgcctggc gagcacgggc    3120
agaggctgcc catcagcagg aacacctttg cagaagtcac cgggctgtcc cctgggtca    3180 cctattactt caaagtcttt gcagtgagcc atgggaggga gagcaagcct ctgactgctc    3240
aacagacaac caaactggat gctcccacta acctccagtt tgtcaatgaa actgattcta    3300
ctgtcctggt gagatggact ccacctcggg cccagataac aggataccga ctgaccgtgg    3360
gccttacccg aagaggacag cccaggcagt acaatgtggg tccctctgtc tccaagtacc    3420
cactgaggaa tctgcagcct gcatctgagt acaccgtatc cctcgtggcc ataaagggca    3480
accaagagag ccccaaagcc actggagtct ttaccacact gcagcctggg agctctattc    3540
caccttacaa caccgaggtg actgagacca ccattgtgat cacatggacg cctgctccaa    3600
gaattggttt taagctgggt gtacgaccaa gccaggagg agaggcacca cgagaagtga    3660
cttcagactc aggaagcatc gttgtgtccg gcttgactcc aggagtagaa tacgtctaca    3720
ccatccaagt cctgagagat ggacaggaaa gagatgcgcc aattgtaaac aaagtggtga    3780
caccattgtc tccaccaaca aacttgcatc tggaggcaaa ccctgacact ggagtgctca    3840
cagtctcctg ggagagggc accaccccag acattactgg ttatagaatt accacaaccc    3900
ctacaaacgg ccagcaggga aattctttgg aagaagtggt ccatgctgat cagagctcct    3960
```

```
gcacttttga taacctgagt cccggcctgg agtacaatgt cagtgtttac actgtcaagg   4020
atgacaagga aagtgtccct atctctgata ccatcatccc agctgttcct cctcccactg   4080
acctgcgatt caccaacatt ggtccagaca ccatgcgtgt cacctgggct ccaccccat   4140 ccattgattt aaccaacttc ctggtgcgtt actcacctgt gaaaaatgag gaagatgttg   4200
cagagttgtc aatttctcct tcagacaatg cagtggtctt aacaaatctc ctgcctggta   4260
cagaatatgt agtgagtgtc tccagtgtct acgaacaaca tgagagcaca cctcttagag   4320
gaagacagaa aacaggtctt gattccccaa ctggcattga cttttctgat attactgcca   4380
actcttttac tgtgcactgg attgctcctc gagccaccat cactggctac aggatccgcc   4440
atcatcccga gcacttcagt gggagacctc gagaagatcg ggtgccccac tctcggaatt   4500
ccatcaccct caccaacctc actccaggca cagagtatgt ggtcagcatc gttgctctta   4560
atggcagaga ggaaagtccc ttattgattg ccaacaatc aacagtttct gatgttccga   4620
gggacctgga agttgttgct gcgaccccca ccagcctact gatcagctgg gatgctcctg   4680
ctgtcacagt gagatattac aggatcactt acggagagac aggaggaaat agccctgtcc   4740
aggagttcac tgtgcctggg agcaagtcta cagctaccat cagcggcctt aaacctggag   4800
ttgattatac catcactgtg tatgctgtca ctggccgtgg agacagcccc gcaagcagca   4860
agccaatttc cattaattac cgaacagaaa ttgacaaacc atcccagatg caagtgaccg   4920
atgttcagga caacagcatt agtgtcaagt ggctgccttc aagttcccct gttactggtt   4980
acagagtaac caccactccc aaaaatggac caggaccaac aaaaactaaa actgcaggtc   5040
cagatcaaac agaaatgact attgaaggct tgcagcccac agtggagtat gtggttagtg   5100
tctatgctca gaatccaagc ggagagagtc agcctctggt tcagactgca gtaaccaaca   5160
ttgatcgccc taaaggactg gcattcactg atgtggatgt cgattccatc aaaattgctt   5220
gggaaagccc acaggggcaa gtttccaggt acagggtgac ctactcgagc cctgaggatg   5280
gaatccatga gctattccct gcacctgatg gtgaagaaga cactgcagag ctgcaaggcc   5340
tcagaccggg ttctgagtac acagtcagtg tggttgcctt gcacgatgat atggagagcc   5400 agccctgat tggaacccag tccacagcta ttcctgcacc aactgacctg aagttcactc   5460
aggtcacacc cacaagcctg agcgcccagt ggacaccacc caatgttcag ctcactggat   5520
atcgagtgcg ggtgaccccc aaggagaaga ccggaccaat gaaagaaatc aaccttgctc   5580
ctgacagctc atccgtggtt gtatcaggac ttatggtggc caccaaatat gaagtgagtg   5640
tctatgctct taaggacact ttgacaagca gaccagctca gggagttgtc accactctgg   5700
agaatgtcag cccaccaaga agggctcgtg tgacagatgc tactgagacc accatcacca   5760
ttagctggag aaccaagact gagacgatca ctggcttcca agttgatgcc gttccagcca   5820
atggccagac tccaatccag agaaccatca gccagatgt cagaagctac accatcacag   5880
gtttacaacc aggcactgac tacaagatct acctgtacac cttgaatgac aatgctcgga   5940
gctcccctgt ggtcatcgac gcctccactg ccattgatgc accatccaac ctgcgtttcc   6000
tggccaccac acccaattcc ttgctggtat catggcagcc gccacgtgcc aggattaccg   6060
gctacatcat caagtatgag aagcctgggt ctcctccag agaagtggtc cctcggcccc   6120
gccctggtgt cacagaggct actattactg gcctggaacc gggaaccgaa tatacaattt   6180
atgtcattgc cctgaagaat aatcagaaga gcgagccct gattggaagg aaaaagacag   6240
acgagcttcc ccaactggta acccttccac accccaatct tcatggacca gagatcttgg   6300
atgttccttc cacagttcaa aagacccctt tcgtcaccca ccctgggtat gacactggaa   6360
```

-continued

| | |
|---|---|
| atggtattca gcttcctggc acttctggtc agcaacccag tgttgggcaa caaatgatct | 6420 |
| ttgaggaaca tggttttagg cggaccacac cgcccacaac ggccacccccc ataaggcata | 6480 |
| ggccaagacc atacccgccg aatgtaggac aagaagctct ctctcagaca accatctcat | 6540 |
| gggcccccatt ccaggacact tctgagtaca tcatttcatg tcatcctgtt ggcactgatg | 6600 |
| aagaacccctt acagttcagg gttcctggaa cttctaccag tgccactctg acaggcctca | 6660 |
| ccagaggtgc cacctacaac atcatagtgg aggcactgaa agaccagcag aggcataagg | 6720 |
| ttcgggaaga ggttgttacc gtgggcaact ctgtcaacga aggcttgaac caacctacgg | 6780 |
| atgactcgtg ctttgacccc tacacagttt cccattatgc cgttggagat gagtgggaac | 6840 |
| gaatgtctga atcaggcttt aaactgttgt gccagtgctt aggctttgga agtggtcatt | 6900 |
| tcagatgtga ttcatctaga tggtgccatg acaatggtgt gaactacaag attggagaga | 6960 |
| agtgggaccg tcaggagaa atggccaga tgatgagctg cacatgtctt gggaacggaa | 7020 |
| aaggagaatt caagtgtgac cctcatgagg caacgtgtta tgatgatggg aagacatacc | 7080 |
| acgtaggaga acagtggcag aaggaatatc tcggtgccat ttgctcctgc acatgctttg | 7140 |
| gaggccagcg gggctggcgc tgtgacaact gccgcagacc tgggggtgaa cccagtcccg | 7200 |
| aaggcactac tggccagtcc tacaaccagt attctcagag ataccatcag agaacaaaca | 7260 |
| ctaatgttaa ttgcccaatt gagtgcttca tgcctttaga tgtacaggct gacagagaag | 7320 |
| attcccgaga gtaaatcatc tttccaatcc agaggaacaa gcatgtctct ctgccaagat | 7380 |
| ccatctaaac tggagtgatg ttagcagacc cagcttagag ttcttctttc tttcttaagc | 7440 |
| cctttgctct ggaggaagtt ctccagcttc agctcaactc acagcttctc caagcatcac | 7500 |
| cctgggagtt tcctgagggt tttctcataa atgagggctg cacattgcct gttctgcttc | 7560 |
| gaagtattca ataccgctca gtattttaaa tgaagtgatt ctaagatttg gtttgggatc | 7620 |
| aataggaaag catatgcagc caaccaagat gcaaatgttt tgaaatgata tgaccaaaat | 7680 |
| tttaagtagg aaagtcaccc aaacacttct gctttcactt aagtgtctgg cccgcaatac | 7740 |
| tgtaggaaca agcatgatct tgttactgtg atatttaaaa tatccacagt actcactttt | 7800 |
| tccaaatgat cctagtaatt gcctagaaat atctttctct tacctgttat ttatcaattt | 7860 |
| ttcccagtat ttttatacgg aaaaaattgt attgaaaaca cttagtatgc agttgataag | 7920 |
| aggaatttgg tataattatg gtgggtgatt atttttttata ctgtatgtgc caaagcttta | 7980 |
| ctactgtgga aagacaactg ttttaataaa agatttacat ccacaacttt gaagttcatc | 8040 |
| tatttgatat aagacacctt cggggaaat aattcctgtg aatattcttt ttcaattcag | 8100 |
| caaacatttg aaaatctatg atgtgcaagt ctaattgttg atttcagtac aagattttct | 8160 |
| aaaatcagttc ctacaaaaac tgattggttt ttgtcacttc atctcttcac taatggagat | 8220 |
| agctttacac tttctgcttt aatagattta agtggacccc aatatttatt aaaattgcta | 8280 |
| gtttaccgtt cagaagtata atagaaataa tctttagttg ctcttttcta accattgtaa | 8340 |
| ttcttcccctt cttccctcca cctttccttc attgaataaa cctctgttca aagagattgc | 8400 |
| ctgcaaggga aataaaaatg actaagatat taaaaaaaaa aaaaaaaa | 8449 |

<210> SEQ ID NO 35
<211> LENGTH: 4625
<212> TYPE: DNA
<213> ORGANISM: Homo sapiens

<400> SEQUENCE: 35

| | |
|---|---|
| agcgctccgc agtcacgtga cgctcgtccg caacctctgc tgtcctccgc ggcgccccct | 60 |

-continued

```
tccgcctgac gcgccccggg cggcggccgc gcagccctgg ctcctcgcgg gctcgggcgg      120
cggctgcggc ggggctatgg cgagcggcgg tggcggggt aacactggcg cgggtggggg       180
gccggggatg ggcctgagcc tgggcctggg tctgggtctg agcctaggca tgagtgaggc      240
caccagtgag gcagaggagg aggcggccac ggccgaggcg gtgggacgcc tggccacgac      300
gctgtggctg cggctccgcg gctgggaggc ggtgctggcg gcggcgcagc ggttgctggt      360
gtgggagaag ccgctgcaca gcctggtcac ggcggccgcg ctcaacggcc tcttctggtt      420
gctgtcttcc tcgtccctcc ggcccttctt cctactcagc gtctcacttt tggcctattt      480
tctgctggat ctctggcagc ctcgctttct ccctgacgtt tcagcatcat ccccagagga      540
gccacactct gacagtgagg gtgcggggtc aggcgcccgg ccgcacctgc tgagtgtgcc      600
cgagttgtgc agatacctgg ctgagagctg gctcaccttc cagattcacc tgcaggagct      660
gctgcagtac aagaggcaga atccagctca gttctgcgtt cgagtctgct ctggctgtgc      720
tgtgttggct gtgttgggac actatgttcc agggattatg atttcctaca ttgtcttgtt      780
gagtatcctg ctgtggcccc tggtggttta tcatgagctg atccagagga tgtacactcg      840
cctggagccc ctgctcatgc agctggacta cagcatgaag gcagaagcca atgccctgca      900
tcacaaacac gacaagagga agcgtcaggg gaagaatgca cccccaggag gtgatgagcc      960
actggcagag acagagagtg aaagcgaggc agagctggct ggcttctccc cagtggtgga     1020
tgtgaagaaa acagcattgg ccttggccat tacagactca gagctgtcag atgaggaggc     1080
ttctatcttg gagagtggtg gcttctccgt atcccgggcc acaactccgc agctgactga     1140
tgtctccgag gatttggacc agcagagcct gccaagtgaa ccagaggaga ccctaagccg     1200
ggacctaggg gagggagagg agggagagct ggcccctccc gaagacctac taggccgtcc     1260
tcaagctctg tcaaggcaag ccctggactc ggaggaagag gaagaggatg tggcagctaa     1320
ggaaaccttg ttgcggctct catccccct ccactttgtg aacacgcact tcaatggggc      1380
agggtccccc ccagatggag tgaaatgctc ccctggagga ccagtggaga cactgagccc     1440
cgagacagtg agtggtggcc tcactgctct gcccggcacc ctgtcacctc cactttgcct     1500
tgttggaagt gacccagccc cctcccttc cattctccca cctgttcccc aggactcacc      1560
ccagcccctg cctgcccctg aggaagaaga ggcactcacc actgaggact ttgagttgct     1620
ggatcagggg gagctggagc agctgaatgc agagctgggc ttggagccag agacaccgcc     1680 aaaacccct gatgctccac ccctgggcc cgacatccat tctctggtac agtcagacca       1740
agaagctcag gccgtggcag agccatgagc cagccgttga ggaaggagct gcaggcacag     1800
tagggcttcc tggctaggag tgttgctgtt tcctcctttg cctaccactc tggggtgggg     1860
cagtgtgtgg ggaagctggc tgtcggatgg tagctattcc accctctgcc tgcctgcctg     1920
cctgctgtcc tgggcatggt gcagtacctg tgcctaggat tggtttttaaa tttgtaaata    1980 attttccatt tgggttagtg gatgtgaaca gggctaggga agtccttccc acagcctgcg    2040
cttgcctccc tgcctcatct ctattctcat tccactatgc cccaagccct ggtggtctgg    2100 cccttttcttt ttcctcctat cctcaggac ctgtgctgct ctgccctcat gtcccacttg     2160
gttgtttagt tgaggcactt tataattttt ctcttgtctt gtgttccttt ctgctttatt    2220
tccctgctgt gtcctgtcct tagcagctca acccatcct ttgccagctc ctcctatccc     2280
gtgggcactg gccaagcttt agggaggctc ctggtctggg aagtaaagag taaacctggg    2340
gcagtgggtc aggccagtag ttacactctt aggtcactgt agtctgtgta accttcactg    2400
catccttgcc ccattcagcc cggcctttca tgatgcagga gagcagggat cccgcagtac    2460
```

```
atggcgccag cactggagtt ggtgagcatg tgctctctct tgagattagg agcttcctta    2520
ctgctcctct gggtgatcca agtgtagtgg accccctac tagggtcagg aagtggacac    2580
taacatctgt gcaggtgttg acttgaaaaa taaagtgttg attggctaga actgctgcct    2640
ccctgactgt gagctgcctt ccacaccctg cactgcactg tgttctctcc tcacccttaa    2700
cctgcttcac tccagtctgt tctggctgtt tattaccttg ttgcaaaaca gggccgaagc    2760
aaggattacc ttgacaaccc tagcttctcc ttagccatct tccttgacag tgtgatctgt    2820
ttagtgagat ttagcatgtg tgaataaagt atatgcagga ggaaattgct ttgtcttccc    2880
aatcggtaga aattcgggac cataaaaatt gtgttttacc atgtggccta caaccttaac    2940
actgctttct taagaagtct tcacccatct acatgctaac aactcactca gcctggattt    3000
atctttactg gggaagccaa acaagcaata gaggaccttt acctgtgtta gaaatgagtt    3060
ggagccaagg aacactgaag aaatagtatc ttaacagtta ctgagtccat tgtatgtgct    3120
tggctctgct ctgagtgatt tatatgtatt aagattttc ctcacaggtc agatatatac    3180
tgttactaac ttcattttat agacaggtta agcttcctga aggccacagg tcccagtaaa    3240
ttgtggagcc agaacccaaa cccaagaagt tttggcttca gcaaatgcat cagacagccc    3300
ctgtccatta atagggcaca ggtaggaaga tgcacaagga tgtgggaact atagagaacc    3360
aatctgatgc cttggcttaa caaagagtgg acatggcaag ccttcctctt tggggaagaa    3420
aagcccagaa ctgagcagat ggcctccttt atgagttcat gtcctccgcc ttcagctgga    3480
ggtaccatat ggcgatgcta cctgtctttc tgctggaggt accatatggt aatgctgcct    3540
ggctgtctgc tggaggtacc atatggtaat gctgcctgtc tttctgaggt tgacttttat    3600
gccatgtctt tcctaagtgt gtaagaattt ttctgtttgc ttcacatttg actgagaatc    3660
attctagggt ttgattgagc ccctgtcctg tgccactaaa ggaactcgaa cttttcatca    3720
cttagagatt tcagggga atggaaaaac agttctaatc aataagcaag caattcaaga    3780
aaaatagaat taatcaggca atgactgcaa catgtcctat ctttaatcta ttttcttatt    3840
aagcttggac attgacaata gaaccagaag cttgtagctg gatcaaaata ttctccatag    3900
gcctggagtt tcatgagggt ctattctttt gttgttgttg ttttggtttt ttgttttttg    3960
tgggtttttt tttttttttt tttgagacgg agtcttgttc tgttgcccag gctggagtgc    4020
aatggtgcag tcttggttca ctgcaacctc tgcctcccag gttcaaacaa ttctcctgcc    4080
tcagccgtcc aagtagctgg gattacaggt gcatgccacg atgcctggct atttttgta    4140
ttttagtag aggtgggtt tcaccatgtt ggccaggctg gtctcgaact cctgacctca    4200
ggtgattcac ccacctcggc ctcccaaagt gctgggatta caggtgtgag ccacggcgcc    4260
cagcctcatg agggtctatt ctttacattc accatggtct gatggttgct acatgtttgt    4320
ctatgatttt ttttttctat tatcaggtgt cttggccggt tcatgcccca cgatgaaagg    4380
gccagaggtt ttcatatgag taaaagaaaa aagcagaaat gtgaaaccta caattaggct    4440
aaacaaaaat caactggaaa agtacaggct gaggggagaa gagttggcta catgtttatg    4500
ttaggggagg agggagtaca ttttagctat gtattcaaac agctaatagt ttaatgttgc    4560
tgcttataaa cttaatttta ggctgcatta ataaaagtgt agtctcccaa acaaaaaaaa    4620
aaaaa                                                                4625
```

<210> SEQ ID NO 36
<211> LENGTH: 7556
<212> TYPE: DNA
<213> ORGANISM: Homo sapiens

<400> SEQUENCE: 36

```
gcaggcgcct tcgcggaccg agcctgacgg agccggaggc tgggagccgc ggcggcctgg      60
ggaagtgttt ggattgtgag ctatttcaga actgttctca ggactcatta ttttaacatt     120
tgggagaaac acagccagaa gatgcacact tgactgaagg aggacaggga atctgaagac     180
tccggatgac atcagagcta cttttcaaca gccttctcaa ttttctttct cagaaagcag     240
aggctcagag cttggagaca gacgaacact gatatttgca tttaatgggg aacaaaagat     300
gaagaaggaa aaggaatata ttcactaagg attctatctg cttactgcta cagacctatg     360
tgttaaggaa ttcttctcct cctccttgcg tagaagttga tcagcactgt ggtcagactg     420
catttatctt gtcattgcca gaagaaatct tggacagaat gtaacagtac gtctctctct     480
gattgcgatg gaaggtgata aactgatact cctttattaa agttacatcg cactcaccac     540
agaaaaccat tctttaaagt gaatagaaac caagcccttg tgaacacttc tattgaacat     600
gactcatgga gaagagcttg gctctgatgt gcaccaggat tctattgttt taacttacct     660
agaaggatta ctaatgcatc aggcagcagg gggatcaggt actgccgttg acaaaaagtc     720
tgctgggcat aatgaagagg atcagaactt aacatttct ggcagtgcat ttcccacctg      780
tcaaagtaat ggtccagttc tcaatacaca tacatatcag gggtctggca tgctgcacct     840
caaaaaagcc agactgttgc agtcttctga ggactggaat gcagcaaagc ggaagaggct     900
gtctgattct atcatgaatt taaacgtaaa gaaggaagct ttgctagctg gcatggttga     960
cagtgtgcct aaaggcaaac aggatagcac attactggcc tctttgcttc agtcattcag    1020
ctctaggctg cagactgttg ctctgtcaca acaaatcagg cagagcctca aggagcaagg    1080
atatgccctc agtcatgatt ctttaaaagt ggagaaggat ttaaggtgct atggtgttgc    1140
atcaagtcac ttaaaaactt tgttgaagaa aagtaaagtt aaagatcaaa agcctgatac    1200
gaatcttcct gatgtgacta aaaacctcat cagagatagg tttgcagagt ctcctcatca    1260
tgttggacaa agtggaacaa aggtcatgag tgaaccgttg tcatgtgctg caagattaca    1320
ggctgttgca agcatggtgg aaaaaagggc tagtcctgcc acctcaccta aacctagtgt    1380
tgcttgtagc cagttagcat tacttctgtc aagcgaagcc catttgcagc agtattctcg    1440
agaacacgct ttaaaaacgc aaaatgcaaa tcaagcagca agtgaaagac ttgctgctat    1500
ggccagattg caagaaaatg gccagaagga tgttggcagt taccagctcc caaaaggaat    1560
gtcaagccat cttaatggtc aggcaagaac atcatcaagc aaactgatgg ctagcaaaag    1620
tagtgctaca gtgtttcaaa atccaatggg tatcattcct tcttccccta aaaatgcagg    1680
ttataagaac tcactggaaa gaaacaatat aaaacaagct gctaacaata gtttgctttt    1740
acatcttctt aaaagccaga ctatacctaa gccaatgaat ggcacagtc acagtgagag     1800
aggaagcatt tttgaggaaa gtagtacacc tacaactatt gatgaatatt cagataacaa    1860
tcctagtttt acagatgaca gcagtggtga tgaaagttct tattccaact gtgttcccat    1920
agacttgtct tgcaaacacc gaactgaaaa atcagaatct gaccaacctg tttccctgga    1980
taacttcact caatccttgc taaacacttg ggatccaaaa gtcccagatg tagatatcaa    2040
agaagatcaa gatacctcaa agaattctaa gctaaactca caccagaaag taacacttct    2100
tcaattgcta cttggccata agaatgaaga aaatgtagaa aaaaacacca gccctcaggg    2160
agtacacaat gatgtgagca agttcaatac acaaaattat gcaaggactt ctgtgataga    2220
aagccccagt acaaatcgga ctactccagt gagcactcca cctttactta catcaagcaa    2280
agcagggtct cccatcaatc tctctcaaca ctctctggtc atcaaatgga attccccacc    2340
```

```
atatgtctgc agtactcagt ctgaaaagct aacaaatact gcatctaacc actcaatgga    2400
ccttacaaaa agcaaagacc caccaggaga gaaaccagcc caaaatgaag gtgcacagaa    2460
ctctgcaacg tttagtgcca gtaagctgtt acaaaattta gcacaatgtg gaatgcagtc    2520
atccatgtca gtggaagagc agagacccag caaacagctg ttaactggaa acacagataa    2580
accgataggt atgattgata gattaaaatag cccctttgctc tcaaataaaa caaatgcagt    2640
tgaagaaaat aaagcattta gtagtcaacc aacaggtcct gaaccagggc tttctggttc    2700
tgaaatagaa aatctgcttg aaagacgtac tgtcctccag ttgctcctgg ggaaccccaa    2760
caaagggaag agtgaaaaaa aagagaaaac tcccttaaga gatgaaagta ctcaggaaca    2820
ctcagagaga gctttaagtg aacaaatact gatggtgaaa ataaaatctg agccttgtga    2880
tgacttacaa attcctaaca caaatgtgca cttgagccat gatgctaaga gtgccccatt    2940
cttgggtatg gctcctgctg tgcagagaag cgcacctgcc ttaccagtgt ccgaagactt    3000
taaatcggag cctgtttcac ctcaggattt ttctttctcc aagaatggtc tgctaagtcg    3060
attgctaaga caaaatcaag atagttacct ggcagatgat tcagacagga gtcacagaaa    3120
taatgaaatg gcacttctag aatcaaagaa tctttgcatg gtccctaaga aaaggaagct    3180
ttatactgag ccattagaaa atccatttaa aaagatgaaa aacaacattg ttgatgctgc    3240
aaacaatcac agtgccccag aagtactgta tgggtccttg cttaaccagg aagagctgaa    3300
atttagcaga aatgatcttg aatttaaata tcctgctggt catggctcag ccagcgaaag    3360
tgaacacagg agttgggcca gagagagcaa aagctttaat gttctgaaac agctgcttct    3420
ctcagaaaac tgtgtgcgag atttgtcccc gcacagaagt aactctgtgg ctgacagtaa    3480
aaagaaagga cacaaaaata atgtgaccaa cagcaaacct gaatttagca tttcttcttt    3540
aaatggactg atgtacagtt ccactcagcc cagcagttgc atggataaca ggacatttc    3600 atacccaggt gtagtaaaaa ctcctgtgag tcctactttc cctgagcact gggctgtgc    3660 agggtctaga ccagaatctg ggcttttgaa tgggtgttcc atgcccagtg agaaaggacc    3720
cattaagtgg gttatcactg atgcggagaa gaatgagtat gaaaaagact ctccaagatt    3780
gaccaaaacc aacccaatac tatattacat gcttcaaaaa ggaggcaatt ctgttaccag    3840
tcgagaaaca caagacaagg acatttggag ggaggcttca tctgctgaaa gtgtctcaca    3900
ggtcacagcc aaagaagagt tacttcctac tgcagaaacg aaagcttctt tctttaattt    3960
aagaagccct tacaatagcc atatgggaaa taatgcttct cgcccacaca gcgcaaatgg    4020
agaagtttat ggacttctgg gaagcgtgct aacgataaag aaagaatcag aataaaatgt    4080
acctgccatc cagttttgga tcttttaaa actaatgagt atgaacttga gatctgtata    4140
aataagagca tgatttgaaa aaaagcatgg tataattgaa actttttca ttttgaaaag    4200 tattggttac tggtgatgtt gaaatatgca tactaatttt tgcttaacat tagatgtcat    4260
gaggaaacta ctgaactagc aattggttgt ttaacacttc tgtatgcatc agataacaac    4320
tgtgagtagc ctatgaatga aattctttta taaatattag gcataaatta aaatgtaaaa    4380
ctccattcat agtggattaa tgcatttttgc tgcctttatt agggtacttt attttgcttt    4440
tcagaagtca gcctacataa cacatttta aagtctaaac tgttaaacaa ctctttaaag    4500
gataattatc caataaaaaa aaacctagtg ctgattcaca gcttattatc caattcaaaa    4560
ataaattaga aaatatatg cttacatttt tcactttgc taaaaagaaa aaaaaaggt    4620 gtttatttt aactcttgga agaggttttg tggttcccaa tgtgtctgtc ccaccctgat    4680
ccttttcaat atatatttct ttaaaccttg tgctactag taaaaattga ttacaattga    4740
```

```
gggaagtttg atagatcctt taaaaaaaag gcagatttcc attttttgta ttttaactac    4800
tttactaaat taatactcct cctttttacag aattagaaaa gttaacattt atctttaggt    4860
ggtttcctga aaagttgaat atttaagaaa ttgttttttaa cagaagcaaa atggctttc    4920
tttggacagt tttcaccatc tcttgtaaaa gttaattctc accattcctg tggtacctgc    4980
gagtgttatg accaggattc cttaaacctg aactcagacc acttgcatta gaaccatctg    5040
gagcacttgt tttaaaatgc agattcatag gcagcatctc agatctacag aacaagaatc    5100
tctgctaagt ggacctggaa tcttccatct gcatcttaac atgctctcta ggtgtttctt    5160
gtgtttgaga accatgactt atgactttcc tcagaacatg agactgtaaa acaaaaacaa    5220
aaaactatgt gatgcctcta ttttccccaa tacagtcaca catcagctca aaatttgcaa    5280
tattgtagtt catatattac cgttatgtct ttggaaatcg ggttcagaac acttttttatg   5340
acaaaaattg ggtggagggg ataactttca tatctggctc aacatctcag gaaaatctgt    5400
gattatttgt gtgttctaat gagtaacatc tacttagtta gccttaggga tggaaaaaca    5460
gggccactta ccaaactcag gtgattccag gatggtttgg aaacttctcc tgaatgcatc    5520
cttaacctt attaaaacca ttgtcctaag aacaatgcca acaaagctta caacatttag    5580
tttaaaccca agaagggcac taaactcaga ttgactaaat aaaaagtaca aagggcacat    5640
atacgtgaca gaattgtaca caatcactcc attggatctt ttactttaaa gtagtgatga    5700
aaagtacatg ttgatactgt cttagaagaa attaatatat tagtgaagcc acatggggtt    5760
tcagttgcga aacaggtctg tttttatgtt cagtttgtac aatccacaat tcattcacca    5820
gatattttgt tcttaattgt gaaccaggtt agcaaatgac ctatcaaaaa ttattctata    5880
atcactacta gttaggatat tgatttaaaa ttgttctact tgaagtggtt tctaagattt    5940
ttatattaaa aataggtgtg atttcctaat atgatctaaa accctaaatg gttattttc    6000
ctcagaatga tttgtaaata gctactggaa atattataca gtaataggag tgggtattat    6060
gcaacatcat ggagaagtga aggcataggc ttattctgac ataaaattcc actggccagt    6120
tgaatatatt ctattccatg tccatactat gacaatctta ttgtcaacac tatataaata    6180
agctttaaaa caagtcattt ttcttgatcg ttgtggaagg tttggagcct tagaggtatg    6240
tcagaaaaaa tatgttggta ttctcccttg ggtaggggga aatgaccttt ttacaagaga    6300
gtgaaattta ggtcagggaa aagaccaagg gccagcattg ctacttttgt gtgtgtgtgt    6360
gtgggttttg ttttgttttt ttggttggct ggttgttttc gttgttgtta acaaaggaat    6420
gagaatatgt aatacttaaa taaacatgac cacgaagaat gctgttctga tttactagag    6480
aatgttccca atttgaattt agggtgattt taaagaacag tgagaaaggg catacatcca    6540
cagattcact ttgtttatgc atatgtagat acaaggatgc acatatacac attttcaagg    6600
actatttag atatctagac aatttcttct aataaagtca tttgtgaaag ggtactacag     6660
cttattgaca tcagtaaggt agcattcatt acctgtttat tctctgctgc atcttacaga    6720
agagtaaact ggtgagagta tatatttat atatatatat atatatatat atataatatg    6780
tatatatata tatattgact tgttacatga agatgttaaa atcggttttt aaaggtgatg    6840
taaatagtga tttccttaat gaaaaataca tattttgtat tgttctaatg caacagaaaa    6900
gccttttaat ctctttggtt cctgtatatt ccatgtataa gtgtaaatat aatcagacag    6960
gtttaaaagt tgtgcatgta tgtatacagt tgcaagtctg gacaaatgta tagaataaac    7020
cttttattta agttgtgatt acctgctgca tgaaaagtgc atgggggacc ctgtgcatct    7080
gtgcatttgg caaaatgtct taacaaatca gatcagatgt tcatcctaac atgacagtat    7140
```

```
tccatttctg  dacatgacgt  ctgtggttta  agctttgtga  aagaatgtgc  tttgattcga    7200
agggtcttaa  agaattttt   taatcgtcaa  ccacttttaa  acataaagaa  ttcacacaac    7260
tactttcatg  aattttttaa  tcccattgca  aacattattc  caagagtatc  ccagtattag    7320
caatactgga  ataggcac    attaccattc  atagtaagaa  ttctggtgtt  tacacaacca    7380
aatttgatgc  gatctgctca  gtaatataat  ttgccatttt  tattagaaat  ttaatttctt    7440
catgtgatgt  catgaaactg  tacatactgc  agtgtgaatt  ttttgtttt   gtttttaat     7500 cttttagtgt  ttacttcctg  cagtgaattt  gaataaatga  gaaaaatgc   attgtc        7556

<210> SEQ ID NO 37
<211> LENGTH: 1516
<212> TYPE: DNA
<213> ORGANISM: Homo sapiens

<400> SEQUENCE: 37
tgccccacca  ccgctgctcc  tcagcaggcg  cctcaccagc  ctccacaccc  cttgcgcccg      60
cagaaacgcg  cctggccctg  agctgtcacc  accgacactc  tccaggctcc  ggacacgatg     120
caggccatca  agtgtgtggt  ggtgggagat  ggggccgtgg  gcaagacctg  ccttctcatc     180
agctacacca  ccaacgcctt  tcccggagag  tacatcccca  ccgtgtttga  caactattca     240
gccaatgtga  tggtggacag  caagccagtg  aacctggggc  tgtgggacac  tgctgggcag     300
gaggactacg  accgtctccg  gccgctctcc  tatccacaga  cggacgtctt  cctcatctgc     360 ttctcctcg   tcagcccagc  ctcttatgag  aacgtccgcg  ccaagtggtt  cccagaagtg     420
cggcaccact  gccccagcac  acccatcatc  ctggtgggca  ccaagctgga  cctgcgggac     480
gacaaggaca  ccatcgagaa  actgaaggag  aagaagctgg  ctcccatcac  ctacccgcag     540
ggcctggcac  tggccaagga  gattgactcg  gtgaaatacc  tggagtgctc  agctctcacc     600
cagagaggcc  tgaaaaccgt  gttcgacgag  gccatccggg  ccgtgctgtg  ccctcagccc     660
acgcggcagc  agaagcgcgc  ctgcagcctc  ctctaggggt  tgcaccccag  cgctcccacc     720
tagatgggtc  tgatcctcca  ggatccccac  ccaaagcctg  atggcacccc  ggctggccat     780 gctgtccct   cctgtggcg   tttcttagca  gatggctgca  gagcttcgtt  gatggtcttt     840
tctgtactgg  aggcctcctg  aggccaggaa  cgtgcaaatt  tgcaggtgct  gcatcccaag     900
cccctcatgc  tcctgccttc  ctgagggcca  gaggggagcc  ccaggaccca  ttaagccacc     960
cccgtgttcc  tgccgtcagt  gccaactgcc  gcatgtggaa  gcatctaccc  gttcactcca    1020
gtcccacccc  acgcctgact  cccctctgga  aactgcaggc  cagatggttg  ctgccacaac    1080
ttgtgtacct  tcaggatgg   ggctcttact  ccctcctgag  gccagctgct  ctaatatcga    1140
tggtcctgct  tgccagagag  ttcctctacc  cagcaaaaat  gagtgtctca  gaagtgtgct    1200
cctctggcct  cagttctcct  cttttggaac  aacataaaac  aaatttaatt  ttctacgcct    1260
ctggggatat  ctgctcagcc  aatgaaaat   ctggttcaa   ccagccctg   ccatttctta    1320 agactttctg  ctgcactcac  aggatcctga  gctgcactta  cctgtgagag  tcttcaaact    1380
tttaaacctt  gccagtcagg  acttttgcta  ttgcaaatag  aaaacccaac  tcaacctgct    1440
taagcagaaa  ataaatttat  tgattcaaaa  aaaaaaaaaa  aaaaaaaaa   aaaaaaaaa     1500 aaaaaaaaaa  aaaaaa                                                        1516

<210> SEQ ID NO 38
<211> LENGTH: 1641
<212> TYPE: DNA
<213> ORGANISM: Homo sapiens
```

-continued

```
<400> SEQUENCE: 38
ctccctgtgt tggtggagga tgtctgcagc agcatttaaa ttctgggagg gcttggttgt     60
cagcagcagc aggaggaggc agagcacagc atcgtcggga ccagactcgt ctcaggccag    120
ttgcagcctt ctcagccaaa cgccgaccaa ggaaaactca ctaccatgag aattgcagtg    180
atttgctttt gcctcctagg catcacctgt gccataccag ttaaacaggc tgattctgga    240
agttctgagg aaaagcagct ttacaacaaa tacccagatg ctgtggccac atggctaaac    300
cctgacccat ctcagaagca gaatctccta gccccacaga atgctgtgtc ctctgaagaa    360
accaatgact ttaaacaaga gacccttcca agtaagtcca acgaaagcca tgaccacatg    420
gatgatatgg atgatgaaga tgatgatgac catgtggaca gccaggactc cattgactcg    480
aacgactctg atgatgtaga tgacactgat gattctcacc agtctgatga gtctcaccat    540
tctgatgaat ctgatgaact ggtcactgat tttcccacgg acctgccagc aaccgaagtt    600
ttcactccag ttgtccccac agtagacaca tatgatggcc gaggtgatag tgtggtttat    660
ggactgaggt caaaatctaa gaagtttcgc agacctgaca tccagtaccc tgatgctaca    720
gacgaggaca tcacctcaca catggaaagc gaggagttga atggtgcata caaggccatc    780
cccgttgccc aggacctgaa cgcgccttct gattgggaca gccgtgggaa ggacagttat    840
gaaacgagtc agctggatga ccagagtgct gaaaccccaca gccacaagca gtccagatta    900
tataagcgga aagccaatga tgagagcaat gagcattccg atgtgattga tagtcaggaa    960
ctttccaaag tcagccgtga attccacagc catgaatttc acagccatga agatatgctg   1020
gttgtagacc ccaaaagtaa ggaagaagat aaacacctga aatttcgtat ttctcatgaa   1080
ttagatagtg catcttctga ggtcaattaa aaggagaaaa aatacaattt ctcactttgc   1140
atttagtcaa agaaaaaaat gctttatagc aaaatgaaag agaacatgaa atgcttcttt   1200
ctcagtttat tggttgaatg tgtatctatt tgagtctgga ataactaat gtgtttgata   1260
attagtttag tttgtggctt catggaaact ccctgtaaac taaaagcttc agggttatgt   1320
ctatgttcat tctatagaag aaatgcaaac tatcactgta ttttaatatt tgttattctc   1380
tcatgaatag aaatttatgt agaagcaaac aaaatacttt tacccactta aaagagaat   1440
ataacatttt atgtcactat aatcttttgt tttttaagtt agtgtatatt ttgttgtgat   1500
tatctttttg tggtgtgaat aaatctttta tcttgaatgt aataagaatt tggtggtgtc   1560
aattgcttat ttgttttccc acggttgtcc agcaattaat aaaacataac cttttttact   1620
gcctaaaaaa aaaaaaaaaa a                                              1641

<210> SEQ ID NO 39
<211> LENGTH: 6463
<212> TYPE: DNA
<213> ORGANISM: Homo sapiens

<400> SEQUENCE: 39
ctctcttgct cgctcgctcc ctctctctcc tgctggctgc ctgttctagg aagccagcgc     60
ggagagggg gggatgcaca gcacagggga gagagattgc gcatgttggt cagtcgtgtt    120
ttaaagagta cagtgcgggg aggctgagag gggcgcatgc aacaacaact tttggaagga    180
tggaagagaa gaggcgaaaa tactccatca gcagtgacaa ctctgacacc actgacagtc    240
atgcgacatc tacatccgca tcaagatgct ccaaactgcc cagcagcacc aagtcgggct    300
ggccccgaca gaacgaaaag aagcccctccg aggttttccg gacagacttg atcacagcca    360
tgaagatccc ggactcatac cagctcagcc cggatgacta ctacatcctg gcagacccat    420
```

| | |
|---|---|
| ggcgacagga atgggagaaa ggtgtgcagg tgcctgccgg ggcagaggcc atcccagagc | 480 |
| ccgtggtgag gatcctccca ccactggaag gccccctgc ccaggcatcc ccgagcagca | 540 |
| ccatgcttgg tgagggctcc cagcctgatt ggccagggg cagccgctat gacttggacg | 600 |
| agattgatgc ctactggctg gagctcatca actcggagct taaggagatg gagaggccgg | 660 |
| agctggacga gctgacatta gagcgtgtgc tggaggagct ggagaccctg tgccaccaga | 720 |
| atatggccag ggccattgag acgcaggagg ggctgggcat cgagtacgac gaggatgttg | 780 |
| tctgcgacgt gtgtcgctct cctgagggcg aggatggcaa cgagatggtc ttctgtgaca | 840 |
| agtgcaacgt ctgtgtgcat caggcatgct acgggatcct caaggtgccc acgggcagct | 900 |
| ggctgtgccg gacgtgtgcc ctgggtgtcc agccaaagtg cctgctctgc cccaagcgag | 960 |
| gaggagcctt gaagcccact agaagtggga ccaagtgggt gcatgtcagc tgtgccctat | 1020 |
| ggattcctga ggtcagcatc ggctgcccag agaagatgga gcccatcacc aagatctcgc | 1080 |
| atatcccagc cagccgctgg gctctgtcct gcagcctctg caaggaatgc acaggcacct | 1140 |
| gcatccagtg ttccatgcct tcctgcgtca cagcgttcca tgtcacatgc gcctttgacc | 1200 |
| acggcctgga aatgcggact atattagcag acaacgatga ggtcaagttc aagtcattct | 1260 |
| gccaggagca cagtgacggg ggcccacgta atgagcccac atctgagccc acggaaccca | 1320 |
| gccaggctgg cgaggacctg gaaaaggtga ccctgcgcaa gcagcggctg cagcagctag | 1380 |
| aggaggactt ctacgagctg gtggagccgg ctgaggtggc tgagcggctg gacctggctg | 1440 |
| aggcactggt cgacttcatc taccagtact ggaagctgaa gaggaaagcc aatgccaacc | 1500 |
| agccgctgct gaccccaag accgacgagg tggacaacct ggcccagcag gagcaggacg | 1560 |
| tcctctaccg ccgcctgaag ctcttcaccc atctgcggca ggacctagag aggttagaa | 1620 |
| atctgtgcta catggtgaca aggcgcgaga gaacgaaaca cgccatctgc aaactccagg | 1680 |
| agcagatatt ccacctgcag atgaaactta ttgaacagga tctgtgtcga ggcctgtcca | 1740 |
| cctcattccc catcgatggc accttcttca acagctggct ggcacagtcg gtgcagatca | 1800 |
| cagcagagaa catggccatg agcgagtggc cactgaacaa tgggcaccgc gaggaccctg | 1860 |
| ctccagggct gctgtcagag gaactgctgc aggacgagga gacactgctc agcttcatgc | 1920 |
| gggacccctc gctgcgacct ggtgaccctg ctaggaaggc ccgaggccgc acccgcctgc | 1980 |
| ctgccaagaa gaaaccacca ccaccaccac cgcaggacgg gcctggttca cggacgactc | 2040 |
| cagacaaagc ccccaagaag acctggggcc aggatgcagg cagtggcaag gggggtcaag | 2100 |
| ggccacctac caggaagcca ccacgtcgga catcttctca cttgccgtcc agccctgcag | 2160 |
| ccggggactg tcccatccta gccacccctg aaagcccccc gccactggcc cctgagaccc | 2220 |
| cggacgaggc agcctcagta gctgctgact cagatgtcca agtgcctggc cctgcagcaa | 2280 |
| gccctaagcc tttgggccgg ctccggccac ccgcgagag caaggtaacc cggagattgc | 2340 |
| cgggtgccag gctgatgct gggatgggac caccttcagc tgtggctgag aggcccaagg | 2400 |
| tcagcctgca ttttgacact gagactgatg ctacttctc tgatggggag atgagcgact | 2460 |
| cagatgtaga ggccgaggac ggtggggtgc agcgggtcc ccgggaggca ggggcagagg | 2520 |
| aggtggtccg catgggcgta ctggcctcct aactcacccc cttccctgtc ccaggccctg | 2580 |
| ccctggtccc cccacaaggc ctcagcccag tcacaactgc catttccagt ctctgctgag | 2640 |
| tgtcccagac cctcgaggct gccactccgt cgtggtttta tttttaatat agagagagtt | 2700 |
| ttgaattcta cactgttgtc tttcctctgt gctggcctag acattaagga ttccttccac | 2760 |
| ggctccggcc gctaggaccc tgccaggtcc cgcgcaccat ccctgccctg cccacgtggt | 2820 |

-continued

| | | | | |
|---|---|---|---|---|
| attgctgggc | tcctggctag | atgcaagcaa | ggtggacaag | agctcaggac | tccagcccac | 2880 |
| tgccactggg | tgacacagac | tgtcgtttgg | gcattatttc | atggcagatg | ggccagtcca | 2940 |
| gggcctaccc | cgccttgccc | ccagatccca | ctggggtcca | tttggggggt | cctgctacac | 3000 |
| tccaccgatc | cccaaggaag | tataataaac | gatacccagc | cagagtctac | tcactgtcac | 3060 |
| aagcacaacg | agtttatatg | agaaagcact | gagggggtgc | agagggcccg | ctagttccag | 3120 |
| gggaactgaa | agctgttcct | gatcagcccg | tatcatctga | ggcctgcctg | cccaccctgc | 3180 |
| caccctcccc | tcccttgctg | ctctgcccct | gccagtgccc | agcccagcgg | ctctgggaag | 3240 |
| gggttcccag | aatccctcct | gagctgtgcc | atttactcag | gggactccca | aacagccagc | 3300 |
| tgccagtgca | ggtggagggc | tgtaggggag | ggccagtgcc | cagacagggt | catgggctc | 3360 |
| agaccagccc | actgtagaga | atcactctga | ggctccaact | tccttccttc | cttcggggcc | 3420 |
| agtctcggcc | gaagtctggt | cacgctcaga | cagagctgac | cagaccagac | cgtttgcctt | 3480 |
| ttcaagtttc | ctagtcctgc | tacaagatga | gcttcttccg | tggttttcctt | ttggaaactc | 3540 |
| ctccttccaa | caagcagtgg | gatcccgggg | cccagggcgg | gccggtgttg | gccgctgggg | 3600 |
| ctgttgtaag | tcttgctgga | tgttcccctg | ttcctgagcc | ttaacccctc | gcacagccat | 3660 |
| cccccccccc | gtcctgccat | cccccccgc | cgtcctgcct | tccccacccc | acccttaggt | 3720 |
| cccaggtagt | tgctctgaag | agtttcagta | gagtggcccc | aggtgatag | ctcagggaac | 3780 |
| aacaaaaaag | gaattccgtg | aaaacatttt | tttttctttg | atgaattact | cctgggtcac | 3840 |
| ttccaccact | ggtaaagcca | gaacttctcc | aaaaagaacc | ttgcaaaaag | tccagtgaat | 3900 |
| cagtcgaatc | attctgtgga | tgccaaagaa | tattttgacc | ataatacagc | acagcctgga | 3960 |
| cctgacaact | tgtcatttgg | actttttttt | aaatggagtt | ctttagcaac | aaagtataga | 4020 |
| aacatgttca | ttgcacacac | ccaaggagaa | gagctcaagc | gcttggaaga | ggatgctttg | 4080 |
| ctgctgctga | agtgtacctg | ggtgttagat | ttcagatcct | gggctgagcc | cactgtgagc | 4140 |
| tttcctaaac | tgtgagactc | acagagggga | aagatactga | cggtgaaacc | agcatggaaa | 4200 |
| acgtctttac | catgtggttc | cctcctcccc | aaatacataa | agcaaataag | caggatgggg | 4260 |
| aacagcttga | ccttcatcca | cccctaactc | caaaactatc | aaggtacgac | agtggcattg | 4320 |
| tcatcgacac | tcaatttcat | gtgaatttta | gcaaaacagg | aaacaaagat | aatgactcag | 4380 |
| ttcagaggat | cggacaaatg | tgtctagtcc | gggtggactc | ggagggagtg | gggtgggctt | 4440 |
| caaggattct | gggcgttggg | atggcatgag | ctaccctgta | gagtttagtc | tgcctgcccg | 4500 |
| ccttggtagt | agtgaccagt | cagtgtcagc | atcagtgtcc | caaccccagt | ctctgtttac | 4560 |
| tgcctttgaa | cagaacttct | tccttcccca | tgctttgggt | cacctcgggc | tgcaaccctg | 4620 |
| tctgtgccag | attgcccggt | ctgaccctgc | aggaagcaaa | gaggtgagct | taaagaacaa | 4680 |
| ccaaactctg | ccaggggtcc | cagaaagccc | agggtccagc | agtctcagca | cttggcccct | 4740 |
| tgccccttca | caccatcctg | ggcaggggc | tgggcctccc | tggtggcagg | ggtgggtgga | 4800 |
| gaattaggga | gagggtgcaa | cgagtctggc | cccttgcctc | gggctggctg | gtgttcttcc | 4860 |
| aagagcctct | gctcacattg | ttggcctctg | gattctggcc | cttcttcatt | ggctgttgct | 4920 |
| ttggactgga | ctgttgctga | gcctgtgtcc | tgcagaaccc | agatgtctgt | taggctggct | 4980 |
| ggctgctgcg | aggggagggg | ggtggccttt | catttgggt | gccctttcac | tcccaggcca | 5040 |
| agccctggag | caatcttctt | caggcagctg | tctccacctc | caggatgtcc | agcaggctgc | 5100 |
| aaggagaagg | atgccagcca | cccatcctcc | cccagttccc | agcctttccc | ctgttggtca | 5160 |
| cagccgcttc | tgtctttttc | cggtctactg | tccccagtgt | agagggcttt | gctgtccctg | 5220 |

| | |
|---|---:|
| agactgaggc aggttccttt tccaggtcag aggtggaggt agatctttct ctcaaccaca | 5280 |
| tctgcctcca cacacagctc ctccgcaggg aaggagaagc tgctctgtaa ctcattctgg | 5340 |
| ctatcgtccc ccttctcact gacctgaccg cccaccacct ccttcccct catcacatga | 5400 |
| caaaggataa tgtgcaagaa aagtattttt atgtatcata aatgtatttt gaaacaaatg | 5460 |
| agaagaagaa aggtagaagg gtttatttta ttaaatgagc ctgacttagt gacagtgtgt | 5520 |
| gagcatttgc aatgtaaggg cctcagcttc cttggagaag ccaccccagg tttccagaca | 5580 |
| tagatgttga attgtttgtg gggggtgtgc caggccacgt ctcgtgtgtc cgtatgcagg | 5640 |
| catgcctgtg tatactgtgt atgggcacac tgggactagc tgggacaatt cctagagatt | 5700 |
| caactgccca attctaacca acattggcag cggctgaact tggcatttcc ttgctaactg | 5760 |
| ccagatgtgg ccaacctttg tccatatgca aaccactgaa aaatgatctg gatttctata | 5820 |
| gcaaggccct tggggagggc actctcccat gcccttggcc tcgctggcca cattggccaa | 5880 |
| tgagccaggg ctggagtctg agacctttgg ttgttcttta aggcacctcc tgccactttc | 5940 |
| tccctcagag gcacaaacac tttgtgttcc acgtcagttt gaggggacgg tggggggatg | 6000 |
| atatgaatgt cacaggagga gacaccttct gtctttgttt caaagaaagt gatgtgccat | 6060 |
| ttgttaatat acaagagaaa tattgaaaat atattgaaaa gagcaatttt aaattatttt | 6120 |
| tggcttatgt tgcaatattt attttcttgt attagaaaag attcctttgt agagaaaaaa | 6180 |
| tgtattttc attaacgcaa agacctattt ctccttttg tacattgtcc atgtgcgcaa | 6240 |
| cccttaacga gcaatagaat gtatggtcac ctgggtgtgg ccagtgcccg ctgtgccctg | 6300 |
| catgattctg tgttgccgct gctgcatagt tcccagcccc atcctgtcct gctcactcat | 6360 |
| gggggcttcc agaccccggc cccaccaggg cttgtgtcat agggagccct ttgcactcct | 6420 |
| cgtgtgttgg caaacgcagt taataaagca gtgttttctg tgc | 6463 |

<210> SEQ ID NO 40
<211> LENGTH: 2828
<212> TYPE: DNA
<213> ORGANISM: Homo sapiens

<400> SEQUENCE: 40

| | |
|---|---:|
| catagatgaa aatggcaagt tccctggctt tccttctgct caactttcat gtctccctcc | 60 |
| tcttggtcca gctgctcact ccttgctcag ctcagttttc tgtgcttgga ccctctgggc | 120 |
| ccatcctggc catggtgggt gaagacgctg atctgccctg tcacctgttc ccgaccatga | 180 |
| gtgcagagac catggagctg aagtgggtaa gttccagcct aaggcaggtg gtgaacgtgt | 240 |
| atgcagatgg aaaggaagtg gaagacaggc agagtgcacc gtatcgaggg agaacttcga | 300 |
| ttctgcggga tggcatcact gcaggaaggc tgctctccg aatacacaac gtcacagcct | 360 |
| ctgacagtgg aaagtacttg tgttatttcc aagatggtga cttctatgaa aaagccctgg | 420 |
| tggagctgaa ggttgcagca ctgggttcta atcttcacgt cgaagtgaag ggttatgagg | 480 |
| atggagggat ccatctggag tgcaggtcca ccggctggta cccccaaccc caaatacagt | 540 |
| ggagcaacgc caagggagag aacatcccag ctgtggaagc acctgtggtt gcagatggag | 600 |
| tgggcctata tgaagtagca gcatctgtga tcatgagagg cggctccggg gagggtgtat | 660 |
| cctgcatcat cagaaattcc ctcctcggcc tggaaaagac agccagcatt tccatcgcag | 720 |
| accccttctt caggagcgcc cagccctgga tcgcagccct ggcagggacc ctgcctatct | 780 |
| tgctgctgct ctcgccggga gccagttact tcttgtggag acaacagaag gaaataactg | 840 |
| ctctgtccag tgagatagaa agtgagcaag agatgaaaga aatgggatat gctgcaacag | 900 |

-continued

| | |
|---|---|
| agcgggaaat aagcctaaga gagagcctcc aggaggaact caagaggaaa aaaatccagt | 960 |
| acttgactcg tggagaggag tcttcgtccg ataccaataa gtcagcctga tgctctaatg | 1020 |
| gaaaaatggc cctcttcaag cctggaaaaa tggctgaccc catggacacc tcctcaaact | 1080 |
| ctctgcagca gatgtaattc tgtatccaga catggcaaat gccatcctcc ttgtttctga | 1140 |
| ggaccagagg agtgtacagc gtgctgagga gccccatgac ctaccagaca accctgagag | 1200 |
| atttgaatgg cgttactgtg tgcttggctg tgaaagcttc atgtcagaga gacactactg | 1260 |
| ggaggtggaa gtgggggaca gaaaagagtg gcatattggg gtatgtagta agaacgtgga | 1320 |
| gaggaaaaaa gtttgggtca aaatgacacc ggagaacgga tactggacta tgggcctgac | 1380 |
| tgatgggaat aagtatcggg ctctcactga gcccagaacc aacctgaaac ttcctgagcc | 1440 |
| tcctaggaaa gtgggggtca tcctggacta tgagactgga catatctcgt tctacaatgc | 1500 |
| cacggatgga tctcatatct acacatttct gcacgcctct tcctctgagc ctctgtatcc | 1560 |
| tgtattcaga attttgacct tggagcccac tgccctgacc gtttgcccaa taccaaaagt | 1620 |
| agagagttcc cccgatcccg acctagtgcc tgatcattcc ctggagatac cactgacccc | 1680 |
| aggcttagct aatgaaagtg gggagcctca ggctgaagta acatctctgc ttctccctgc | 1740 |
| ccagcctgga gctaagggtc tcaccctcca caacagccag tcagaaccat aaagctacag | 1800 |
| gcacacactg aagcacttta ctgatattca ttcaattatt cataggaca gttgtttgag | 1860 |
| tttggtgcca ccttattggc ccctttatac agataaggaa actggggtgt agaaaagtgt | 1920 |
| attgacttta caaagcagac aggaatagtg aacaacagag ctgggatctg aacaacaatg | 1980 |
| actaacatta atggagaatt taaaacgttc tgagtgctgt gttatgagct ttggtgggtg | 2040 |
| tcactccttt aatcctcaca acaccctgtc aggtagtctc atttggcaag tatggaagca | 2100 |
| gaggcagggc aacattaagt agcttacata actcacacgg taatttgtgc agttgggaga | 2160 |
| tgttcagctt cagtccctgg ccaattgccc gttcttttcc agcctgattt ttcctgcatg | 2220 |
| ggaagagccc acatgtagcc ctgaggttcc cttcccagga cagctccagg atcgagatca | 2280 |
| ctgtgagtgg ttgtggagtt aagacccta tggactcctt cccagctgat tatcagagcc | 2340 |
| ttagacccag cactccttgg attggctctg cagagtgtct tggttgagag aataacgttg | 2400 |
| cagttcccac agggcatgtg actttgaaag agactagagg ccacactcag ttaataatgg | 2460 |
| ggcacagatg tgttcccacc caacaaatgt gataagtgat cgtgcagcca gagccagcct | 2520 |
| tccttcagtc aaggtttcca ggcagagcaa ataccctaga gattctctgt aatattggta | 2580 |
| atttggatga aggaagctag aagaattaca gggatgtttt taatcccact atggactcag | 2640 |
| tctcctggaa aaggatctgt ccactcctgg tcattggtgg atgttaaacc catattcctt | 2700 |
| tcaactgctg cctgctaggg aaaactgctc tcattatca tcactattat tgctcaccac | 2760 |
| tgtatcccct ctactgggca agtgcttgtc aagttctagt tgttcaataa atttgttaat | 2820 |
| aatgctga | 2828 |

<210> SEQ ID NO 41
<211> LENGTH: 2698
<212> TYPE: DNA
<213> ORGANISM: Homo sapiens

<400> SEQUENCE: 41

| | |
|---|---|
| gccgtccgtg ctgactgagg cgctgcagcc aggagccgcg gccggctgcc cagcgctcgc | 60 |
| cgcctccgcg cgtccgcagc cgtccccgcg ccgacatgcg cttggccgcc gccgcgaacg | 120 |
| aggcgtacac ggccccttg gcggtctcgg ggctgctggg ctgcaagcag tgcggcgggg | 180 |

```
gccgcgacca ggacgaggaa cttggcatta gaattcctcg accactagga cagggaccaa    240
gcagattcat cccagaaaag gagatcctcc aagtggggag tgaagacgca cagatgcatg    300
ctttatttgc agattctttt gctgctttgg gccgtttgga taacattacg ttagtgatgg    360
ttttccaccc acaatattta gaaagtttct taaaaactca gcactatcta ctgcaaatgg    420
atgggccgtt accctacat tatcgtcact acattggaat aatggctgcg gcaagacatc     480
agtgctccta cttagtgaac ctgcatgtaa atgatttcct tcatgttggt ggggaccca    540 agtggctcaa tggtttagag aatgctcctc aaaaactaca gaatttagga gaacttaaca    600
aagtgttagc ccatagacct tggcttatta ccaaagaaca cattgaggga cttttaaaag    660
ctgaagagca cagctggtcc cttgcggaat tggtacatgc agtagtttta ctcacacact    720
atcattctct tgcctcattc acattcggct gtggaatcag tccagaaatt cattgtgatg    780
gtggccacac attcagacct ccttctgtta gcaactactg catctgtgac attacaaatg    840
gcaatcacag tgtggatgag atgccggtca actcagcaga aaatgtttct gtaagtgatt    900 cttctttga ggttgaagcc ctcatggaaa agatgaggca gttacaggaa tgtcgagatg     960
aagaagaggc aagtcaggaa gagatggctt cacgttttga aatagaaaaa agagagagta   1020
tgtttgtctt ctcttcagat gatgaagaag ttacaccagc aagagctgta tctcgtcatt   1080
ttgaggatac tagttatggc tataaagatt tctctagaca tgggatgcat gttccaacat   1140 tcgtgtcca ggactattgc tgggaagatc atggttattc tttggtaaat cgcctttatc    1200
cagatgtggg acagttgatt gatgaaaaat ttcacattgc ttacaatctt acttataata   1260
caatggcaat gcacaaagat gttgatacct caatgcttag acgggcaatt tggaactata   1320
ttcactgcat gtttggaata agatatgatg attatgacta tggtgaaatt aaccagctat   1380
tggatcgtag ctttaaagtt tatatcaaaa ctgttgtttg cactcctgaa aaggttacca   1440
aaagaatgta tgatagcttc tggaggcagt tcaagcactc tgagaaggtt catgttaatc   1500
tgcttcttat agaagctagg atgcaagcag aactcctta tgctctgaga gccattaccc    1560
gctatatgac ctgatgcctt ccttcatta aagatgattc tggaatgatc agcagatata    1620
gtctacaagg gggaaggtac taagccccag gaccaatggt agacaaaata attcagaaat   1680
ccattgtgcc atgattcctt tagtttctgc tattttctg tggaaaacca ctgctggcac    1740
aagcagtgac tgtttggcag cttcaagttt agagctgtga agacaggctg ccattcacag   1800
tattttgctt tttgacagta caagatgctg tgtaactgtt ttaatacagc aaatagtaac   1860
tctccaaatc ctgttgcttt tatgttaaat aagataacaa gaattggagc atgcaaagaa   1920
tgggacttgg ataatgactt aagctttata tgtaaagaat tttagaagat cttggtgctg   1980
ctattcctgc tggaggaatg aatagatggc tgtttcagtt aagctattag taataaaagt   2040
gaacattgct actatctgag cctacataca taacttgtgt gatttcaaat taaacttgca   2100
ttatgtgtta atttcttgc atctaaaaaa gcatagaatt cctactcaca cagctcagca    2160
acaaccattt tgatggtaac agttaatttc tttcattagt tttttaaatt cagggttctg   2220
gatattaaat taaatggca ttcttaaaga ttttcttcaa aaagcaatcc taaatgaaag    2280
tgtgtaaatt ataagaagct ggcgatcttt tgatatgctg tttcacagga tcctgacact   2340
ggagggcagc tgtcttgtgc attacttgtg tttccagcac caaagttgtg ggacatgttg   2400
ctgtagactg ctgcgcagtc ctgggtgcat tcagtctctc tgcctctgcc tgcctcctgg   2460
tccccacttt aaaggctgtg cagctcctta aataataaag ctggaaaata ttttagtcg    2520 ggttatcaaa tttgatttac aaaaacgcta acttgtttg aaatgcaaac aggtttgaaa    2580
```

```
atatgtatta agtactttgt attctggaag cgtgaattgc ttttgaagtc tgtcagtatt    2640
actggtattt ttaaataaag aagaattttt ctccaattt  aaaaaaaaaa aaaaaaa       2698

<210> SEQ ID NO 42
<211> LENGTH: 5215
<212> TYPE: DNA
<213> ORGANISM: Homo sapiens

<400> SEQUENCE: 42
cgagcgcggc gcccttgagc tgcaccgcgg cgcaggtttg cgagccgact tgtcagccgg      60
ccaagaaaag gaagctccgt cccttcccgc tcacccggct tccccacccc ttgtactcta     120
aactctgcag agggcgagcg gcgcggccac ggaggcgccg aggaggagcg agccgccgcc     180
gggcagcggc gtgccctcgg gggagagggc gccggagagg aggcggcggc gcggcggcga     240
gggcgcggcg cgcgatggca gctgcttagc ccggcgggcg cggagcagcc ccgagctgtg     300
gctggccagg cggtgcggct gggcggggga cgccgccgcc gttgctgccc ggcccggaga     360
gatgagcacg gaggcggacg agggcatcac tttctctgtg ccaccctctcg ccccctcggg    420 cttctgcacc atccccgagg gcggcatctg caggagggga ggagcggcgg cggtgggcga    480
gggcgaggag caccagctgc caccgccgcc gccgggcagc ttctggaacg tggagagcgc    540
cgctgcccct ggcatcggtt gtccggcggc cacctcctcg agcagtgcca cccgaggccg    600
gggcagctct gttggcgggg gcagccgacg gaccacggtg gcatatgtga tcaacgaagc    660
gagccaaggg caactggtgg tggccgagag cgaggccctg cagagcttgc gggaggcgtg    720
cgagacagtg ggcgccaccc tggaaaccct gcattttggg aaactcgact ttggagaaac    780
caccgtgctg gaccgctttt acaatgcaga tattgcggtg gtggagatga gcgatgcctt    840
ccggcagccg tccttgtttt accaccttgg ggtgagagaa agtttcagca tggccaacaa    900
catcatcctc tactgtgata ctaactcgga ctctctgcag tcactgaagg aaataatttg    960
ccagaagaat actatgtgca ctgggaacta caccttttgtt ccttacatga taactccaca   1020
taacaaagtc tactgctgtg acagcagctt catgaagggg ttgacagagc tcatgcaacc   1080
gaacttcgag ctgcttcttg gacccatctg cttacctctt gtggatcgtt ttattcaact   1140
tttgaaggtg gcacaagcaa gttctagcca gtacttccgg gaatctatac tcaatgacat   1200
caggaaagct cgtaatttat acactggtaa agaattggca gctgagttgg caagaattcg   1260
gcagcgagta gataatatcg aagtcttgac agcagatatt gtcataaatc tgttactttc   1320
ctacagagat atccaggact atgattctat tgtgaagctg gtagagactt tagaaaaact   1380
gccaaccttt gatttggcct cccatcacca tgtgaagttt cattatgcat ttgcactgaa   1440
taggagaaat ctccctggtg acagagcaaa agctcttgat attatgattc ccatggtgca   1500
aagcgaagga caagttgctt cagatatgta ttgcctagtt ggtcgaatct acaaagatat   1560 gttttttggac tctaatttca cggacactga aagcagagac catggagctt cttggttcaa   1620
aaaggcattt gaatctgagc caacactaca gtcaggaatt aattatgcgg tcctcctcct   1680
ggcagctgga caccagtttg aatcttcctt tgagctccgg aaagtggggg tgaagctaag   1740
tagtcttctt ggtaaaaagg gaaacttgga aaaactccag agctactggg aagttggatt   1800
ttttctgggg gccagcgtcc tagccaatga ccacatgaga gtcattcaag catctgaaaa   1860 gcttttaaa  ctgaagacac cagcatggta cctcaagtct attgtagaga caattttaat   1920
atataagcat tttgtgaaac tgaccacaga acagcctgtg gccaagcaag aacttgtgga   1980
cttttggatg gatttcctgg tcgaggccac aaagacagat gttactgtgg ttaggtttcc   2040
```

```
agtattaata ttagaaccaa ccaaaatcta tcaaccttct tatttgtcta tcaacaatga    2100
agttgaggaa aagacaatct ctatttggca cgtgcttcct gatgacaaga aaggtataca    2160
tgagtggaat tttagtgcct cttctgtcag gggagtgagt atttctaaat ttgaagaaag    2220
atgctgcttt ctttatgtgc ttcacaattc tgatgatttc caaatctatt tctgtacaga    2280
acttcattgt aaaaagtttt ttgagatggt gaacaccatt accgaagaga aggggagaag    2340
cacagaggaa ggagactgtg aaagtgactt gctggagtat gactatgaat atgatgaaaa    2400
tggtgacaga gtcgttttag gaaaaggcac ttatgggata gtctacgcag gtcgggactt    2460
gagcaaccaa gtcagaattg ctattaagga aatcccagag agagacagca gatactctca    2520 gccctgcat gaagaaatag cattgcataa acacctgaag cacaaaaata ttgtccagta     2580
tctgggctct ttcagtgaga atggtttcat taaaatcttc atggagcagg tccctggagg    2640
aagtctttct gctctccttc gttccaaatg gggtccatta aaagacaatg agcaaacaat    2700
tggcttttat acaaagcaaa tactggaagg attaaaatat ctccatgaca atcagatagt    2760
tcaccgggac ataaagggtg acaatgtgtt gattaatacc tacagtggtg ttctcaagat    2820
ctctgacttc ggaacatcaa agaggcttgc tggcataaac ccctgtactg aaacttttac    2880
tggtaccctc cagtatatgg caccagaaat aatagataaa ggaccaagag gctacggaaa    2940
agcagcagac atctggtctc tgggctgtac aatcattgaa atggccacag gaaaaccccc    3000 atttatgaa ctgggagaac cacaagcagc tatgttcaag gtgggaatgt ttaaagtcca     3060
ccctgagatc ccagagtcca tgtctgcaga ggccaaggca ttcatactga aatgttttga    3120
accagatcct gacaagagag cctgtgctaa cgacttgctt gttgatgagt ttttaaaagt    3180
ttcaagcaaa aagaaaaaga cacaacctaa gctttcagct ctttcagctg atcaaaatga    3240
atatctcagg agtatatcct tgccggtacc tgtgctggtg gaggacacca gcagcagcag    3300
tgagtacggc tcagtttcac ccgacacgga gttgaaagtg gacccttct ctttcaaaac     3360 aagagccaag tcctgcggag aaagagatgt caagggaatt cggacactct ttttgggcat    3420
tccagatgag aattttgaag atcacagtgc tcctccttcc cctgaagaaa agattctgg     3480 attcttcatg ctgaggaagg acagtgagag gcgagctacc cttcacagga tcctgacgga    3540
agaccaagac aaaattgtga gaaacctaat ggaatcttta gctcaggggg ctgaagaacc    3600
gaaactaaaa tgggaacaca tcacaaccct cattgcaagc ctcagagaat tgtgagatc     3660 cactgaccga aaaatcatag ccaccacact gtcaaagctg aaactggagc tggacttcga    3720
cagccatggc attagccaag tccaggtggt actctttggt tttcaagatg ctgtcaataa    3780
agttcttcgg aatcataaca tcaagccgca ctggatgttt gccttagaca gtatcattcg    3840
gaaggcggta cagacagcca ttaccatcct ggttccagaa ctaaggccac atttcagcct    3900
tgcatctgag agtgatactg ctgatcaaga agacttggat gtagaagatg accatgagga    3960
acagccttca aatcaaactg tccgaagacc tcaggctgtc attgaagatg ctgtggctac    4020
ctcaggcgtg agcacgctca gttctactgt gtctcatgat tcccagagtg ctcaccggtc    4080
actgaatgta cagcttggaa ggatgaaaat agaaaccaat agattactgg aagaattggt    4140
tcggaaagag aaagaattac aagcactcct tcatcgagct attgaagaaa aagaccaaga    4200
aattaaacac ctgaagctta gtcccaacc catagaaatt cctgaattgc ctgtatttca     4260
tctaaattct tctggcacaa atactgaaga ttctgaactt accgactggc tgagagtgaa    4320
tggagctgat gaagacacta taagccggtt tttggctgaa gattatacac tattggatgt    4380
tctctactat gttacacgtg atgacttaaa atgcttgaga ctaaggggag ggatgctgtg    4440
```

-continued

| | |
|---|---|
| cacactgtgg aaggctatca ttgactttcg aaacaaacag acttgactgt tgctcaatct | 4500 |
| aatcttcgat ggaaattcta aaaattaata cagagctgat cttcttgggg gtgggaaaat | 4560 |
| cgaagggaga ggagaaaggc gctgcacttt aaatccagta tttgtttact catgttaaaa | 4620 |
| aaaaaaaaaa cagacaaaac acactgaaat ttcctaacta catctatttc tataatttt | 4680 |
| aaggactctt cataaggact cttaaaataa tcctgaacat tagaacccta atgttcagga | 4740 |
| agattttaat ctaagcattt ttatggaaat attttttaatg cagcagctat tgcacttcag | 4800 |
| ccaaatgttt atttcacaca aaacggatgt aacatttcat gtgatcgtgc accactggaa | 4860 |
| caaaaccaaa atgtgaccat aactgtttag gcttctgtgt gtttgtaata tgctctaata | 4920 |
| atctgagtag aaatgcgtaa tttcaattac tgtataaagt ttatgttttt ttaagtgtgc | 4980 |
| agaatctgag agcaatggtt tttacttctc tgtgttaatt gtaatattga ctctattttg | 5040 |
| taacttaagt ttctgacctg tcgtacattt gtttgagtcg tttatgtact actgaactgt | 5100 |
| accagttgca catgcttgaa ctgtagtaat gttagcttgt tctaaagcta tccattgtgt | 5160 |
| catatttact ctaaaaatta aagagactct caacaaaaaa aaaaaaaaaa aaaaa | 5215 |

<210> SEQ ID NO 43
<211> LENGTH: 4655
<212> TYPE: DNA
<213> ORGANISM: Homo sapiens

<400> SEQUENCE: 43

| | |
|---|---|
| tctgtgcacc ttgcggtggg cggcgaacgg cagccgcggc agcagctagg gggcttgtgc | 60 |
| acacagcgag ggagacttag ggactggcag acggacggac ggacggcgag gaccctaccc | 120 |
| gagcccccga gccatggccg agagaaagca atccgggaag gcggcagagg acgaagaggt | 180 |
| ccctgctttt tttaaaaacc tgggctccgg cagccccaag ccccggcaga aattctgtgg | 240 |
| catgttctgc ccggtggaag ggtcctcgga gaacaagacc atcgacttcg actcgctgtc | 300 |
| ggtgggccgg ggctcggggc aggtggtggc tcagcagcgg gacgtcgccc acttgggccc | 360 |
| ggacccgcag ccgccgtact cgcggcaggg ccggcgcgcc ggcggagagc catctgttga | 420 |
| atcgggccgg aaggtggaga tccggagggc ctcgggcaaa gaagccctgc agaacatcaa | 480 |
| cgaccagagc gatcgtcttc tgatcaaagg aggtaaaatt gttaatgatg accagtcgtt | 540 |
| ctatgcagac atatacatgg aagatggggtt gatcaagcaa ataggagaaa atctgattgt | 600 |
| gccaggagga gtgaagacca tcgaggccca ctcccggatg gtgatccccg gaggaattga | 660 |
| cgtccacact cgtttccaga tgcctgatca gggaatgacg tctgctgatg atttcttcca | 720 |
| aggaaccaag gcggccctgg ctgggggaac cactatgatc attgaccacg ttgttcctga | 780 |
| gcctgggaca agcctgctcg ctgcctttga ccagtggagg gaatgggccg acagcaagtc | 840 |
| ctgctgtgac tactctctgc atgtggacat cagcgagtgg cataagggca tccaggagga | 900 |
| gatggaagcg cttgtgaagg atcacggggt aaattccttc ctcgtgtaca tggctttcaa | 960 |
| agatcgcttc cagctaacgg attgccagat ttatgaagta ctgagtgtga tccgggatat | 1020 |
| tggcgccata gcccaagtcc acgcagaaaa tggcgacatc attgcagagg agcagcagag | 1080 |
| gatcctggat ctgggcatca cgggccccga gggacatgtg ctgagccgac tgaggaggt | 1140 |
| cgaggccgaa gccgtgaatc gtgccatcac catcgccaac cagaccaact gcccgctgta | 1200 |
| tatcaccaag gtgatgagca aaagctctgc tgaggtcatc gcccaggcac ggaagaaggg | 1260 |
| aactgtggtg tatggcgagc ccatcactgc cagcttggga acggacggct cccattactg | 1320 |
| gagcaagaac tgggccaagg ctgctgcctt tgtcacctcc ccaccccttga gccctgatcc | 1380 |

```
aaccactcca gactttctca actccttgct gtcctgtgga gacctccagg tcacgggcag    1440
tgcccattgc acgtttaaca ctgcccagaa ggctgtagga aaggacaact tcaccctgat    1500
tccggagggc accaatggca ctgaggagcg gatgtccgtc atctgggaca aggctgtggt    1560
cactgggaag atggatgaga accagtttgt ggctgtgacc agcaccaatg cagccaaagt    1620
cttcaacctt taccccggga aaggccgcat tgctgtggga tccgatgccg acctggtcat    1680
ctgggacccc gacagcgtta aaaccatctc tgccaagaca cacaacagct ctctcgagta    1740
caacatcttt gaaggcatgg agtgccgcgg ctccccactg gtggtcatca gccaggggaa    1800
gattgtcctg gaggacggca ccctgcatgt caccgaaggc tctggacgct acattccccg    1860
gaagcccttc cctgattttg tttacaagcg tatcaaggca aggagcaggc tggctgagct    1920
gagaggggtt cctcgtggcc tgtatgacgg acctgtgtgt gaagtgtctg tgacgcccaa    1980
gacagtcact ccagcctcct cggccaagac gtctcctgcc aagcagcagg ccccacctgt    2040
ccggaacctg caccagtctg gattcagttt gtctggtgct cagattgatg acaacattcc    2100
ccgccgcacc acccagcgta tcgtggcgcc ccccggtggc cgtgccaaca tcaccagcct    2160
gggctagagc tcctgggctg tgccgtccac tggggactgg ggatgggaca cctgaggaca    2220
ttctgagact tctttcttcc ttccttttt tttttttgtt ttttttttta agagcctgtg    2280
atagttactg tggagcagcc agttcatggg gtcccccttg gggccccaca cccgtctct    2340 caccaagagt tactgatttt gctcatccac ttccctacac atctatgggt atcacaccca    2400
agactaccca ccaagctcat acagggaacc acacccaaca cttagacatg cgaacaagca    2460
gcccccagcg agggtctcct tcgccttcaa cctcctagtg tctgttagca tcttcctttt    2520
catgggggga gggaagataa agtgaattgc ccagagctgc cttttctttt tcttttaaa    2580 aattttaaga agttttcttt gtggggctgg ggaggggccg gggtcaggga gagtcttttt    2640
tttttttttt tttaaatact aaattggaac atttaattcc atattaatac aagggtttg    2700 aactggacat cctaatgatg caattacgtc atcacccagc tgattccggg tggttggcaa    2760
actcatcgtg tctgtcctga gaggctccac aatgcccacc cgcatcgcca ttctgtagtc    2820
ttcagggtca gctgttgata aaggggcagg cttgcgttat tggcctagat tttgctgcag    2880
attaaatcct ttgaggattc tcttctcttt taccattttt ctgcgtgctc tcactctctc    2940
tttctctctc tagcttttta attcatgaat attttcgtgt ctgtctctct ctctctctgt    3000
gtttcctcca gcccttgtct cggagacggt gttttcctcc cttgcccat tatctttttca   3060 cctcccaggt ctaccatttc atggtggtcg ttgggtccgc ctaaaggatt tgagcgtttg    3120
ccattgcaag catagtgctg tgtcatcctg gtccatgtag gactggtgct aaccacctgc    3180
catcatgagg atgtgtgcta gagtgtggga ccctggccaa gtgcaggaat gggccatgcc    3240
gtctcaccca cagtatcaca cgtggaaccg cagacagggc ccagaagctt tagaggtatg    3300
aggctgcaga accggagaga ttttcctctg tgcagtgctc tctggctaaa gtcacggtca    3360
aacctaaaca ccgagcctca ttaacccaag tgaaccaacc aaagtcacca gttcagaagt    3420
gctaagctaa taggagtctg acccgagggc ctgctgcttc ctggttaagt atcttttgag    3480
attctagaac acatgggagc ttttatttt cggggaaaaa ccgtattttt ttcttgtcca    3540
attatttcta aagacacact acatagaaag aggccctata aactcaaaaa gtcattggga    3600
aacttaaagt ctattctact ttgcaagagg agaaatgtgt tttatgaacg atagatcaca    3660
tcagaactcc tgtggggagg aaaccttata aattaaacac atggccccct tagagaccac    3720
aggtgatgtc tgtctccatc cttccctctc cttttctgtc acctttcccc ctagctggct    3780
```

-continued

| | |
|---|---|
| cctttggacc tacccctgtc cttgctgact tgtgttgcat tgtattccaa acgtgtttac | 3840 |
| aggttctctt aagcaatgtt gtatttgcag gcttttctga ataccaaatc tgcttttttgt | 3900 |
| aaagcgtaaa aacatcacaa agtaggtcat tccatcacca cccttgtctc tctacacatt | 3960 |
| ttgcctttgg ggatctggtt ggggttttgg gttttttgtt gttgttgttt atttgttatt | 4020 |
| ttaaaggtaa attgcacttt taaaaaaata attggttgac ttaatatatt tgctttttttt | 4080 |
| ctcacctgca cttagaggaa atttgaacaa gttggaaaaa acaatttttt gtttcaattc | 4140 |
| taagaaacac ttgcagctct agtattcact tgagtcttcc tgttttttcct gtaccgggtc | 4200 |
| atggtaattt ttggttgttt tggttgtttt cttaaaaaac aagttaaaac ctgacgattt | 4260 |
| ctgcaggctg tgtaagcatg tttacctgtt ggcttgcttt gtgtgtctgt taaatgaatg | 4320 |
| tcatatgtaa atgctaaaat aaatcgacag tgtctcagaa ctgaataact gcagtgactt | 4380 |
| gatgctctaa aacagtgtag gatttaagaa tagatggttt ttaatcctgg aaattgtgat | 4440 |
| tgtgacccat gagtggagga actttcagtt ctaaagctga taaagtgtgt agccagaaga | 4500 |
| gtactttttt ttttgtaacc actgtcttga tggcaaaata attatggtaa aaaacaagtc | 4560 |
| tcgtgtttat tattccttaa gaactctgtg ttatattacc atggaacgcc taataaagca | 4620 |
| aaatgtggtt gtttcaggaa aaaaaaaaaa aaaaa | 4655 |

<210> SEQ ID NO 44
<211> LENGTH: 4417
<212> TYPE: DNA
<213> ORGANISM: Homo sapiens

<400> SEQUENCE: 44

| | |
|---|---|
| gctgtaacac tcaccgtgaa ggtctgcagc ttcactcccg agccagcgag accacgaacc | 60 |
| caccagaagg aagaaactct gaacacatct gaacatcaga agggacagac tccagacgcg | 120 |
| ccaccactct gctaacacca gatagtggaa agaaaccatg tgctgaaatg tttgacgaca | 180 |
| ctgatggttt gactctgcta actggaatgg cttattgtgc aagaaagtac acctggtcgg | 240 |
| gtcctggggc tcatctctag caccagcaaa gatttctgaa gacgtctttc tagaaatgac | 300 |
| tggaaagttt caagaggcat aagatacagc atttcttctg aggccctgaa gaagtatcaa | 360 |
| gtgggctttg acattgcggt ggtgagagcg acccctcctc acctggagaa ctgggaaatg | 420 |
| tggattctca gggaccgcgc tgttcacgag ctccaggctg tgctgctggc cctggtcctg | 480 |
| gggcgctgag ccgcatctgc aatagcacac ttgcccggcc acctgctgcc gtgagccttt | 540 |
| gctgctgaag cccctggggt cgcctctacc tgatgaggat gtgcaccccc attaggggc | 600 |
| tgctcatggc ccttgcagtg atgtttggga cagcgatggc atttgcaccc ataccccgga | 660 |
| tcacctggga gcacagagag gtgcacctgg tgcagtttca tgagccagac atctacaact | 720 |
| actcagcctt gctgctgagc gaggacaagg acaccttgta cataggtgcc cggaggcgg | 780 |
| tcttcgctgt gaacgcactc aacatctccg agaagcagca tgaggtgtat tggaaggtct | 840 |
| cagaagacaa aaaagcaaaa tgtgcagaaa aggggaaatc aaaacagaca gagtgcctca | 900 |
| actacatccg ggtgctgcag ccactcagcg ccacttccct ttacgtgtgt gggaccaacg | 960 |
| cattccagcc ggcctgtgac cacctgaact taacatcctt taagtttctg gggaaaaatg | 1020 |
| aagatggcaa aggaagatgt cccttttgacc cagcacacag ctacacatcc gtcatggttg | 1080 |
| atggagaact ttattcgggg acgtcgtata attttttggg aagtgaaccc atcatctccc | 1140 |
| gaaattcttc ccacagtcct ctgaggacag aatatgcaat cccttggctg aacgagccta | 1200 |
| gtttcgtgtt tgctgacgtg atccgaaaaa gcccagacag ccccgacggc gaggatgaca | 1260 |

```
gggtctactt cttcttcacg gaggtgtctg tggagtatga gtttgtgttc agggtgctga    1320
tcccacggat agcaagagtg tgcaaggggg accagggcgg cctgaggacc ttgcagaaga    1380
aatggacctc cttcctgaaa gcccgactca tctgctcccg gccagacagc ggcttggtct    1440
tcaatgtgct gcgggatgtc ttcgtgctca ggtccccggg cctgaaggtg cctgtgttct    1500
atgcactctt cacccacag ctgaacaacg tggggctgtc ggcagtgtgc gcctacaacc     1560
tgtccacagc cgaggaggtc ttctcccacg ggaagtacat gcagagcacc acagtggagc    1620
agtcccacac caagtgggtg cgctataatg gcccggtacc caagccgcgg cctggagcgt    1680
gcatcgacag cgaggcacgg gccgccaact acaccagctc cttgaatttg ccagacaaga    1740
cgctgcagtt cgttaaagac cacccttga tggatgactc ggtaaccca atagacaaca      1800
ggcccaggtt aatcaagaaa gatgtgaact acacccagat cgtggtggac cggacccagg    1860
ccctggatgg gactgtctat gatgtcatgt tgtcagcac agaccgggga gctctgcaca     1920
aagccatcag cctcgagcac gctgttcaca tcatcgagga acccagctc ttccaggact     1980
ttgagccagt ccagaccctg ctgctgtctt caaagaaggg caacaggtttt gtctatgctg   2040
gctctaactc gggcgtggtc caggcccgc tggccttctg tgggaagcac ggcacctgcg     2100
aggactgtgt gctggcgcgg gacccctact gcgcctggag cccgcccaca gcgacctgcg    2160
tggctctgca ccagaccgag agccccagca ggggtttgat tcaggagatg agcggcgatg    2220
cttctgtgtg cccggcctcg tctcctaagc ccctccctcc tcctggctcc tcttccctgt    2280
cctgtctggg ccatgtgggg gacaggaggc tttcctctcc ctggaccccc tggccagcct    2340
cgggtgcggg gcccgacagc agctcgaggg tctccttgct gccgcccttc ctgagtgacc    2400
aggcacagca cgtgcacgcc ctggggaact tctacctctt ctgccaggcc acaggtcctg    2460
cagacattcg ctttgtctgg gagaagaatg ggcgagctct ggagacctgt gtccctgtgc    2520
agacccatgc actgcccgat ggcagggccc atgcactcag ctggctgcag gacgccatca    2580
gggaaagcgc tgagtatcgc tgctctgtcc tctcctcagc agggaacaag acttcgaagg    2640
tgcaggttgc tgtgatgaga cctgaagtga cccaccagga gaggtggacc agagagctct    2700
ctgcctggag ggctgtggct ggggagcacg accggatgat gcagagctgg aggaaggcgt    2760
gggaaagctg tagcaaggac accctgtagc caccaggaag gagtccctga caccgacctc    2820
aaccccaaca gaccctgct gccactgacc acagccaccc ccggagaagg cctggtcccc     2880
cacaactgtg aactgtcttg cccaagcctg ctctgaacac agccattggg ccaccacctg    2940
atgggcagag gcgggacagt ggagaagcct ggaacccaag tgggcctgtg acaggaacta    3000
agacttaaaa aattaggtgc ttacctggga cagtaagttc tgtctggcac aagcaggtaa    3060
ccaggatggc taacaggctt tgatagctgc tcgtgaacta aaacagcagg gtgtgtgcag    3120
gttcctcctc tacggtcagg cagcaggctc tgaaggctga tcctacaccg tcccagtgac    3180
tccccttgac agagtgcccc cacccctaa tagccaacag ggttagcatg ccagcacag     3240
atcgctgctt ttattgatgc aaatcaagcc tgctgcttct cctccctgca gacttagcca    3300
aggaactcca agatgcatga ctgggacaag aaaaggtgag actccacatg gaaatgcctt    3360
gccctaaacc ttgaatgact gtgagatgcg atctgggagt gcatctgtca agtctttgtg    3420
ttttcttcac taacctcaga atactgggct ctattttatc aagcgctgca gtttatgcct    3480
ctgtcccgtc aatgctcagc ttctgcaaca ggacaccaaa cttgatgcag aaagccaaat    3540
aggtcaatta tgcaaatctc ctggtgccat attaaatttc ttgacgatgg aatgagtctc    3600
atgagtgttt tgttctacct gctttcaagt ctctaattat taaagctgta tctctgaaga    3660
```

```
ctgtgtcact gtgtgtgtga acttgtccta aagctactca gcctttaatc ttacacacac    3720
gtctcttctt gtctgttgaa tgacagtttt catgtctatc ataaaaccaa agcctctgtt    3780
aaaagtcaag ccgcacccct ctggtgatcc tagcaaatac tgagtgtctt cccagcagtg    3840
tgacaatgac ctgttttgca tcccctcttt ctggagctgg acaaattctc taccagcctt    3900
tgtgtgggat cagcatacat cgcctgctaa ttccttcagg atccatcaca acaggtgtcc    3960
tgaagatgct ggagacaccc tggttgtctc cacacgttcc ccctccgcac cccaagtcga    4020
gaggcccagc tgcctgtgag gtgtgtgctt gcccatccag ccaaggatgc cagtcttgct    4080
cacggaacca tcacatactc ataacctgaa gttttcctgt aaaatatcca tcagctcact    4140
gtggttcttg ctttgggtgt ggcttcaacc actacaaact gatgagtgaa atgctatggg    4200
ctttaggctt atattcttgg tgctgttttc tgtctcttct cctgaagtct ggatttcaag    4260
cactttcaca cttaacaaaa taattacata cttgaagttt tcgtaatgtg gagtgttcta    4320
ctgggaaatg gagttatgag gatgaatttc tgagtctttc tttgctctgc tggaaaaaat    4380
aaaaatagag ttgtacattg aaaaaaaaaa aaaaaaa                            4417

<210> SEQ ID NO 45
<211> LENGTH: 3108
<212> TYPE: DNA
<213> ORGANISM: Homo sapiens

<400> SEQUENCE: 45
gcctctggct cctcagggca ttcccggcgg ctccgggttt ggcaacgagg acggggagt       60 gcgactgcgt ctcgggcagc atggccgaga agcggcacac acgggactcc gaagcccagc     120
ggctccccga ctccttcaag gacagcccca gtaagggcct tggaccttgc ggatggattt     180
tggtggcgtt ctcattctta ttcaccgtta taactttccc aatctcaata tggatgtgca     240
taaagattat aaaagagtat gaaagagcca tcatctttag attgggtcgc atttttacaag    300 gaggagccaa aggacctggt ttgttttta ttctgccatg cactgacagc ttcatcaaag      360
tggacatgag aactatttca tttgatattc ctcctcagga gatcctcaca aaggattcag     420
tgacaattag cgtggatggt gtggtctatt accgcgttca gaatgcaacc ctggctgtgg     480
caaatatcac caacgctgac tcagcaaccc gtcttttggc acaaactact ctgaggaatg     540
ttctgggcac caagaatctt tctcagatcc tctctgacag agaagaaatt gcacacaaca     600
tgcagtctac tctggatgat gccactgatg cctggggaat aaaggtggag cgtgtggaaa     660
ttaaggatgt gaaactacct gtgcagctcc agagagctat ggctgcagaa gcagaagcgt     720
cccgcgaggc ccgcgccaag gttattgcag ccgaaggaga aatgaatgca tccagggctc     780
tgaaagaagc ctccatggtc atcactgaat ctcctgcagc ccttcagctc cgatacctgc     840
agacactgac caccattgct gctgagaaaa actcaacaat tgtcttccct ctgcccatag     900
atatgctgca aggaatcata ggggcaaaac acagccatct aggctagtgt agagatgagc     960
gctagccttc caagcatgaa gtcggggacc aaattagcct ttaactcata aagagagggt    1020
agggcttttc ttttttccata tgtcaattgt ggtgttccca gaatgtatag cagttataaa   1080
aataggtgaa agaattgtta gcttgtaaat actgagagat tggtgattta tataaggtaa    1140
tctgttagtc ttaaaatagt taaaagtttg tattttaga ttattatgta gtaggttaga     1200
tccctcttgt tttgacttcc actgactcat tctgaacccc ctaagcaccc aggccagagg    1260
caagaacctg ggctgtaact gccacctgac accgctgact ggctaaatgc tttgcagaaa    1320
gtgatgacct tacaccacaa ccagcttctc caggtcatat gtgccttacc tccagagagt    1380
```

-continued

```
cttttttttt tttttctga gatggagttt cactcttgtt gcccaggctg gagtgcaata      1440
gcatgatctc ggctcactgc aacctccgcc tcctgggttc aagagattct cctgcctcag      1500
cctccccagt agctgggatt acaggctcat gccaccatgc ccagctaatt tttgtattat      1560
tattattgtt ttttagtaga gacggggttt caccatgttg gccaggctag tcacgaactc      1620
ctaacctcag gtgatccacc cacctctgcc tcccaaagtg ctgggattac aggcatgagc      1680
taccacacct ggtttggaga gtcttaatta aggaaatttc cctaatgttc atttattttc      1740
taaatccaga ccgtgtttca gaataatcct tacttgagag tagccatttt cttgcctgta      1800
cttgtcagaa ctagaggaaa tagccaagac taatgaaaaa gattactcta acccttaaaa      1860
gacttttaaa ttcactacta gagtggtcat tttaaaaata catccatgtt ttaacttatt      1920
tgagccttct ttatgagtaa atgattcctc cttgttctgt ctttcaaacc agctaaatat      1980
ttgtcacaaa agtgcttttt tctcactgtt gcctattttc atatatcagg ttttaaatag      2040
ttttaatttt ttaataaaat tttctctacg ttctatatgc aattgttata tatctatttg      2100
aatagctgaa ggactaaaat actttttaa gagataactt caggaaacca ttatatttta      2160
ctatctgcat gctgttaact gtggtacact gtgaaatatg ttgattacaa acccattcat      2220
tacatagtat aaggaattca cagtatattg actatatagt gtctaatgat cttgggcaga      2280
tactgtcaaa cttacaatat ctatatagat gtaggtcttt ttaaatttac ctagtcattc      2340
ttctatcatg tatattgatg ctgaaagagg aactggtcag ctcctctgga caacaaattc      2400
ttagtctata atattaggag acatcttctg ttttgcaaat gtctgtgaat ctgagcaacc      2460
tggcattctg cttactggcc agaaagctgg cgggtgacat ttgtaacatt tcctctttga      2520
gactctgagt tcacctagag aagtctaagc ataacagctt tctttcccag cacgagcctt      2580
tatagctctc tttagctcaa ccactctgtc catccagcca atggatgtcc cttcccctgt      2640
accccaattt caagcttatt ttaggaagcc ttgaactacc atgtatcctg gctcctagct      2700
gagtttatta gaggtatgga gcagtgcaac ttaaactcaa gttgcactta cattttgaat      2760
tttaaaatga tggttttatc tgttgtgtga agtggttcac ccttgaggac caggagcctc      2820
catatcctga ctgaaaacct tttctgagac ttagagtaac agtgcttttg gttccttgag      2880
ttctcctgtc tccagatacc aaatgacctt gacttttctg ccttgtgaat tcgtagtcca      2940
atcagctgaa attaaatcac ttgggaggga cgcatagaag gagctctagg aacacagtgc      3000
cagtgcagaa gtttctccag gtggcctccc tttccaacaa tgtacataat aaagtgtatg      3060
cactttcact aataaaaaaa aaaaaaaaaa aaaaaaaaaa aaaaaaaa                   3108
```

<210> SEQ ID NO 46
<211> LENGTH: 4090
<212> TYPE: DNA
<213> ORGANISM: Homo sapiens

<400> SEQUENCE: 46

```
gggcgctccc ggagtatcag caaaagggtt cgccccgccc acagtgcccg gctcccccg        60 ggtatcaaaa gaaggatcgg ctccgccccc gggctcccg ggggagttga tagaagggtc       120
cttcccaccc tttgccgtcc ccactcctgt gcctacgacc caggagcgtg tcagccaaag      180
catggagaat caagagaagg cgagtatcgc gggccacatg ttcgacgtag tcgtgatcgg      240
aggtggcatt tcaggactat ctgctgccaa actcttgact gaatatggcg ttagtgtttt      300
ggttttagaa gctcgggaca gggttggagg aagaacatat actataagga atgagcatgt      360
tgattacgta gatgttggtg gagcttatgt gggaccaacc caaaacagaa tcttacgctt      420
```

```
gtctaaggag ctgggcatag agacttacaa agtgaatgtc agtgagcgtc tcgttcaata    480
tgtcaagggg aaaacatatc catttcgggg cgcctttcca ccagtatgga atcccattgc    540
atatttggat tacaataatc tgtggaggac aatagataac atggggaagg agattccaac    600
tgatgcaccc tgggaggctc aacatgctga caaatgggac aaaatgacca tgaaagagct    660
cattgacaaa atctgctgga caaagactgc taggcggttt gcttatcttt tgtgaatat     720 caatgtgacc tctgagcctc acgaagtgtc tgccctgtgg ttcttgtggt atgtgaagca    780
gtgcgggggc accactcgga tattctctgt caccaatggt ggccaggaac ggaagtttgt    840
aggtggatct ggtcaagtga gcgaacggat aatggacctc ctcggagacc aagtgaagct    900
gaaccatcct gtcactcacg ttgaccagtc aagtgacaac atcatcatag agacgctgaa    960
ccatgaacat tatgagtgca atacgtaat taatgcgatc cctccgacct tgactgccaa    1020
gattcacttc agaccagagc ttccagcaga gagaaaccag ttaattcagc ggcttccaat    1080
gggagctgtc attaagtgca tgatgtatta caaggaggcc ttctggaaga agaaggatta    1140
ctgtggctgc atgatcattg aagatgaaga tgctccaatt tcaataaccct tggatgacac    1200 caagccagat gggtcactgc ctgccatcat gggcttcatt cttgcccgga agctgatcg     1260 acttgctaag ctacataagg aaataaggaa gaagaaaatc tgtgagctct atgccaaagt    1320
gctgggatcc caagaagctt tacatccagt gcattatgaa gagaagaact ggtgtgagga    1380
gcagtactct gggggctgct acacggccta cttccctcct gggatcatga ctcaatatgg    1440
aagggtgatt cgtcaacccg tgggcaggat tttctttgcg ggcacagaga ctgccacaaa    1500
gtggagcggc tacatggaag gggcagttga ggctggagaa cgagcagcta gggaggtctt    1560
aaatggtctc gggaaggtga ccgagaagga tatctgggta caagaacctg aatcaaagga    1620
cgttccagcg gtagaaatca cccacacctt ctgggaaagg aacctgccct ctgtttctgg    1680
cctgctgaag atcattggat tttccacatc agtaactgcc ctggggtttg tgctgtacaa    1740
atacaagctc ctgccacggt cttgaagttc tgttcttatg ctctctgctc actggttttc    1800
aataccacca agaggaaaat attgacaagt ttaaaggctg tgtcattggg ccatgtttaa    1860
gtgtactgga tttaactacc tttggcttaa ttccaatcat tgttaaagta aaaacaattc    1920
aaagaatcac ctaattaatt tcagtaagat caagctccat cttatttgtc agtgtagatc    1980
aactcatgtt aattgataga ataaagcctt gtgatcactt tctgaaattc acaaagttaa    2040
acgtgatgtg ctcatcagaa acaatttctg tgtcctgttt ttattccctt caatgcaaaa    2100
tacatgatga tttcagaaac aaagcatttg actttctgtc tgtggaggtg gagtaggtga    2160
aggcccagcc tgtaactgtc cttttttcttc ccttaggcaa tggtgaactg tcattacaga    2220
gcctagaggc tcacagcctc ctggaggaag cagcctccac tttggatcag gaaatagtaa    2280
aggaaagcag tgttgggggt agcggcatgc agaccctcag accagaatgg ggacatcttg    2340
tggtctgctg cctcaggaat ctcctgacca cttgtagtcc ctccgacttc tctagacatc    2400
tagtctcagt gctagcttat ttgtattttt cctctttcac ttcttatgga ggagagtgtt    2460
taactgagtt agaatgttga aactgacttg ctgtgactta tgtgcagctt tccagttgag    2520
cagaggaaaa tagtggcagg actgtccccc aggaggactc cctgcttagc tctgtgggag    2580
accaactacg actggcatct tctcttcccc ctggaaggca gctagacacc aatggatcct    2640
tgtcagttgt aacattctat ttcaacttca ggaaagcagc agttttcttt taattttttcc    2700 tatgaccata aaattagaca tacctctcaa cttacatatg tcttcaacat ggttacctct    2760
gcataaatat tagcaaagca tgccaatttc tcttaagtac tgaaatacat atgataaatt    2820
```

```
tgactgttat ttgttgagac tatcaaacag aaaagaaatt agggctctaa tttccttaaa      2880
gcaagctcac ttgctttagt tgttaagttt tataaaagac atgaaattga gtcattttat      2940
atatgaaaac taagttctct atcttaggag taatgtcggc ccacaagggt gcccacctct      3000
tgttttcccc ttttaaaaac tcagattttt aaaagcccct tccaaaggtt tcaactgtaa      3060
aatacttctt tttacaatgt atcaacatat ttttatttaa ggggaattaa caattgccag      3120
ggaaaccagc caacccaagt ttattatatc attaaccttta tcataaattc aaacctaagt      3180
tgctggaccc tggtgtgagg acataaatct tccaaagttt tgcctatcct aagagctgca      3240
tttttctact gctctttacc ttgcatttta gctaatttag gagttttgag aatgtattgg      3300
atacgctcca gtacataagg agttgccgca tattatatca gactgctttg agaaatctca      3360
tccctagtct attgcagttg tttctattag cttactgatt aactcagtcc tgacacacct      3420
tttgggaaat gctgatttaa acttcttaac tggcaacagt tggaacagta atcagtttgc      3480
taacatattt aaagtcttga atgttgaaga actcatgtga tttacccttt tcaacttttt      3540
ggaaaacgat ttaatttatt ctaattagat taaccctatt aatctatgga ttgggtatca      3600
aaatgaatgc cagtccagat gtgcctagac acgaaattgg agctgaggac tctcacgata      3660
tgcaagttca tccaacgtga agataccata agcttttct ctgaaccaga gaaatgaaag      3720
tcagtttaag aggctgatag atcttggccc tgttaaggca tccacttcac agttctgaag      3780
gctgagtcag ccccactcca cagttaggcc aagaattaga ttttaaaact tcatctgtct      3840
gtcccagtta actgttaaat aaggcctcat cctccactga agagtatgga ttgaaggatt      3900
gtgaactatg tttagtgtga ttgtgaactt ggtgcctaat gttccatgtc tgaagtttgc      3960
cccagtgcta cacgttggag tatacctatg tgtgtgcttt gccactgaag taagattttg      4020
cctgtatggt actgttttgt ttgttaataa agtgcactgc caccccaat gcaaaaaaaa      4080 aaaaaaaaaa                                                              4090
```

METHODS AND COMPOSITIONS RELATED TO GLUCOCORTICOID RECEPTOR ANTAGONISTS AND BREAST CANCER

This application claims priority to U.S. Provisional Patent application Ser. No. 61/317,182 filed on Mar. 24, 2010, which is hereby incorporated by reference.

This invention was made with government support under CA089208 awarded by the National Institutes of Health. The government has certain rights in the invention.

BACKGROUND OF THE INVENTION

I. Field of the Invention

Embodiments of this invention are directed generally to biology and medicine. In certain aspects methods involve determining the prognosis for a breast cancer patient. In other embodiments, there are methods and compositions for treating a breast cancer patient with a glucocorticoid antagonist.

II. Background

There are over 1 million cases of breast cancer per year on a global basis, of which around 0.5 million are in the US, 40,000 are in the UK and nearly 2,000 in Ireland. It is the leading cause of cancer deaths among women (Keen and Davidson, 2003). Although the overall incidence of the disease is increasing within the western world, wider screening and improved treatments have led to a gradual decline in the fatality rate of about 1% per year since 1991. Inheritance of susceptibility genes, such as BRCA1 and BRCA2, account for only 5% of breast cancer cases and the factors responsible for the other 95% remain obscure (Grover and Martin, 2002). In the absence of a strategy to reduce causative agents of breast cancer, early detection remains the best approach to reducing the mortality rate of this disease. It is widely held that breast cancer initiates as the pre-malignant stage of atypical ductal hyperplasia (ADH), progresses into the pre-invasive stage of ductal carcinoma in situ (DCIS), and culminates in the potentially lethal stage of invasive ductal carcinoma (IDC). This linear model of breast cancer progression has been the rationale for the use of detection methods such as mammography in the hope of diagnosing and treating breast cancer at earlier clinical stages (Ma et al., 2003).

As more molecular information is being collated, diseases such as breast cancer are being sub-divided according to genetic signatures linked to patient outcome, providing valuable information for the clinician. Emerging novel technologies in molecular medicine have already demonstrated their power in discriminating between disease sub-types that are not recognizable by traditional pathological criteria (Sorlie et al., 2001) and in identifying specific genetic events involved in cancer progression (Srinivas et al., 2002).

Endocrine therapy is a popular mode of treatment for all stages of breast cancer. A majority of breast cancers belong to the type in which growth is stimulated by the female sex hormones, estrogens and progesterone. Therefore some of the therapies are based on depriving the tumor of the hormone-induced growth stimulus. Some of the current modes of endocrine treatments include blockade of the estrogen receptor with an antiestrogen, e.g. tamoxifen; hormonal ablation by surgery (oophorectomy, adrenalectomy or hypophysectomy), radiotherapy or medically by administration of a luteinizing hormone-releasing hormone analogue (LH-RHa), e.g., goserelin; suppression of estrogen synthesis with aromatase inhibitors, e.g., anastrozole; pharmacological doses of estrogens and progestagens, e.g., megestrol acetate.

Despite recent advances, the challenge of cancer treatment, including breast cancer therapy remains. Progress is limited with respect to the development of specific treatment regimens to clinically distinct tumor types, and to personalize tumor treatment in order to maximize outcome and efficiency. Moreover, a number of patients exhibit chemotherapy resistance.

Mere classification of breast cancers into a few subgroups characterized by low to absent gene expression of the estrogen receptor (ER) alone may not reflect the cellular and molecular heterogeneity of breast cancer, and may not allow the design of treatment strategies maximizing patient response. Once a patient is diagnosed with cancer, such as breast or ovarian cancer, or an individual wants predisposition analysis, there is a strong need for methods that allow the physician to predict the expected course of disease, including the likelihood of cancer recurrence, long-term survival of the patient, and the like, and accordingly select an appropriate treatment option that is effective.

SUMMARY OF THE INVENTION

Embodiments concern methods, compositions, and apparatuses related to assessing, prognosing, and/or treating breast cancer patients. It concerns using information related to glucocorticoid receptor (GR) activity and/or expression in conjunction with information related to estrogen receptor (ER) activity or expression to identify patients with the least favorable prognosis based on current standards of care for breast cancer. Patients with relatively low levels of estrogen receptor expression and relatively high levels of glucocorticoid expression fall into a group of breast cancer patients with the least favorable prognosis (i.e., mortality rate).

Accordingly, methods concern evaluating a patient with breast cancer. Embodiments include evaluating a biological sample from a patient; evaluating breast cancer cells from a patient; evaluating a biological sample from a breast cancer patient; assessing a breast cancer patient; testing a breast cancer sample or biopsy; testing a breast tumor; prognosing a breast cancer patient; treating a breast cancer patient, particularly a patient with a particular profile related to ER and GR; determining a treatment for a breast cancer patient; altering a treatment plan for a breast cancer patient; reporting prognosis of a breast cancer patient; determining a prognosis score for a breast cancer patient; generating a prognosis score for a breast cancer patient; assessing the risk of mortality of a breast cancer patient generally or within a certain time frame, such as 150 months from end of cancer treatment; generating an ER and GR expression profile for a breast cancer patient; comparing a patient's ER and GR expression profile to a standardized profile; and/or, determining a breast cancer patient has a poor prognosis based on the patient's ER and GR status.

Embodiments also cover apparatuses, kits, and computer readable medium and systems for assessing the level or activity of ER and/or GR in a patient's breast cancer sample and determining a prognosis; and/or treating the patient accordingly. It is specifically contemplated that a breast cancer patient is a human. Accordingly, in human patients, ER refers to an estrogen receptor in a human and GR refers to a glucocorticoid receptor in a human.

Some embodiments include generating an expression profile for glucocorticoid receptor, which means obtaining the level of expression of OR directly or indirectly by measuring or assaying activity or expression. Methods include directly measuring or assaying the level of expression or activity refers to measuring or assaying a sample to determine the level of GR expression (protein or transcript) in the cell. Indirectly obtaining the level of expression includes measuring or assaying expression or activity of a gene or protein that correlates with GR expression or activity. In some embodiments, the level of GR expression can be indirectly obtained by measuring or assaying expression of a GR-responsive gene, which refers to a gene whose expression is affected in a dose-dependent manner by GR expression or activity. Expression refers to either protein expression or RNA (transcript) expression. Methods may involve either type of expression and a variety of assays are well known to those of skill in the art. For example, quantitative PCR may be performed to obtain RNA expression levels. The Affymetrix chip used in the Examples also provides information regarding RNA expression levels. Alternatively, reagents to detect protein expression levels may be employed in embodiments. Methods may involve probes, primers, and/or antibodies that are specific to GR or ER in order to assess expression levels.

In some embodiments, the activity level of GR is measured by assaying the level of GR expression. In additional embodiments, GR expression is GR transcript expression. In other embodiments, GR expression is GR protein expression. As discussed above, in some embodiments, the activity level of GR is measured by assaying the expression level of one or more GR-responsive genes. A GR-responsive gene may be one or more of the following: MCL1, SAP30, DUSP1, SGK1, SMARCA2, PTGDS, TNFRSF9, SFN, LAPTM5, GPSM2, SORT1, DPT, NRP1, ACSL5, BIRC3, NNMT, IGFBP6, PLXNC1, SLC46A3, C14orf139, PIAS1, SERPINF1, ERBB2, PECAM1, LBH, ST3GAL5, IL1R1, BIN1, WIPF1, TFP1, FN1, FAM134A, NRIP1, RAC2, SPP1, PHF15, BTN3A2, SESN1, MAP3K5, DPYSL2, SEMA4D, STOM, or MAOA.

In some embodiments, there is a step of assaying or measuring the activity level of glucocorticoid receptor (GR) in a biological sample from the patient containing breast cancer cells. As discussed above, the activity level of GR can be obtained directly or indirectly. It is specifically contemplated that levels of glucocorticoid activity or expression refers to activity or expression of GR α, GR β, or both. Unless specifically stated otherwise, the terms "glucocorticoid receptor" or "GR" refer to both forms. Embodiments discussed with respect to glucocorticoid receptor or GR may also be implemented solely with GRα or solely with GRβ.

Methods may also include obtaining a level of estrogen receptor (ER) expression in breast cancer cells from the patient. The level can be obtained by obtaining the results of an assay that measured the level of ER expression. In some embodiments, the level is obtained by measuring or assaying the level of ER expression.

In some embodiments, the level of estrogen receptor expression in breast cancer cells from patient is obtained by measuring the level of estrogen receptor expression from the biological sample from the patient. In other embodiments, the level is obtained by receiving qualitative and/or quantitative data regarding the level.

In some embodiments, methods include identifying the patient as having or not having a risk factor for cancer recurrence based on the levels of ER and GR expression. Methods may involve categorizing the patient as ER+ or ER− based the level of estrogen receptor expression and a predetermined threshold value for ER expression. The term "ER+" refers to a classification of ER expression that indicates the patient expresses estrogen receptor in breast cancer cells at or above a certain level. The term "ER−" refers to a classification of ER expression that indicates the patient expresses estrogen receptor at a relatively low level in breast cancer cells, meaning at or below a certain level. In embodiments of the invention, that certain level or a predetermined threshold value is at, below, or above 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percentile, or any range derivable therein.

Methods may involve measuring the activity level of glucocorticoid receptor in a biological sample from the patient containing breast cancer cells and measuring the expression level of estrogen receptor in the biological sample.

In certain embodiments, the predetermined threshold value for ER expression identifies a patient as ER+ if the patient's ER expression level is in the $25^{th}$ percentile or greater compared to a normalized sample. This means the patient may be designated as having a level of ER expression that is at or above 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percentile, or any range derivable therein. It is contemplated that in some cases, a patient may be designated as ER+ if the patient's ER expression level is at or above 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or any range derivable therein. The patient may also be referred to as having a normal or high ER expression level. The higher the percentile, the higher the relative expression level.

In embodiments, methods may also involve categorizing the patient as GR+ or GR− based on a predetermined threshold value for GR activity. In some cases, a predetermined threshold value for GR activity is dependent on whether the patient is categorized as ER+ or ER−. Embodiments may involve a predetermined threshold value for GR activity that identifies a patient as GR+ if the patient is ER− and GR activity level is in the $65^{th}$ percentile or greater compared to a normalized sample. It is contemplated that in some cases, a patient may be designated as GR+ if the patient's GR expression level is at or above 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or any range derivable therein. The threshold value may or may not be dependent on ER expression levels or status. In some embodiments, the threshold value depends on whether the patient is ER− or not. The higher the percentile, the higher the relative expression level.

Methods may involve the use of a normalized sample or control that is based on one or more breast cancer samples that are not from the patient being tested.

In some embodiments, methods involve calculating a prognosis score for the patient based on the levels of ER and/or GR expression. Methods may alternatively or additionally involve reporting a prognosis score or report the levels of ER and/or GR expression. The score or report may contain or reflect raw data regarding expression levels or it may reflect a categorization of the expression levels obtained. A score could indicate the risk factor for mortality, recurrennce, and/or both. The score could be a number within a numeric scale in which one end of the scale is most favorable and the other end is the least favorable with respect to a prognosis for breast cancer.

In certain embodiments, methods may involve identifying the patient as having a poor prognosis if the patient is determined to have a glucocorticoid receptor activity level at or above a certain threshold level and a level of estrogen receptor that is at or below a second threshold level. In each case, the threshold levels are specific for each of GR and ER. In certain embodiments, it is contemplated that a GR level in the 65th percentile or above based on breast cancer patients whose are in the 35$^{th}$ percentile or below is indicative of a poor prognosis. In some embodiments, patients with a poor prognosis include a population of breast cancer patients that numbers approximately 10% or less.

Methods also include identifying the patient as having a poor prognosis if the patient is determined to have i) an activity level of glucocorticoid receptor that is higher than the activity level of glucocorticoid receptor in normalized control sample and ii) a expression level of estrogen receptor expression that is lower than the expression level of estrogen receptor in a normalized control sample. Consequently, methods of the invention include prognosing a breast cancer patient. In some cases, a patient is identified as having a relatively good prognosis.

Other embodiments include methods of treating a patient for breast cancer comprising: treating the patient for breast cancer after a biological sample from the patient containing breast cancer cells is analyzed for i) the activity level of glucocorticoid receptor and ii) the expression level of estrogen receptor. A patient may be treated with a different treatment protocol than the patient would have been treated with if the patient's biological sample had not been analyzed. In some embodiments, the patient is categorized as ER− and GR+ based on the activity level of the glucocorticoid receptor and the expression level of estrogen receptor. In some cases, the patient is treated with a more aggressive therapy than the patient would have been treated with if the patient had not been categorized as ER− and GR+. The term "more aggressive" refers to a treatment regimen that may include more drugs or drugs with more severe side effects and/or it may include an increased dosage or increased frequency of drugs. It may also include radiation or a combination of therapies. In some cases, the therapy includes one or more chemotherapeutics and/or biologics. In some embodiments, the patient is treated with a therapy comprising an anti-angiogenic agent. In additional embodiments, the therapy further comprises a chemotherapeutic agent in addition to the anti-angiogenic agent. Embodiments also include administering a glucocorticoid receptor antagonist and/or tyrosine kinase inhibitor.

Embodiments may also include where the patient is treated with more than one type of cancer therapy. This may be after the patient is determined to have a particular prognosis or after the status of the patient's GR and ER expression profile is known. In some embodiments, certain treatments are provided to an ER−/GR+ breast cancer patient who might have otherwise been treated with a less aggressive treatment for breast cancer. In some embodiments, a patient is treated with at least two of the following: radiation, chemotherapy, or a biologic. In particular embodiments, the patient may be treated with a kinase inhibitor and/or anti-angiogenic agent.

Methods may also involve obtaining a biological sample comprising breast cancer cells from the patient and categorizing the patient as i) GR+ or GR− based on the level of glucocorticoid activity assayed in the sample and compared to a predetermined threshold value for GR activity; and ii) ER+ or ER− based on the level of estrogen receptor expression assayed in the sample and compared to a predetermined threshold value for ER expression.

Any method may also include treating the patient for breast cancer, which may include directly administering or providing a cancer therapy. In some embodiments, a practitioner or doctor may prescribe a cancer therapy that the patient administers to herself.

To achieve these methods, a doctor, medical practitioner, or their staff may retrieve a biological sample from a patient for evaluation. The sample may be a biopsy, such as a breast tissue or tumor biopsy. The sample may be analyzed by the practitioner or their staff, or it may be sent to an outside or independent laboratory. The medical practitioner may be cognizant of whether the test is providing information regarding the patient's level of GR and/or ER expression or activity, or the medical practitioner may be aware only that the test indicates directly or indirectly that the test reflects that the patient has a particular prognosis or can be given a particular prognosis score. Furthermore, the practitioner may know the patient's ER or GR status, such as ER+ or ER−, or GR+ or GR−. Alternatively, she may be aware only that the test or assay indicates the patient has a poor prognosis, or the worst prognosis.

Embodiments also concern kits to determine glucocorticoid receptor status in breast cancer cells comprising: (a) one or more reagents for determining expression levels of NR3C1 in a biological sample; and (b) an algorithm and software encoding the algorithm for calculating a risk factor index from the expression of NR3C1 in a sample and the estrogen receptor status of the breast cancer cells to determine a prognosis or a prognosis score. Kits may also include one or more reagents for determining expression levels of ESR1 in the biological sample to provide estrogen receptor status.

Other embodiments include a computer readable medium having software modules for performing a method comprising the acts of: (a) comparing glucocorticoid receptor data obtained from a patient's breast cancer sample with a reference; and (b) providing an assessment of glucocorticoid receptor status to a physician for use in determining an appropriate therapeutic regimen for a patient. In further embodiments, the computer readable medium further comprises a software module for assessing estrogen receptor status of the patient's breast cancer sample.

Computer systems are also included. In some embodiments, they have a processor, memory, external data storage, input/output mechanisms, a display, for assessing glucocorticoid receptor activity, comprising: (a) a database; (b) logic mechanisms in the computer generating for the database a GR-responsive gene expression reference; and (c) a comparing mechanism in the computer for comparing the GR-responsive gene expression reference to expression data from a patient sample using a comparison model to determine a GR gene expression profile of the sample.

Other embodiments include an internet accessible portal for providing biological information constructed and arranged to execute a computer-implemented method for providing: (a) a comparison of gene expression data of one or more GR-responsive genes in a patient sample with a calculated reporter index; and (b) providing an assessment of GR activity or expression to a physician for use in determining an appropriate therapeutic regime for a patient.

In addition to compiling, collecting and or processing data related to GR status, methods, media and systems may also include the same embodiments with respect to data related to ER status. Such aspects may be instead of or in addition to the aspects related to GR status or data.

Embodiments also include methods of killing breast cancer cells comprising administering to a breast cancer patient an effective amount of a combination of anti-cancer compounds, wherein the anticancer compounds comprise a glucocorticoid receptor antagonist and a chemotherapeutic.

In other embodiments, there are methods for treating breast cancer in a patient comprising administering to the patient an effective amount of glucocorticoid receptor antagonist and a chemotherapeutic.

In further embodiments, methods are provided for treating chemotherapy-insensitive breast cancer cells comprising administering to a breast cancer patient an effective amount of a glucocorticoid receptor antagonist followed by chemotherapy.

Other methods include methods for treating breast cancer in a patient comprising: a) administering radiation or at least a first chemotherapeutic to the patient; b) subsequently administering an effective amount of a glucocorticoid receptor antagonist to the patient; and, c) administering radiation again or at least a second chemotherapeutic to the patient after the glucocorticoid receptor antagonist is administered to the patient.

In some embodiments, there are methods for treating breast cancer in a patient comprising: a) administering an effective amount of a glucocorticoid receptor antagonist to the patient, wherein the patient expresses detectable levels of GR prior to administration of the GR antagonist; h) then administering an effective amount of radiation or at least one chemotherapeutic.

It is contemplated that in methods described herein, breast cancer cells may undergo apoptosis following treatment set forth herein. Moreover, in some embodiments, the combination of a glucocorticoid receptor antagonist and an anticancer agent or compound induces more apoptosis than treatment with just the anticancer treatment alone. In other methods, it is specifically contemplated to exclude treatment with a synthetic glucocorticoid, such as dexamethasone.

Glucocorticoid receptor antagonists are known to those of skill in the art. It refers to a compound or substance that that does not provoke a biological response itself upon binding to the glucocorticoid receptor, but blocks or dampens agonist-mediated responses. Examples include, but are not limited to, beclometasone, betamethasone, budesonide, ciclesonide, flunisolide, fluticasone, mifepristone, mometasone, and triamcinolone. In additional embodiments, the glucocorticoid receptor antagonist has undetectable level or a lower level of activity as a progesterone receptor antagonist. In certain embodiments, the glucocorticoid receptor antagonist has greater than 10-fold, 50-fold, 100-fold, 200-fold, 300-fold, 400-fold, 500-fold, 1000-fold lower binding activity (or any range derivable therein) for another hormone receptor compared to its binding activity for glucocorticoid receptor. In specific embodiments the hormone receptor is estrogen receptor or progesterone receptor.

In some embodiments, a patient had been previously treated with an anti-cancer therapy, such as radiation, chemotherapy, or immunotherapy (or a combination or multiple therapies thereof). In certain embodiments, a first anti-cancer therapy prior to therapy with glucocorticoid receptor antagonist was last administered more than two weeks prior to the glucocorticoid receptor antagonist or its combination with a second anti-cancer therapy. In certain embodiments, this first anti-cancer therapy that does not include a glucocorticoid receptor antagonist was last administered to the breast cancer patient at least 7, 8, 9, 10, 11, 12, 13, 14 days, and/or 1, 2, 3, 4, or 5 weeks, and/or 1, 2, 3, 4, 5, 6, 7, 8, 9, 10, 11, or 12 months prior to treatment with a glucocorticoid receptor antagonist. Treatment methods may be applied to breast cancer or breast cancer cells that are chemo-resistant or breast cancer cells that are not chemo-sensitive. Moreover, treatment may be applied to breast cancer or to breast cancer cells that were previously administered a first apoptosis inducing agent, but were resistant to apoptosis.

In some embodiments, the breast cancer cells are determined to be resistant to apoptosis. In additional embodiments, the breast cancer or the breast cancer cells are determined not to be chemo-sensitive or are determined to be chemo-resistant. This determination may be based on the results of a genetic test or based on information obtained from an assessment of a tumor or the breast cancer after treatment with a first anti-cancer therapy. In specific embodiments, the first anti-cancer therapy is a chemotherapeutic, Herceptin®, radiation, a combination of chemotherapeutics, or a combination of one or more chemotherapeutic agents and Herceptin®.

In additional embodiments, the breast cancer cells express a detectable level of glucocorticoid receptor or its transcript. In some embodiments, the patient is determined to have breast cancer cells that express a detectable level of glucocorticoid receptor or its transcript. This may be determined directly or indirectly.

It is contemplated that breast cancer cells may be treated with a glucocorticoid receptor antagonist regardless of estrogen receptor status. Therefore, breast cancer cells may be estrogen receptor-negative (ER−) or estrogen receptor-positive (ER+), accordingly to a standardized and industry accepted test for ER status. In certain embodiments, the breast cancer cells do not express any detectable levels of ER; in other embodiments, ER expression is detectable in the breast cancer cells.

It is contemplated that breast cancer cells may be treated with a glucocorticoid receptor antagonist depending on or regardless of progesterone receptor status. Therefore, breast cancer cells may be progesterone receptor-negative (PR−) or progesterone receptor-positive (PR+); accordingly to a standardized and industry accepted test for ER status. In certain embodiments, the breast cancer cells do not express any detectable levels of PR; in other embodiments, PR expression is detectable in the breast cancer cells.

Methods involve treating breast cancer, particularly a chemo-resistant breast cancer, with a combination of therapies that includes a glucocorticoid receptor antagonist and an anticancer therapy that induces apoptosis (together they may be referred to as a combination of anti-cancer agents or compounds), such as a chemotherapeutic. In some embodiments, the chemotherapeutic is capecitabine, carboplatin, cyclophosphamide (Cytoxan), daunorubicin, docetaxel (Taxotere), doxorubicin (Adriamycin), epirubicin (Ellence), fluorouracil (also called 5-fluorouracil or 5-FU), gemcitabine, eribulin, ixabepilone, methotrexate, mitomycin C, mitoxantrone, paclitaxel (Taxol), thiotepa, vincristine, or vinorelbin, or a combination of these agents. In other embodiments, therapy with a glucocorticoid receptor antagonist is combined Herceptin®, radiation, chemotherapeutic(s) and radiation, a combination of chemotherapeutics, or a combination of one or more chemotherapeutic agents and Herceptin®.

It is contemplated that in some embodiments of the combination therapy the glucocorticoid receptor antagonist is administered within 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof within administration of at least one or the combination of the anti-cancer agents or compounds. In specific embodiments, the glucocorticoid receptor antagonist is administered within 2 hours, 12 hours or 24 hours of administration of a anticancer agent or compound (or a combination of such agents or compounds).

It is specifically contemplated that treatment may continue or be repeated. In some embodiments, once treated with the combination of a glucocorticoid receptor antagonist and at least one anticancer agent or compound, all or part of the treatment may be repeated alone or in combination with a different anticancer agent or compound.

In certain embodiments, the glucocorticoid receptor antagonist is administered prior to as the other agent or therapy included in the combination therapy. In certain embodiments, the glucocorticoid receptor antagonist is administered 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof prior to administration of at least one or the combination of the anti-cancer agents or compounds. It is specifically contemplated that in some embodiments, the glucocorticoid receptor antagonist is given prior to administration of the anticancer agent or compound but that the glucocorticoid receptor antagonist is also given concurrently with or after administration of the initial or a subsequent dose of the anticancer agent or compound. As discussed throughout, the anticancer agent or compound may be in a combination of such agents or compounds. In certain embodiments, the glucocorticoid receptor antagonist is administered up to three days prior to administering the anticancer agent or compound.

Additionally or alternatively, the glucocorticoid receptor antagonist is administered after administration of the other agent or therapy included in the combination therapy. In certain embodiments, the glucocorticoid receptor antagonist is administered 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof after administration of at least one or the combination of the anti-cancer agents or compounds. It is specifically contemplated that in some embodiments, the glucocorticoid receptor antagonist is given after to administration of the anticancer agent or compound; such administration may be repeated. As discussed throughout, the anticancer agent or compound may be in a combination of such agents or compounds. In certain embodiments, the glucocorticoid receptor antagonist is administered up to three days after administering the anticancer agent or compound.

In certain embodiments, the breast cancer is an unresectable breast cancer. In further embodiments, the breast cancer is inflammatory breast cancer.

It is specifically contemplated that in some methods, dexamethasone has not been administered to the patient within 24 hours of administration of the glucocorticoid receptor antagonist.

Compositions are contemplated to include a glucocorticoid receptor antagonist and any other anticancer compound discussed herein, such a Herceptin or one or more chemotherapeutic compounds. In some embodiments, the composition is in a pharmaceutically acceptable formulation.

Use of the one or more compositions may be employed based on methods described herein. Other embodiments are discussed throughout this application. Any embodiment discussed with respect to one aspect of the invention applies to other aspects of the invention as well and vice versa. The embodiments in the Example section are understood to be embodiments of that are applicable to all aspects of the technology described herein.

"Cancer prognosis" generally refers to a forecast or prediction of the probable course or outcome of the cancer. As used herein, cancer prognosis includes the forecast or prediction of any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, and/or duration of response in a patient or a group of patients susceptible to or diagnosed with a cancer.

In certain aspects, prognosis is an estimation of the likelihood of metastasis free survival of said patient over a predetermined period of time, e.g., over a period of 5 years.

In further aspects, prognosis is an estimation of the likelihood of death of disease of said patient over a predetermined period of time, e.g., over a period of 5 years.

The term "recurrence" refers to the detection of breast cancer in form of metastatic spread of tumor cells, local recurrence, contralateral recurrence or recurrence of breast cancer at any site of the body of the patient after breast cancer had been substantially undetectable or responsive to treatments.

As used herein, "prognostic for cancer" means providing a forecast or prediction of the probable course or outcome of the cancer. In some embodiments, "prognostic for cancer" comprises providing the forecast or prediction of (prognostic for) any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, and/or duration of response in a patient or a group of patients susceptible to or diagnosed with a cancer.

By "gene" is meant any polynucleotide sequence or portion thereof with a functional role in encoding or transcribing a protein or regulating other gene expression. The gene may consist of all the nucleic acids responsible for encoding a functional protein or only a portion of the nucleic acids responsible for encoding or expressing a protein. The polynucleotide sequence may contain a genetic abnormality within exons, introns, initiation or termination regions, promoter sequences, other regulatory sequences or unique adjacent regions to the gene.

As used herein, "treatment" or "therapy" is an approach for obtaining beneficial or desired clinical results. This includes: reduce the number of cancer cells; reduce the tumor size; inhibit (i.e., slow to some extent and/or stop) cancer cell infiltration into peripheral organs; inhibit (i.e., slow to some extent and/or stop) tumor metastasis; inhibit, to some extent, tumor growth; and/or relieve to some extent one or more of the symptoms associated with the disorder, shrinking the size of the tumor, decreasing symptoms resulting from the disease, increasing the quality of life of those suffering from the disease, decreasing the dose of other medications required to treat the disease, delaying the progression of the disease, and/or prolonging survival of patients.

The term "therapeutically effective amount" refers to an amount of the drug that may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The terms "overexpress", "overexpression", "overexpressed", "up-regulate", or "up-regulated" interchangeably refer to a biomarker that is transcribed or translated at a detectably greater level, usually in a cancer cell, in comparison to a non-cancer cell or cancer cell that is not associated with the worst or poorest prognosis. The term includes overexpression due to transcription, post transcriptional processing, translation, post-translational processing, cellular localization, and/or RNA and protein stability, as compared to a non-cancer cell or cancer cell that is not associated with the worst or poorest prognosis. Overexpression can be detected using conventional techniques for detecting mRNA (i.e., RT-PCR, PCR, hybridization) or proteins (i.e., ELISA, immunohistochemical techniques, mass spectroscopy). Overexpression can be 10%, 20%, 30%, 40%, 50%, 60%, 70%, 80%, 90% or more in comparison to a normal cell or cancer cell that is not associated with the worst or poorest prognosis. In certain instances, overexpression is 1-fold, 2-fold, 3-fold, 4-fold 5, 6, 7, 8, 9, 10, or 15-fold or more higher levels of transcription or translation in comparison to a non-cancer cell or cancer cell that is not associated with the worst or poorest prognosis.

"Biological sample" includes sections of tissues such as biopsy and autopsy samples, and frozen sections taken for histologic purposes. Such samples include breast cancer tissues, cultured cells, e.g., primary cultures, explants, and transformed cells. A biological sample is typically obtained from a mammal, such as a primate, e.g., human.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., breast), the size and type of the tumor, among other factors. Representative biopsy techniques include, but are not limited to, excisional biopsy, incisional biopsy, needle biopsy, and surgical biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy", or a "fine-needle aspiration biopsy" which generally obtains a suspension of cells from within a target tissue. Biopsy techniques are discussed, for example, in Harrison's Principles of Internal Medicine, 2005. Obtaining a biopsy includes both direct and indirect methods, including obtaining the biopsy from the patient or obtaining the biopsy sample after it is removed from the patient.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 7. Schematic of glucocorticoid receptor (GR) isoforms.

DETAILED DESCRIPTION OF THE INVENTION

Figure 1:
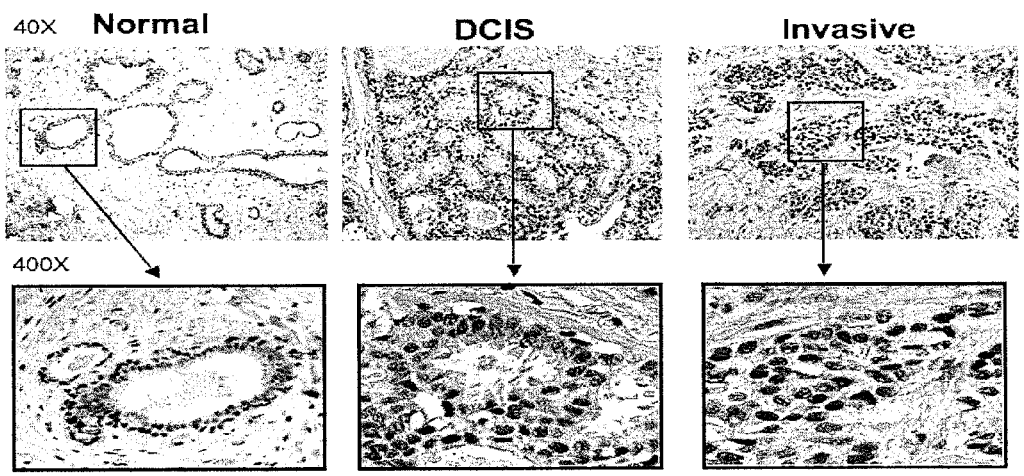
FIG. 1. Primary human breast ductal epithelium, DCIS (60%) invasive human cancers ('30-40%) exhibit significant glucocorticoid receptor expression.
Figure 2:
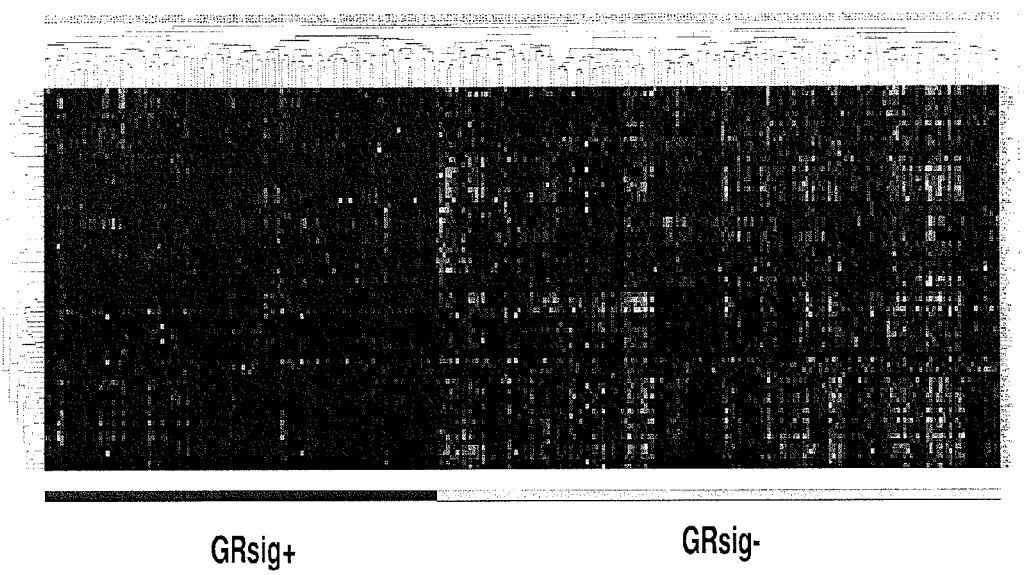
FIG. 2. Unsupervised cluster analysis identifies GR target gene signature (Sig+) vs Sig− tumors (n=68 genes) A GR-regulated gene expression set from MCF10A-Myc (ER−/GR−) cells treated+/−Dex from 30m-24 h was used to perform a two dimensional unsupervised clustering analysis on the NKI-295 early breast cancer gene expression data set (n=2034 starting genes). GR-regulated genes (n=68) that separate these tumors into two groups (GRsig+=Red and GRsig−=Green) are shown in rows while each column represents a patient. Several EMT genes (e.g. Snail) and known anti-apoptotic genes are included.
Figure 3:
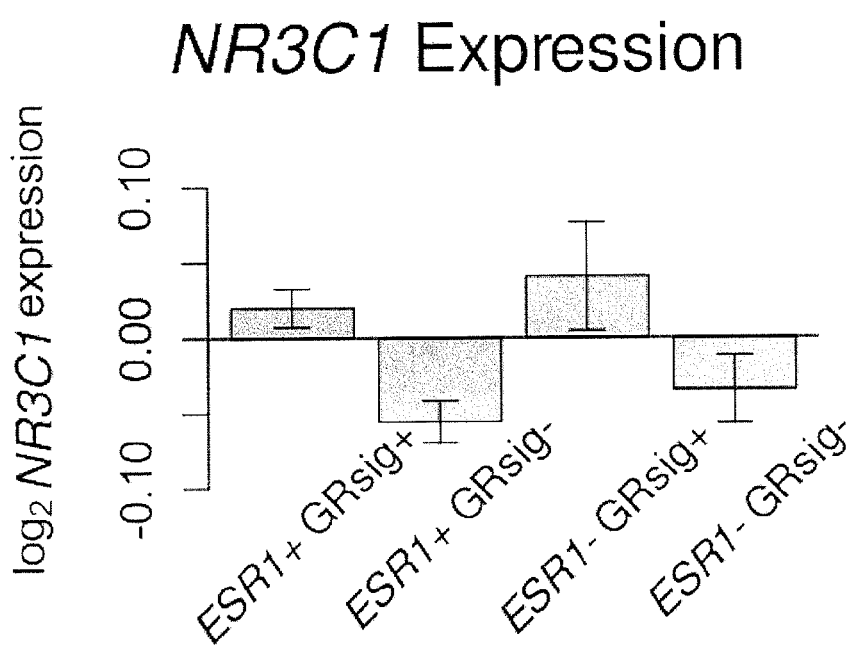
FIG. 3. NR3C1 expression correlates with GR signature gene expression. The GRsig+ vs. GRsig− tumor designations correlate with higher NR3C1 vs. lower expression, respectively. For ESR1+ tumors (orange) the P<0.00001 and for ESR1− tumors (green) p=0.7 (t test). Error bars are +/−SD.
Figure 4:
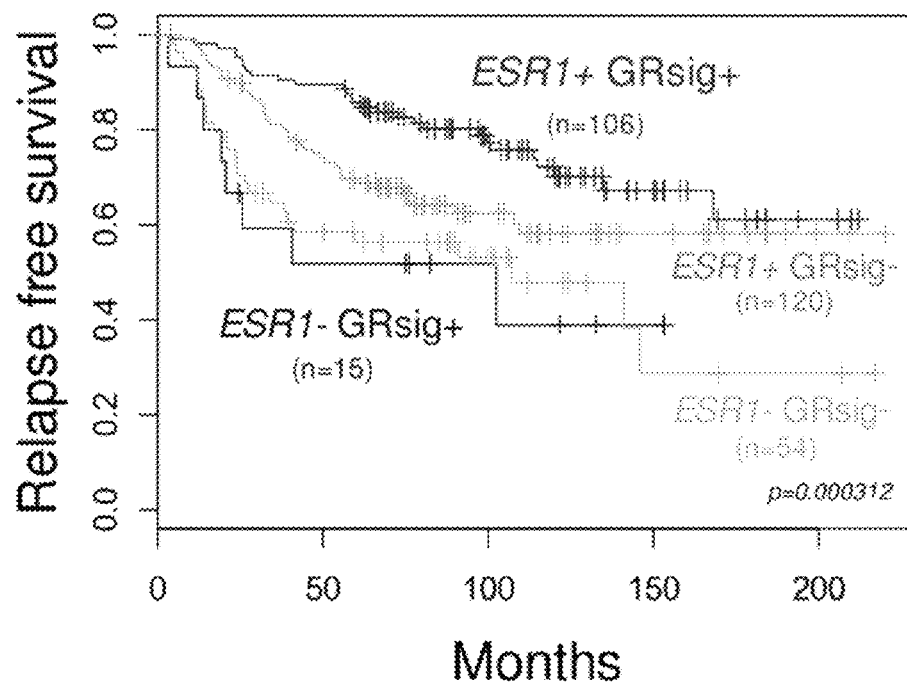
FIG. 4. RFS of GR gene expression signature. The GR signature predicts a differential prognosis for ESR1+ patients and ESR1− pts with respect to GR-signature expression. ESR1−/GR+ signature patients have the worst prognosis.
Figure 5:
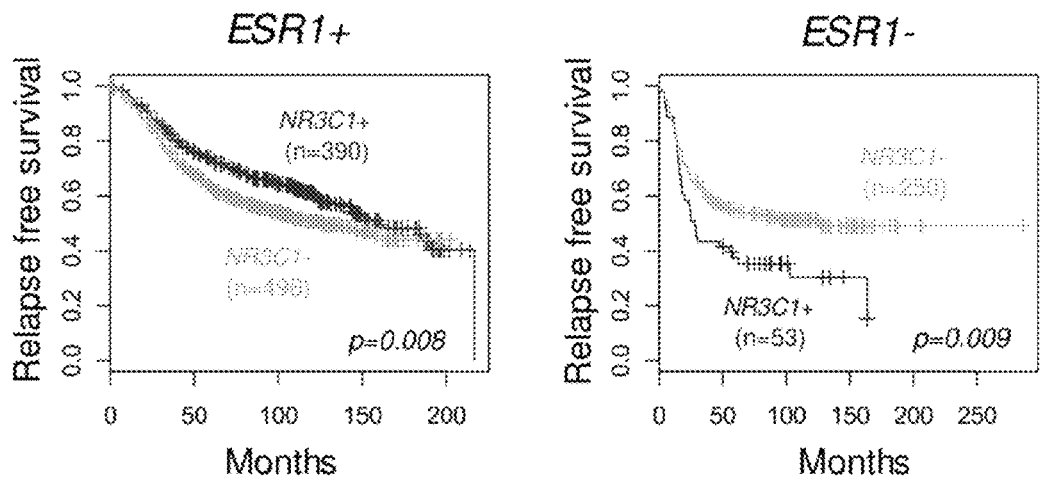
FIG. 5. Meta-analysis of NR3C1 expression and RFS.
Figure 6:
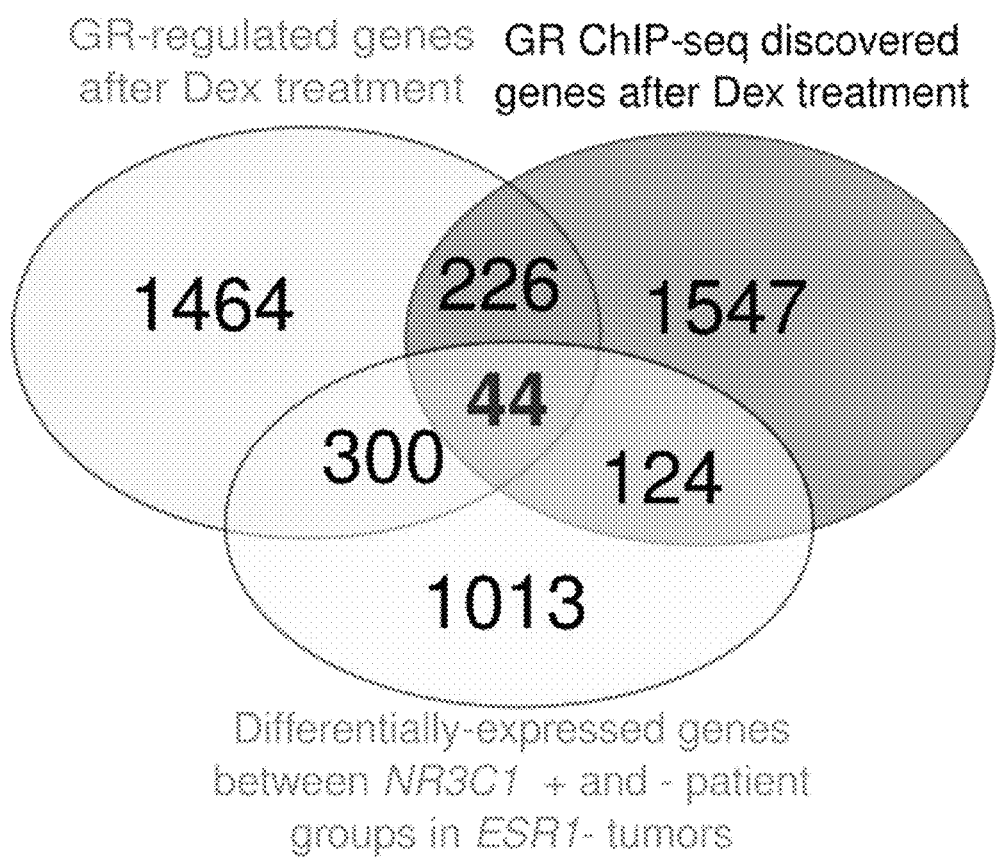
FIG. 6. Common genes differentially expressed in ESR1− and NR3C1+/− tumors, ChIP-seq and gene expression in Dex-treated MCF10A-Myc cells.

Glucocorticoid receptor (GR) activation initiates a potent cell survival signal in ER-breast cancer models. However, GR activity has not been previously examined in primary human breast cancers. Because anti-apoptotic signaling is believed to be an important determinant of breast cancer viability and relapse, the inventors contemplate that early stage primary human breast cancer demonstrates a correlation between high GR (NR3C1) and GR-mediated gene expression and cancer recurrence.

The Dutch NKI 295 data set was examined and the inventors determined that a gene expression signature of 68 GR-regulated genes (based on in vitro data) could cluster patients into different groups with differential outcome. In addition, it was found that GR-mediated gene expression correlated with NR3C1 expression levels. The inventors examined NR3C1 tumor expression in a much larger meta-dataset and again found that ER−/GR (NR3C1)+ patients did the worst. Moreover, key cell survival genes identified as GR gene targets from ChIP-seq experiments were differentially expressed.

I. Hormone Receptor Status of Breast Cancer

Intracellular receptors (IRs) form a class of structurally-related genetic regulators scientists have named "ligand dependent transcription factors" (R. M. Evans, Science, 240: 889, 1988). Steroid receptors are a recognized subset of the IRs, including androgen receptor (AR), progesterone receptor (PR), estrogen receptor (ER), glucocorticoid receptor (GR), and mineralocorticoid receptor (MR). Regulation of a gene by such factors requires both the IR itself and a corresponding ligand, which has the ability to selectively bind to the IR in a way that affects gene transcription.

Naturally occurring as well as synthetic steroidal glucocorticoids (e.g., cortisol, cortisone, prednisolone, dexamethasone) have been widely used for over fifty years for the treatment of acute and chronic inflammatory and immune disorders. In particular, glucocorticoids have been prescribed for the treatment of rheumatoid arthritis, osteoarthritis, rheumatic fever, asthma, allergic rhinitis, systemic lupus erythematosus, chronic obstructive pulmonary disease, Crohn's disease, inflammatory bowel disease, and ulcerative colitis. However, the use of glucocorticoids is often associated with severe and sometimes irreversible side effects such as bone loss/osteoporosis, hyperglycemia, diabetes mellitus, hypertension, glaucoma, muscle atrophy, Cushing's syndrome, and psychosis.

Glucocorticoids exert their pharmacological effects by regulating gene transcription after the formation of a complex with the glucocorticoid receptor (GR). GR-glucocorticoid complex affects gene transcription by translocating to the nucleus after binding of the glucocorticoid where it acts as a dimer in binding to DNA glucocorticoid hormone response elements (GREs) in the promoter regions of particular genes. The GR-glucocorticoid/GRE complex then, in turn, activates (transactivation) or inhibits transcription of proximally located genes. Conversely, the GR-glucocorticoid complex may negatively regulate gene transcription by a process that does not involve binding to DNA. In this process, termed transrepression, following binding of the glucocorticoid, the complexed GR enters the nucleus where it acts as a monomer to directly interact (via protein-protein interaction) with other transcription factors, repressing their ability to induce gene transcription and thus protein expression.

Estrogen, mediated through the estrogen receptor (ER), plays a major role in regulating the growth and differentiation of normal breast epithelium (Pike et al. Epidemiologic Reviews (1993) 15(1):17-35; Henderson et al. Cancer Res. (1988) 48:246-253). It stimulates cell proliferation and regulates the expression of other genes, including the progesterone receptor (PgR). PgR then mediates the mitogenic effect of progesterone, further stimulating proliferation (Pike et al., 1993; Henderson et al., 1988). The molecular differences between estrogen receptor ("ER") negative and ER positive tumors are significant in light of clinical observations which indicate that the nature and biological behavior of ER positive and ER negative tumors are distinct even in the absence of hormonal therapy. For example, ER negative cancers tend to recur sooner and show a different rate of recurrence in distant organ sites compared to ER positive tumors. Clinical observations and molecular profiling data suggest that tumors not expressing both ER and PgR represent a different clinical entity in terms of chemotherapy responsiveness. (Colleoni et al., Annals of Oncology 11(8):1057 (2000)). Thus, ER negative and ER positive breast cancers are two distinct disease entities rather than phenotypic variations of the same disease.

Relatively increased expression of these genes in primary ER-negative human breast tumors is associated with high OR expression and with an earlier relapse in ER-negative breast cancer patients (described herein). Activation of the glucocorticoid receptor (GR) in epithelial cells has been shown to initiate an anti-apoptotic (i.e., cell survival) signaling pathway that prevents breast (Wu et al, 2004) and ovarian cancer (Melhem et al, 2009) cell death in vitro and in vivo (Pang et al, 2006). Blocking or antagonizing GR activation with a GR antagonist such as mifepristone reverses cell survival signaling pathways initiated by the GR (Moran et al., 2000). Other GR antagonists (e.g., dexamethasone oxetanone) also reverse GR-mediated cell survival and potentiate apoptosis in response to cell stressors such as growth factor withdrawal (Mikosz et al, 2001). The mechanism(s) whereby GR activation protects from cell death includes the transcriptional upregulation of genes encoding anti-apoptotic proteins such as SGK1, MKP1, MCL1, and BIRC3. However, experiments with a glucocorticoid receptor antagonist, RU486, in conjunction with dexamethasone did not increase the number of apoptotic cells induced by paclitaxel, compared to paclitaxel alone (Wu et al., 2004).

II. Biomarkers and Evaluating Levels of Biomarkers

Biomarkers for prognosing human breast cancer patients have been identified. They include estrogen receptor (ER) in combination with the activity of the glucocorticoid receptor (GR) activity. It is contemplated that these biomarkers may be evaluated based on their gene products. In some embodiments, the gene product is the RNA transcript. In other embodiments, the gene product is the protein expressed by the RNA transcript. In still another embodiment is the evaluation of surrogate genes or gene targets of ER, GR, or ER and GR.

In certain aspects a meta-analysis of expression or activity can be performed. In statistics, a meta-analysis combines the results of several studies that address a set of related research hypotheses. This is normally done by identification of a common measure of effect size, which is modeled using a form of meta-regression. Generally, three types of models can be distinguished in the literature on meta-analysis: simple regression, fixed effects meta-regression and random effects meta-regression. Resulting overall averages when controlling for study characteristics can be considered meta-effect sizes, which are more powerful estimates of the true effect size than those derived in a single study under a given single set of assumptions and conditions. A meta-gene expression value, in this context, is to be understood as being the median of the normalized expression of a marker gene or activity. Normalization of the expression of a marker gene is preferably achieved by dividing the expression level of the individual marker gene to be normalized by the respective individual median expression of this marker genes, wherein said median expression is preferably calculated from multiple measurements of the respective gene in a sufficiently large cohort of test individuals. The test cohort preferably comprises at least 3, 10, 100, 200, 1000 individuals or more including all values and ranges thereof. Dataset-specific bias can be removed or minimized allowing multiple datasets to be combined for meta-analyses (See Sims et al., BMC Medical Genomics (1:42), 1-14, 2008, which is incorporated herein by reference in its entirety).

The calculation of a meta-gene expression value is performed by: (i) determining the gene expression value of at least two, preferably more genes (ii) "normalizing" the gene expression value of each individual gene by dividing the expression value with a coefficient which is approximately the median expression value of the respective gene in a representative breast cancer cohort (iii) calculating the median of the group of normalized gene expression values.

A gene shall be understood to be specifically expressed in a certain cell type if the expression level of said gene in said cell type is at least 2-fold, 5-fold, 10-fold, 100-fold, 1000 fold, or 10000-fold higher than in a reference cell type, or in a mixture of reference cell types. Reference cell types include non-cancerous breast tissue cells or a heterogenous population of breast cancers.

In certain algorithms a suitable threshold level is first determined for a marker gene. The suitable threshold level can be determined from measurements of the marker gene expression in multiple individuals from a test cohort. The median expression of the marker gene in said multiple expression measurements is taken as the suitable threshold value.

Comparison of multiple marker genes with a threshold level can be performed as follows:

1. The individual marker genes are compared to their respective threshold levels.
2. The number of marker genes, the expression level of which is above their respective threshold level, is determined.
3. If a marker genes is expressed above its respective threshold level, then the expression level of the marker gene is taken to be "above the threshold level".

"A sufficiently large number", in this context, means preferably 30%, 50%, 80%, 90%, or 95% of the marker genes used.

In certain aspects, the determination of expression levels is on a gene chip, such as an Affymetrix™ gene chip.

In another aspect, the determination of expression levels is done by kinetic real time PCR.

In certain aspects, the methods can relate to a system for performing such methods, the system comprising (a) apparatus or device for storing data on the ER or nodal status of the patient; (b) apparatus or device for determining the expression level of at least one marker gene or activity; (c) apparatus or device for comparing the expression level of the first marker gene or activity with a predetermined first threshold value; (d) apparatus or device for determining the expression level of at least one second marker gene or activity; and (e) computing apparatus or device programmed to provide a unfavorable or poor prognosis if the data indicates a negative ER status and an increased or decreased expression level of said first marker gene or activity (e.g., GR expression or activity) with the predetermined first threshold value and, alternatively, the expression level of said second marker gene is above or below a predetermined second threshold level.

The person skilled in the art readily appreciates that an unfavorable or poor prognosis can be given if the expression level of the first marker gene with the predetermined first threshold value indicates a tumor that is likely to recur or not respond well to standard therapies.

The expression patterns can also be compared by using one or more ratios between the expression levels of different breast cancer biomarkers. Other suitable measures or indicators can also be employed for assessing the relationship or difference between different expression patterns.

The GR nucleic acid and protein sequences are provided in GenBank accession number AY436590. The ER nucleic acid and protein sequences are provided in GenBank accession number NO_008493. The content of all of these GenBank Accession numbers is specifically incorporated herein by reference as of the filing date of this application.

The following biomarkers are provided for implementation with embodiments discussed herein. All of them designate nucleic acid sequences for the particular gene identifier. Nucleic acid sequences related to these gene designation can be found in the Genbank sequence databases. Additional biomarkers include the MCL1, SAP30, DUSP1, SGK1, SMARCA2, PTGDS, TNFRSF9, SFN, LAPTM5, GPSM2, SORT1, DPT, NRP1, ACSL5, BIRC3, NNMT, IGFBP6, PLXNC1, SLC46A3, C14orf139, PIAS1, IDH2, SERPINF1, ERBB2, PECAM1, LBH; ST3GAL5, IL1R1, BIN1, WIPF1, TFP1, FN1, FAM134A, NRIP1, RAC2, SPP1, PHF15, BTN3A2, SESN1, MAP3K5, DPYSL2, SEMA4D, STOM, and MAOA genes.

One or more of the biomarkers can be used to prognose a human patient with breast cancer. The expression pattern of these biomarkers in breast cancer cells may be used to evaluate a patient to determine whether they are likely to respond to standard chemotherapy, likely not to respond to standard chemotherapy, or likely to relapse after standard chemotherapy.

The expression levels of breast cancer biomarkers can be compared to reference expression levels using various methods. These reference levels can be determined using expression levels of a reference based on all breast cancer patients or all breast cancer patients determined to be ER+ and/or ER−. Alternatively, it can be based on an internal reference such as a gene that is expressed in all cells. In some embodiments, the reference is a gene expressed in breast cancer cells at a higher level than any biomarker. Any comparison can be performed using the fold change or the absolute difference between the expression levels to be compared. One or more breast cancer biomarkers can be used in the comparison. It is contemplated that 1, 2, 3, 4, 5, 6, 7, 8, and/or 9 biomarkers may be compared to each other and/or to a reference that is internal or external. A person of ordinary skill in the art would know how to do such comparisons.

Comparisons or results from comparisons may reveal or be expressed as x-fold increase or decrease in expression relative to a standard or relative to another biomarker or relative to the same biomarker but in a different class of prognosis. In some embodiments, patients with a poor prognosis have a relatively high level of expression (overexpression) or relatively low level of expression (underexpression) when compared to patients with a better or favorable prognosis, or vice versa.

Fold increases or decreases may be, be at least, or be at most 1-, 2-, 3-, 4-, 5-, 6-, 7-, 8-, 9-, 10-, 11-, 12-, 13-, 14-, 15-, 16-, 17-, 18-, 19-, 20-, 25-, 30-, 35-, 40-, 45-, 50-, 55-, 60-, 65-, 70-, 75-, 80-, 85-, 90-, 95-, 100- or more, or any range derivable therein. Alternatively, differences in expression may be expressed as a percent decrease or increase, such as at least or at most 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900, 1000% difference, or any range derivable therein.

Other ways to express relative expression levels are by normalized or relative numbers such as 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, or any range derivable therein.

Algorithms, such as the weighted voting programs, can be used to facilitate the evaluation of biomarker levels. In addition, other clinical evidence can be combined with the biomarker-based test to reduce the risk of false evaluations. Other cytogenetic evaluations may be considered in some embodiments of the invention.

Any biological sample from the patient that contains breast cancer cells may be used to evaluate the expression pattern of any biomarker discussed herein. In some embodiments, a biological sample from a breast tumor is used. Evaluation of the sample may involve, though it need not involve, panning (enriching) for cancer cells or isolating the cancer cells.

A. Nucleic Acids

Screening methods based on differentially expressed gene products are well known in the art. In accordance with one aspect of the present invention, the differential expression patterns of breast cancer biomarkers can be determined by measuring the levels of RNA transcripts of these genes, or genes whose expression is modulated by the these genes, in the patient's breast cancer cells. Suitable methods for this purpose include, but are not limited to, RT-PCR, Northern Blot, in situ hybridization, Southern Blot, slot-blotting, nuclease protection assay and oligonucleotide arrays.

In certain aspects, RNA isolated from breast cancer cells can be amplified to cDNA or cRNA before detection and/or quantitation. The isolated RNA can be either total RNA or mRNA. The RNA amplification can be specific or non-specific. Suitable amplification methods include, but are not limited to, reverse transcriptase PCR, isothermal amplification, ligase chain reaction, and Qbeta replicase. The amplified nucleic acid products can be detected and/or quantitated through hybridization to labeled probes. In some embodiments, detection may involve fluorescence resonance energy transfer (FRET) or some other kind of quantum dots.

Amplification primers or hybridization probes for a breast cancer biomarker can be prepared from the gene sequence or obtained through commercial sources, such as Affymatrix. In certain embodiments the gene sequence is identical or complementary to at least 8 contiguous nucleotides of the coding sequence.

Sequences suitable for making probes/primers for the detection of their corresponding breast cancer biomarkers include those that are identical or complementary to all or part of genes or SEQ ID NOs described herein. These sequences are all nucleic acid sequences of breast cancer biomarkers.

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

In one embodiment, each probe/primer comprises at least 15 nucleotides. For instance, each probe can comprise at least or at most 20, 25, 50, 75, 100, 125, 150, 175, 200, 225, 250, 275, 300, 325, 350, 400 or more nucleotides (or any range derivable therein). They may have these lengths and have a sequence that is identical or complementary to a gene or SEQ II) NO described herein. Preferably, each probe/primer has relatively high sequence complexity and does not have any ambiguous residue (undetermined "n" residues). The probes/primers preferably can hybridize to the target gene, including its RNA transcripts, under stringent or highly stringent conditions. In some embodiments, because each of the biomarkers has more than one human sequence, it is contemplated that probes and primers may be designed for use with each on of these sequences. For example, inosine is a nucleotide frequently used in probes or primers to hybridize to more than one sequence. It is contemplated that probes or primers may have inosine or other design implementations that accommodate recognition of more than one human sequence for a particular biomarker.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

In another embodiment, the probes/primers for a gene are selected from regions which significantly diverge from the sequences of other genes. Such regions can be determined by checking the probe/primer sequences against a human genome sequence database, such as the Entrez database at the NCBI. One algorithm suitable for this purpose is the BLAST algorithm. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence to increase the cumulative alignment score. Cumulative scores are calculated using, for nucleotide sequences, the parameters M (reward score for a pair of matching residues; always>0) and N (penalty score for mismatching residues; always<0). The BLAST algorithm parameters W, T, and X determine the sensitivity and speed of the alignment. These parameters can be adjusted for different purposes, as appreciated by one of ordinary skill in the art.

In one embodiment, quantitative RT-PCR (such as Taq-Man, ABI) is used for detecting and comparing the levels of RNA transcripts in breast cancer samples. Quantitative RT-PCR involves reverse transcription (RT) of RNA to cDNA followed by relative quantitative PCR (RT-PCR). The concentration of the target DNA in the linear portion of the PCR process is proportional to the starting concentration of the target before the PCR was begun. By determining the concentration of the PCR products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived may be determined for the respective tissues or cells. This direct proportionality between the concentration of the PCR products and the relative mRNA abundances is true in the linear range portion of the PCR reaction. The final concentration of the target DNA in the plateau portion of the curve is determined by the availability of reagents in the reaction mix and is independent of the original concentration of target DNA. Therefore, the sampling and quantifying of the amplified PCR products preferably are carried out when the PCR reactions are in the linear portion of their curves. In addition, relative concentrations of the amplifiable cDNAs preferably are normalized to some independent standard, which may be based on either internally existing RNA species or externally introduced RNA species. The abundance of a particular mRNA species may also be determined relative to the average abundance of all mRNA species in the sample.

In one embodiment, the PCR amplification utilizes one or more internal PCR standards. The internal standard may be an abundant housekeeping gene in the cell or it can specifically be GAPDH, GUSB and β-2 microglobulin. These standards may be used to normalize expression levels so that the expression levels of different gene products can be compared directly. A person of ordinary skill in the art would know how to use an internal standard to normalize expression levels.

A problem inherent in clinical samples is that they are of variable quantity and/or quality. This problem can be overcome if the RT-PCR is performed as a relative quantitative RT-PCR with an internal standard in which the internal standard is an amplifiable cDNA fragment that is similar or larger than the target cDNA fragment and in which the abundance of the mRNA encoding the internal standard is roughly 5-100 fold higher than the mRNA encoding the target. This assay measures relative abundance, not absolute abundance of the respective mRNA species.

In another embodiment, the relative quantitative RT-PCR uses an external standard protocol. Under this protocol, the PCR products are sampled in the linear portion of their amplification curves. The number of PCR cycles that are optimal for sampling can be empirically determined for each target cDNA fragment. In addition, the reverse transcriptase products of each RNA population isolated from the various samples can be normalized for equal concentrations of amplifiable cDNAs.

Nucleic acid arrays can also be used to detect and compare the differential expression patterns of breast cancer biomarkers in breast cancer cells. The probes suitable for detecting the corresponding breast cancer biomarkers can be stably attached to known discrete regions on a solid substrate. As used herein, a probe is "stably attached" to a discrete region if the probe maintains its position relative to the discrete region during the hybridization and the subsequent washes. Construction of nucleic acid arrays is well known in the art. Suitable substrates for making polynucleotide arrays include, but are not limited to, membranes, films, plastics and quartz wafers.

A nucleic acid array of the present invention can comprise at least 1, 2, 3, 4, 5, 6, 7, 8, 9, 10, 15, 20, 25, 30, 35, 40, 45, 50, 60, 70, 80, 90, 100, 150, 200, 250 or more different polynucleotide probes, which may hybridize to different and/or the same biomarkers. Multiple probes for the same gene can be used on a single nucleic acid array. Probes for other disease genes can also be included in the nucleic acid array. The probe density on the array can be in any range. In some embodiments, the density may be 50, 100, 200, 300, 400, 500 or more probes/cm$^2$.

Specifically contemplated by the present inventors are chip-based nucleic acid technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see also, Pease et al., 1994; and Fodor et al, 1991). It is contemplated that this technology may be used in conjunction with evaluating the expression level of one or more breast cancer biomarkers with respect to diagnostic, prognostic, and treatment methods of the invention.

The present invention may involve the use of arrays or data generated from an array. Data may be readily available. Moreover, an array may be prepared in order to generate data that may then be used in correlation studies.

An array generally refers to ordered macroarrays or microarrays of nucleic acid molecules (probes) that are fully or nearly complementary or identical to a plurality of mRNA molecules or cDNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass and silicon. Such arrays may vary in a number of different ways, including average probe length, sequence or types of probes, nature of bond between the probe and the array surface, e.g. covalent or non-covalent, and the like. The labeling and screening methods of the present invention and the arrays are not limited in its utility with respect to any parameter except that the probes detect expression levels; consequently, methods and compositions may be used with a variety of different types of genes.

Representative methods and apparatus for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 5,492,806; 5,525,464; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112;

6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000; the disclosures of which are all herein incorporated by reference.

It is contemplated that the arrays can be high density arrays, such that they contain 100 or more different probes. It is contemplated that they may contain 1000, 16,000, 65,000, 250,000 or 1,000,000 or more different probes. The probes can be directed to targets in one or more different organisms. The oligonucleotide probes range from 5 to 50, 5 to 45, 10 to 40, or to 40 nucleotides in length in some embodiments. In certain embodiments, the oligonucleotide probes are 20 to 25 nucleotides in length.

The location and sequence of each different probe sequence in the array are generally known. Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$.

Moreover, a person of ordinary skill in the art could readily analyze data generated using an array. Such protocols include information found in WO 9743450; WO 03023058; WO 03022421; WO 03029485; WO 03067217; WO 03066906; WO 03076928; WO 03093810; WO 03100448A1, all of which are specifically incorporated by reference.

In one embodiment, nuclease protection assays are used to quantify RNAs derived from the breast cancer samples. There are many different versions of nuclease protection assays known to those practiced in the art. The common characteristic that these nuclease protection assays have is that they involve hybridization of an antisense nucleic acid with the RNA to be quantified. The resulting hybrid double-stranded molecule is then digested with a nuclease that digests single-stranded nucleic acids more efficiently than double-stranded molecules. The amount of antisense nucleic acid that survives digestion is a measure of the amount of the target RNA species to be quantified. An example of a nuclease protection assay that is commercially available is the RNase protection assay manufactured by Ambion, Inc. (Austin, Tex.).

B. Proteins and Polypeptides

In other embodiments, the differential expression patterns of breast cancer biomarkers can be determined by measuring the levels of polypeptides encoded by these genes in breast cancer cells. Methods suitable for this purpose include, but are not limited to, immunoassays such as ELISA, RIA, FACS, dot blot, Western Blot, immunohistochemistry, and antibody-based radioimaging. Protocols for carrying out these immunoassays are well known in the art. Other methods such as 2-dimensional SDS-polyacrylamide gel electrophoresis can also be used. These procedures may be used to recognize any of the polypeptides encoded by the breast cancer biomarker genes described herein.

One example of a method suitable for detecting the levels of target proteins in peripheral blood samples is ELISA. In an exemplifying ELISA, antibodies capable of binding to the target proteins encoded by one or more breast cancer biomarker genes are immobilized onto a selected surface exhibiting protein affinity, such as wells in a polystyrene or polyvinylchloride microtiter plate. Then, breast cancer cell samples to be tested are added to the wells. After binding and washing to remove non-specifically bound immunocomplexes, the bound antigen(s) can be detected. Detection can be achieved by the addition of a second antibody which is specific for the target proteins and is linked to a detectable label. Detection may also be achieved by the addition of a second antibody, followed by the addition of a third antibody that has binding affinity for the second antibody, with the third antibody being linked to a detectable label. Before being added to the microtiter plate, cells in the peripheral blood samples can be lysed using various methods known in the art. Proper extraction procedures can be used to separate the target proteins from potentially interfering substances.

In another ELISA embodiment, the breast cancer cell samples containing the target proteins are immobilized onto the well surface and then contacted with the antibodies of the invention. After binding and washing to remove non-specifically bound immunocomplexes, the bound antigen is detected. Where the initial antibodies are linked to a detectable label, the immunocomplexes can be detected directly. The immunocomplexes can also be detected using a second antibody that has binding affinity for the first antibody, with the second antibody being linked to a detectable label.

Another typical ELISA involves the use of antibody competition in the detection. In this ELISA, the target proteins are immobilized on the well surface. The labeled antibodies are added to the well, allowed to bind to the target proteins, and detected by means of their labels. The amount of the target proteins in an unknown sample is then determined by mixing the sample with the labeled antibodies before or during incubation with coated wells. The presence of the target proteins in the unknown sample acts to reduce the amount of antibody available for binding to the well and thus reduces the ultimate signal.

Different ELISA formats can have certain features in common, such as coating, incubating or binding, washing to remove non-specifically bound species, and detecting the bound immunocomplexes. For instance, in coating a plate with either antigen or antibody, the wells of the plate can be incubated with a solution of the antigen or antibody, either overnight or for a specified period of hours. The wells of the plate are then washed to remove incompletely adsorbed material. Any remaining available surfaces of the wells are then "coated" with a nonspecific protein that is antigenically neutral with regard to the test samples. Examples of these nonspecific proteins include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means can also be used. After binding of a protein or antibody to the well, coating with a non-reactive material to reduce background, and washing to remove unbound material, the immobilizing surface is contacted with the control and/or clinical or biological sample to be tested under conditions effective to allow immunocomplex (antigen/antibody) formation. These conditions may include, for example, diluting the antigens and antibodies with solutions such as BSA, bovine gamma globulin (BGG) and phosphate buffered saline (PBS)/Tween and incubating the antibodies and antigens at room temperature for about 1 to 4 hours or at 49° C. overnight. Detection of the immunocomplex then requires a labeled secondary binding ligand or antibody, or a secondary binding ligand or antibody in conjunction with a labeled tertiary antibody or third binding ligand.

After all of the incubation steps in an ELISA, the contacted surface can be washed so as to remove non-complexed material. For instance, the surface may be washed with a solution such as PBS/Tween, or borate buffer. Following the formation of specific immunocomplexes between the test sample and the originally bound material, and subsequent washing, the occurrence of the amount of immunocomplexes can be determined.

To provide a detecting means, the second or third antibody can have an associated label to allow detection. In one embodiment, the label is an enzyme that generates color development upon incubating with an appropriate chromogenic substrate. Thus, for example, one may contact and incubate the first or second immunocomplex with a urease, glucose oxidase, alkaline phosphatase or hydrogen peroxidase-conjugated antibody for a period of time and under conditions that favor the development of further immunocomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl)-benzhiazoline-6-sulfonic acid (ABTS) and hydrogen peroxide, in the case of peroxidase as the enzyme label. Quantitation can be achieved by measuring the degree of color generation, e.g., using a spectrophotometer.

Another suitable method is RIA (radioimmunoassay). An example of RIA is based on the competition between radiolabeled-polypeptides and unlabeled polypeptides for binding to a limited quantity of antibodies. Suitable radiolabels include, but are not limited to, $I^{125}$. In one embodiment, a fixed concentration of $I^{125}$-labeled polypeptide is incubated with a series of dilution of an antibody specific to the polypeptide. When the unlabeled polypeptide is added to the system, the amount of the $I^{125}$-polypeptide that binds to the antibody is decreased. A standard curve can therefore be constructed to represent the amount of antibody-bound $I^{125}$-polypeptide as a function of the concentration of the unlabeled polypeptide. From this standard curve, the concentration of the polypeptide in unknown samples can be determined. Various protocols for conducting RIA to measure the levels of polypeptides in breast cancer cell samples are well known in the art.

Suitable antibodies for this invention include, but are not limited to, polyclonal antibodies, monoclonal antibodies, chimeric antibodies, humanized antibodies, single chain antibodies, Fab fragments, and fragments produced by a Fab expression library.

Antibodies can be labeled with one or more detectable moieties to allow for detection of antibody-antigen complexes. The detectable moieties can include compositions detectable by spectroscopic, enzymatic, photochemical, biochemical, bioelectronic, immunochemical, electrical, optical or chemical means. The detectable moieties include, but are not limited to, radioisotopes, chemiluminescent compounds, labeled binding proteins, heavy metal atoms, spectroscopic markers such as fluorescent markers and dyes, magnetic labels, linked enzymes, mass spectrometry tags, spin labels, electron transfer donors and acceptors, and the like.

Protein array technology is discussed in detail in Pandey and Mann (2000) and MacBeath and Schreiber (2000), each of which is herein specifically incorporated by reference. These arrays typically contain thousands of different proteins or antibodies spotted onto glass slides or immobilized in tiny wells and allow one to examine the biochemical activities and binding profiles of a large number of proteins at once. To examine protein interactions with such an array, a labeled protein is incubated with each of the target proteins immobilized on the slide, and then one determines which of the many proteins the labeled molecule binds. In certain embodiments such technology can be used to quantitate a number of proteins in a sample, such as a breast cancer biomarker proteins.

The basic construction of protein chips has some similarities to DNA chips, such as the use of a glass or plastic surface dotted with an array of molecules. These molecules can be DNA or antibodies that are designed to capture proteins. Defined quantities of proteins are immobilized on each spot, while retaining some activity of the protein. With fluorescent markers or other methods of detection revealing the spots that have captured these proteins, protein microarrays are being used as powerful tools in high-throughput proteomics and drug discovery.

The earliest and best-known protein chip is the ProteinChip by Ciphergen Biosystems Inc. (Fremont, Calif.). The Protein-Chip is based on the surface-enhanced laser desorption and ionization (SELDI) process. Known proteins are analyzed using functional assays that are on the chip. For example, chip surfaces can contain enzymes, receptor proteins, or antibodies that enable researchers to conduct protein-protein interaction studies, ligand binding studies, or immunoassays. With state-of-the-art ion optic and laser optic technologies, the ProteinChip system detects proteins ranging from small peptides of less than 1000 Da up to proteins of 300 kDa and calculates the mass based on time-of-flight (TOF).

The ProteinChip biomarker system is the first protein biochip-based system that enables biomarker pattern recognition analysis to be done. This system allows researchers to address important clinical questions by investigating the proteome from a range of crude clinical samples (i.e., laser capture microdissected cells, biopsies, tissue, urine, and serum). The system also utilizes biomarker pattern software that automates pattern recognition-based statistical analysis methods to correlate protein expression patterns from clinical samples with disease phenotypes.

In other aspects, the levels of polypeptides in samples can be determined by detecting the biological activities associated with the polypeptides. If a biological function/activity of a polypeptide is known, suitable in vitro bioassays can be designed to evaluate the biological function/activity, thereby determining the amount of the polypeptide in the sample.

III. Breast Cancer Therapy

Certain embodiments are directed to methods of treating breast cancer based on OR status of the breast cancer tissue. In some embodiments, the hormone receptor status is determined based on the expression of a hormone receptor such as the estrogen receptor (ER) in combination with the glucocorticoid receptor (OR).

In certain aspects, the hormone receptor status is high for GR and may also be low for one or more other hormone receptors such as the estrogen receptor. An individual having an elevated GR and low ER is likely to have a poor prognosis. In the event of a poor prognosis the physician may pursue a more aggressive therapy for those patients. In some embodiments, the method comprises identifying a breast cancer patient based on a hormone receptor status of patients having tumor tissue with elevated levels of GR expression.

In certain aspects, there may be provided methods for treating a subject determined to have cancer and with a predetermined expression profile of one or more biomarkers disclosed herein.

In a further aspect, biomarkers and related systems that can establish a prognosis of cancer patients in this invention can be used to identify patients who may get benefit of conventional single or combined modality therapy. In the same way, the invention can identify those patients who do not get much benefit from such conventional single or combined modality therapy and can offer them alternative treatment(s).

In certain aspects of the present invention, conventional cancer therapy may be applied to a subject wherein the subject is identified or reported as having a good prognosis based on the assessment of the biomarkers as disclosed. On the other hand, at least an alternative cancer therapy may be prescribed, as used alone or in combination with conventional cancer therapy, if a poor prognosis is determined by the disclosed methods, systems, or kits.

Embodiments concern a glucocorticoid receptor antagonist. In some embodiments, the glucocorticoid receptor antagonist is a selective glucocorticoid receptor antagonist, as set forth in Clark, 2008, which is hereby incorporated by reference. In other embodiments, the glucocorticoid receptor antagonist is a non-selective glucocorticoid receptor antagonist, such as mifepristone. In certain embodiments, the glucocorticoid receptor antagonist is steroidal. In other embodiments, the glucocorticoid receptor antagonist is nonsteroidal. A glucocorticoid receptor antagonist includes those in the following classes of chemical compounds: octahydrophenanthrenes, spirocyclic dihydropyridines, triphenylmethanes and diaryl ethers, chromenes, dibenzyl anilines, dihydroisoquinolines, pyrimidinediones, azadecalins, and aryl pyrazolo azadecalins, and which are described in more detail in Clark, 2008, which is hereby incorporated by reference. Some embodiments of steroidal antagonists from Clark, 2008 are: RU-486, RU-43044, 11-monoaryl and 11,21 bisaryl steroids (including 11β-substituted steroids), 10β-substituted steroids, 11β-aryl conjugates of mifepristone, and phosphorous-containing mifepristone analogs. Further embodiments of nonsteroidal antagonists from Clark, 2008 are: octahydrophenanthrenes, spirocyclic dihydropyridines, triphenylmethanes and diaryl ethers, chromenes, dibenzyl anilines, dihyrdroquinolines, pyrimidinediones, azadecalins, aryl pyrazolo azadecalins (including 8a-benzyl isoquinolones, N-substituted derivatives, bridgehead alcohol and ethers, bridgehead amines). Additional specific examples include, but are not limited to the following specific antagonists: beclometasone, betamethasone, budesonide, ciclesonide, flunisolide, fluticasone, mifepristone, mometasone, and triamcinolone. Other examples include those described and/or depicted in U.S. Patent Application Publication 2010/0135956, which is hereby incorporated by reference. Even further examples include ORG-34517 (Merck), RU-43044, dexamethasone mesylate (Dex-Mes), dexamethasone oxetanone (Dex-Ox), deoxycorticosterone (DOC) (Peeters et al., 2008, which is hereby incorporated by reference in its entirety and Cho et al. 2005, which is hereby incorporated by reference in its entirety). In additional embodiments the glucocorticoid receptor antagonist may be CORT 0113083 or CORT 00112716, which are described in Belanoff et al. (2011), which is hereby incorporated by reference. It is specifically contemplated that one or more of the antagonists discussed herein or in the incorporated references may be excluded in embodiments of the invention. It is also contemplated that in some embodiments, more than one glucocorticoid receptor antagonist is employed, while in other embodiments, only one is employed as part of the therapeutic method (though it may be administered multiple times). It is contemplated that the second one may be administered concurrently with the first one or they may be administered at different times.

Conventional cancer therapies include one or more selected from the group of chemical or radiation based treatments and surgery. Chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, navelbine, farnesyl-protein transferase inhibitors, transplatinum, 5-fluorouracil, vincristin, vinblastin and methotrexate, or any analog or derivative variant of the foregoing.

Suitable therapeutic agents include, for example, vinca alkaloids, agents that disrupt microtubule formation (such as colchicines and its derivatives), anti-angiogenic agents, therapeutic antibodies, EGFR targeting agents, tyrosine kinase targeting agent (such as tyrosine kinase inhibitors), serine kinase targeting agents, transitional metal complexes, proteasome inhibitors, antimetabolites (such as nucleoside analogs), alkylating agents, platinum-based agents, anthracycline antibiotics, topoisomerase inhibitors, macrolides, therapeutic antibodies, retinoids (such as all-trans retinoic acids or a derivatives thereof); geldanamycin or a derivative thereof (such as 17-AAG), and other standard chemotherapeutic agents well recognized in the art.

Certain chemotherapeutics are well known for use against breast cancer. These breast cancer chemotherapeutics are capecitabine, carboplatin, cyclophosphamide (Cytoxan), daunorubicin, docetaxel (Taxotere), doxorubicin (Adriamycin), epirubicin (Ellence), fluorouracil (also called 5-fluorouracil or 5-FU), gemcitabine, eribulin, ixabepilone, methotrexate, mitomycin C, mitoxantrone, paclitaxel (Taxol), thiotepa, vincristine, vinorelbine.

In some embodiments, the chemotherapeutic agent is any of (and in some embodiments selected from the group consisting of) adriamycin, colchicine, cyclophosphamide, actinomycin, bleomycin, daunorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof (e.g., paclitaxel and derivatives thereof, taxotere and derivatives thereof, and the like), topetecan, vinblastine, vincristine, tamoxifen, pipo-sulfan, nab-5404, nab-5800, nab-5801, Irinotecan, HKP, Ortataxel, gemcitabine, Herceptin®, vinorelbine, Doxil®, capecitabine, Gleevec®, Alimta®, Avastin®, Velcade®, Tarceva®, Neulasta®, Lapatinib, STI-571, ZD1839, Iressa® (gefitinib), SH268, genistein, CEP2563, SU6668, SU11248, EMD121974, and Sorafenib.

In some embodiments, the chemotherapeutic agent is a composition comprising nanoparticles comprising a thiocolchicine derivative and a carrier protein (such as albumin).

In further embodiments a combination of chemotherapeutic agents is administered to breast cancer cells. The chemotherapeutic agents may be administered serially (within minutes, hours, or days of each other) or in parallel; they also may be administered to the patient in a pre-mixed single composition. The composition may or may not contain a glucocorticoid receptor antagonist. Combinations of breast cancer therapeutics include, but are not limited to the following: AT (Adriamycin and Taxotere), AC±T: (Adriamycin and Cytoxan, with or without Taxol or Taxotere), CMF (Cytoxan, methotrexate, and fluorouracil), CEF (Cytoxan, Ellence, and fluorouracil), FAC (fluorouracil, Adriamycin, and Cytoxan), CAF (Cytoxan, Adriamycin, and fluorouracil) (the FAC and CAF regimens use the same medicines but use different doses and frequencies), TAC (Taxotere, Adriamycin, and Cytoxan), and GET (Gemzar, Ellence, and Taxol). In some embodiments trastuzumab (Herceptin®) is administered to a breast cancer patient with a glucocorticoid receptor antagonist, which may be with or without a chemotherapeutic or a combination of chemotherapeutics.

Various combinations with a glucocorticoid receptor antagonist and an anticancer agent or compound (or a combination of such agents and/or compounds) may be employed, for example glucocorticoid receptor antagonist is "A" and the anticancer agent or compound (or a combination of such agents and/or compounds) given as part of an anticancer therapy regime, is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A B/A/B/A B/A/A/B A/A/A/B B/A/A/A A/B/A/A A/A/B/A

Administration of the therapeutic compounds or agents to a patient will follow general protocols for the administration of such compounds, taking into account the toxicity, if any, of the therapy. It is expected that the treatment cycles would be repeated as necessary. It also is contemplated that various standard therapies, as well as surgical intervention, may be applied in combination with the described therapy.

The term "a serine/threonine kinase inhibitor", as used herein, relates to a compound which inhibits serine/threonine kinases. An example of a target of a serine/threonine kinase inhibitor includes, but is not limited to, dsRNA-dependent protein kinase (PKR). Examples of indirect targets of a serine/threonine kinase inhibitor include, but are not limited to, MCP-1, NF-kappaB, eIF2alpha, COX2, RANTES, IL8, CYP2A5, IGF-1, CYP2B1, CYP2B2, CYP2H1, ALAS-1, HIF-1, erythropoietin and/or CYP1A1. An example of a serine/theronin kinase inhibitor includes, but is not limited to, Sorafenib and 2-aminopurine, also known as 1H-purin-2-amine(9CI). Sorafenib is marketed as NEXAVAR.

The term "an angiogenesis inhibitor", as used herein, relates to a compound which targets, decreases or inhibits the production of new blood vessels. Targets of an angiogenesis inhibitor include, but are not limited to, methionine aminopeptidase-2 (MetAP-2), macrophage inflammatory protein-1 (MIP-1a), CCL5, TGF-.beta., lipoxygenase, cyclooxygenase, and topoisomerase. Indirect targets of an angiogenesis inhibitor include, but are not limited to, p21, p53, CDK2 and collagen synthesis. Examples of an angiogenesis inhibitor include, but are not limited to, Fumagillin, which is known as 2,4,6,8-decatetraenedioic acid, mono[3R,4S,5S,6R)-5-methoxy-4-[(2R,3R)-2-methyl-3-(3-methyl-2-butenyl)oxi-ranyl]-1-oxaspiro[2.5]oct-6-yl]ester, (2E,4E,6E,8E)-(9CI); Shikonin, which is also known as 1,4-naphthalenedione, 5,8-dihydroxy-2-[(1R)-1-hydroxy-4-methyl-3-pentenyl]-(9CI); Tranilast, which is also known as benzoic acid, 2-[[3-(3,4-dimethoxyphenyl)-1-oxo-2-propenyl]amino]-(9CI); ursolic acid; suramin; thalidomide and lenalidomide, and marketed as REVLIMID.

Radiation therapy that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Laser therapy is the use of high-intensity light to destroy tumor cells. Laser therapy affects the cells only in the treated area. Laser therapy may be used to destroy cancerous tissue and relieve a blockage in the esophagus when the cancer cannot be removed by surgery. The relief of a blockage can help to reduce symptoms, especially swallowing problems.

Photodynamic therapy (PDT), a type of laser therapy, involves the use of drugs that are absorbed by cancer cells; when exposed to a special light, the drugs become active and destroy the cancer cells. PDT may be used to relieve symptoms of esophageal cancer such as difficulty swallowing.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well. A patient may be administered a single compound or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg (or any range derivable therein). A patient may be administered a single compound or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500 mg/kg/day (or any range derivable therein).

Alternative cancer therapy include any cancer therapy other than surgery, chemotherapy and radiation therapy in the present invention, such as immunotherapy, gene therapy, hormonal therapy or a combination thereof. Subjects identified with poor prognosis using the present methods may not have favorable response to conventional treatment(s) alone and may be prescribed or administered one or more alternative cancer therapy per se or in combination with one or more conventional treatments.

For example, the alternative cancer therapy may be a targeted therapy. The targeted therapy may be an anti-EGFR treatment. In one embodiment of the method of the invention, the anti-EGFR agent used is a tyrosine kinase inhibitor. Examples of suitable tyrosine kinase inhibitors are the quinazoline derivatives described in WO 96/33980, in particular gefitinib (Iressa). Other examples include quinazoline derivatives described in WO 96/30347, in particular erlotinib (Tarceva), dual EGFR/HER2 tyrosine kinase inhibitors, such as lapatinib, or pan-Erb inhibitors. In a preferred embodiment of the method or use of the invention, the anti-EGFR agent is an antibody capable of binding to EGFR, i.e. an anti-EGFR antibody.

In a further embodiment, the anti-EGFR antibody is an intact antibody, i.e. a full-length antibody rather than a fragment. An anti-EGFR antibody used in the method of the present invention may have any suitable affinity and/or avidity for one or more epitopes contained at least partially in EGFR. Preferably, the antibody used binds to human EGFR with an equilibrium dissociation constant ($K_D$) of $10^{-8}$ M or less, more preferably $10^{-10}$ M or less.

Particularly antibodies for use in the present invention include zalutumumab (2F8), cetuximab (Erbitux), nimotuzumab (h-R3), panitumumab (ABX-EGF), and matuzumab (EMD72000), or a variant antibody of any of these, or an antibody which is able to compete with any of these, such as an antibody recognizing the same epitope as any of these. Competition may be determined by any suitable technique. In one embodiment, competition is determined by an ELISA assay. Often competition is marked by a significantly greater relative inhibition than 5% as determined by ELISA analysis.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Gene therapy is the insertion of polynucleotides, including DNA or RNA, into an individual's cells and tissues to treat a disease. Antisense therapy is also a form of gene therapy in the present invention. A therapeutic polynucleotide may be administered before, after, or at the same time of a first cancer therapy. Delivery of a vector encoding a variety of proteins is encompassed within the invention. For example, cellular expression of the exogenous tumor suppressor oncogenes would exert their function to inhibit excessive cellular proliferation, such as p53, p16 and C-CAM.

Additional agents to be used to improve the therapeutic efficacy of treatment include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

II. Kits

Certain aspects of the present invention also encompass kits for performing the diagnostic and prognostic methods of the invention. Such kits can be prepared from readily available materials and reagents. For example, such kits can comprise any one or more of the following materials: enzymes, reaction tubes, buffers, detergent, primers, probes, antibodies. In a preferred embodiment, these kits allow a practitioner to obtain samples of neoplastic cells in blood, tears, semen, saliva, urine, tissue, serum, stool, sputum, cerebrospinal fluid and supernatant from cell lysate. In another preferred embodiment these kits include the needed apparatus for performing RNA extraction, RT-PCR, and gel electrophoresis. Instructions for performing the assays can also be included in the kits.

In a particular aspect, these kits may comprise a plurality of agents for assessing the differential expression of a plurality of biomarkers, for example, GR and/or ER, wherein the kit is housed in a container. The kits may further comprise instructions for using the kit for assessing expression, means for converting the expression data into expression values and/or means for analyzing the expression values to generate prognosis. The agents in the kit for measuring biomarker expression may comprise a plurality of PCR probes and/or primers for qRT-PCR and/or a plurality of antibody or fragments thereof for assessing expression of the biomarkers. In another embodiment, the agents in the kit for measuring biomarker expression may comprise an array of polynucleotides complementary to the mRNAs of the biomarkers of the invention. Possible means for converting the expression data into expression values and for analyzing the expression values to generate scores that predict survival or prognosis may be also included.

Kits may comprise a container with a label. Suitable containers include, for example, bottles, vials, and test tubes. The containers may be formed from a variety of materials such as glass or plastic. The container may hold a composition which includes a probe that is useful for prognostic or non-prognostic applications, such as described above. The label on the container may indicate that the composition is used for a specific prognostic or non-prognostic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

anti-apoptotic signaling, and that those ER– patients with high NR3C1 gene expression have a significantly worse outcome than NR3C1-low patients. Interestingly, the high NR3C1 gene expression in the ER+ (ESR1-high) subset of patients suggests a slight better outcome, implying a crosstalk between the ER and the GR that is absent in ER– tumors.

Using a global approach of gene expression studies merged with data from OR ChIP-sequencing in ER– pre-malignant breast cells (MCF10A-Myc), the inventors have identified direct GR target genes are significantly associated with cell survival signaling pathways. Interestingly, a meta-analysis of the high NR3C1-expressing ER– tumors reveals that many genes identified by ChIP-sequencing/gene expression analysis are indeed differentially expressed in high versus low NR3C1-primary breast cancers. These results suggest that GR expression may be a functional biomarker in ER– breast cancer.

TABLE 1

Clinical studies used for meta-analysis

| GEO ID | # of pts | Reference |
|---|---|---|
| GSE9195 | 77 | Loi S, et al |
| GSE7390 | 189 | Desmedt C, et al |
| GSE6532 | 212 | Loi S, et al |
| GSE2603 | 73 | Minn AJ, et al |
| GSE2990 | 183 | Sotiriou C, et al |
| GSE2034 | 280 | Wang YX, et al |
| TOTAL | 1206 | |

TABLE 2

Differentially expressed genes with concordant expression by all three methods (33/44 genes)

| Gene expression after Dex-treatment in MCF10A-Myc | Gene expression in NR3C1 + vs. – tumors | GR-binding within distance to TSS after Dex-treatment in MCF10A-Myc | Genes |
|---|---|---|---|
| Up | Up | 10 kb | DUSP1, SGK1, SMARCA2, PTGDS, MCL1 |
| | | 10-100 kb | DPYSL2, STOM, LAPTM5, NNMT, SERPINF1, NRIP1, WIPF1, BIN1, IL1R1, ST3GAL5, SEMA4D, MAP3K5, SMARCA2, DPT, BIRC3, PTGDS, PHF15, MAOA, TFPI, SLC46A3, PIAS1, ACSL5, SESN1, C14orf139, LBH |
| | | 10 kb | NONE |
| Down | Down | 10-100 kb | SFN, SPP1, ERBB2 |
| Overlapping genes with NKI-295 gene signature | | | DUSP1, DPT, NNMT, SERPINF1, IL1R1, FN1, DPYSL2 |

Example 1

Tumor Biomarker Status

A. Results

The glucocorticoid receptor (GR) is highly expressed in the myoepithelium of the normal human breast and in a subset of both ERalpha-positive and negative human breast cancers. In vitro and in vivo experiments suggest that activation of the GR in ER– pre-malignant breast epithelial and cancer cells triggers cell survival pathways under stress conditions (e.g. chemotherapy) that usually induce apoptosis. The inventors examined the association between NR3C1 gene expression and GR target gene expression in human ER– breast cancers and found that ER– breast cancers with high NR3C1 expression also express GR target genes associated with EMT and B. Materials and Methods Cell Culture and Glucocorticoid Treatment:

MCF10A-Myc cells were cultured in a 1:1 mixture of DMEM and Hams/F12 medium supplemented with 10% fetal bovine serum, hydrocortisone (0.5 µg/ml), EGF (10 ng/ml), insulin (5 ng/ml) and 100 U/ml penicillin/streptomycin were also added. The cells were then starved for three days of all growth factors and treated with dexamethasone (10-6M) and ethanol of the same volume as a control.

Microarray Gene Expression:

MCF10A-Myc Cells: Time course (0.5 h, 2 h, 4 h and 24 h) microarray data were obtained using Affymetrix gene arrays (HG-U133A) (Wu et al., 2006). Genes that were induced or repressed≥1.5 fold-change were considered to be regulated.

GR ChIP-Seq Experiment and Analysis for MCF10A-Myc Cells:

Cells were collected for the ChIP assay following 1 hour of Dex (10-6M) or EtOH treatment. The ChIP assay was done basically following Millipore's ChIP Assay Kit instructions. The DNA input (1%) was also sequenced using Illumina's Solexa Sequencer. Short-tag reads (36 bp) were mapped to the Human Genome (UCSC, hg18) by using Maq aligner. GR-binding peaks were called by using MACS software. Known SGK1 and GILZ promoter GR binding-regions (GBRs) were used as positive controls to determine the FDR threshold for retrieving significant GBRs.

Human Primary Breast Cancer Analysis:

1) Data Collection: All the clinical data and raw CEL files (all Affymetrix HU-133A and HU-133+2) were obtained from GEO (see Table 1). Low quality arrays were removed by AffyPLM. Arrays were normalized by using RMA and then centered by mean within each study and pooled together. 2) Determination of ESR1 and NR3C1 positivity: Expression data of tumors with known ER IHC status were analyzed using ROC analysis. The Youden Index of the best ESR1 probe's ROC curve was used as the cut-off point to separate ESR1+ and ESR1- tumors. Due to the lack of tumors with both GR IHC and NR3C1 gene expression information, we were unable to use ROC analysis to determine the NR3C1 cutoff. Therefore, based on published and our unpublished GR IHC data, we used the percentiles of NR3C1 gene expression levels that correspond to the observed proportion of GR+ patients. 3) Clustering: Un-supervised clustering was performed by Cluster using Pearson correlation distance and complete-linkage method. Heat-maps were plotted by Treeview. 4) Statistical analysis: Relapse-free survival (RFS) Kaplan-Meier plot and log-rank test were done by using R's "survival" package. Microarray SAM analysis was performed by using R's "siggenes" package.

Tumor Assessment.

pAUC areas were calculated for all the probes on the chip by setting p=0.2 (meaning can separate at least 80% patients) for tumors with known ER status (n=1000). A probe was then selected that has biggest pAUC area, which is the ESR1 probe 205225_at. So, this probe is the best one that can separate ER IHC+versus−. Using the 205225_at probe, the Youden Index of its ROC curve was calculated, that is the max (sensitivity+specificity−1) as the cut-off value for ESR1+ and −. The range of ESR1 expression after normalization was [−5.223868− 3.944120]. The Youden Index, i.e. the cut-off is −1.257434. In the n=1000, training set, n=773>−1.257434 (ESR1+), and n=227<=−1.257434. (ESR1−) or i.e. 77.3% quantile This cut-off was applied to the entire dataset, n=898 (ESR+), n=308 (ESR−). In addition to the method, the ACTUAL Log 2 value cutoff is needed for ESR1 positivity in normalized meta-dataset, as well as the range of ESR1 values encountered following batched mean normalization. If in one study, samples are obtained from different hospitals, they were normalized separately. So, to be precisely accurate, the normalization is done within the samples from the same source.

The ESR1 probe ID from Affymetrix is 205225_at.
The NR3C1 probe ID from Affymetrix is 216321_s_at
The range for NR3C1 probe (216321_s_at) is [−3.145456 to 2.158716] for the entire data set. For ESR1+, the range is [−3.009359 2.158716] and for ESR1−, the range is [−3.145456 1.917823] Thus, the cut-off for ESR1+, is 0.172189, 55.98% quantile (or about 44% NR3C1+ percentage) and the cut-off for ESR1−, is 0.47332, 82.51% quantile (or about 17.5% NR3C1+ percentage). All the cut-off are log 2 values.

The cutoffs used are the best cut-off that can separate patients with a p<0.01. If the p-value is loosened to 0.05, the range can be widened.

For ESR1+ patients, NR3C1+ patients can be from about 35% to 60% (about 44% is the best). For ESR1− patients, NR3C1+ patients can be from about 30% to 15% (about 17.5% is the best)

Example 2

Figure 8:
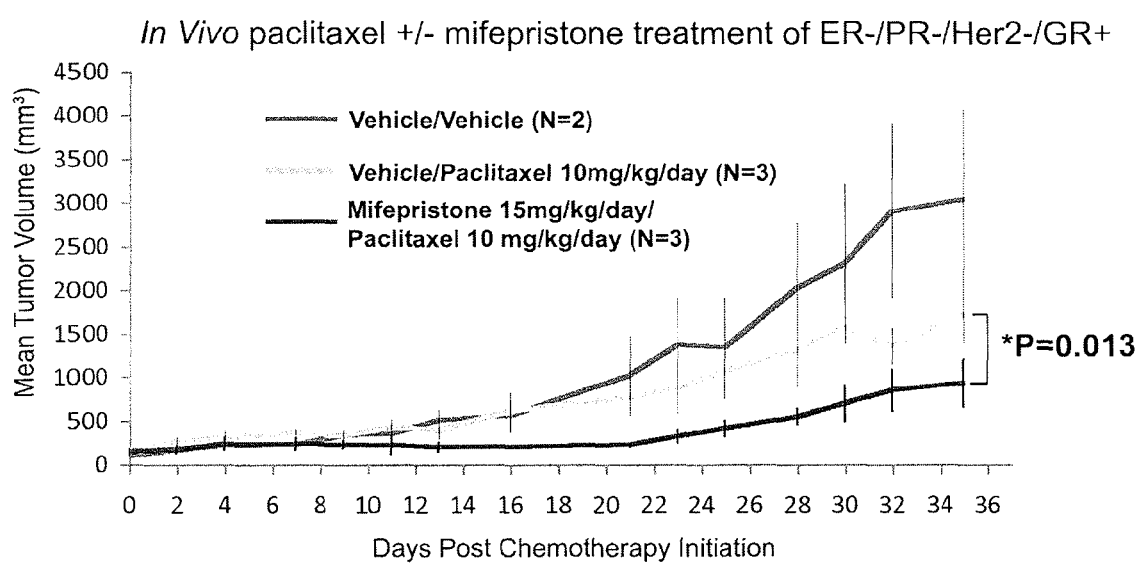
FIG. 8. Administration of mifepristone increases MDA-MB-231 tumor susceptibility to paclitaxel treatment in vivo.

Mifepristone Pretreatment Enhances Paclitaxel Anti-Tumor Effectiveness in Models of Human Breast Cancer Xenografted ER−/PR−/HER2− (GR+) MDA-MB-231 human breast cancer cells ($1 \times 10^7$ cells in 50 µl of PBS) were injected into the mammary fat pad of female Severe Combined Immunodeficient Mice (SCID) mice and allowed to grow until reaching approximately 100 mm$^3$. Mice were then injected intraperitoneally with either both vehicles, paclitaxel (10 mg/kg)+the mifepristone vehicle, or the combination of mifepristone (15 mg/kg) administered two hours prior to paclitaxel (10 mg/kg) for five successive days. The longest (L) and shortest (S) diameters of the tumors were measured bi-weekly with electronic calipers and tumor volume was calculated using the formula for an ellipsoid sphere: volume=S2×L×0.52. Mifepristone pretreatment significantly decreased tumor volume over time (P=0.013) compared to treatment with paclitaxel alone (FIG. 8).

Example 3

Figure 9:
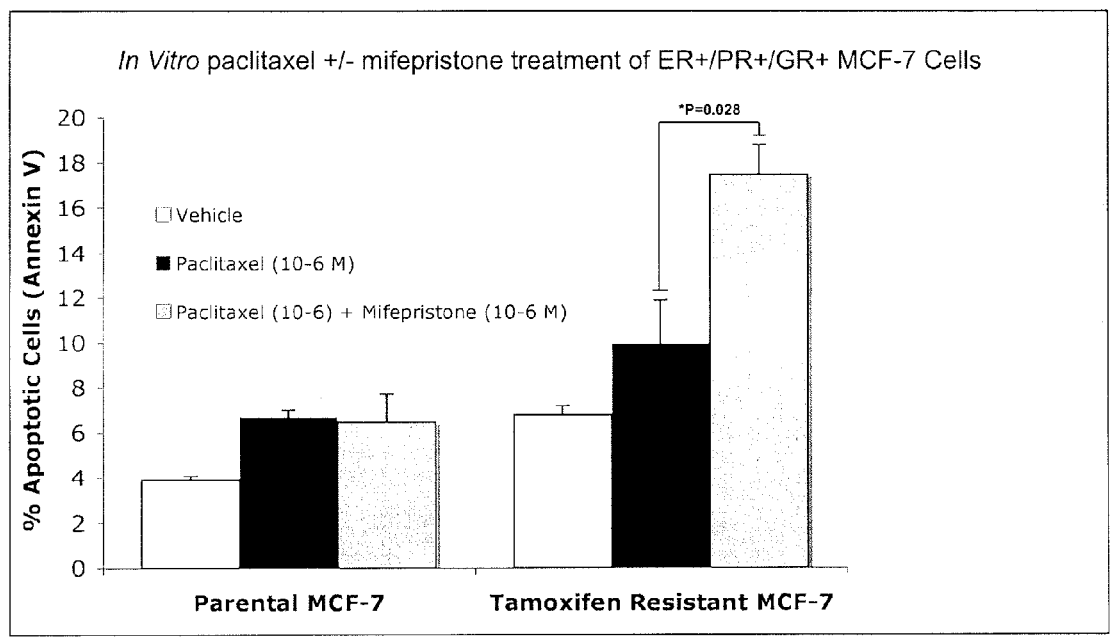
FIG. 9. Mifepristone pretreatment increases tamoxifen-resistant MCF-7 (T-R-MCF-7), but not parental MCF-7 cell susceptibility to paclitaxel in vitro.

Mifepristone Pretreatment Increases Tamoxifen-Resistant MCF-7 (T-R-MCF-7), but not Parental MCF-7 Cell Susceptibility to Paclitaxel In Vitro Parental MCF-7 (ER+/PR+/GR+) and T-R MCF-7 (ER+/PR+/GR+) cells were treated with the appropriate vehicle (ethanol for mifepristone and castor oil/saline for paclitaxel), paclitaxel alone ($10^{-6}$ M), and paclitaxel/mifepristone ($10^{-6}$ M). Apoptosis was measured using FITC conjugated-anti-Annexin V antibody labeling followed FACS analysis to determine the percentage of the total cell population undergoing apoptosis after 20 hours of treatment. Mean+/−SE is shown. Significantly more apoptosis (P=0.028) was observed in the T-R MCF-7 cells when treated with mifepristone/paclitaxel compared to paclitaxel alone (FIG. 9). No difference was seen in the parental MCF-7 cells.

REFERENCES

The following references, to the extent that they provide exemplary procedural or other details supplementary to those set forth herein, are specifically incorporated herein by reference.

U.S. Pat. No. 5,143,854
U.S. Pat. No. 5,202,231
U.S. Pat. No. 5,242,974
U.S. Pat. No. 5,288,644
U.S. Pat. No. 5,324,633
U.S. Pat. No. 5,384,261
U.S. Pat. No. 5,405,783
U.S. Pat. No. 5,412,087
U.S. Pat. No. 5,424,186
U.S. Pat. No. 5,429,807
U.S. Pat. No. 5,432,049

U.S. Pat. No. 5,436,327
U.S. Pat. No. 5,445,934
U.S. Pat. No. 5,468,613
U.S. Pat. No. 5,470,710
U.S. Pat. No. 5,472,672
U.S. Pat. No. 5,492,806
U.S. Pat. No. 5,503,980
U.S. Pat. No. 5,510,270
U.S. Pat. No. 5,525,464
U.S. Pat. No. 5,525,464
U.S. Pat. No. 5,527,681
U.S. Pat. No. 5,529,756
U.S. Pat. No. 5,532,128
U.S. Pat. No. 5,545,531
U.S. Pat. No. 5,547,839
U.S. Pat. No. 5,554,501
U.S. Pat. No. 5,556,752
U.S. Pat. No. 5,561,071
U.S. Pat. No. 5,571,639
U.S. Pat. No. 5,580,726
U.S. Pat. No. 5,580,732
U.S. Pat. No. 5,593,839
U.S. Pat. No. 5,599,672
U.S. Pat. No. 5,599,695
U.S. Pat. No. 5,610,287
U.S. Pat. No. 5,624,711
U.S. Pat. No. 5,631,134
U.S. Pat. No. 5,639,603
U.S. Pat. No. 5,654,413
U.S. Pat. No. 5,658,734
U.S. Pat. No. 5,661,028
U.S. Pat. No. 5,665,547
U.S. Pat. No. 5,667,972
U.S. Pat. No. 5,695,940
U.S. Pat. No. 5,700,637
U.S. Pat. No. 5,744,305
U.S. Pat. No. 5,800,992
U.S. Pat. No. 5,807,522
U.S. Pat. No. 5,830,645
U.S. Pat. No. 5,837,196
U.S. Pat. No. 5,847,219
U.S. Pat. No. 5,871,928
U.S. Pat. No. 5,876,932
U.S. Pat. No. 5,919,626
U.S. Pat. No. 6,004,755
U.S. Pat. No. 6,087,102
U.S. Pat. No. 6,368,799
U.S. Pat. No. 6,383,749
U.S. Pat. No. 6,617,112
U.S. Pat. No. 6,638,717
U.S. Pat. No. 6,720,138
U.S. Patent Publn. 2010/0135956
Belanoff et al., *Eur. J. Pharmacol.*, 655(1-3):117-20, 2011.
Cho et al. *Biochemistry*, 44(9):3547-61, 2005.
Clark, *Curr. Top. Med. Chem.* 8(9):813-838, 2008.
Colleoni et al., *Annals of Oncology*, 11(8):1057, 2000.
Euopean Appln. EP 373 203
Euopean Appln. EP 785 280
Euopean Appln. EP 799 897
Evans, *Science*, 240:889, 1988.
Fodor et al., *Science*, 251:767-777, 1991.
Grover and Martin, *Carcinogenesis*, 23(7):1095-102, 2002.
Hacia et al., *Nature Genet.*, 14:441-449, 1996.
Harrison's Principles of Internal Medicine, Kasper et al. (Eds.), 16th Ed., Chapter 70, 2005.
Henderson et al. *Cancer Res.*, 48:246-253, 1988.
Keen and Davidson, *Cancer*, 97(3 Suppl):825-33, 2003.
Ma et al., *J. Immunol.*, 171(2):608-615, 2003.
MacBeath and Schreiber, *Science*, 289(5485):1760-3, 2000.
Melhem et al, *Clin. Cancer Res.*, 15(9):3196-204, 2009.
Mikosz et al., *J. Biol. Chem.*, 276:16649-54, 2001.
Moran et al., *Cancer Res.*, 60:867-872, 2000.
Pandey and Mann, *Nature*, 405(6788):837-46, 2000.
Pang and Conzen, *Cancer Biol. Ther. Cancer Biol. Ther.*, 5(8):933-40, 2006.
PCT Appln. WO 01/68255
PCT Appln. WO 03/020898
PCT Appln. WO 03/022421
PCT Appln. WO 03/023058
PCT Appln. WO 03/029485
PCT Appln. WO 03/040410
PCT Appln. WO 03/053586
PCT Appln. WO 03/066906
PCT Appln. WO 03/067217
PCT Appln. WO 03/076928
PCT Appln. WO 03/087297
PCT Appln. WO 03/091426
PCT Appln. WO 03/093810
PCT Appln. WO 03/100448A1
PCT Appln. WO 04/020085
PCT Appln. WO 04/027093
PCT Appln. WO 09/923,256
PCT Appln. WO 09/936,760
PCT Appln. WO 93/17126
PCT Appln. WO 95/11995
PCT Appln. WO 95/21265
PCT Appln. WO 95/21944
PCT Appln. WO 95/35505
PCT Appln. WO 96/30347
PCT Appln. WO 96/31622
PCT Appln. WO 96/33980
PCT Appln. WO 97/10365
PCT Appln. WO 97/27317
PCT Appln. WO 9743450
PCT Appln. WO 99/35505
PCT Appln. WO 01/38580
PCT Appln. WO 03/100012
Pease et al., *Proc. Natl. Acad. Sci. USA*, 91:5022-5026, 1994.
Peeters et al., Ann. NY Acad Sci., 1148:536-41, 2008.
Pike et al., *Epidemiologic Revi.*, 15(1):17-35, 1993.
Shoemaker et al., *Nature Genetics*, 14:450-456, 1996.
Sims et al. *BMC Medical Genomics*, 1(42):1-14, 2008.
Sorlie et al., *Proc. Natl. Acad. Sci. USA*, 98:10869-10874, 2001.
Srinivas et al., *Clin. Chem.*, 48(8):1160-9, 2002.
UK Appln. 8 803 000
Wu et al., *Cancer Res.*, 64:1757-64, 2004.
Wu et al., *J. Clin. Invest.*, 114:560-568, 2004.
Wu et al., *Mol Endocrinol.*, 2006

What is claimed is:

1. A method of killing breast cancer cells comprising administering to a breast cancer patient an effective amount of a combination of a chemotherapeutic agent and mifepristone, wherein the breast cancer cells do not express estrogen receptor alpha at a level detectable by immunohistochemistry (IHC), wherein the breast cancer cells were previously administered a first chemotherapeutic more than two weeks prior to the combination of anti-cancer compounds.

2. The method of claim 1, wherein the breast cancer cells that were previously administered a first chemotherapeutic are chemo-resistant.

3. The method of claim 2, wherein the breast cancer cells are determined not to be chemo-sensitive or are determined to be chemo-resistant.

4. The method of claim 1, wherein the breast cancer cells are glucocorticoid receptor-positive (GR+).

5. The method of claim 1, further comprising determining whether the breast cancer cells do not express detectable levels of estrogen receptor alpha by IHC.

6. The method of claim 1, wherein the glucocorticoid receptor antagonist is administered prior to the chemotherapeutic.

7. The method of claim 1, wherein the glucocorticoid receptor antagonist is administered after the chemotherapeutic is administered.

8. The method of claim 1, wherein the glucocorticoid receptor antagonist is administered prior to and after administration of the chemotherapeutic.

9. The method of claim 1, wherein the glucocorticoid receptor antagonist has undetectable or a lower level of activity as a progesterone receptor antagonist.

10. The method of claim 9, wherein the glucocorticoid receptor antagonist does not have detectable progesterone receptor antagonist activity.

11. The method of claim 1, wherein the breast cancer is an unresectable breast cancer.

12. The method of claim 1, wherein the breast cancer cells are PR− and HER2−.

13. A method of treating chemotherapy-insensitive breast cancer cells comprising administering to a breast cancer patient an effective amount of a glucocorticoid receptor antagonist followed by chemotherapy, wherein the glucocorticoid receptor antagonist is mifepristone, and wherein the breast cancer cells do not express estrogen receptor alpha at a level detectable by immunohistochemistry (IHC).

14. The method of claim 13, wherein the glucocorticoid receptor antagonist is not specific for progesterone receptor.

15. The method of claim 13, wherein the patient was previously treated with chemotherapy.

16. The method of claim 13, wherein the breast cancer cells are PR− and HER2−.

17. A method of treating breast cancer cells comprising administering to a breast cancer patient an effective amount of a glucocorticoid receptor antagonist followed by at least one apoptosis-inducing agent, wherein the glucocorticoid receptor antagonist is mifepristone, and wherein the breast cancer cells do not express estrogen receptor alpha at a level detectable by immunohistochemistry (IHC) and are determined to be resistant to apoptosis.

18. The method of claim 17, wherein at least one apoptosis inducing agent is radiation, a chemotherapeutic, or an immunotherapy.

19. The method of claim 17, wherein the breast cancer cells are PR− and HER2−.

20. A method for treating breast cancer in a patient comprising:
   a) administering radiation or at least a first chemotherapeutic to the patient;
   b) subsequently administering an effective amount of a glucocorticoid receptor antagonist to the patient;
   c) administering radiation again or at least a second chemotherapeutic to the patient after the glucocorticoid receptor antagonist is administered to the patient, wherein the glucocorticoid receptor antagonist is mifepristone, and wherein breast cancer cells do not express estrogen receptor alpha at a level detectable by immunohistochemistry (IHC).

21. The method of claim 20, wherein the breast cancer cells are PR− and HER2−.

\* \* \* \* \*